US008426174B2

(12) United States Patent
Bramucci et al.

(10) Patent No.: US 8,426,174 B2
(45) Date of Patent: Apr. 23, 2013

(54) METHOD FOR THE PRODUCTION OF 2-BUTANOL

(75) Inventors: Michael G. Bramucci, Boothwyn, PA (US); Dennis Flint, Newark, DE (US); Edward S. Miller, Jr., Knoxville, TN (US); Vasantha Nagarajan, Wilmington, DE (US); Natalia Sedkova, Cherry Hill, NJ (US); Manjari Singh, West Chester, PA (US); Tina K. Van Dyk, Wilmington, DE (US)

(73) Assignee: Butamax(TM) Advanced Biofuels LLC, Wilmington, DE (US)

( * ) Notice: Subject to any disclaimer, the term of this patent is extended or adjusted under 35 U.S.C. 154(b) by 865 days.

(21) Appl. No.: 12/110,510

(22) Filed: Apr. 28, 2008

(65) Prior Publication Data

US 2008/0274525 A1   Nov. 6, 2008

Related U.S. Application Data

(60) Provisional application No. 60/915,459, filed on May 2, 2007.

(51) Int. Cl.
*C12P 7/16* (2006.01)

(52) U.S. Cl.
USPC .......................................................... 435/160

(58) Field of Classification Search ........................ None
See application file for complete search history.

(56) References Cited

U.S. PATENT DOCUMENTS

| | | | |
|---|---|---|---|
| 2,198,104 | A | 4/1940 | Carnarius |
| 5,063,156 | A | 11/1991 | Glassner et al. |
| 5,192,673 | A | 3/1993 | Jain et al. |
| 5,424,202 | A | 6/1995 | Ingram et al. |
| 5,686,276 | A | 11/1997 | Laffend et al. |
| 5,763,236 | A | 6/1998 | Kojima et al. |
| 6,358,717 | B1 | 3/2002 | Blaschek et al. |
| 6,432,688 | B1 | 8/2002 | Ito et al. |
| 6,514,733 | B1 | 2/2003 | Emptage et al. |
| 6,960,465 | B1 | 11/2005 | Papoutsakis et al. |
| 2002/0028492 | A1 | 3/2002 | Leuke et al. |
| 2004/0157305 | A1 | 8/2004 | Stampfer et al. |
| 2004/0234649 | A1 | 11/2004 | Lewis et al. |
| 2005/0003500 | A1 | 1/2005 | Kudoh et al. |
| 2007/0259410 | A1* | 11/2007 | Donaldson et al. ............ 435/148 |
| 2007/0259411 | A1 | 11/2007 | Bramucci et al. |
| 2007/0265477 | A1 | 11/2007 | Gupta et al. |
| 2007/0292927 | A1* | 12/2007 | Donaldson et al. ............ 435/160 |
| 2008/0124774 | A1 | 5/2008 | Bramucci et al. |

FOREIGN PATENT DOCUMENTS

| | | |
|---|---|---|
| AU | 620802 | 10/1988 |
| EP | 315949 | 5/1989 |
| EP | 0 645 453 B1 | 3/1995 |
| EP | 1 149 918 A1 | 10/2001 |
| WO | WO 90/02193 | 3/1990 |
| WO | WO 98/51813 | 11/1998 |
| WO | WO 03/078615 A1 | 9/2003 |
| WO | WO 2007/130518 | 11/2007 |
| WO | WO 2008/006038 | 1/2008 |

OTHER PUBLICATIONS

Berovic et al., Food Technol. Biotechnol., 2003, vol. 41, No. 4, p. 353-359.*
See KEGG *S. bayanus* 18810, 1 page.*
Poulsen et al. J. Biochem., 1989, vol. 185, p. 433, 435-439.*
KEGG, *S. bayanus* 18810, downloaded on Dec. 9, 2011, 1 page.*
Butanols, Ullmann'S Encyclopedia of Industrial Chemistry, 6th Edition, 2003, vol. 5:716-719.
Speranza et al., Conversion of Meso-2,3-Butanediol Into 2-Butanol by Lactobacilli, Stereochemical and Enzymatic Aspects, J. Agric. Food Chem., 1997, vol. 45:3476-3480.
Amartey et al., Effects of Temperature and Medium Composition on the Ethanol Tolerance of *Bacillus stearothermophilus*, Biotechnol. Lett., 1991, vol. 13:627-632.
Herrero et al., Development of Ethanol Tolerance in *Clostridium thermocellum*: Effect of Growth Temperature, Appl. Environ. Microbiol., 1980, vol. 40:571-577.
Brown et al., The Effect of Temperature on the Ethanol Tolerance of the Yeast, *Saccharomyces uvarum*, Biotechnol. Lett., 1982, vol. 4:269-274.
Van Uden, Effects of Ethanol on the Temperature Relations of Viability and Growth in Yeast, CRC Crit. Rev. Biotechnol., 1984, vol. 1:263-273.
Harada, On the Butanol-Rich Production in Acetone-Butanol Fermentation of Molasses. (Part 2) Temperature, Hakkp Kyokaishi, 1962, vol. 20:155-156.
Jones et al., Acetone-Butanol Fermentation Revisted, Microbiol. Rev., 1986, vol. 50:484-524.
Bermjeo, et al., Expression of *Clostridium acetobutylicum* ATCC 824 Genes in *Escherichia coli* for Acetone Production . . . , Appl. Environ. Microbiol. 64:1079-1085, 1998.
Blomqvist, et al., Characterization of the Genes of the 2,3-Butanediol Operons from *Klebsielle terrigena* and *Enterobacter aerogenes*, J. Bacteriol. 175:1392-1404, 1993.
Cornillot, et al., The Genes for Butanol and Acetone Formation in *Clostridium acetbutylicum* ATCC 824 Reside on a Large Plasmid Whose Loss . . . , J. Bacterial. 179:5442-5447, 1997.
Durre, New Insights and Novel Developments in Clostridial Acetone/Butanol/Isopropanol Fermentation, Appl. Microbiol. Biotechnol. 49:639-648, 1998.
Fontaine, et al., Molecular Characterization and Transc iptional Analysis of acihE2, the Gene Encoding the NADH-dependent Aldehyde/Alcohol . . . , J. Bacteriol. 184:821-830, 2002.
Garcia-Alles, et al., Phosphoenolpyruvate- and ATP-Dependent Dihydroxyacetone Kinases: Covalent Substrate-Binding and Kinetic Mechanism, Biochemistry 43:13037-13045, 2004.
Girbal, et al., Regulation of Solvent Production in *Clostridium acetobutylicum*, TIBTech 16:11-16, 1998.
Harris, et al., Characterization of Recombinant Strains of the *Clostridium acetobutylicum* Butyrate Kinase Inactivation Mutant:Need for New . . . Biotechnol. Bioeng, 67:1-11, 2000.
Keen, et al., The Formation of 2-Butanone and 2-Butanol in Cheddar Cheese, J. Dairy Res. 41:249-257, 1974.
O'Brien, et al., Insight into the Mechanism of the B12-independent Glycerol Dehydratase from *Clostridium butyricum*: Preliminary Biochemical . . . , Biochemistry 43:4635-4645, 2004.

(Continued)

*Primary Examiner* — Kade Ariani

(74) *Attorney, Agent, or Firm* — Christine M. Lhulier

(57) ABSTRACT

A method for the production of 2-butanol by fermentation using a microbial production host is disclosed. The method employs a reduction in temperature during the fermentation process that results in a more robust tolerance of the production host to the butanol product.

50 Claims, 1 Drawing Sheet

OTHER PUBLICATIONS

Peng, et al., Cloning, Sequencing and Heterologous Expression of a *Klebsiella pneumoniae* Gene Encoding an FAD-independent Acetoiactate Synthase, Gene 117:125-130, 1992.

Radler, et al., Characterization of the Enzyme Involved in Formation of 2-Butanol from meso-2,3-Butanediol by Lactic Acid Bacteria, Am. J. Enol. Vitic. 37:206-210, 1986.

Scott, et al., Whole-Geneome Transcription Profiling Reveals Genes Up-Regulated by Growth on Fucosen in the Human Gut Bacterium . . . , J. Bacteriol. 188:4340-4349, 2006.

Seyfried, et al., Cloning, Sequencing, and Overexpression of the Genes Encoding Coenzyme B12-dependent Glycerol Dehydratase of . . . , J. Bacteriol. 178:5793-5796, 1996.

Shin, et al., Purification, Characterization, and Molecular Cloning of a Novel Amine: Pyruvate Transaminase from Vibrio . . . , Appl. Microbiol. Biotechnol. 61:463-471, 2003.

Stewart, A Chemist's Perspective on the Use of Genetically Engineered Microbes as Reagent for Organic Synthesis, Biotechnol. Genetic Eng. Rev. 14:67-143, 1997.

Tobimatsu, et al., Molecular Cloning, Sequencing, and Expression of the Genes Encoding Adenosylcobalamin-dependent Diol Dehydrase . . . , J. Biol. Chem. 270:7142-7148, 1995.

Ul, et al., Production of L-2,3-butanediol by a New Pathway Constructed in *Escherichia coli*, Lett. Appl. Microbiol. 39:533-537, 2004.

Voloch, et al., Reduction of Acetoin to 2,3-Butanediol in *Klebsiella pneumoniae*: A New Model, Biotech. Bioeng. 25:173-183, 1983.

Woods, The Genetic Engineering of Microbial Solvent Production, TiBTech 13:259-264, 1995.

Baer, et al. Effect of Butanol Challenge and Temperature on Lipid Composition and Membrane Fluidity of Butanol-tolerant . . . , Appl. Environ. Microbiol. 53:2854-2861, 1987.

* cited by examiner

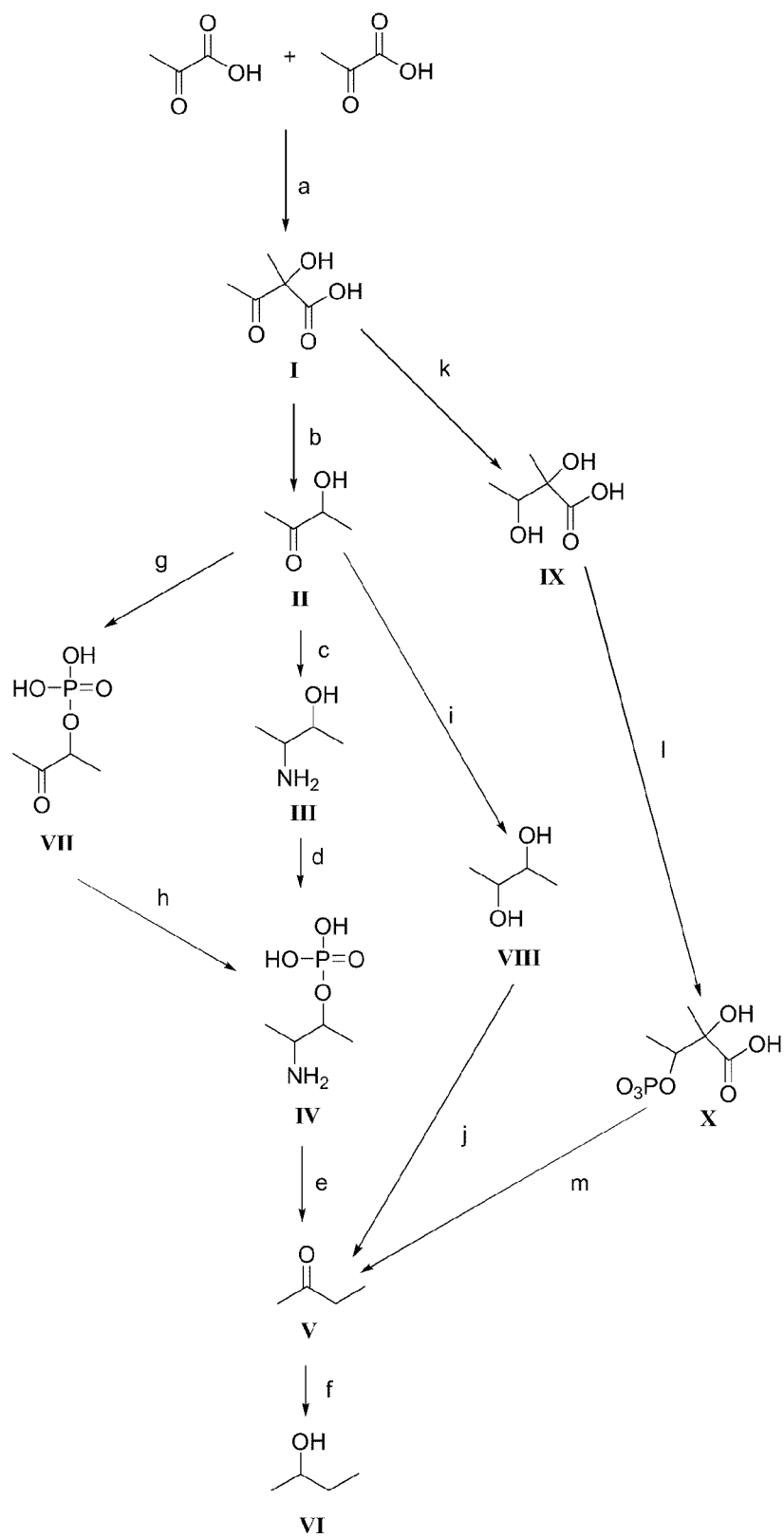

METHOD FOR THE PRODUCTION OF 2-BUTANOL

CROSS-REFERENCE TO RELATED APPLICATIONS

This application claims the benefit of priority to U.S. Provisional Application Ser. No. 60/915,459, filed on May 2, 2007.

FIELD OF THE INVENTION

The invention relates to a method for the production of 2-butanol by fermentation using a recombinant microbial host. Specifically, the method employs a decrease in temperature during fermentation that results in more robust tolerance of the production host to the 2-butanol product.

BACKGROUND OF THE INVENTION

Butanol is an important industrial chemical, useful as a fuel additive, as a feedstock chemical in the plastics industry, and as a foodgrade extractant in the food and flavor industry. Each year 10 to 12 billion pounds of butanol are produced by petrochemical means and the need for this commodity chemical will likely increase.

Methods for the chemical synthesis of 2-butanol are known, such as n-butene hydration (*Ullmann's Encyclopedia of Industrial Chemistry*, 6$^{th}$ edition, 2003, Wiley-VCH Verlag GmbH and Co., Weinheim, Germany, Vol. 5, pp. 716-719). These processes use starting materials derived from petrochemicals and are generally expensive, and are not environmentally friendly. The production of 2-butanol from plant-derived raw materials would minimize greenhouse gas emissions and would represent an advance in the art.

Methods for producing 2-butanol by biotransformation of other organic chemicals are also known. For example, Stampfer et al. (WO 03/078615) describe the production of secondary alcohols, such as 2-butanol, by the reduction of ketones which is catalyzed by an alcohol dehydrogenase enzyme obtained from *Rhodococcus ruber*. Similarly, Kojima et al. (EP 0645453) describe a method for preparing secondary alcohols, such as 2-butanol, by reduction of ketones which is catalyzed by a secondary alcohol dehydrogenase enzyme obtained from *Candida parapsilosis*. Additionally, Kuehnle et al. (EP 1149918) describe a process that produces both 1-butanol and 2-butanol by the oxidation of hydrocarbons by various strains of *Rhodococcus ruber*. The process favored 1-butanol production with a selectivity of 93.8%.

The production of 2-butanol by certain strains of *Lactobacilli* is also known (Speranza et. al. *J. Agric. Food Chem.* (1997) 45:3476-3480). The 2-butanol is produced by the transformation of meso-2,3-butanediol. The production of 2-butanol from acetolactate and acetoin by these *Lactobacilli* strains was also demonstrated.

Recombinant microbial production hosts expressing 2-butanol biosynthetic pathways are described in co-pending and commonly owned U.S. Patent Application Publication No. US20070259410A1. However, biological production of 2-butanol is believed to be limited by 2-butanol toxicity to the host microorganism used in the fermentation.

Some microbial strains that are tolerant to 2-butanol are known in the art (co-pending and commonly owned U.S. patent application Ser. Nos. 11/743,220 and 11/761,497). However, biological methods of producing 2-butanol to higher levels are required for cost effective commercial production.

There have been reports describing the effect of temperature on the tolerance of some microbial strains to ethanol. For example, Amartey et al. (*Biotechnol. Lett.* 13(9):627-632 (1991)) disclose that *Bacillus stearothermophillus* is less tolerant to ethanol at 70° C. than at 60° C. Herrero et al. (*Appl. Environ. Microbiol.* 40(3):571-577 (1980)) report that the optimum growth temperature of a wild-type strain of *Clostridium thermocellum* decreases as the concentration of ethanol challenge increases, whereas the optimum growth temperature of an ethanol-tolerant mutant remains constant. Brown et al. (*Biotechnol. Lett.* 4(4):269-274 (1982)) disclose that the yeast *Saccharomyces uvarum* is more resistant to growth inhibition by ethanol at temperatures 5° C. and 10° C. below its growth optimum of 35° C. However, fermentation became more resistant to ethanol inhibition with increasing temperature. Additionally, Van Uden (*CRC Crit. Rev. Biotechnol.* 1 (3):263-273 (1984)) report that ethanol and other alkanols depress the maximum and the optimum growth temperature for growth of *Saccharomyces cerevisiae* while thermal death is enhanced. Moreover, Lewis et al. (U.S. Patent Application Publication No. 2004/0234649) describe methods for producing high levels of ethanol during fermentation of plant material comprising decreasing the temperature during saccharifying, fermenting, or simultaneously saccharifying and fermenting Much less is known about the effect of temperature on the tolerance of microbial strains to butanols. Harada (*Hakko Kyokaishi* 20:155-156 (1962)) discloses that the yield of 1-butanol in acetone-butanol-ethanol (ABE) fermentation is increased from 18.4%-18.7% to 19.1%-21.2% by lowering the temperature from 30° C. to 28° C. when the growth of the bacteria reaches a maximum. Jones et al. (*Microbiol. Rev.* 50(4):484-524 (1986)) review the role of temperature in ABE fermentation. They report that the solvent yields of three different solvent producing strains remains fairly constant at 31% at 30° C. and 33° C., but decreases to 23 to 25% at 37° C. Similar results were reported for *Clostridium acetobutylicum* for which solvent yields decreased from 29% at 25° C. to 24% at 40° C. In the latter case, the decrease in solvent yield was attributed to a decrease in acetone production while the yield of 1-butanol was unaffected. However, Carnarius (U.S. Pat. No. 2,198,104) reports that an increase in the butanol ratio is obtained in the ABE process by decreasing the temperature of the fermentation from 30° C. to 24° C. after 16 hours. However, the effect of temperature on the production of 2-butanol by recombinant microbial hosts is not known in the art.

There is a need, therefore, for a cost-effective process for the production of 2-butanol by fermentation that provides higher yields than processes known in the art. The present invention addresses this need through the discovery of a method for producing 2-butanol by fermentation using a recombinant microbial host, which employs a decrease in temperature during fermentation, resulting in more robust tolerance of the production host to the 2-butanol product.

SUMMARY OF THE INVENTION

The invention provides a method for the production of 2-butanol by fermentation using a recombinant microbial host, which employs a decrease in temperature during fermentation that results in more robust tolerance of the production host to the 2-butanol product.

Accordingly, the invention provides a method for the production of 2-butanol comprising:
a) providing a recombinant microbial production host which produces 2-butanol;
b) seeding the production host of (a) into a fermentation medium comprising a fermentable carbon substrate to create a fermentation culture;
c) growing the production host in the fermentation culture at a first temperature for a first period of time;
d) lowering the temperature of the fermentation culture to a second temperature; and
e) incubating the production host at the second temperature of step (d) for a second period of time;
whereby 2-butanol is produced.

BRIEF DESCRIPTION OF THE FIGURES AND SEQUENCE DESCRIPTIONS

The invention can be more fully understood from the following detailed description, FIGURE, and the accompanying sequence descriptions, which form a part of this application.

FIG. 1 shows four different pathways for biosynthesis of 2-butanone and 2-butanol.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5 (a-bis), and Section 208 and Annex C of the Administrative Instructions). The symbols and format used for nucleotide and amino acid sequence data comply with the rules set forth in 37 C.F.R. §1.822.

TABLE 1

Summary of Nucleic Acid and Protein SEQ ID Numbers

| Description | SEQ ID Nucleic acid | SEQ ID Protein |
|---|---|---|
| budA, acetolactate decarboxylase from Klebsiella pneumoniae ATCC 25955 | 1 | 2 |
| alsD, acetolactate decarboxylase from Bacillus subtilis | 80 | 81 |
| budA, acetolactate decarboxylase from Klebsiella terrigena | 82 | 83 |
| budB, acetolactate synthase from Klebsiella pneumoniae ATCC 25955 | 3 | 4 |
| alsS, acetolactate synthase from Bacillus subtilis | 76 | 77 |
| budB, acetolactate synthase from Klebsiella terrigena | 78 | 79 |
| budC butanediol dehydrogenase from Klebsiella pneumoniae IAM1063 | 5 | 6 |
| butanediol dehydrogenase from Bacillus cereus | 84 | 85 |
| butanediol dehydrogenase from Bacillus cereus | 86 | 87 |
| butB, butanediol dehydrogenase from Lactococcus lactis | 88 | 89 |
| pddA, butanediol dehydratase alpha subunit from Klebsiella oxytoca ATCC 8724 | 7 | 8 |
| pddB, butanediol dehydratase beta subunit from Klebsiella oxytoca ATCC 8724 | 9 | 10 |
| pddC, butanediol dehydratase gamma subunit from Klebsiella oxytoca ATCC 8724 | 11 | 12 |
| pduC, B12 dependent diol dehydratase large subunit from Salmonella typhimurium | 92 | 93 |
| pduD, B12 dependent diol dehydratase medium subunit from Salmonella typhimurium | 94 | 95 |
| pduE, B12 dependent diol dehydratase small subunit from Salmonella typhimurium | 96 | 97 |
| pduC, B12 dependent diol dehydratase large subunit from Lactobacillus collinoides | 98 | 99 |

TABLE 1-continued

Summary of Nucleic Acid and Protein SEQ ID Numbers

| Description | SEQ ID Nucleic acid | SEQ ID Protein |
|---|---|---|
| pduD, B12 dependent diol dehydratase medium subunit from Lactobacillus collinoides | 100 | 101 |
| pduE, B12 dependent diol dehydratase small subunit from Lactobacillus collinoides | 102 | 103 |
| pddC, adenosylcobalamin-dependent diol dehydratase alpha subunit from Klebsiella pneumoniae | 104 | 105 |
| pddD, adenosylcobalamin-dependent diol dehydratase beta subunit from Klebsiella pneumoniae | 106 | 107 |
| pddD, adenosylcobalamin-dependent diol dehydratase gamma subunit from Klebsiella pneumoniae | 108 | 109 |
| ddrA, diol dehydratase reactivating factor large subunit from Klebsiella oxytoca | 110 | 111 |
| ddrB, diol dehydratase reactivating factor small subunit from Klebsiella oxytoca | 112 | 113 |
| pduG, diol dehydratase reactivating factor large subunit from Salmonella typhimurium | 114 | 115 |
| pduH, diol dehydratase reactivating factor small subunit from Salmonella typhimurium | 116 | 117 |
| pduG, diol dehydratase reactivating factor large subunit from Lactobacillus collinoides | 118 | 119 |
| pduH, diol dehydratase reactivating factor small subunit from Lactobacillus collinoides | 120 | 121 |
| sadH, butanol dehydrogenase from Rhodococcus ruber 219 | 13 | 14 |
| adhA, butanol dehydrogenase from Pyrococcus furiosus | 90 | 91 |
| chnA, cyclohexanol dehydrogenase from Acinteobacter sp. | 71 | 72 |
| yqhD, butanol dehydrogenase from Escherichia coli | 74 | 75 |
| amine: pyruvate transaminase from Vibrio fluvialis (an acetoin aminase) | 144 codon opt. | 122 |
| amino alcohol kinase from Erwinia carotovora subsp. atroseptica | 123 | 124 |
| amino alcohol O-phosphate lyase from Erwinia carotovora subsp. atroseptica | 125 | 126 |
| budC, acetoin reductase (butanediol dehydrogenase) from Klebsiella terrigena (now Raoultella terrigena) | 133 | 134 |
| glycerol dehydratase alpha subunit from Klebsiella pneumoniae | 145 | 146 |
| glycerol dehydratase beta subunit from Klebsiella pneumoniae | 147 | 148 |
| glycerol dehydratase gamma subunit from Klebsiella pneumoniae | 149 | 150 |
| glycerol dehydratase reactivase large subunit from Klebsiella pneumoniae | 151 | 152 |
| glycerol dehydratase reactivase small subunit from Klebsiella pneumoniae | 153 | 154 |

SEQ ID NOs:15-65 are the nucleotide sequences of oligonucleotide PCR, cloning, screening, and sequencing primers used in the Examples.

SEQ ID NO:66 is nucleotide sequence of the deleted region of the yqhD gene in E. coli strain MG1655 ΔyqhCD, described in Example 15.

SEQ ID NO:67 is the nucleotide sequence of a variant of the glucose isomerase promoter 1.6GI.

SEQ ID NO:68 is the nucleotide sequence of the 1.5GI promoter.

SEQ ID NO:69 is the nucleotide sequence of the diol dehydratase operon from Klebsiella oxytoca.

SEQ ID NO:70 is the nucleotide sequence of the diol dehydratase reactivating factor operon from Klebsiella oxytoca.

SEQ ID NO:73 is the nucleotide sequence of pDCQ2, which is described in Example 13.

SEQ ID NOs:127-132 are the nucleotide sequences of additional oligonucleotide PCR and cloning primers used in the Examples.

SEQ ID NO: 55 is a codon optimized coding region for the amino alcohol kinase of *Erwinia carotovora* subsp. *atroseptica*.

SEQ ID NO:156 is a codon optimized coding region for the amino alcohol O-phosphate lyase of *Erwinia carotovora* subsp. *atroseptica*.

SEQ ID NOs:157-163 are the nucleotide sequences of additional oligonucleotide PCR and cloning primers used in the Examples.

SEQ ID NO:164 is the nucleotide sequence of an operon from *Erwinia carotovora* subsp. *atroseptica*.

TABLE 2

Additional glycerol and diol dehydratase large, medium and small subunits

| [a]Description | [b]subunit | protein SEQ ID |
|---|---|---|
| Corresponding subunits from same organism[c] | | |
| Glycerol dehydratase alpha subunit from *Clostridium pasteurianum* | L | 135 |
| Glycerol dehydratase beta subunit from *Clostridium pasteurianum* | M | 136 |
| Glycerol dehydratase gamma subunit from *Clostridium pasteurianum* | S | 137 |
| Glycerol dehydratase alpha subunit from *Escherichia blattae* | L | 138 |
| Glycerol dehydratase beta subunit from *Escherichia blattae* | M | 139 |
| Glycerol dehydratase gamma subunit from *Escherichia blattae* | S | 140 |
| Glycerol dehydratase alpha subunit from *Citrobacter freundii* | L | 141 |
| Glycerol dehydratase beta subunit from *Citrobacter freundii* | M | 142 |
| Glycerol dehydratase gamma subunit from *Citrobacter freundii* | S | 143 |

[a]Description: from the Genbank annotation of the sequence and may not be correct including the glycerol or diol designation, or may not include subunit information.
[b]Subunit: identified by sequence homology to the large, medium, or small subunit. of the *Klebsiella oxytoca* enzyme.
[c]Subunts are listed together that are from the same organism and have annotations as the same enzyme, or have Genbank numbers close together indicating proximity in the genome.

DETAILED DESCRIPTION OF THE INVENTION

The present invention relates to a method for the production of 2-butanol using recombinant microorganisms that employs a decrease in temperature during fermentation, resulting in more robust tolerance of the production host to the 2-butanol product and therefore a higher titer of 2-butanol. The present invention meets a number of commercial and industrial needs. 2-Butanol is an important industrial commodity chemical with a variety of applications, where its potential as a fuel or fuel additive is particularly significant. Although only a four-carbon alcohol, butanol has an energy content similar to that of gasoline and can be blended with any fossil fuel. Butanol is favored as a fuel or fuel additive as it yields only $CO_2$ and little or no $SO_X$ or $NO_X$ when burned in the standard internal combustion engine. Additionally butanol is less corrosive than ethanol, the most preferred fuel additive to date.

In addition to its utility as a biofuel or fuel additive, butanol has the potential of impacting hydrogen distribution problems in the emerging fuel cell industry. Fuel cells today are plagued by safety concerns associated with hydrogen transport and distribution. Butanol can be easily reformed for its hydrogen content and can be distributed through existing gas stations in the purity required for either fuel cells or combustion engines in vehicles.

Finally the present invention produces 2-butanol from plant derived carbon sources, avoiding the negative environmental impact associated with standard petrochemical processes for butanol production.

The following definitions and abbreviations are to be used for the interpretation of the claims and the specification.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "2-butanol biosynthetic pathway" refers to the enzyme pathways to produce 2-butanol from pyruvate.

The term "2-butanone biosynthetic pathway" refers to the enzyme pathways to produce 2-butanone from pyruvate.

The term "acetolactate synthase", also known as "acetohydroxy acid synthase", refers to a polypeptide (or polypeptides) having an enzyme activity that catalyzes the conversion of two molecules of pyruvic acid to one molecule of alpha-acetolactate. Acetolactate synthase, known as EC 2.2.1.6 [formerly 4.1.3.18] (*Enzyme Nomenclature* 1992, Academic Press, San Diego) may be dependent on the cofactor thiamin pyrophosphate for its activity. Suitable acetolactate synthase enzymes are available from a number of sources, for example, *Bacillus subtilis* [GenBank Nos: AAA22222 NCBI (National Center for Biotechnology Information) amino acid sequence (SEQ ID NO:77), L04470 NCBI nucleotide sequence (SEQ ID NO:76)], *Klebsiella terrigena* [GenBank Nos: AAA25055 (SEQ ID NO:79), L04507 (SEQ ID NO:78)], and *Klebsiella pneumoniae* [GenBank Nos: AAA25079 (SEQ ID NO:4), M73842 (SEQ ID NO:3)].

The term "acetolactate decarboxylase" refers to a polypeptide (or polypeptides) having an enzyme activity that catalyzes the conversion of alpha-acetolactate to acetoin. Acetolactate decarboxylases are known as EC 4.1.1.5 and are available, for example, from *Bacillus subtilis* [GenBank Nos: AAA22223 (SEQ ID NO:81), L04470 (SEQ ID NO:80)], *Klebsiella terrigena* [GenBank Nos: AAA25054 (SEQ ID NO:83), L04507 (SEQ ID NO:82)] and *Klebsiella pneumoniae* [GenBank Nos: AAU43774 (SEQ ID NO:2), AY722056 (SEQ ID NO:1)].

The term "acetoin aminase" refers to a polypeptide (or polypeptides) having an enzyme activity that catalyzes the conversion of acetoin to 3-amino-2-butanol. Acetoin aminase may utilize the cofactor pyridoxal 5'-phosphate or NADH (reduced nicotinamide adenine dinucleotide) or NADPH (reduced nicotinamide adenine dinucleotide phosphate). The resulting product may have (R) or (S) stereochemistry at the 3-position. The pyridoxal phosphate-dependent enzyme may use an amino acid such as alanine or glutamate as the amino donor. The NADH- and NADPH-dependent enzymes may use ammonia as a second substrate. A suitable example of an NADH-dependent acetoin aminase, also known as amino alcohol dehydrogenase, is described by Ito et al. (U.S. Pat. No. 6,432,688). An example of a pyridoxal-dependent acetoin aminase is the amine:pyruvate aminotransferase (also called amine:pyruvate transaminase) described by Shin and Kim (*J. Org. Chem.* 67:2848-2853 (2002)).

The term "butanol dehydrogenase" refers to a polypeptide (or polypeptides) having an enzyme activity that catalyzes the interconversion of 2-butanone and 2-butanol. Butanol dehydrogenases are a subset of a broad family of alcohol dehydrogenases. Butanol dehydrogenase may be NAD- or NADP-dependent. The NAD-dependent enzymes are known as EC 1.1.1.1 and are available, for example, from *Rhodococcus ruber* [GenBank Nos: CAD36475 (SEQ ID NO:14), AJ491307 (SEQ ID NO:13)]. The NADP-dependent enzymes are known as EC 1.1.1.2 and are available, for example, from *Pyrococcus furiosus* [GenBank Nos: AAC25556 (SEQ ID NO:91), AF013169 (SEQ ID NO:90)]. Additionally, a butanol dehydrogenase is available from *Escherichia coli* [GenBank Nos:NP_417-484 (SEQ ID NO:75), NC_000913 (SEQ ID NO:74)] and a cyclohexanol dehydrogenase with activity towards 2-butanol is available from *Acinetobacter* sp. [GenBank Nos: AAG10026 (SEQ ID NO:72), AF282240 (SEQ ID NO:71)].

The term "acetoin kinase" refers to a polypeptide (or polypeptides) having an enzyme activity that catalyzes the conversion of acetoin to phosphoacetoin. Acetoin kinase may utilize ATP (adenosine triphosphate) or phosphoenolpyruvate as the phosphate donor in the reaction. Although there are no reports of enzymes catalyzing this reaction on acetoin, there are enzymes that catalyze the analogous reaction on the similar substrate dihydroxyacetone, for example, enzymes known as EC 2.7.1.29 (Garcia-Alles et al. (2004) *Biochemistry* 43:13037-13046).

The term "acetoin phosphate aminase" refers to a polypeptide (or polypeptides) having an enzyme activity that catalyzes the conversion of acetoin phosphate (also called phosphoacetoin) to 3-amino-2-butanol O-phosphate. Acetoin phosphate aminase may use the cofactor pyridoxal 5'-phosphate, NADH or NADPH. The resulting product may have (R) or (S) stereochemistry at the 3-position. The pyridoxal phosphate-dependent enzyme may use an amino acid such as alanine or glutamate. The NADH- and NADPH-dependent enzymes may use ammonia as a second substrate. Although there are no reports of enzymes catalyzing this reaction on acetoin phosphate, there is a pyridoxal phosphate-dependent enzyme that is proposed to carry out the analogous reaction on the similar substrate serinol phosphate (Yasuta et al. (2001) *Appl. Environ. Microbiol.* 67:4999-5009).

The term "aminobutanol phosphate phospho-lyase", also called "amino alcohol O-phosphate lyase", refers to a polypeptide (or polypeptides) having an enzyme activity that catalyzes the conversion of 3-amino-2-butanol O-phosphate to 2-butanone. Aminobutanol phosphate phospho-lyase may utilize the cofactor pyridoxal 5'-phosphate. There are reports of enzymes that catalyze the analogous reaction on the similar substrate 1-amino-2-propanol phosphate (Jones et al. (1973) *Biochem J.* 134:167-182). Disclosed in co-owned and co-pending US Patent Application Publication No. 20070259410A1 is an aminobutanol phosphate phospho-lyase (SEQ ID NO: 126) from the organism *Erwinia carotovora*, with demonstrated aminobutanol phosphate phospho-lyase activity.

The term "aminobutanol kinase" refers to a polypeptide (or polypeptides) having an enzyme activity that catalyzes the conversion of 3-amino-2-butanol to 3-amino-2-butanol O-phosphate. Aminobutanol kinase may utilize ATP as the phosphate donor. There are reports of enzymes that catalyze the analogous reaction on the similar substrates ethanolamine and 1-amino-2-propanol (Jones et al., supra). Disclosed in co-owned and co-pending US Patent Application Publication No. 20070259410A1 is an amino alcohol kinase of *Erwinia carotovora* subsp. *atroseptica* (SEQ ID NO:124).

The term "butanediol dehydrogenase" also known as "acetoin reductase" refers to a polypeptide (or polypeptides) having an enzyme activity that catalyzes the conversion of acetoin to 2,3-butanediol. Butanediol dehydrogenases are a subset of the broad family of alcohol dehydrogenases. Butanediol dehydrogenase enzymes may have specificity for production of (R)- or (S)-stereochemistry in the alcohol product. (S)-specific butanediol dehydrogenases are known as EC 1.1.1.76 and are available, for example, from *Klebsiella pneumoniae* (GenBank Nos: BBA13085 (SEQ ID NO:6), D86412 (SEQ ID NO:5)). (R)-specific butanediol dehydrogenases are known as EC 1.1.1.4 and are available, for example, from *Bacillus cereus* [GenBank Nos. NP_830481 (SEQ ID NO:85), NC_004722 (SEQ ID NO:84); AAP07682 (SEQ ID NO:87), AE017000 (SEQ ID NO:86)], and *Lactococcus lactis* [GenBank Nos. AAK04995 (SEQ ID NO:89), AE006323 (SEQ ID NO:88)].

The term "butanediol dehydratase", also known as "diol dehydratase" or "propanediol dehydratase" refers to a polypeptide (or polypeptides) having an enzyme activity that catalyzes the conversion of 2,3-butanediol to 2-butanone. Butanediol dehydratase may utilize the cofactor adenosyl cobalamin (vitamin B12). Adenosyl cobalamin-dependent enzymes are known as EC 4.2.1.28 and are available, for example, from *Klebsiella oxytoca* [GenBank Nos: BAA08099 (alpha subunit) (SEQ ID NO:8), D45071 (SEQ ID NO:7); BAA08100 (beta subunit) (SEQ ID NO:10), D45071 (SEQ ID NO:9); and BBA08101 (gamma subunit) (SEQ ID NO:12), D45071 (SEQ ID NO:11) (Note all three subunits are required for activity)], and *Klebsiella pneumoniae* [GenBank Nos: AAC98384 (alpha subunit) (SEQ ID NO:105), AF102064 (SEQ ID NO:104); GenBank Nos: AAC98385 (beta subunit) (SEQ ID NO:107), AF102064 (SEQ ID NO:106), GenBank Nos: AAC98386 (gamma subunit) SEQ ID NO:109), AF102064 (SEQ ID NO:108)]. Other suitable diol dehydratases include, but are not limited to, B12-dependent diol dehydratases available from *Salmonella typhimurium* [GenBank Nos: AAB84102 (large subunit) (SEQ ID NO:93), AF026270 (SEQ ID NO:92); GenBank Nos: AAB84103 (medium subunit) (SEQ ID NO:95), AF026270 (SEQ ID NO:94); GenBank Nos: AAB84104 (small subunit) (SEQ ID NO:97), AF026270 (SEQ ID NO:96)]; and *Lactobacillus collinoides* [GenBank Nos: CAC82541 (large subunit) (SEQ ID NO:99), AJ297723 (SEQ ID NO:98); GenBank Nos: CAC82542 (medium subunit) (SEQ ID NO:101); AJ297723 (SEQ ID NO:100); GenBank Nos: CAD01091 (small subunit) (SEQ ID NO:103), AJ297723 (SEQ ID NO:102)]; and enzymes from *Lactobacillus brevis* (particularly strains CNRZ 734 and CNRZ 735, Speranza et al., supra), and nucleotide sequences that encode the corresponding enzymes. Methods of diol dehydratase gene isolation are well known in the art (e.g., U.S. Pat. No. 5,686,276).

The term "glycerol dehydratase" refers to a polypeptide (or polypeptides) having an enzyme activity that catalyzes the conversion of glycerol to 3-hydroxypropionaldehyde. Adenosyl cobalamin-dependent glycerol dehydratases are known as EC 4.2.1.30. The glycerol dehydratases of EC 4.2.1.30 are similar to the diol dehydratases in sequence and in having three subunits. The glycerol dehydratases can also be used to convert 2,3-butanediol to 2-butanone. Some examples of glycerol dehydratases of EC 4.2.1.30 include those from *Klebsiella pneumoniae* (alpha subunit, SEQ ID NO:145, coding region and SEQ ID NO:146, protein; beta subunit, SEQ ID NO:147, coding region and SEQ ID NO:148, protein; and gamma subunit SEQ ID NO:149, coding region and SEQ ID NO:150, protein); from *Clostridium pasteurianum* [GenBank Nos: 3360389 (alpha subunit, SEQ ID NO:135), 3360390 (beta subunit, SEQ ID NO:136), and 3360391 (gamma subunit, SEQ ID NO:137)]; from *Escherichia blattae* [GenBank Nos: 60099613 (alpha subunit, SEQ ID NO:138), 57340191 (beta subunit, SEQ ID NO:139), and 57340192 (gamma subunit, SEQ ID NO:140)]; and from *Citrobacter freundii* [GenBank Nos: 1169287 (alpha subunit, SEQ ID NO:141), 1229154 (beta subunit, SEQ ID NO:142), and 1229155 (gamma subunit, SEQ ID NO:143)]. Note that all three subunits are required for activity. Additional glycerol dehydratases are listed in Table 2.

Diol and glycerol dehydratases may undergo suicide inactivation during catalysis. A reactivating factor protein, also referred to herein as "reactivase", can be used to reactivate the inactive enzymes (Mori et al., *J. Biol. Chem.* 272:32034 (1997)). Preferably, the reactivating factor is obtained from the same source as the diol or glycerol dehydratase used. For example, suitable diol dehydratase reactivating factors are available from *Klebsiella oxytoca* [GenBank Nos: AAC15871 (large subunit) (SEQ ID NO:11), AF017781 (SEQ ID NO:10); GenBank Nos: AAC15872 (small subunit) (SEQ ID NO:113), AF017781 (SEQ ID NO:112)]; *Salmonella typhimurium* [GenBank Nos: AAB84105 (large subunit) (SEQ ID NO:115), AF026270 (SEQ ID NO:114), GenBank Nos: AAD39008 (small subunit) (SEQ ID NO:117), AF026270 (SEQ ID NO:116)]; and *Lactobacillus collinoides* [GenBank Nos: CAD01092 (large subunit) (SEQ ID NO:119), AJ297723 (SEQ ID NO:118); GenBank Nos: CAD01093 (small subunit) (SEQ ID NO:121), AJ297723 (SEQ ID NO:120)]. Both the large and small subunits are required for activity. For example, suitable glycerol dehydratase reactivating factors are available from *Klebsiella pneumoniae* (large subunit, SEQ ID NO:151, coding region and SEQ ID NO:152, protein; and small subunit, SEQ ID NO:153, coding region and SEQ ID NO:154, protein).

The term "a facultative anaerobe" refers to a microorganism that can grow in both aerobic and anaerobic environments.

The term "carbon substrate" or "fermentable carbon substrate" refers to a carbon source capable of being metabolized by host organisms disclosed herein and particularly carbon sources selected from the group consisting of monosaccharides, oligosaccharides, polysaccharides, and one-carbon substrates or mixtures thereof.

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, an "isolated nucleic acid fragment" or "isolated nucleic acid molecule" or "genetic construct" will be used interchangeably and will mean a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, $2^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Altschul, S. F., et al., J. Mol. Biol., 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine.

The terms "homology" and "homologous" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that homologous nucleic acid sequences encompassed by this invention are also defined by their ability to hybridize, under moderately stringent conditions (e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein.

"Codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (described by Higgins and Sharp, *CABIOS.* 5:151-153 (1989); Higgins, D. G. et al., *Comput. Appl. Biosci.,* 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS.* 5:151-153 (1989); Higgins, D. G. et al., *Comput. Appl. Biosci.* 8:189-191 (1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, from other species, wherein such polypeptides have the same or similar function or activity. Useful examples of percent identities include, but are not limited to: 24%, 30%, 35%, 40%, 45%, 50%, 55%, 60%, 65%, 70%, 75%, 80%, 85%, 90%, or 95%, or any integer percentage from 24% to 100% may be useful in describing the present invention, such as 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.,* 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.,* [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

As used herein the term "coding sequence" or "CDS" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment disclosed herein. Expression may also refer to translation of mRNA into a polypeptide.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid" and "vector" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation vector" refers to a specific vector containing a foreign gene and having elements in addition to the foreign gene that facilitates transformation of a particular host cell.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

The term "fermentation product medium" refers to a medium in which fermentation has occurred such that product is present in the medium.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et al., *Current Protocols in Molecular Biology*, published by Greene Publishing Assoc. and Wiley-Interscience (1987).

2-Butanol Biosynthetic Pathways

Carbohydrate utilizing microorganisms employ the Embden-Meyerhof-Parnas (EMP) pathway, the Entner-Doudoroff pathway and the pentose phosphate cycle as the central, metabolic routes to provide energy and cellular precursors for growth and maintenance. These pathways have in common the intermediate glyceraldehyde 3-phosphate, and, ultimately, pyruvate is formed directly or in combination with the EMP pathway. The combined reactions of sugar conversion to pyruvate produce energy (e.g. adenosine 5'-triphosphate, ATP) and reducing equivalents (e.g. reduced nicotinamide adenine dinucleotide, NADH, and reduced nicotinamide adenine dinucleotide phosphate, NADPH). NADH and NADPH must be recycled to their oxidized forms (NAD$^+$ and NADP$^+$, respectively). In the presence of inorganic electron acceptors (e.g. $O_2$, $NO_3^-$ and $SO_4^{2-}$), the reducing equivalents may be used to augment the energy pool; alternatively, a reduced carbon by-product may be formed.

As described in co-owned and co-pending US Patent Application Publication Nos. 20070259410A1 and 20070292927A1,2-butanol can be produced from carbohydrate sources in recombinant microorganisms comprising a complete 2-butanol biosynthetic pathway. Four biosynthetic pathways including all steps starting with pyruvate for production of 2-butanol are shown in FIG. 1. The letters and roman numerals cited below correspond to the letters and roman numerals in FIG. 1, which are used to depict the conversion steps and products, respectively. As described below, 2-butanone is an intermediate in all of these 2-butanol biosynthetic pathways.

All of the pathways begin with the initial reaction of two pyruvate molecules to yield alpha-acetolactate (I), shown as the substrate to product conversion (a) in FIG. 1. From alpha-acetolactate, there are 4 possible pathways to 2-butanone (V), referred to herein as 2-butanone biosynthetic pathways:

Pathway 1) I->II->III->IV->V (substrate to product conversions b, c, d, e)
2) I->II->VII->IV->V (substrate to product conversions b, g, h, e)
3) I->II->VIII->V (substrate to product conversions b, i, j)
4) I->IX->X->V (substrate to product conversions k, l, m)

The 2-butanol biosynthetic pathways conclude with the conversion of 2-butanone (V) to 2-butanol (VI). A detailed discussion of the substrate to product conversions in each pathway is given below.

Pathway 1:

(a) pyruvate to alpha-acetolactate

The initial step in pathway 1 is the conversion of two molecules of pyruvate to one molecule of alpha-acetolactate (compound I in FIG. 1) and one molecule of carbon dioxide catalyzed by a thiamin pyrophosphate-dependent enzyme. Enzymes catalyzing this substrate to product conversion (generally called either acetolactate synthase or acetohydroxy acid synthase; EC 2.2.1.6 [switched from 4.1.3.18 in 2002]) are well-known, and they participate in the biosynthetic pathway for the proteinogenic amino acids leucine and valine, as well as in the pathway for fermentative production of 2,3-butanediol and acetoin of a number of organisms.

The skilled person will appreciate that polypeptides having acetolactate synthase activity isolated from a variety of sources will be useful in pathway 1 independent of sequence homology. Some examples of suitable acetolactate synthase enzymes are available from a number of sources, for example, *Bacillus subtilis* [GenBank Nos: AAA22222 NCBI (National Center for Biotechnology Information) amino acid sequence (SEQ ID NO:77), L04470 NCBI nucleotide sequence (SEQ ID NO:76)], *Klebsiella terrigena* [GenBank Nos: AAA25055 (SEQ ID NO:79), L04507 (SEQ ID NO:78)], and *Klebsiella pneumoniae* [GenBank Nos: AAA25079 (SEQ ID NO:4), M73842 (SEQ ID NO:3)]. Preferred acetolactate synthase enzymes are those that have at least 80%-85% identity to SEQ ID NO's 4, 77, and 79, where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

(b) alpha-acetolactate to acetoin

Alpha-acetolactate (I) is converted to acetoin (II) by the action of an enzyme such as acetolactate decarboxylase (EC 4.1.1.5). Like acetolactate synthase, this enzyme is thiamin pyrophosphate-dependent and is also involved in the production of 2,3-butanediol and acetoin by a number of organisms. The enzymes from different sources vary quite widely in size (25-50 kilodaltons), oligomerization (dimer-hexamer), localization (intracellular of extracellular), and allosteric regulation (for example, activation by branched-chain amino acids). An intracellular location is preferable to extracellular, but other variations are generally acceptable.

The skilled person will appreciate that polypeptides having acetolactate decarboxylase activity isolated from a variety of sources will be useful in pathway 1 independent of sequence homology. Some example of suitable acetolactate decarboxylase enzymes are available from a number of sources, for example, *Bacillus subtilis* [GenBank Nos: AAA22223 (SEQ ID NO:81), L04470 (SEQ ID NO:80)], *Klebsiella terrigena* [GenBank Nos: AAA25054 (SEQ ID NO:83), L04507 (SEQ ID NO:82)] and *Klebsiella pneumoniae* [GenBank Nos: AAU43774 (SEQ ID NO:2), AY722056 (SEQ ID NO:1)].

Preferred acetolactate decarboxylase enzymes are those that have at least 80%-85% identity to SEQ ID NO's 2, 81 and 83, where at least 85%-90% identity is more preferred and where at least 95% identity based on the Clustal W method of alignment using the default parameters of GAP PEN- ALTY=10, GAP LENGTH PENALTY=0.1, and Gonnet 250 series of protein weight matrix, is most preferred.

(c) acetoin to 3-amino-2-butanol

There are two known types of biochemical reactions that could effect the substrate to product conversion of acetoin (II) to 3-amino-2-butanol (III), specifically, pyridoxal phosphate-dependent transamination utilizing an accessory amino donor and direct reductive amination with ammonia. In the latter case, the reducing equivalents are supplied in the form of a reduced nicotinamide cofactor (either NADH or NADPH). An example of an NADH-dependent enzyme catalyzing this reaction with acetoin as a substrate is reported by Ito et al. (U.S. Pat. No. 6,432,688). Any stereospecificity of this enzyme has not been assessed. An example of a pyridoxal phosphate-dependent transaminase that catalyzes the conversion of acetoin to 3-amino-2-butanol has been reported by Shin and Kim (supra). This enzyme was shown in co-owned and co-pending US Patent Application Publication No. 20070259410A1 to convert both the (R) isomer of acetoin to the (2R,3S) isomer of 3-amino-2-butanol and the (S) isomer of acetoin to the (2S,3S) isomer of 3-amino-2-butanol. Either type of enzyme (i.e., transaminase or reductive aminase) is considered to be an acetoin aminase and may be utilized in the production of 2-butanol. Other enzymes in this group may have different stereospecificities.

The skilled person will appreciate that polypeptides having acetoin aminase activity isolated from a variety of sources will be useful in the present invention independent of sequence homology. One example of a protein having this activity is described in co-owned and co-pending US Patent Application Publication No. 20070259410A1 (SEQ ID NO:122). Accordingly preferred acetoin aminase enzymes are those that have at least 80%-85% identity to SEQ ID NO:122, where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

(d) 3-amino-2-butanol to 3-amino-2-butanol O-phosphate

There are no enzymes known in the art that catalyze the substrate to product conversion of 3-amino-2-butanol (III) to 3-amino-2-butanol phosphate (IV). However, a few *Pseudomonas* and *Erwinia* species have been shown to express an ATP-dependent ethanolamine kinase (EC 2.7.1.82) which allows them to utilize ethanolamine or 1-amino-2-propanol as a nitrogen source (Jones et al. (1973) *Biochem. J.* 134:167-182). It is likely that this enzyme also has activity towards 3-amino-2-butanol or could be engineered to do so, thereby providing an aminobutanol kinase. Disclosed in co-owned and co-pending US Patent Application Publication No. 20070259410A1 is a gene of *Erwinia carotovora* subsp. *atroseptica* (SEQ ID NO:123) that encodes a protein (SEQ ID NO:24) identified as an amino alcohol kinase. This enzyme may be used to convert 3-amino-2-butanol to 3-amino-2-butanol O-phosphate.

The skilled person will appreciate that polypeptides having aminobutanol kinase activity isolated from a variety of sources will be useful in the present invention independent of sequence homology. One example of this activity is described in co-owned and co-pending US Patent Application Publication No. 20070259410A1 (SEQ ID NO:124). Accordingly preferred aminobutanol kinase enzymes are those that have at least 80%-85% identity to SEQ ID NO:124, where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

(e) 3-amino-2-butanol phosphate to 2-butanone

Although there are no enzymes reported to catalyze the substrate to product conversion of 3-amino-2-butanol phosphate (IV) to 2-butanone (V), the substrate is very similar to those utilized by the pyridoxal phosphate-dependent phosphoethanolamine phospho-lyase enzyme, which has been found in a small number of *Pseudomonas* and *Erwinia* species. These enzymes have activity towards phosphoethanolamine and both enantiomers of 2-phospho-1-aminopropane (Jones et al. (1973) *Biochem. J.* 134:167-182), and may also have activity towards 3-amino-2-butanol O-phosphate. Applicants have identified a gene of *Erwinia* carotovora subsp. *atroseptica* (SEQ ID NO:125) that encodes a protein (SEQ ID NO:126) with homology to class III aminotransferases was identified. It was shown to have activity on both aminopropanol phosphate and aminobutanol phosphate substrates. The enzyme was able to catalyze the conversion of a mixture of (R)-3-amino-(S)-2-butanol and (S)-3-amino-(R)-2-butanol O-phosphate, and a mixture of (R)-3-amino-(R)-2-butanol and (S)-3-amino-(S)-2-butanol O-phosphate to 2-butanone. The enzyme was also able to catalyze the conversion of both (R) and (S)-2-amino-1-propanol phosphate to propanone, with a preference for (S)-2-amino-1-propanol phosphate. The highest activity was with the proposed natural substrate DL-1-amino-2-propanol phosphate, which was converted to propionaldehyde.

The skilled person will appreciate that polypeptides having aminobutanol phosphate phospho-lyase activity isolated from a variety of sources will be useful in the present invention independent of sequence homology. One example of a suitable aminobutanol phosphate phospho-lyase enzyme is described in co-owned and co-pending US Patent Application Publication No. 20070259410A1 (SEQ ID NO: 126). Accordingly preferred aminobutanol phosphate phospho-lyase enzymes are those that have at least 80%-85% identity to SEQ ID NO's 126, where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

(f) 2-butanone to 2-butanol

The final step in all pathways to produce 2-butanol from pyruvic acid is the reduction of 2-butanone (V) to 2-butanol (VI). This substrate to product conversion is catalyzed by some members of the broad class of alcohol dehydrogenases (types utilizing either NADH or NADPH as a source of hydride, depending on the enzyme) that may be called butanol dehydrogenases. Enzymes of each type that catalyze the reduction of 2-butanone are well known, as described above in the definition for butanol dehydrogenase.

The skilled person will appreciate that polypeptides having butanol dehydrogenase activity isolated from a variety of sources will be useful in the present invention independent of sequence homology. Some example of suitable butanol dehydrogenase enzymes are available from a number of sources, for example, *Rhodococcus ruber* [GenBank Nos: CAD36475 (SEQ ID NO:14), AJ491307 (SEQ ID NO:13)]. The NADP-dependent enzymes are known as EC 1.1.1.2 and are available, for example, from *Pyrococcus furiosus* [GenBank Nos: AAC25556 (SEQ ID NO:91), AF013169 (SEQ ID NO:90)]. Additionally, a butanol dehydrogenase is available from *Escherichia coli* [GenBank Nos:NP_417-484 (SEQ ID NO:75), NC_000913 (SEQ ID NO:74)] and a cyclohexanol dehydrogenase is available from *Acinetobacter* sp. [GenBank Nos: AAG10026 (SEQ ID NO:72), AF282240 (SEQ ID NO:71)]. Preferred butanol dehydrogenase enzymes are those that have at least 80%-85% identity to SEQ ID NO's 14, 91, 75, and 72, where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

Pathway 2:

(a) pyruvate to alpha-acetolactate

This substrate to product conversion is the same as described above for Pathway 1.

(b) alpha-acetolactate to acetoin

This substrate to product conversion is the same as described above for Pathway 1.

(g) acetoin to phosphoacetoin

Although enzymes that catalyze the substrate to product conversion of acetoin (II) to phosphoacetoin (VII) have not been described, the structure of the substrate acetoin is very similar to that of dihydroxyacetone, and therefore acetoin may be an acceptable substrate for dihydroxyacetone kinase (EC 2.7.1.29), an enzyme which catalyzes phosphorylation of dihydroxyacetone. Protein engineering techniques for the alteration of substrate specificity of enzymes are well known (Antikainen and Martin (2005) *Bioorg. Med. Chem.* 13:2701-2716) and may be used to generate an enzyme with the required specificity. In this conversion, the phosphate moiety may be supplied by any high energy biological phosphate donor, with the common substrates being phosphoenolpyruvate (as in the *E. coli* dihydroxyacetone kinase) and ATP (as in the *Citrobacter freundii* dihydroxyacetone kinase) (Garcia-Alles et al. (2004) *Biochemistry* 43:13037-13045).

(h) phosphoacetoin to 3-amino-2-butanol O-phosphate

Although enzymes that catalyze the substrate to product conversion of phosphoacetoin (VII) to 3-amino-2-butanol O-phosphate (IV) have not been described, the structure of the substrate is very similar to that of dihydroxyacetone phosphate, a substrate for the proposed serinol phosphate aminotransferase encoded by the 5' portion of the rtxA gene in some species of *Bradyrhizobium* (Yasuta et al., supra). Thus a serinol phosphate aminotransferase may be functional in this step.

(e) 3-amino-2-butanol O-phosphate to 2-butanone

This substrate to product conversion is the same as described above for Pathway 1.

(f) 2-butanone to 2-butanol

This substrate to product conversion is the same as described above for Pathway 1.

Pathway 3:

(a) pyruvate to alpha-acetolactate

This substrate to product conversion is the same as described above for Pathway 1.

(b) alpha-acetolactate to acetoin

This substrate to product conversion is the same as described above for Pathway 1.

(i) acetoin to 2,3-butanediol

The substrate to product conversion of acetoin (II) to 2,3-butanediol (VII) may be catalyzed by a butanediol dehydrogenase that may either utilize NADH or NADPH as the source of reducing equivalents when carrying out reductions. Enzymes with activity towards acetoin participate in the pathway for production of 2,3-butanediol in organisms that produce that compound. The reported enzymes (e.g., BudC from *Klebsiella pneumoniae* (Ui et al. (2004) *Letters in Applied Microbiology* 39:533-537) generally utilize NADH. Either cofactor is acceptable for use in the production of 2-butanol by this pathway.

(j) 2,3-butanediol to 2-butanone

The substrate to product conversion of 2,3-butanediol (VIII) to 2-butanone (V) may be catalyzed by diol dehydratase enzymes (EC 4.2.1.28) and glycerol dehydratase enzymes (EC 4.2.1.30). The best characterized diol dehydratase is the coenzyme B12-dependent *Klebsiella oxytoca* enzyme, but similar enzymes are found in many enteric bacteria. The *K. oxytoca* enzyme has been shown to accept meso-2,3-butanediol as a substrate (Bachovchin et al. (1977) *Biochemistry* 16:1082-1092), producing the desired product 2-butanone. Applicants describe a *Klebsiella pneumoniae* glycerol dehydratase able to convert meso-2,3-butanediol to 2-butanone. The three subunit of the *Klebsiella pneumoniae* glycerol dehydratase (alpha: SEQ ID NO:145 (coding region) and 146 (protein); beta: SEQ ID NO: 147 (coding region) and 148 (protein); and gamma: SEQ ID NO: 149 (coding region) and 150 (protein)) were expressed in conjunction with the two subunits of the *Klebsiella pneumoniae* glycerol dehydratase reactivase (large subunit, SEQ ID NO: 151 (coding region) and 152 (protein); and small subunit, SEQ ID NO: 153 (coding region) and 154 (protein)) to provide activity.

There are also reports in the literature of a B12-independent diol dehydratase from *Clostridium glycolicum* (Hartmanis et al. (1986) *Arch. Biochem. Biophys.* 245:144-152). This enzyme has activity towards 2,3-butanediol, although this activity is less than 1% of the activity towards ethanediol, but the enzyme may be engineered to improve that activity. A better-characterized B12-independent dehydratase is the glycerol dehydratase from *Clostridium butyricum* (O'Brien et al. (2004) *Biochemistry* 43:4635-4645), which has high activity towards 1,2-propanediol as well as glycerol. This enzyme uses S-adenosylmethionine as a source of adenosyl radical. There are no reports of activity towards 2,3-butanediol, but such activity, if not already present, may possibly be engineered.

The skilled person will appreciate that polypeptides having butanediol dehydrogenase activity isolated from a variety of sources will be useful in the present invention independent of sequence homology. As noted above a variety of diol and glycerol dehydratases have been described in the literature and will be suitable for use in the present invention. Accordingly, in one aspect of the invention preferred diol and glycerol dehydratase enzymes are those that have at least 80%-85% identity to enzymes having the large, medium and small subunits, respectively of the sequences listed below:
 a) SEQ ID NO:8, SEQ ID NO:10, and SEQ ID NO:12;
 b) SEQ ID NO:93, SEQ ID NO:95, and SEQ ID NO:97;
 c) SEQ ID NO:99, SEQ ID NO:101, and SEQ ID NO:103;
 d) SEQ ID NO:105, SEQ ID NO:107, and SEQ ID NO:109;
 e) SEQ ID NO:135, SEQ ID NO:136, and SEQ ID NO:137;
 f) SEQ ID NO:138, SEQ ID NO:139, and SEQ ID NO:140;
 g) SEQ ID NO:146, SEQ ID NO:148, and SEQ ID NO:150;
 h) SEQ ID NO:141, SEQ ID NO:142, and SEQ ID NO:143; and
 i) SEQ ID NO:164, SEQ ID NO:165, and SEQ ID NO:166.
where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

Similarly preferred diol and glycerol dehydratase enzymes are those that have at least 80%-85% identity to enzymes having the large, medium and small subunits, respectively of the sequences listed below: Large subunit: SEQ ID NOs: 8, 99, 105, 135, 138, 141, 146, and 164; Medium subunit: SEQ ID NOs: 10, 101, 107, 136, 139, 142, 148, and 165; Small subunit: SEQ ID NOs:12, 103, 109, 137, 140, 143, 150, and 166; where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

(f) 2-butanone to 2-butanol

This substrate to product conversion is the same as described above for Pathway 1.
Pathway 4:

(a) pyruvate to alpha-acetolactate

This substrate to product conversion is the same as described above for Pathway 1.

(k) alpha-acetolactate to 2,3-dihydroxy-2-methylbutanoic acid

The substrate to product conversion of acetolactate (I) to 2,3-dihydroxy-2-methylbutanoic acid (IX) is not known in the art. However, the product of this conversion has been reported as a component of fermentation broths (Ziadi et al. (1973) Comptes Rendus des Seances de l'Academie des Sciences, Serie D: Sciences Naturelles 276:965-8), but the mechanism of formation is unknown. The likely mechanism of formation is reduction of acetolactate with NADH or NADPH as the electron donor. To utilize this pathway for production of 2-butanol, an enzyme catalyzing this reaction needs to be identified or engineered. However, the precedent for enzymatic reduction of ketones to alcohols is well established.

(l) 2,3-dihydroxy-2-methylbutanoic acid to 2-hydroxy-2-methyl-3-phosphobutanoic acid There are no enzymes known that catalyze the substrate to product conversion of 2,3-dihydroxy-2-methylbutanoic acid (IX) to 2-hydroxy-2-methyl-3-phosphobutanoic acid (X). However, there are a large number of kinases in Nature that possess varying specificity. It is therefore likely that an enzyme could be isolated or engineered with this activity.

(m) 2-hydroxy-2-methyl-3-phosphobutanoic acid to 2-butanone

There are no known enzymes that catalyze the substrate to product conversion of 2-hydroxy-2-methyl-3-phosphobutanoic acid (X) to 2-butanone (V). The combination of this reaction with the previous one is very similar to the multi-step reaction catalyzed by mevalonate-5-pyrophosphate (M5PP) decarboxylase, which consists of initial phosphorylation of M5PP to 3-phosphomevalonate-5-PP, followed by decarboxylation-dependent elimination of phosphate (Alvear et al. (1982) Biochemistry 21:4646-4650).

(f) 2-butanone to 2-butanol

This substrate to product conversion is the same as described above for Pathway 1.

Thus, in providing multiple recombinant pathways from pyruvate to 2-butanol, there exists a number of choices to fulfill the individual conversion steps, and the person of skill in the art will be able to utilize publicly available sequences and sequences disclosed herein to construct the relevant pathways. A listing of a representative number of genes known in the art and useful in the construction of 2-butanol biosynthetic pathways is given above in Tables 1 and 2.

Microbial Hosts for 2-Butanol and 2-Butanone Production

Microbial hosts for 2-butanol or 2-butanone production may be selected from bacteria, cyanobacteria, filamentous fungi and yeasts. The microbial host used for 2-butanol or 2-butanone production should be tolerant to the product produced, so that the yield is not limited by toxicity of the product to the host. The selection of a microbial host for 2-butanol production is described in detail below.

Microbes that are metabolically active at high titer levels of 2-butanol are not well known in the art. Although butanol-tolerant mutants have been isolated from solventogenic Clostridia, little information is available concerning the butanol tolerance of other potentially useful bacterial strains. Most of the studies on the comparison of alcohol tolerance in bacteria suggest that butanol is more toxic than ethanol (de Cavalho et al., Microsc. Res. Tech. 64:215-22 (2004) and Kabelitz et al., FEMS Microbiol. Lett. 220:223-227 (2003)). Tomas et al. (J. Bacteriol. 186:2006-2018 (2004)) report that the yield of 1-butanol during fermentation in Clostridium acetobutylicum may be limited by butanol toxicity. The primary effect of 1-butanol on Clostridium acetobutylicum is disruption of membrane functions (Hermann et al., Appl. Environ. Microbiol. 50:1238-1243 (1985)).

The microbial hosts selected for the production of 2-butanol should be tolerant to 2-butanol and should be able to convert carbohydrates to 2-butanol using the introduced biosynthetic pathway. The criteria for selection of suitable microbial hosts include the following: intrinsic tolerance to 2-butanol, high rate of carbohydrate utilization, availability of genetic tools for gene manipulation, and the ability to generate stable chromosomal alterations.

Suitable host strains with a tolerance for 2-butanol may be identified by screening based on the intrinsic tolerance of the strain. The intrinsic tolerance of microbes to 2-butanol may be measured by determining the concentration of 2-butanol that is responsible for 50% inhibition of the growth rate (IC50) when grown in a minimal medium. The IC50 values may be determined using methods known in the art. For example, the microbes of interest may be grown in the presence of various amounts of 2-butanol and the growth rate monitored by measuring the optical density at 600 nanometers. The doubling time may be calculated from the logarithmic part of the growth curve and used as a measure of the growth rate. The concentration of 2-butanol that produces 50% inhibition of growth may be determined from a graph of the percent inhibition of growth versus the 2-butanol concentration. Preferably, the host strain should have an IC50 for 2-butanol of greater than about 0.5%. More suitable is a host strain with an IC50 for 2-butanol that is greater than about 1.5%. Particularly suitable is a host strain with an IC50 for 2-butanol that is greater than about 2.5%.

The microbial host for 2-butanol production should also utilize glucose and/or other carbohydrates at a high rate. Most microbes are capable of utilizing carbohydrates. However, certain environmental microbes cannot efficiently use carbohydrates, and therefore would not be suitable hosts.

The ability to genetically modify the host is essential for the production of any recombinant microorganism. Modes of gene transfer technology that may be used include by electroporation, conjugation, transduction or natural transformation. A broad range of host conjugative plasmids and drug resistance markers are available. The cloning vectors used with an organism are tailored to the host organism based on the nature of antibiotic resistance markers that can function in that host.

The microbial host also may be manipulated in order to inactivate competing pathways for carbon flow by inactivating various genes. This requires the availability of either transposons or chromosomal integration vectors to direct inactivation. Additionally, production hosts that are amenable to chemical mutagenesis may undergo improvements in intrinsic 2-butanol tolerance through chemical mutagenesis and mutant screening.

Based on the criteria described above, suitable microbial hosts for the production of 2-butanol include, but are not limited to, members of the genera *Clostridium, Zymomonas, Escherichia, Salmonella, Rhodococcus, Pseudomonas, Bacillus, Lactobacillus, Enterococcus, Pediococcus, Alcaligenes, Klebsiella, Paenibacillus, Arthrobacter, Corynebacterium, Brevibacterium, Pichia, Candida, Hansenula* and *Saccharomyces*. Preferred hosts include: *Escherichia coli, Alcaligenes eutrophus, Bacillus licheniformis, Paenibacillus macerans, Rhodococcus erythropolis, Pseudomonas putida, Lactobacillus plantarum, Enterococcus faecium, Enterococcus gallinarium, Enterococcus faecalis, Pediococcus pentosaceus, Pediococcus acidilactici, Bacillus subtilis* and *Saccharomyces cerevisiae*.

Construction of Production Host

Recombinant organisms containing the necessary genes that encode the enzymatic pathway for the conversion of a fermentable carbon substrate to 2-butanol may be constructed using techniques well known in the art. Genes encoding the enzymes of, for example, the 2-butanol biosynthetic Pathway 1: acetolactate synthase, acetolactate decarboxylase, acetoin aminase (or amine:pyruvate transaminase), aminobutanol kinase, aminobutanol O-phosphate lyase and butanol dehydrogenase may be isolated from various sources, as described above.

Methods of obtaining desired genes from a bacterial genome are common and well known in the art of molecular biology. For example, if the sequence of the gene is known, primers may be designed and the desired sequence amplified using standard primer-directed amplification methods such as polymerase chain reaction (U.S. Pat. No. 4,683,202) to obtain amounts of DNA suitable for cloning into expression vectors. If a gene that is heterologous to a known sequence is to be isolated, suitable genomic libraries may be created by restriction endonuclease digestion and may be screened with probes having complementary sequence to the desired gene sequence. Once the sequence is isolated, the DNA may be amplified using standard primer-directed amplification methods such as polymerase chain reaction (U.S. Pat. No. 4,683,202) to obtain amounts of DNA suitable for cloning into expression vectors, which are then transformed into appropriate host cells.

In addition, given the amino acid sequence of a protein with desired enzymatic activity, the coding sequence may be ascertained by reverse translating the protein sequence. A DNA fragment containing the coding sequence may be prepared synthetically and cloned into an expression vector, then transformed into the desired host cell.

In preparing a synthetic DNA fragment containing a coding sequence, this sequence may be optimized for expression in the target host cell. Tools for codon optimization for expression in a heterologous host are readily available. Some tools for codon optimization are available based on the GC content of the host organism. The GC contents of some exemplary microbial hosts are given Table 3.

TABLE 3

| GC Contents of Microbial Hosts | |
|---|---|
| Strain | % GC |
| *B. licheniformis* | 46 |
| *B. subtilis* | 42 |
| *C. acetobutylicum* | 37 |
| *E. coli* | 50 |
| *P. putida* | 61 |
| *A. eutrophus* | 61 |
| *Paenibacillus macerans* | 51 |
| *Rhodococcus erythropolis* | 62 |
| *Brevibacillus* | 50 |
| *Paenibacillus polymyxa* | 50 |

Once the relevant pathway genes are identified and isolated they may be transformed into suitable expression hosts by means well known in the art. Vectors useful for the transformation of a variety of host cells are common and commercially available from companies such as EPICENTRE® (Madison, Wis.), Invitrogen Corp. (Carlsbad, Calif.), Stratagene (La Jolla, Calif.), and New England Biolabs, Inc. (Beverly, Mass.). Typically the vector contains a selectable marker and sequences allowing autonomous replication or chromosomal integration in the desired host. In addition, suitable vectors comprise a promoter region which harbors transcriptional initiation controls and a transcriptional termination control region, between which a coding region DNA fragment may be inserted, to provide expression of the inserted coding region. Both control regions may be derived from genes homologous to the transformed host cell, although it is to be understood that such control regions may also be derived from genes that are not native to the specific species chosen as a production host.

Initiation control regions or promoters, which are useful to drive expression of the relevant pathway coding regions in the desired host cell are numerous and familiar to those skilled in the art. Virtually any promoter capable of driving these genetic elements is suitable for use including, but not limited to, promoters derived from the following genes: CYC1, HIS3, GAL1, GAL10, ADH1, PGK, PHO5, GAPDH, ADC1, TRP1, URA3, LEU2, ENO, TPI, CUP1, FBA, GPD, and GPM (useful for expression in *Saccharomyces*); AOX1 (useful for expression in *Pichia*); as well as the lac, ara, tet, trp, $IP_L$, $IP_R$, T7, tac, and trc promoters (useful for expression in *Escherichia coli, Alcaligenes*, and *Pseudomonas*); the amy, apr, and npr promoters, and various phage promoters useful for expression in *Bacillus subtilis, Bacillus licheniformis*, and *Paenibacillus macerans*; nisA (useful for expression Gram-positive bacteria, Eichenbaum et al. *Appl. Environ. Microbiol.* 64(8):2763-2769 (1998)); and the synthetic P11 promoter (useful for expression in *Lactobacillus plantarum*, Rud et al., *Microbiology* 152:1011-1019 (2006)).

Termination control regions may also be derived from various genes native to the preferred hosts. Optionally, a termination site may be unnecessary, however, it is most preferred if included.

Certain vectors are capable of replicating in a broad range of host bacteria and can be transferred by conjugation. The complete and annotated sequence of pRK404 and three related vectors: pRK437, pRK442, and pRK442 (H), are available. These derivatives have proven to be valuable tools for genetic manipulation in Gram-negative bacteria (Scott et al., *Plasmid* 50(1):74-79 (2003)). Several plasmid derivatives of broad-host-range Inc P4 plasmid RSF1010 are also available with promoters that can function in a range of Gram-negative bacteria. Plasmid pAYC36 and pAYC37, have active promoters along with multiple cloning sites to allow for heterologous gene expression in Gram-negative bacteria.

Chromosomal gene replacement tools are also widely available. For example, a thermosensitive variant of the broad-host-range replicon pWV101 has been modified to construct a plasmid pVE6002 which can be used to effect gene replacement in a range of Gram-positive bacteria (Maguin et al., *J. Bacteriol.* 174(17):5633-5638 (1992)). The expression of a 2-butanol biosynthetic pathway in various preferred microbial hosts is described in more detail below.

Expression of a 2-butanol Biosynthetic Pathway in *E. coli*

Vectors useful for the transformation of *E. coli* are common and commercially available from the companies listed above. For example, the genes of a 2-butanol biosynthetic pathway may be isolated from various sources, as described above, cloned onto a modified pUC19 vector and transformed into *E. coli* NM522, as described in Examples 10 and 11. Alternatively, the genes encoding a 2-butanol biosynthetic pathway may be divided into multiple operons, cloned onto expression vectors, and transformed into various *E. coli* strains, as described in Examples 13, 15, and 15.

Expression of a 2-butanol Biosynthetic Pathway in *Rhodococcus erythropolis*

A series of *E. coli*-Rhodococcus shuttle vectors are available for expression in *R. erythropolis*, including, but not limited to pRhBR17 and pDA71 (Kostichka et al., *Appl. Microbiol. Biotechnol.* 62:61-68 (2003)). Additionally, a series of promoters are available for heterologous gene expression in *R. erythropolis* (see for example Nakashima et al., *Appl. Environ. Microbiol.* 70:5557-5568 (2004), and Tao et al., *Appl. Microbiol. Biotechnol.* 2005, DOI 10.1007/s00253-005-0064). Targeted gene disruptions in chromosomal genes of *R. erythropolis* may be created using the methods described by Tao et al., supra, and Brans et al. (*Appl. Envion. Microbiol.* 66: 2029-2036 (2000)).

The heterologous genes required for the production of 2-butanol, as described above, may be cloned initially in pDA71 or pRhBR71 and transformed into *E. coli*. The vectors may then be transformed into *R. erythropolis* by electroporation, as described by Kostichka et al., supra. The recombinants may be grown in synthetic medium containing glucose and the production of 2-butanol can be followed using fermentation methods known in the art.

Expression of a 2-butanol Biosynthetic Pathway in *B. Subtilis*

Methods for gene expression and creation of mutations in *B. subtilis* are also well known in the art. For example, the genes of a 2-butanol biosynthetic pathway may be isolated from various sources, as described above, cloned into a modified *E. coli*-Bacillus shuttle vector and transformed into *Bacillus subtilis* BE1010, as described in Example 12, The desired genes may be cloned into a *Bacillus* expression vector and transformed into a strain to make a production host. Alternatively, the genes may be integrated into the *Bacillus* chromosome using conditional replicons or suicide vectors that are known to one skilled in the art. For example, the *Bacillus* Genetic Stock Center carries numerous integration vectors.

Expression of a 2-butanol Biosynthetic Pathway in *B. licheniformis*

Most of the plasmids and shuttle vectors that replicate in *B. subtilis* may be used to transform *B. licheniformis* by either protoplast transformation or electroporation. The genes required for the production of 2-butanol may be cloned in plasmids pBE20 or pBE60 derivatives (Nagarajan et al., *Gene* 114:121-126 (1992)). Methods to transform *B. licheniformis* are known in the art (for example see Fleming et al. *Appl. Environ. Microbiol.*, 61(11):3775-3780 (1995)). The plasmids constructed for expression in *B. subtilis* may be transformed into *B. licheniformis* to produce a recombinant microbial host that produces 2-butanol.

Expression of a 2-butanol Biosynthetic Pathway in *Paenibacillus macerans*

Plasmids may be constructed as described above for expression in *B. subtilis* and used to transform *Paenibacillus macerans* by protoplast transformation to produce a recombinant microbial host that produces 2-butanol.

Expression of a 2-butanol Biosynthetic Pathway in *Alcaligenes (Ralstonia) eutrophus*

Methods for gene expression and creation of mutations in *Alcaligenes* eutrophus are known in the art (see for example Taghavi et al., *Appl. Environ. Microbiol.*, 60(10):3585-3591 (1994)). The genes for a 2-butanol biosynthetic pathway may be cloned in any of the broad host range vectors described above, and electroporated into *Alcaligenes* eutrophus to generate recombinants that produce 2-butanol. The poly(hydroxybutyrate) pathway in *Alcaligenes* has been described in detail, a variety of genetic techniques to modify the *Alcaligenes* eutrophus genome are known, and those tools can be applied for engineering a 2-butanol biosynthetic pathway.

Expression of a 2-butanol Biosynthetic Pathway in *Pseudomonas putida*

Methods for gene expression in *Pseudomonas putida* are known in the art (see for example Ben-Bassat et al., U.S. Pat. No. 6,586,229, which is incorporated herein by reference). The genes of a 2-butanol biosynthetic pathway may be inserted into pPCU18, and this ligated DNA may be electroporated into electrocompetent *Pseudomonas putida* DOT-T1 C5aAR1 cells to generate recombinants that produce 2-butanol.

Expression of a 2-butanol Biosynthetic Pathway in *Lactobacillus plantarum*

The *Lactobacillus* genus belongs to the Lactobacillales family and many plasmids and vectors used in the transformation of *Bacillus subtilis* and *Streptococcus* may be used for *Lactobacillus*. Non-limiting examples of suitable vectors include pAMβ1 and derivatives thereof (Renault et al., *Gene* 183:175-182 (1996); and O'Sullivan et al., *Gene* 137:227-231 (1993)); pMBB1 and pHW800, a derivative of pMBB1 (Wyckoff et al. *Appl. Environ. Microbiol.* 62:1481-1486 (1996)); pMG1, a conjugative plasmid (Tanimoto et al., *J. Bacteriol.* 184:5800-5804 (2002)); pNZ9520 (Kleerebezem et al., *Appl. Environ. Microbiol.* 63:4581-4584 (1997)); pAM401 (Fujimoto et al., *Appl. Environ. Microbiol.* 67:1262-1267 (2001)); and pAT392 (Arthur et al., *Antimicrob. Agents Chemother.* 38:1899-1903 (1994)). Several plasmids from *Lactobacillus plantarum* have also been reported (van Kranenburg et al., *Appl. Environ. Microbiol.* 71(3):1223-1230 (2005)).

The various genes for a 2-butanol biosynthetic pathway may be assembled into any suitable vector, such as those described above. The codons can be optimized for expression based on the codon index deduced from the genome sequences of *Lactobacillus plantarum* or *Lactobacillus arizonensis*. The plasmids may be introduced into the host cell using methods known in the art, such as electroporation (Cruz-Rodz et al. *Molecular Genetics and Genomics* 224: 1252-154 (1990), Bringel, et al. *Appl. Microbiol. Biotechnol.* 33: 664-670 (1990), Alegre et al., *FEMS Microbiology letters* 241:73-77 (2004)), and conjugation (Shrago et al., *Appl. Environ. Microbiol.* 52:574-576 (1986)). The 2-butanol biosynthetic pathway genes can also be integrated into the chromosome of *Lactobacillus* using integration vectors (Hols et al., *Appl. Environ. Microbiol.* 60:1401-1403 (1990), Jang et al., *Micro. Lett.* 24:191-195 (2003)).

Expression of a 2-butanol Biosynthetic Pathway in *Enterococcus faecium*, *Enterococcus gallinarium*, and *Enterococcus faecalis*

The *Enterococcus* genus belongs to the Lactobacillales family and many plasmids and vectors used in the transformation of *Lactobacillus, Bacillus subtilis*, and *Streptococcus*, described above, may be used for *Enterococcus*. Expression vectors for *E. faecalis* using the nisA gene from *Lactococcus* may also be used (Eichenbaum et al., *Appl. Environ. Microbiol.* 64:2763-2769 (1998). Additionally, vectors for gene replacement in the *E. faecium* chromosome may be used (Nallaapareddy et al., *Appl. Environ. Microbiol.* 72:334-345 (2006)).

The various genes for a 2-butanol biosynthetic pathway may be assembled into any suitable vector, such as those described above. The codons can be optimized for expression based on the codon index deduced from the genome sequences of *Enterococcus faecalis* or *Enterococcus faecium*. The plasmids may be introduced into the host cell using methods known in the art, such as electroporation, as described by Cruz-Rodz et al. (*Molecular Genetics and Genomics* 224:1252-154 (1990)) or conjugation, as described by Tanimoto et al. (*J. Bacteriol.* 184:5800-5804 (2002)) and Grohamann et al. (*Microbiol. Mol. Biol. Rev.* 67:277-301 (2003)).

Expression of a 2-butanol Biosynthetic Pathway in *Pediococcus pentosaceus* and *Pediococcus acidilactici*

The *Pediococcus* genus belongs to the Lactobacillales family and many plasmids and vectors used in the transformation of *Bacillus subtilis* and *Streptococcus*, described above, may be used for *Pediococcus*. A non-limiting example of a suitable vector is pHPS9 (Bukhtiyarova et al. Appl. Environ. Microbiol. 60:3405-3408 (1994)). Several plasmids from *Pediococcus* have also been reported (Alegre et al., FEMS Microbiol. Lett. 250:151-156 (2005); Shareck et al. *Crit. Rev Biotechnol.* 24:155-208 (2004)).

The genes for a 2-butanol biosynthetic pathway may be assembled into any suitable vector, such as those described above. The codons can be optimized for expression based on the codon index deduced from the genome sequence of *Pediococcus pentosaceus*. The plasmids may be introduced into the host cell using methods known in the art, such as electroporation (see for example, Osmanagaoglu et al., *J. Basic Microbiol.* 40:233-241 (2000); Alegre et al., *FEMS Microbiol. Lett.* 250:151-156 (2005)) and conjugation (Gonzalez and Kunka, *Appl. Environ. Microbiol.* 46:81-89 (1983)). The 2-butanol biosynthetic pathway genes can also be integrated into the chromosome of *Pediococcus* using integration vectors (Davidson et al. *Antonie van Leeuwenhoek* 70:161-183 (1996)).

Fermentation Media

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity. For example, methylotrophic yeasts are known to utilize the carbon from methylamine to form trehalose or glycerol (Bellion et al., *Microb. Growth C1 Compd.*, [Int. Symp.], 7th (1993), 415-32, Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, preferred carbon substrates are glucose, fructose, and sucrose. Sucrose may be derived from renewable sugar sources such as sugar cane, sugar beets, cassava, sweet sorghum, and mixtures thereof. Glucose and dextrose may be derived from renewable grain sources through saccharification of starch based feedstocks including grains such as corn, wheat, rye, barley, oats, and mixtures thereof. In addition, fermentable sugars may be derived from renewable cellulosic or lignocellulosic biomass through processes of pretreatment and saccharification, as described, for example, in co-owned and co-pending U.S. Patent Application Publication No. 2007/0031918A1, which is herein incorporated by reference. Biomass refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

In addition to an appropriate carbon source, fermentation media must contain suitable minerals, salts, cofactors, buffers and other components, known to those skilled in the art, suitable for the growth of the cultures and promotion of an enzymatic pathway necessary for 2-butanol production.

Culture Conditions with Temperature Lowering

In the present method, the recombinant microbial production host which produces 2-butanol is seeded into a fermentation medium comprising a fermentable carbon substrate to create a fermentation culture. The production host is grown in the fermentation culture at a first temperature for a first period of time. The first temperature is typically from about 25° C. to about 40° C.

Suitable fermentation media in the present invention include common commercially prepared media such as Luria Bertani (LB) broth, Sabouraud Dextrose (SD) broth or Yeast Medium (YM) broth. Other defined or synthetic growth media may also be used, and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are between pH 5.0 to pH 9.0, where pH 6.0 to pH 8.0 is preferred as the initial condition.

Fermentations may be performed under aerobic or anaerobic conditions, where anaerobic or microaerobic conditions are preferred.

The first period of time to grow the production host at the first temperature may be determined in a variety of ways. For example, during this period of growth a metabolic parameter of the fermentation culture may be monitored. The metabolic parameter that is monitored may be any parameter known in the art, including, but not limited to the optical density, pH, respiratory quotient, fermentable carbon substrate utilization, $CO_2$ production, and 2-butanol production. During this period of growth, additional fermentable carbon substrate may be added, the pH may be adjusted, oxygen may be added for aerobic cells, or other culture parameters may be adjusted to support the metabolic activity of the culture. Though nutrients and culture conditions are supportive of growth, after a period of time the metabolic activity of the fermentation culture decreases as determined by the monitored parameter described above. For example, a decrease in metabolic activity may be indicated by a decrease in one or more of the following parameters: rate of optical density change, rate of pH change, rate of change in respiratory quotient (if the host cells are aerobic), rate of fermentable carbon substrate utilization, rate of 2-butanol production, rate of change in $CO_2$ production, or rate of another metabolic parameter. The decrease in metabolic activity is related to the sensitivity of the host cells to the production of 2-butanol and/or the presence of 2-butanol in the culture. When decreased metabolic activity is detected, the temperature of the fermentation culture is lowered to reduce the sensitivity of the host cells to 2-butanol and thereby allow further production of 2-butanol. In one embodiment, the lowering of the temperature coincides with a change in the metabolic parameter that is monitored.

In one embodiment, the change in metabolic activity is a decrease in the rate of 2-butanol production. 2-Butanol production may be monitored by analyzing the amount of 2-butanol present in the fermentation culture medium as a function of time using methods well known in the art, such as using high performance liquid chromatography (HPLC) or gas chromatography (GC), which are described in the Examples herein. GC is preferred due to the short assay time.

Alternatively, the lowering of the temperature of the fermentation culture may occur at a predetermined time. The first period of time may be predetermined by establishing a correlation between a metabolic parameter of the fermentation culture and time in a series of test fermentations runs. A correlation between a metabolic parameter, as described above, and time of culture growth may be established for any 2-butanol producing host by one skilled in the art. The specific correlation may vary depending on conditions used including, but not limited to, carbon substrate, fermentation conditions, and the specific recombinant 2-butanol producing microbial production host. The correlation is most suitably made between 2-butanol production or specific glucose consumption rate and time of culture growth. Once the predetermined time has been established from the correlation, the temperature of the fermentation culture in subsequent fermentation runs is lowered at the predetermined time. For example, if it is determined by monitoring a metabolic parameter in the test fermentation runs that the rate of production of 2-butanol decreases after 12 hours, the temperature in subsequent fermentations runs is lowered after 12 hours without the need to monitor 2-butanol production in the subsequent runs.

After the first period of time, the temperature of the fermentation culture is lowered to a second temperature. Typically, the second temperature is about 3° C. to about 25° C. lower than the first temperature. Reduction in temperature to enhance tolerance of the host cells to 2-butanol is balanced with maintaining the temperature at a level where the cells continue to be metabolically active for 2-butanol production. For example, a fermentation culture that has been grown at about 35° C. may be reduced in temperature to about 28° C.; or a culture grown at about 30° C. may be reduced in temperature to about 25° C. The change in temperature may be done gradually over time or may be made as a step change. The production host is incubated at the second temperature for a second period of time, so that 2-butanol production continues. The second period of time may be determined in the same manner as the first period of time described above, e.g., by monitoring a metabolic parameter or by using a predetermined time.

Additionally, the temperature lowering and incubation steps may be repeated one or more times to more finely balance metabolic activity for 2-butanol production and 2-butanol sensitivity. For example, a culture that has been grown at about 35° C. may be reduced in temperature to about 32° C., followed by an incubation period. During this period a metabolic parameter of the fermentation culture may be monitored as described above, or a predetermined time may be used. It is particularly suitable to monitor the production of 2-butanol during this incubation period. When monitoring indicates a decrease in metabolic activity or at a predetermined time, the temperature may be reduced a second time. For example, the temperature may be reduced from about 32° C. to about 28° C. The temperature lowering and incubation steps may be repeated a third time where the temperature is reduced, for example, to about 20° C. The production host is incubated at the lowered temperature so that 2-butanol production continues. The steps may be repeated further as necessary to obtain the desired 2-butanol titer.

Industrial Batch and Continuous Fermentations

The present process employs a batch method of fermentation. A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the fed-batch system. Fed-batch fermentation processes are also suitable in the present invention and comprise a typical batch system with the exception that the substrate is added in increments as the fermentation progresses. Fed-batch systems are useful when catabolite repression is apt to inhibit the metabolism of the cells and where it is desirable to have limited amounts of substrate in the media. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36:227, (1992), herein incorporated by reference.

Although the present invention is performed in batch mode it is contemplated that the method would be adaptable to continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by the turbidity of the culture medium, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for 2-butanol production.

Methods for 2-Butanol Isolation from the Fermentation Medium

The bioproduced 2-butanol may be isolated from the fermentation medium using methods known in the art for ABE fermentations (see for Example, Durre, *Appl. Microbiol. Biotechnol.* 49:639-648 (1998), Groot et al., *Process Biochem.* 27:61-75 (1992), and references therein). For example, solids may be removed from the fermentation medium by centrifugation, filtration, decantation, or the like. Then, the 2-butanol may be isolated from the fermentation medium using methods such as distillation, azeotropic distillation, liquid-liquid extraction, adsorption, gas stripping, membrane evaporation, or pervaporation.

EXAMPLES

The present invention is further defined in the following Examples. It should be understood that these Examples, while indicating a preferred embodiment of the invention, are given by way of illustration only. From the above discussion and these Examples, one skilled in the art can ascertain the essential characteristics of this invention, and, without departing from the spirit and scope thereof, can make various changes and modifications of the invention to adapt it to various uses and conditions.

General Methods

Standard recombinant DNA and molecular cloning techniques described in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, N.Y., (1989) (Maniatis) and by T. J. Silhavy, M. L. Bennan, and L. W. Enquist, *Experiments with Gene Fusions*, Cold Spring Harbor Laboratory Press, Cold Spring Harbor, N.Y. (1984) and by Ausubel, F. M. et al., *Current Protocols in Molecular Biology*, pub. by Greene Publishing Assoc. and Wiley-Interscience (1987).

Materials and methods suitable for the maintenance and growth of bacterial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials described for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.) unless otherwise specified. Bacterial strains are obtained from the American Type Culture Collection (ATCC, Manassas, Va.) unless otherwise noted.

Oligonucleotide Primers Described in the Following Examples are Given in

TABLE 4

All oligonucleotide primers were synthesized by Sigma-Genosys (Woodlands, TX). Table 4 Cloning and Screening Primers

| Gene | Primer Name | Sequence | SEQ ID NO: | Description |
|---|---|---|---|---|
| budB | B1 | CACCATGGACAAACAGTATCCGGTACGCC | 15 | budB forward |
| budB | B2 | CGAAGGGCGATAGCTTTACCAATCC | 16 | budB reverse |
| budA | B3 | CACCATGAATCATTCTGCTGAATGCACCTGCG | 17 | budA forward |
| budA | B4 | GATACTGTTTGTCCATGTGACC | 18 | budA reverse |
| budC | B5 | CACCATGAAAAAGTCGCACTTGTTACC | 19 | budC forward |
| budC | B6 | TTAGTTAAATACCAT | 20 | budC reverse |
| pddA | B7 | CACCATGAGATCGAAAAGATTTG | 21 | pddABC forward |
| pddC | B8 | CTTAGAGAAGTTAATCGTCGCC | 22 | pddABC reverse |
| sadh | B9 | CACCATGAAAGCCCTCCAGTACACC | 23 | sadh forward |
| sadh | B10 | CGTCGTGTCATGCCCGGG | 24 | sadh reverse |
| budA | B11 | GATCGAATTCGTTTAAACTTAGTTTTCTACCGCACG | 25 | budABC forward |
| budC | B12 | GATCGCATGCAAGCTTTCATATAGTCGGAATTCC | 26 | budABC reverse |
| pddA | B13 | GATCGAATTCGTTTAAACAAAGGAGGTCTGATTCATGAGATCG | 27 | pddABC forward |
| pddC | B14 | GATCGGATTCTTAATCGTCGCC | 28 | pddABC reverse |
| sadh | B15 | GATCGGATCCAAAGGAGGTCGGGCGCATGAAAGCCC | 29 | sadh forward |
| sadh | B16 | GATCTCTAGAAAGCTTTCAGCCCGGGACGACC | 30 | sadh reverse |
| — | BenF | ACTTTCTTTCGCCTGTTTCAC | 31 | — |
| — | BenBPR | CATGAAGCTTGTTTAAACTCGGTGACCTTGAAAATAATGAAAACTTATATTGTTTTGAAAATAATGAAAACTTATATTG | 32 | — |
| budAB | BABC F | GAGCTCGAATTCAAAGGAGGAAGTGTATATGAATCATTC | 33 | budAB forward |
| budAB | BAB R | GGATCCTCTAGAATTAGTTAAATACCATCCCGCCG | 34 | budAB reverse |
| budC | BC Spe F | ACTAGTAAAGGAGGAAAGAGTATGAAGAAGGTCGCACT | 40 | budC forward |
| budC | BC Xba R | TCTAGAAAGCAGGGGCAAGCCATGTC | 41 | budC reverse |
| pddABC-ddrAB | DDo For | AAGCTTAAAGGAGGCTGATTCATGAGATCGAAAAGATT | 44 | pddABC-ddrAB forward |
| pddABC-ddrAB | DDo Rev | TCTAGATTATTCATCCTGCTGTTCTCC | 45 | pddABC-ddrAB reverse |
| chnA | ChnA F | CATCAATTGACTACGTAGTCGTACGTGTAAGGAGGTTTGAAATGGAAAAATTATG | 54 | chnA forward |
| chnA | ChnA R | CATGCTAGCCCCGGGTATCTTCTACTCATTTTTTATTTCG | 55 | chnA reverse |
| — | Top ter F1 | CTAGAAGTCAAAAGCCTCCGACCGGAGGCTTTTGA | 58 | forward |
| — | Top ter F2 | CTGCTCGAGTTGCTAGCAAGTTTAAACAAAAAAAAGCCCGCTCATTAGGCGGGCTGAGCT | 59 | forward |
| — | Bot ter R1 | CAGCCCGCCTAATGAGCGGGCTTTTTTTTGTTTAAAC | 60 | reverse |
| — | Bot ter R2 | TTGCTAGCAACTCGAGCAGTCAAAAGCCTCCGGTCGGAGGCTTTTGACTT | 61 | reverse |
| KA-AT | OT872 | CTCCGGAATTCATGTCTGACGGACGACTCACCGCA | 127 | Aminoalcohol kinase/lyase operon forward |
| KA-AT | OT873 | TTCCAATGCATTGGCTGCAGTTATCTCTGTGCACGAGTGCCGATGA | 128 | Aminoalcohol kinase/lyase operon reverse |
| KA | OT879 | AACAGCCAAGCTTGGCTGCAGTCATCGCGCATTCTCCGGG | 129 | Aminoalcohol kinase reverse |
| AT | OT880 | TCTCCGGAATTCATGACGTCTGAAATGACAGCGACAGAAG | 130 | Aminoalcohol lyase forward |
| pBAD.HisB | OT909 | GCTAACAGGAGGAAGAATTCATGGGGGTTCTC | 131 | Adds EcoRI site to replace NcoI site |
| pBAD.HisB | OT910 | GAGAACCCCCCATGAATTCTTCCTCCTGTTAGC | 132 | Adds EcoRI site to replace NcoI site |
| BudAB | N84seqR3 | GGACCTGCTTCGCTTTATCG | 159 | reverse |

TABLE 4-continued

All oligonucleotide primers were synthesized by Sigma-Genosys (Woodlands, TX). Table 4 Cloning and Screening Primers

| Gene | Primer Name | Sequence | SEQ ID NO: | Description |
|---|---|---|---|---|
| APT | APTfor | GCGCGCCCGGGAAGAAGGAGCTCTTCACCATGAACAAACCACAGTCTTGG | 162 | APT forward |
| APT | APTrev | GCGCGCCCGGGTTCATGCCACCTCTGCG | 163 | APT reverse |

TABLE 5

Sequencing Primers

| Name | Sequence | Gene-specific | SEQ ID NO: |
|---|---|---|---|
| M13 Forward | GTAAAACGACGGCCAGT | — | 35 |
| M13 Reverse | AACAGCTATGACCATG | — | 36 |
| N83 SeqF2 | GCTGGATTACCAGCTCGACC | — | 37 |
| N83 SeqF3 | CGGACGCATTACCGGCAAAG | — | 38 |
| N84 SeqR2 | GCATCGAGATTATCGGGATG | — | 65 |
| N84 SeqR4 | CGAAGCGAGAGAAGTTATCC | — | 39 |
| Trc F | TTGACAATTAATCATCCGGC | all | 42 |
| Trc R | CTTCTCTCATCCGCCAAAAC | all | 43 |
| DDko seq F2 | GCATGGCGCGGATTTGACAAC | pddABC-ddrAB | 46 |
| DDko seq F5 | CATTAAAGAGACCAAGTACGTG | pddABC-ddrAB | 47 |
| DDko seq F7 | ATATCCTGGTGGTGTCGTCGGCGT | pddABC-ddrAB | 48 |
| DDko seq F9 | TCTTTGTCACCAACGCCCTGCG | pddABC-ddrAB | 49 |
| DDko seq R1 | GCCCACCGCGCTCGCCGCCGCG | pddABC-ddrAB | 50 |
| DDko seq R3 | CCCCCAGGATGGCGGCTTCGGC | pddABC-ddrAB | 51 |
| DDko seq R7 | GGGCCGACGGCGATAATCACTT | pddABC-ddrAB | 52 |
| DDko seq R10 | TTCTTCGATCCACTCCTTAACG | pddABC-ddrAB | 53 |
| chnSeq F1 | CTCAACAGGGTGTAAGTGTAGT | chnA | 56 |
| chnSeq R1 | CGTTTTGATATAGCCAGGATGT | chnA | 57 |
| pCL1925 vec F | CGGTATCATCAACAGGCTTACC | all | 62 |
| pCL1925 vec R1 | AGGGTTTTCCCAGTCACGACGT | all | 63 |
| pCL1925 vec R2 | CGCAATAGTTGGCGAAGTAATC | all | 64 |
| APTseqRev | GCTAGAGATGATAGC | APT | 160 |
| APTseqFor | GGAAGAGACTATCCAGCG | APT | 161 |

Methods for Determining 2-Butanol and 2-Butanone Concentration in Culture Media

The concentration of 2-butanol and 2-butanone in the culture media can be determined by a number of methods known in the art. For example, a specific high performance liquid chromatography (HPLC) method utilized a Shodex SH-1011 column with a Shodex SH-G guard column, both purchased from Waters Corporation (Milford, Mass.), with refractive index (RI) detection. Chromatographic separation was achieved using 0.01 M $H_2SO_4$ as the mobile phase with a flow rate of 0.5 mL/min and a column temperature of 50° C. Under the conditions used, 2-butanone and 2-butanol had retention times of 39.5 and 44.3 min, respectively. Alternatively, gas chromatography (GC) methods are available. For example, a specific GC method utilized an HP-INNOWax column (30 m×0.53 mm id, 1 µm film thickness, Agilent Technologies, Wilmington, Del.), with a flame ionization detector (FID). The carrier gas was helium at a flow rate of 4.5 mL/min, measured at 150° C. with constant head pressure; injector split was 1:25 at 200° C.; oven temperature was 45° C. for 1 min, 45 to 220° C. at 10° C./min, and 220° C. for 5 min; and FID detection was employed at 240° C. with 26 mL/min helium makeup gas. The retention times of 2-butanone and 2-butanol were 3.61 and 5.03 min, respectively.

2-Butanone can also be detected by derivatization with 3-methyl-2-benzothiazolinone hydrazone (MBTH). An aqueous solution containing 2-butanone is mixed with an equal volume of an aqueous solution of 6 mg/mL MBTH in 375 mM glycine-HCl (pH 2.7) and incubated at 100° C. for 3 min. The resulting MBTH-derivatized samples are analyzed on a 25 cm×4.6 mm (id) Supelosil LC-18-D5 5 µm column (Supelco) using a mobile phase of 55% acetonitrile in water at a flow rate of 1 mL/min. The 2-butanone derivative appears as two peaks (cis and trans isomers) with retention times of approximately 12.3 and 13.3 min and absorbance maxima of 230 and 307 nm.

The meaning of abbreviations is as follows: "s" means second(s), "min" means minute(s), "h" means hour(s), "psi" means pounds per square inch, "nm" means nanometers, "d" means day(s), "µL" means microliter(s), "mL" means milliliter(s), "L" means liter(s), "mm" means millimeter(s), "nm" means nanometers, "mM" means millimolar, "M" means molar, "mmol" means millimole(s), "µmol" means micromole(s)", "g" means gram(s), "µg" means microgram(s) and "ng" means nanogram(s), "PCR" means polymerase chain reaction, "OD" means optical density, "$OD_{600}$" means the optical density measured at a wavelength of 600 nm, "kDa" means kilodaltons, "g" means the gravitation constant, "bp" means base pair(s), "kbp" means kilobase pair(s), "% w/v" means weight/volume percent, % v/v" means volume/volume percent, "wt %" means percent by weight, "nt" means not tested, "HPLC" means high performance liquid chromatography, and "GC" means gas chromatography. The term "molar selectivity" is the number of moles of product produced per mole of sugar substrate consumed and is reported as a percent.

Example 1

Increased Tolerance of *Lactobacillus plantarum* PN0512 to 1-butanol, iso-butanol and 2-butanol at Decreased Growth Temperatures Tolerance levels of bacterial strain *Lactobacillus plantarum* PN0512 (ATCC # PTA-7727) were determined at 25° C., 30° C. and 37° C. as follows. The strain was cultured in S30L medium (i.e., 10 mM ammonium sulfate, 5 mM potassium phosphate buffer, pH 7.0, 50 mM MOPS, pH 7.0, 2 mM $MgCl_2$, 0.7 mM $CaCl_2$, 50 µM $MnCl_2$, 1 µM $FeCl_3$, 1 µM $ZnCl_2$, 1.72 µM $CuCl_2$, 2.53 µM $CoCl_2$, 2.42 µM $Na_2MoO_4$, 2 µM thiamine hydrochloride, 10 mM glucose, and 0.2% yeast extract). An overnight culture in the absence of any test compound was started in 15 mL of the S30L medium in a 150 mL flask, with incubation at 37° C. in a shaking water bath. The next morning, the overnight culture was diluted into three 500 mL flasks containing 150 mL of fresh medium to an initial $OD_{600}$ of about 0.08. Each flask was incubated in a shaking water bath, one each at 25° C., 30° C. and 37° C. Each large culture was allowed to acclimate at the test temperature for at least 0.5 h. After the acclimation period, each large culture was split into flasks in the absence (control) and in the presence of various amounts of 1-butanol, isobutanol or 2-butanol, as listed in Tables 6, 7, and 8, respectively. Growth was followed by measuring $OD_{600}$ for six hours after addition of the compounds. The results are summarized in Tables 6, 7, and 8 below.

TABLE 6

Growth of *L. plantarum* PN0512 in the presence of 1-butanol at different temperatures

| Concentration 1-butanol (% w/v) | 37° C. | 30° C. | 25° C. |
|---|---|---|---|
| 0.0 | +[1] | + | + |
| 1.0 | + | nt[3] | nt |
| 1.2 | + | nt | nt |
| 1.4 | + | nt | nt |
| 1.5 | + | + | + |
| 1.6 | + | nt | nt |
| 1.8 | + | nt | nt |
| 2.0 | + | + | + |
| 2.1 | + | nt | nt |
| 2.2 | + | nt | nt |
| 2.3 | + | nt | nt |
| 2.4 | −[2] | + | + |
| 2.5 | − | nt | nt |
| 2.7 | − | + | nt |
| 2.9 | − | − | + |
| 3.1 | − | − | + |
| 3.2 | nt | − | − |
| 3.3 | nt | nt | − |
| 3.4 | nt | − | − |

[1]"+" = growth observed as an increase in $OD_{600}$.
[2]"−" = no growth observed, i.e. no change in $OD_{600}$.
[3]"nt" = not tested

TABLE 7

Growth of *L. plantarum* PN0512 in the presence of isobutanol at different temperatures

| Concentration isobutanol (% w/v) | 37° C. | 30° C. | 25° C. |
|---|---|---|---|
| 0.0 | +[1] | + | + |
| 0.5 | + | nt[3] | nt |
| 1.0 | + | nt | nt |
| 1.5 | + | + | + |
| 1.6 | + | nt | nt |
| 1.8 | + | nt | nt |
| 2.0 | + | + | + |
| 2.1 | + | nt | nt |
| 2.3 | + | nt | nt |
| 2.4 | + | + | + |
| 2.5 | + | nt | nt |
| 2.7 | + | + | + |
| 2.9 | + | + | + |
| 3.1 | + | + | + |
| 3.3 | nt | −[2] | + |
| 3.4 | − | nt | nt |
| 3.5 | nt | nt | + |
| 3.6 | nt | nt | − |
| 3.8 | − | nt | nt |
| 4.3 | − | nt | nt |

[1]"+" = growth observed as an increase in $OD_{600}$.
[2]"−" = no growth observed, i.e. no change in $OD_{600}$.
[3]"nt" = not tested

TABLE 8

Growth of *L. plantarum* PN0512 in the presence of 2-butanol at different temperatures

| Concentration 2-butanol (% w/v) | 37° C. | 30° C. | 25° C. |
|---|---|---|---|
| 0.0 | +[1] | + | + |
| 1.8 | + | nt[3] | nt |
| 2.1 | + | nt | nt |
| 2.5 | + | nt | nt |
| 2.9 | + | + | + |
| 3.1 | + | nt | nt |
| 3.5 | + | nt | nt |
| 3.6 | + | nt | nt |
| 3.8 | + | + | + |
| 4.0 | nt | + | nt |
| 4.3 | + | + | + |
| 4.5 | −[2] | + | nt |
| 4.7 | − | + | + |
| 4.9 | nt | − | + |
| 5.2 | − | nt | + |
| 5.6 | − | nt | − |
| 6.0 | − | nt | nt |
| 6.4 | − | nt | nt |
| 7.3 | − | nt | nt |

[1]"+" = growth observed as an increase in $OD_{600}$.
[2]"−" = no growth observed, i.e. no change in $OD_{600}$.
[3]"nt" = not tested All three butanols showed a similar effect of temperature on growth inhibition of *L. plantarum* PN0512. The concentration that resulted in full growth inhibition was greater at 25° C. than at 37° C. In the case of 1-butanol, growth was observed at 37° C. in 2.3% 1-butanol, but not 2.4%. However, at 30° C. growth was observed in 2.7%, but not 2.9%, and at 25° C. growth was observed even in 3.1% 1-butanol. Thus, the concentration of 1-butanol that completely inhibited growth increased as growth temperature decreased. Likewise, in the case of isobutanol, growth was observed in 3.5% at 25° C. while growth was observed in 3.1% at 30° C. and 37° C., but not in 3.3% or 3.4%. Similarly, in the case of 2-butanol growth was observed at 37° C. in 4.3%, but not in 4.5%; at 30° C. in 4.7%, but not in 4.9%; and at 25° C. in 5.2%. Thus the tolerance of *L. plantarum* PN0512 to butanols increased with decreased growth temperature.

Example 2

Increased Tolerance of *Escherichia coli* to 1-butanol at Decreased Exposure Temperature The effect of growth and exposure temperature on survival of *Escherichia coli* in the presence of 1-butanol was tested using stationary phase cultures in a rich medium and log phase cultures in a defined medium. For the stationary phase studies, *E. coli* strain MG1655 (ATCC #700926) was grown overnight in LB medium (Teknova, Half Moon Bay, Calif.) with shaking at 250 rpm at 42° C., 29° C. or 28° C. Survival of 1-butanol shock was tested at exposure temperatures of 0° C., 28° C. or 42° C. The 1-butanol exposure at 28° C. or 42° C. was started immediately after removing the overnight cultures from the growth incubators. The 1-butanol exposure at 0° C. was done after allowing the overnight cultures to cool on ice for about 15 min. A series of solutions of 1-butanol at different concentrations in LB medium was made and 90 μL aliquots were put in microfuge tubes. To these were added 10 μL of the overnight cultures and the tubes were immediately placed in shaking incubators at 42° C. or 28° C. or left on ice for 30 min. To stop the effect of 1-butanol on the cultures, a $10^{-2}$ dilution was done by placing 2 μL of the treated culture into 198 μL of LB medium in wells of a microplate. Then, 5 μL of the undiluted treated cultures were spotted on LB agar plates. Subsequent 10-fold serial dilutions of $10^{-3}$, $10^{-4}$, $10^{-5}$ and $10^{-6}$ of the exposed cultures were done by serial pipetting of 20 μL, starting with the $10^{-2}$ dilution cultures, into 180 μL of LB medium in the microplate, using a multi-channel pipette. Prior to each transfer, the cultures were mixed by pipetting up and down six times. Each dilution (5 μL) was spotted onto an LB plate using a multi-channel pipette and allowed to soak into the plate. The plates were inverted and incubated overnight at 37° C. The number of colonies for each dilution was counted and the % growth inhibition was calculated by comparison with a control culture that had not been exposed to 1-butanol. Survival of 0% was recorded when no colonies in the spots of the undiluted or any of the serial dilutions were observed. The results are shown in Table 9.

A similar study was done with log-phase cultures of *E. coli* grown in a defined medium. *E. coli* strain MG1655 was allowed to grow overnight in MOPS 0.2% glucose medium (Teknova, Half Moon Bay, Calif.) at 42° C. or 28° C. The following day, the cultures were diluted into fresh medium and allowed to grow at the same temperature until in the log phase of growth. The $OD_{600}$ was 0.74 for the 28° C. culture and was 0.72 for the 42° C. culture. Both of these log phase cultures were exposed to 1-butanol at 42° C., 28° C. and 0° C. as follows. A series of solutions of 1-butanol at different concentrations in MOPS 0.2% glucose medium was made and 90 μL aliquots were put in microfuge tubes. To these were added 10 μL of the log phase cultures and the tubes were immediately placed in shaking incubators at 42° C. or 28° C. or left on ice for 30 min. To stop the effect of 1-butanol on the cultures, a $10^{-2}$ dilution was done by placing 2 μL of the treated culture into 198 μL of LB medium in wells of a microplate. Then 5 μL of the undiluted treated cultures were spotted on LB agar plates. Subsequent 10-fold serial dilutions of $10^{-3}$, $10^{-4}$, $10^{-5}$ and $10^{-6}$ of the exposed cultures were done by serial pipetting of 20 μL, starting with the $10^{-2}$ dilution cultures, into 180 μL of LB medium in the microplate, using a multi-channel pipette. Prior to each transfer, the cultures were mixed by pipetting up and down six times. Each dilution (5 μL) was spotted onto an LB plate using a multi-channel pipette and allowed to soak into the plate. The plates were inverted and incubated overnight at 37° C. The number of colonies for each dilution was counted and the % growth inhibition was calculated by comparison with a control culture that had not been exposed to 1-butanol. Survival of 0% was recorded when no colonies in the spots of the undiluted or any of the serial dilutions were observed. The results are shown in Table 10.

TABLE 9

Survival of stationary phase *E. coli* in 1-butanol at 42° C., 28° C., or 0° C.

| 1-Butanol % (w/v) | Grown at 42° C. | Grown at 29° C. | Grown at 42° C. | Grown at 28° C. | Grown at 42° C. | Grown at 29° C. |
|---|---|---|---|---|---|---|
| | % survival after 30 min exposure at 42° C. | | % survival after 30 min exposure at 28° C. | | % survival after 30 min exposure at 0° C. | |
| 1.0 | 100 | 100 | 100 | 100 | 100 | 100 |
| 1.5 | 0.1 | 0.1 | 100 | 100 | 100 | 100 |
| 2.0 | 0 | 0.1 | 100 | 100 | 100 | 100 |
| 2.5 | 0 | 0 | 100 | 100 | 100 | 100 |
| 3.0 | 0 | 0 | 100 | 100 | 100 | 100 |
| 3.5 | 0 | 0 | 3 | 10 | 100 | 100 |
| 4.0 | 0 | 0 | 0.0004 | 0.0003 | 100 | 100 |
| 5.0 | nt[1] | nt | nt | nt | 1 | 1 |
| 6.0 | nt | nt | nt | nt | 0 | 0.001 |
| 7.0 | nt | nt | nt | nt | 0 | 0 |

[1]"nt" = not tested

TABLE 10

Survival of log-phase E. coli in 1-butanol at 42° C., 28° C., or 0° C.

| 1-Butanol % (w/v) | Grown at 42° C. % survival after 30 min exposure at 42° C. | Grown at 28° C. % survival after 30 min exposure at 42° C. | Grown at 42° C. % survival after 30 min exposure at 28° C. | Grown at 28° C. % survival after 30 min exposure at 28° C. | Grown at 42° C. % survival after 30 min exposure at 0° C. | Grown at 29° C. % survival after 30 min exposure at 0° C. |
|---|---|---|---|---|---|---|
| 1.0 | 100 | 100 | nt[1] | nt | nt | nt |
| 1.5 | 0 | 0 | 100 | 100 | nt | nt |
| 2.0 | 0 | 0 | 100 | 100 | nt | nt |
| 2.5 | 0 | 0 | 0.1 | 50 | 100 | 100 |
| 3.0 | 0 | 0 | 0 | 0 | 100 | 100 |
| 3.5 | 0 | 0 | 0.01 | 0 | 100 | 100 |
| 4.0 | 0 | 0 | 0.001 | 0 | 100 | 100 |
| 4.5 | nt | nt | 0 | 0 | 100 | 100 |
| 5.0 | nt | nt | nt | nt | 10 | 50 |
| 6.0 | nt | nt | nt | nt | 1 | 1 |

[1]"nt" = not tested

For both the stationary phase and log-phase cultures of *E. coli* MG1655, the growth temperature had very little, if any, effect on the survival of a 1-butanol shock. However, the exposure temperature had a major effect on the survival of *E. coli* to 1-butanol shock. As can be seen from the data in Tables 9 and 10, the tolerance of *E. coli* MG1655 to 1-butanol increased with decreasing exposure temperature.

Example 3

Increased Tolerance of *Escherichia coli* to 2-butanone at Decreased Exposure Temperature The effect of exposure temperature on survival of *Escherichia coli* in the presence of 2-butanone (also referred to herein as methyl ethyl ketone or MEK) was tested as follows. *E. coli* strain BW25113 (The Coli Genetic Stock Center (CGSC), Yale University; #7636) was grown overnight in LB medium (Teknova, Half Moon Bay, Calif.) with shaking at 250 rpm at 37° C. Survival of MEK shock was tested at exposure temperatures of 28° C. or 37° C. A series of solutions of MEK at different concentrations in LB medium was made and 90 µL aliquots were put in microfuge tubes. To these were added 10 µL of the overnight culture and the tubes were immediately placed in shaking incubators at 37° C. or 28° C. for 30 min. To stop the effect of MEK on the cultures, a $10^{-2}$ dilution was done by placing 2 µL of the MEK treated culture into 198 µL of LB medium in wells of a microplate. Then 5 µL of the undiluted treated cultures were spotted on LB agar plates. Subsequent 10-fold serial dilutions of $10^{-3}$, $10^{-4}$, $10^{-5}$ and $10^{-6}$ of the exposed cultures were done by serial pipetting of 20 µL, starting with the $10^{-2}$ dilution cultures, into 180 µL of LB medium in the microplate, using a multi-channel pipette. Prior to each transfer, the cultures were mixed by pipetting up and down six times. Each dilution (5 µL) was spotted onto LB plates using a multi-channel pipette and allowed to soak into the plate. The plates were inverted and incubated overnight at 37° C. The number of colonies for each dilution was counted and the % growth inhibition was calculated by comparison with a control culture that had not been exposed to MEK. Survival of 0% was recorded when no colonies in the spots of the undiluted or any of the serial dilutions were observed. The results, given as the average of duplicate experiments, are shown in Table 11.

TABLE 11

Survival of *E. coli* in MEK at 37° C. and 28° C.

| MEK % w/v | % Survival at 37° C. | % Survival at 28° C. |
|---|---|---|
| 0 | 100 | 100 |
| 4 | 100 | 100 |
| 6 | 0 | 100 |
| 8 | 0 | 0.002 |

Reducing the exposure temperature from 37° C. to 28° C. dramatically improved survival of *E. coli* to MEK treatment. At 37° C. there was full survival at 4% w/v and no survival at 6% w/v, while at 28° C. there was full survival at 6% w/v. Thus, the tolerance of *E. coli* to MEK increased with decreasing exposure temperature.

Example 4

Increased Tolerance of *E. coli* and *L. plantarum* PN0512 to 1-Butanol at Decreased Exposure Temperature This Example demonstrates that the toxic effects of 1-butanol and 2-butanol on various microbial cells was reduced at lower temperatures. This was demonstrated by incubating *E. coli* (strain MG1655; ATCC #700926), and *L. plantarum* (strain PN0512; ATCC # PTA-7727) with either 1-butanol or 2-butanol at different temperatures and then determining the fraction of the cells that survived the treatment at the different temperatures.

Using overnight cultures or cells from plates, 30 mL cultures of the microorganisms to be tested were started in the following culture media:

*E. coli*—Miller's LB medium (Teknova, Half Moon Bay, Calif.):

*L. plantarum* PN0512—Lactobacilli MRS Broth (BD Diagnostic Systems, Sparks, Md.).

The *E. coli* and *L. plantarum* cultures were grown at 37° C. aerobically with shaking until the cultures were in log phase and the $OD_{600}$ was between 0.6 and 0.8. A 50 µL aliquot of each culture was removed for a time zero sample. The remainder of the cultures was divided into six 5 mL portions and placed in six small incubation flasks or tubes. Different amounts of 1-butanol or 2-butanol were added to the six flasks to bring the concentration to predetermined values, as listed in the tables below. The flasks or tubes were incubated at a desired temperature, aerobically without shaking for 1 h.

After the incubation with one of the butanols, 2 μL from each of the flasks (and in addition 2 μL of the time zero sample of the culture before exposure to one of the butanols) were pipetted into the "head" wells of a 96 well (8×12) microtiter plate, each containing 198 μL of LB medium to give a $10^{-2}$ dilution of the culture. Subsequently, $10^{-3}$, $10^{-4}$, $10^{-5}$, and $10^{-6}$ serial dilutions of the cultures were prepared as follows. The $10^{-3}$ dilution was prepared by pipetting 20 μL of the sample from the head well into the 180 μL LB medium in the next well using a multi-channel pipette. This procedure was repeated 3 more times on successive wells to prepare the $10^{-4}$, $10^{-5}$, and $10^{-6}$ dilutions. After each liquid transfer, the solution in the well was mixed by pipetting it up and down 10 times with the multi-channel pipetor. A 5 μL aliquot of each dilution was spotted onto an LB plate using a multi-channel pipette starting with the $10^{-6}$ dilution, then the $10^{-5}$, and so on working from more to less dilute without a change of tips. The spots were allowed to soak into the agar by leaving the lid of the plate slightly open for 15 to 30 min in a sterile transfer hood. The plates were covered, inverted, and incubated overnight at 37° C. The following day, the number of colonies in the spots were counted from the different dilutions. The number of living cells/mL in each of the original culture solutions from which the 2 μL was withdrawn was calculated and compared to the number of cells in the control untreated culture to determine the % of the cells surviving.

The results of experiments in which *E. coli* cells were treated with 1-butanol at temperatures of 0, 30, and 37° C. are shown Table 12.

TABLE 12

Percentage of *E. coli* cells surviving in 1-butanol at 0, 30 and 37° C.

| 1-butanol % v/v | % Survival at 0° C. | % Survival at 30° C. | % Survival at 37° C. |
|---|---|---|---|
| 0 | 100 | 100 | 100 |
| 1 | nt[1] | 100 | 72 |
| 1.5 | nt | 100 | 20 |
| 2 | nt | 100 | 0 |
| 2.5 | 100 | 23 | 0 |
| 3 | 100 | 0 | 0 |
| 3.5 | 100 | 0 | nt |
| 4 | 100 | nt | nt |
| 4.5 | 100 | nt | nt |

[1]"nt" = not tested

The concentration at which 1-butanol kills *E. coli* cells was affected by the treatment temperature. At 0° C., concentrations of 1-butanol as high as 4.5% v/v had no toxic effect on *E. coli* cells during a one hour treatment. At 30° C., *E. coli* cells were killed when treated with 3% v/v 1-butanol for one hour. At 37° C., *E. coli* cells were killed when treated with 2% v/v 1-butanol for one hour.

The results of experiments in which *L. plantarum* PN0512 cells were treated with 1-butanol at temperatures of 0, 23, and 37° C. for one hour are shown Table 13.

TABLE 13

Percentage of *L. plantarum* PN0512 cells surviving in 1-butanol at 0, 23 and 37° C.

| 1-butanol % v/v | % Survival at 0° C. | % Survival at 23° C. | % Survival at 37° C. |
|---|---|---|---|
| 0 | 100 | 100 | 100 |
| 1 | nt[1] | nt | 80 |
| 1.5 | nt | nt | 58 |

TABLE 13-continued

Percentage of *L. plantarum* PN0512 cells surviving in 1-butanol at 0, 23 and 37° C.

| 1-butanol % v/v | % Survival at 0° C. | % Survival at 23° C. | % Survival at 37° C. |
|---|---|---|---|
| 2 | nt | 100 | 29 |
| 2.5 | nt | 100 | 8 |
| 3 | 100 | 82 | 0 |
| 3.5 | 100 | 0 | 0 |
| 4 | 100 | 0 | nt |
| 4.5 | 100 | 0 | nt |
| 5 | 0 | nt | nt |
| 5.5 | 0 | nt | nt |

[1]"nt" = not tested

The concentration at which 1-butanol kills *L. plantarum* PN0512 cells was affected by the treatment temperature. At 0° C., concentrations of 1-butanol as high as 4.5% v/v had no toxic effect on *L. plantarum* PN0512 cells during a one hour treatment. At 23° C., *L. plantarum* PN0512 cells were killed when treated with 3.5% v/v 1-butanol for one hour. At 37° C., *L. plantarum* PN0512 cells were killed when treated with 2.5% v/v 1-butanol for one hour.

Example 5

Cloning and Expression of Acetolactate Synthase

The purpose of this Example was to clone and express in *E. coli* the budB gene that encodes the enzyme acetolactate synthase. The budB gene was amplified from *Klebsiella pneumoniae* strain ATCC 25955 genomic DNA using PCR.

The budB sequence which encodes acetolactate synthase was amplified from *Klebsiella pneumoniae* (ATCC 25955) genomic DNA by PCR using the primer pair B1 (SEQ ID NO:15) and B2 (SEQ ID NO:16). Other PCR amplification reagents (e.g. Kod HiFi DNA Polymerase (Novagen Inc., Madison, Wis.; catalog no. 71805-3)) were supplied in manufacturers' kits and used according to the manufacturer's protocol. *Klebsiella pneumoniae* genomic DNA was prepared using the Gentra Puregene Puregene kit (Gentra Systems, Inc., Minneapolis, Minn.; catalog number D-5000A). Amplification was carried out in a DNA Thermocycler GeneAmp 9700 (PE Applied Biosystems, Foster city, CA). The nucleotide sequence of the open reading frame (ORF) and the predicted amino acid sequence of the enzyme are given as SEQ ID NO:3 and SEQ ID NO:4, respectively.

For expression studies the Gateway cloning technology (Invitrogen Corp., Carlsbad, Calif.) was used. The entry vector pENTR/SD/D-TOPO allows directional cloning and provided a Shine-Dalgarno sequence for the gene of interest. The destination vector pDEST14 used a T7 promoter for expression of the gene with no tag. The forward primer incorporated four bases (CACC) immediately adjacent to the translational start codon to allow directional cloning of the budB acetolactate synthase coding region PCR product into pENTR/SD/D-TOPO (Invitrogen), generating the plasmid pENTRSDD-TOPObudB. The PENTR construct was transformed into *E. coli* Top10 (Invitrogen) cells and plated according to the manufacturer's recommendations. Transformants were grown overnight and plasmid DNA was prepared using the QIAprep Spin Miniprep kit (Qiagen, Valencia, Calif.; catalog no. 27106) according to the manufacturer's recommendations. To create an expression clone, the budB coding region from pENTRSDD-TOPObudB was transferred to the PDEST 14 vector by in vitro recombination using the LR Clonase mix (Invitrogen, Corp., Carlsbad, Calif.). The resulting vector, pDEST14budB, was transformed into BL-21-Al cells (Invitrogen Corp.). BL-21-Al cells carry a chromosomal copy of the T7 RNA polymerase under control of the arabinose-inducible araBAD promoter.

Transformants are inoculated into LB medium supplemented with 50 µg/mL of ampicillin and grown overnight. An aliquot of the overnight culture is used to inoculate 50 mL of LB medium supplemented with 50 µg/mL of ampicillin. The culture is incubated at 37° C. with shaking until the $OD_{600}$ reaches 0.6-0.8. The culture is split into two 25-mL portions and arabinose is added to one of the flasks to a final concentration of 0.2% w/v. The negative control flask is not induced with arabinose. The flasks are incubated for 4 h at 37° C. with shaking. Cells are harvested by centrifugation and the cell pellets are resuspended in 50 mM MOPS, pH 7.0 buffer. The cells are disrupted either by sonication or by passage through a French Pressure Cell. Each cell lysate is centrifuged yielding the supernatant and the pellet or the insoluble fraction. An aliquot of each fraction (whole cell lysate, from induced and control cells, is resuspended in SDS (MES) loading buffer (Invitrogen), heated to 85° C. for 10 min and subjected to SDS-PAGE analysis (NuPAGE 4-12% Bis-Tris Gel, catalog no. NP0322Box, Invitrogen). A protein of the expected molecular weight, as deduced from the nucleic acid sequence, is present in the induced culture but not in the uninduced control.

Acetolactate synthase activity in the cell free extracts is measured using the method described by Bauerle et al. (Bauerle et al. (1964) *Biochim. Biophys. Acta* 92:142-149). Protein concentration is measured by either the Bradford method or by the Bicinchoninic Kit (Sigma, catalog no. BCA-1; St. Louis, Mo.) using Bovine serum albumin (BSA) (Bio-Rad, Hercules, Calif.) as the standard.

Example 6

Cloning and Expression of Acetolactate Decarboxylase

The purpose of this Example was to clone and express in *E. coli* the budA gene that encodes the enzyme acetolactate decarboxylase. The budA gene was amplified from *Klebsiella pneumoniae* strain ATCC 25955 genomic DNA using PCR.

The budA sequence which encodes acetolactate decarboxylase, was cloned in the same manner as described for budB in Example 5, except that the primers used for PCR amplification were B3 (SEQ ID NO:17) and B4 (SEQ ID NO:18). The nucleotide sequence of the open reading frame (ORF) and the predicted amino acid sequence of the enzyme are given as SEQ ID NO:1 and SEQ ID NO:2, respectively. The resulting plasmid was named pENTRSDD-TOPObudA.

Acetolactate decarboxylase activity in the cell free extracts is measured using the method described by Bauerle et al., supra.

Example 7

Prophetic

Cloning and Expression of Butanediol Dehydrogenase

The purpose of this prophetic Example is to describe how to clone and express in *E. coli* the budC gene that encodes the enzyme butanediol dehydrogenase. The budC gene is amplified from *Klebsiella pneumoniae* strain IAM1063 genomic DNA using PCR.

The budC sequence encoding butanediol dehydrogenase is cloned and expressed in the same manner as described for budA in Example 5, except that the primers used for PCR amplification are B5 (SEQ ID NO:19) and B6 (SEQ ID NO:20) and the genomic template DNA is from *Klebsiella pneumoniae* IAM1063 (which is obtained from the Institute of Applied Microbiology Culture Collection, Tokyo, Japan). *Klebsiella pneumoniae* IAM1063 genomic DNA is prepared using the Gentra Puregene Puregene kit (Gentra Systems, Inc., Minneapolis, Minn.; catalog number D-5000A). The nucleotide sequence of the open reading frame (ORF) and the predicted amino acid sequence of the enzyme are given as SEQ ID NO:5 and SEQ ID NO:6, respectively.

Butanediol dehydrogenase activity in the cell free extracts is measured spectrophotometrically by following NADH consumption at an absorbance of 340 nm.

Example 8

Prophetic

Cloning and Expression of Butanediol Dehydratase

The purpose of this prophetic Example is to describe how to clone and express in *E. coli* the pddA, pddB and pddC genes that encode butanediol dehydratase. The pddA, pddB and pddC genes are amplified from *Klebsiella oxytoca* ATCC 8724 genomic DNA using PCR.

The pddA, pddB and pddC sequences which encode butanediol dehydratase are cloned and expressed in the same manner as described for budA in Example 5, except that the genomic template DNA is from *Klebsiella oxytoca* ATCC 8724, and the primers are B7 (SEQ ID NO:21) and B8 (SEQ ID NO:22). *Klebsiella oxytoca* genomic DNA is prepared using the Gentra Puregene Puregene kit (Gentra Systems, Inc., Minneapolis, Minn.; catalog number D-5000A). A single PCR product including all three open reading frames (ORFs) is cloned, so that all three coding regions are expressed as an operon from a single promoter on the expression plasmid. The nucleotide sequences of the open reading frames for the three subunits are given as SEQ ID NOs:7, 9, and 11, respectively, and the predicted amino acid sequences of the three enzyme subunits are given as SEQ ID NOs:8, 10, and 12, respectively.

Butanediol dehydratase activity in the cell free extracts is measured by derivatizing the ketone product with 2,4-dinitrophenylhydrazine (DNPH). Briefly, 100 µL of reaction mixture, cell extract containing approximately 0.0005 units of enzyme, 40 mM potassium phosphate buffer (pH 8.0), 2 µg of adenosylcobalamin, 5 µg of 2,3,-butanediol, and 1 µg of bovine serum albumin, is quenched by addition of an equal volume of 0.05 wt % DNPH in 1.0 N HCl. After 15 min at room temperature, the color is developed by addition of 100 µL of 4 N NaOH. The amount of product is determined from the absorbance of the final solution at 550 nm compared to a standard curve prepared with 2-butanone. All reactions are carried out at 37° C. under dim red light.

Example 9

Prophetic

Cloning and Expression of Butanol Dehydrogenase

The purpose of this prophetic Example is to describe how to clone and express in *E. coli* the sadh gene that encodes butanol dehydrogenase. The sadh gene is amplified from *Rhodococcus ruber* strain 219 genomic DNA using PCR.

The sadh sequence encoding butanol dehydrogenase is cloned and expressed in the same manner as described for budA in Example 5, except that the genomic template DNA is from *Rhodococcus ruber* strain 219 (Meens, Institut fuer Mikrobiologie, Universitaet Hannover, Hannover, Germany) and the primers are B9 (SEQ ID NO:23) and B10 (SEQ ID NO:24). *Rhodococcus ruber* genomic DNA is prepared using the Ultra Clean™ Microbial DNA Isolation Kit (MO BIO Laboratories Inc., Carlsbad, Calif.), according to the manufacturer's protocol. The nucleotide sequence of the open reading frame (ORF) and the predicted amino acid sequence of the enzyme are given as SEQ ID NO:13 and SEQ ID NO:14, respectively.

Butanol dehydrogenase activity in cell free extracts is measured by following the increase in absorbance at 340 nm resulting from the conversion of NAD to NADH when the enzyme is incubated with NAD and 2-butanol.

Example 10

Prophetic

Construction of a Transformation Vector for the Genes in a 2-Butanol Biosynthetic Pathway The purpose of this prophetic Example is to describe the preparation of a transformation vector for the genes in a 2-butanol biosynthetic pathway (i.e., Pathway 3 as described above). Like most organisms, *E. coli* converts glucose initially to pyruvic acid. The enzymes required to convert pyruvic acid to 2-butanol following Pathway 3, i.e., acetolactate synthase, acetolactate decarboxylase, butanediol dehydrogenase, butanediol dehydratase, and butanol dehydrogenase, are encoded by the budA, budB, budC, pddA, pddB, pddC and sadh genes. To simplify building the 2-butanol biosynthetic pathway in a recombinant organism, the genes encoding the 5 steps in the pathway are divided into two operons. The upper pathway comprises the first three steps catalyzed by acetolactate synthase, acetolactate decarboxylase, and butanediol dehydrogenase. The lower pathway comprises the last two steps catalyzed by butanediol dehydratase and butanol dehydrogenase.

The coding sequences are amplified by PCR with primers that incorporate restriction sites for later cloning, and the forward primers contain an optimized *E. coli* ribosome binding site (AAAGGAGG). PCR products are TOPO cloned into the pCR4Blunt-TOPO vector and transformed into Top10 cells (Invitrogen). Plasmid DNA is prepared from the TOPO clones, and the sequence of the cloned PCR fragment is verified. Restriction enzymes and T4 DNA ligase (New England Biolabs, Beverly, Mass.) are used according to manufacturer's recommendations. For cloning experiments, restriction fragments are gel-purified using QIAquick Gel Extraction kit (Qiagen).

After confirmation of the sequence, the coding regions are subcloned into a modified pUC19 vector as a cloning platform. The pUC19 vector is modified by a HindIII/SapI digest, followed by treatment with Klenow DNA polymerase to fill in the ends. The 2.4 kB vector fragment is gel-purified and religated creating pUC19dHS. Alternatively the pUC19 vector is modified by a SphI/SapI digest, followed by treatment with Klenow DNA polymerase to blunt the ends. The 2.4 kB vector fragment is gel-purified and religated creating pUC19dSS. The digests remove the lac promoter adjacent to the MCS (multiple cloning sites), preventing transcription of the operons from the vector.

Upper Pathway:

The budABC coding regions are amplified from *Klebsiella pneumoniae* genomic DNA by PCR using primer pair B11 and B12 (Table 4), given as SEQ ID NOs:25 and 26, respectively. The forward primer incorporates an EcoRI restriction site and a ribosome binding site (RBS). The reverse primer incorporates an SphI restriction site. The PCR product is cloned into pCR4Blunt-TOPO creating pCR4Blunt-TOPO-budABC.

To construct the upper pathway operon pCR4Blunt-TOPO-budABC is digested with EcoRI and SphI releasing a 3.2 kbp budABC fragment. The pUC19dSS vector is also digested with EcoRI and SphI, releasing a 2.0 kbp vector fragment. The budABC fragment and the vector fragment are ligated together using T4 DNA ligase (New England Biolabs) to form pUC19dSS-budABC.

Lower Pathway:

The pddABC coding regions are amplified from *Klebsiella oxytoca* ATCC 8724 genomic DNA by PCR using primers B13 and B14 (Table 4), given as SEQ ID NOs:27 and 28, respectively, creating a 2.9 kbp product. The forward primer incorporates EcoRI and PmeI restriction sites and a RBS. The reverse primer incorporates the BamHI restriction site. The PCR product is cloned into pCRBlunt II-TOPO creating pCRBluntII-pdd.

The sadh gene is amplified from *Rhodococcus ruber* strain 219 genomic DNA by PCR using primers B15 and B16 (Table 4), given as SEQ ID NOs:29 and 30, respectively, creating a 1.0 kbp product. The forward primer incorporates a BamHI restriction site and a RBS. The reverse primer incorporates an XbaI restriction site. The PCR product is cloned into pCR-Blunt II-TOPO creating pCRBluntII-sadh.

To construct the lower pathway operon, a 2.9 kbp EcoRI and BamHI fragment from pCRBluntII-pdd, a 1.0 kbp BamHI and XbaI fragment from pCRBluntII-sadh, and the large fragment from an EcoRI and XbaI digest of pUC19dHS are ligated together. The three-way ligation creates pUC19dHS-pdd-sadh.

The pUC19dSS-budABC vector is digested with PmeI and HindIII, releasing a 3.2 kbp fragment that is cloned into pBenBP, an *E. coli-B. subtilis* shuttle vector. Plasmid pBenBP is created by modification of the pBE93 vector, which is described by Nagarajan (WO 93/2463, Example 4). To generate pBenBP, the *Bacillus amyloliquefaciens* neutral protease promoter (NPR) signal sequence and the phoA gene are removed from pBE93 with an NcoI/HindIII digest. The NPR promoter is PCR amplified from pBE93 by primers BenF and BenBPR, given by SEQ ID NOs:31 and 32, respectively. Primer BenBPR incorporates BstEII, PmeI and HindIII sites downstream of the promoter. The PCR product is digested with NcoI and HindIII, and the fragment is cloned into the corresponding sites in the vector pBE93 to create pBenBP. The upper operon fragment is subcloned into the PmeI and HindIII sites in pBenBP creating pBen-budABC.

The pUC19dHS-pdd-sadh vector is digested with PmeI and HindIII releasing a 3.9 kbp fragment that is cloned into the PmeI and HindIII sites of pBenBP, creating pBen-pdd-sadh.

Example 11

Prophetic

Expression of a 2-Butanol Biosynthetic Pathway in *E. coli*

The purpose of this prophetic Example is to describe how to express a 2-butanol biosynthetic pathway in *E. coli*.

The plasmids pBen-budABC and pBen-pdd-sadh, prepared as described in Example 10, are separately transformed into *E. coli* NM522 (ATCC No. 47000), and expression of the genes in each operon is monitored by SDS-PAGE analysis and enzyme assay. After confirmation of expression of all genes, pBen-budABC is digested with EcoRI and HindIII to release the NPR promoter-budABC fragment. The fragment is blunt ended using the Klenow fragment of DNA polymerase (New England Biolabs, catalog no. M0210S). The plasmid pBen-pdd-sadh is digested with EcoRI and similarly blunted to create a linearized, blunt-ended vector fragment. The vector and NPR-budABC fragments are ligated, creating p2BOH. This plasmid is transformed into *E. coli* NM522 to give *E. coli* NM522/p2BOH, and expression of the genes is monitored as previously described.

*E. coli* NM522/p2BOH is inoculated into a 250 mL shake flask containing 50 mL of medium and shaken at 250 rpm and 35° C. The medium is composed of: dextrose, 5 g/L; MOPS, 0.05 M; ammonium sulfate, 0.01 M; potassium phosphate, monobasic, 0.005 M; S10 metal mix, 1% (v/v); yeast extract, 0.1% (w/v); casamino acids, 0.1% (w/v); thiamine, 0.1 mg/L; proline, 0.05 mg/L; and biotin 0.002 mg/L, and is titrated to pH 7.0 with KOH. S10 metal mix contains: $MgCl_2$, 200 mM; $CaCl_2$, 70 mM; $MnCl_2$, 5 mM; $FeCl_3$, 0.1 mM; $ZnCl_2$, 0.1 mM; thiamine hydrochloride, 0.2 mM; $CuSO_4$, 172 µM; $CoCl_2$, 253 µM; and $Na_2MoO_4$, 242 µM. After 18 h, 2-butanol is detected by HPLC or GC analysis using methods that are well known in the art, for example, as described in the General Methods section above.

Example 12

Prophetic

Expression of a 2-Butanol Biosynthetic Pathway in *Bacillus subtilis*

The purpose of this prophetic Example is to describe how to express a 2-butanol biosynthetic pathway in *Bacillus subtilis*.

The plasmids pBen-budABC and pBen-pdd-sadh, prepared as described in Example 10, are separately transformed into *Bacillus subtilis* BE1010 (*J. Bacteriol.* 173:2278-2282 (1991)) and expression of the genes in each operon is monitored as described in Example 11. The plasmid pBen-budABC is digested with EcoRI and HindIII to release the NPR promoter-budABC fragment. The fragment is blunt ended using the Klenow fragment of DNA polymerase (New England Biolabs, catalog no. M0210S). The plasmid pBen-pdd-sadh is digested with EcoRI and similarly blunted to create a linearized, blunt-ended vector fragment. The vector and NPR-budABC fragments are ligated, creating p2BOH. This plasmid is transformed into *Bacillus subtilis* BE1010 to give *Bacillus subtilis* BE1010/p2BOH, and expression of the genes is monitored as previously described.

*Bacillus subtilis* BE1010/p2BOH is inoculated into a 250 mL shake flask containing 50 mL of medium and shaken at 250 rpm and 35° C. for 18 h. The medium is composed of: dextrose, 5 g/L; MOPS, 0.05 M; glutamic acid, 0.02 M; ammonium sulfate, 0.01 M; potassium phosphate, monobasic buffer, 0.005 M; S10 metal mix (as described in Example 11), 1% (v/v); yeast extract, 0.1% (w/v); casamino acids, 0.1% (w/v); tryptophan, 50 mg/L; methionine, 50 mg/L; and lysine, 50 mg/L, and is titrated to pH 7.0 with KOH. After 18 h, 2-butanol is detected by HPLC or GC analysis using methods that are well known in the art, for example, as described in the General Methods section above.

Example 13

Construction of a Transformation Vector for the Genes in a 2-Butanol Biosynthetic Pathway The purpose of this Example was to prepare a recombinant *E. coli* host carrying the genes in a 2-butanol biosynthetic pathway (i.e., Pathway 3 as described above). Like most organisms, *E. coli* converts glucose initially to pyruvic acid. The enzymes required to convert pyruvic acid to 2-butanone in Pathway 3, i.e., acetolactate synthase, acetolactate decarboxylase, butanediol dehydrogenase, and butanediol dehydratase are encoded by the budA, budB, budC, pddA, pddB, and pddC genes. In the last step of the pathway, a butanol dehydrogenase converts 2-butanone to 2-butanol. Dehydrogenases that carry out this last step are promiscuous and may be found in many organisms. To simplify building the 2-butanol biosynthetic pathway in a recombinant organism, the genes encoding the 5 steps in the pathway were divided into multiple operons. The upper pathway operon comprised the first three steps catalyzed by acetolactate synthase, acetolactate decarboxylase, and butanediol dehydrogenase and were cloned onto an expression vector. The lower pathway comprised the last two steps catalyzed by butanediol dehydratase including the reactivating factor (Mori et al., *J. Biol. Chem.* 272:32034 (1997)) and a butanol dehydrogenase. The diol dehydratase can undergo suicide inactivation during catalysis. The reactivating factor protein encoded by ddrA and ddrB (GenBank AF017781, SEQ ID NO:70) reactivates the inactive enzyme. The ddrA and ddrB genes flank the diol dehydratase operon. The operons for the dehydratase/reactivating factor and the butanol dehydrogenase were either cloned onto another expression vector or the dehydratase/reactivating factor operon was cloned singly onto another expression vector and the last step was provided by an endogenous activity in the demonstration host.

Construction of Vector pTrc99a-budABC:

The budAB coding regions were amplified from *K. pneumoniae* ATCC 25955 genomic DNA by PCR using primer pair BABC F and BAB R, given as SEQ ID NOs:33 and 34, respectively (see Table 4), creating a 2.5 kbp product. The forward primer incorporated SacI and EcoRI restriction sites and a ribosome binding site (RBS). The reverse primer incorporated a SpeI restriction site. The PCR product was cloned into pCR4Blunt-TOPO creating pCR4Blunt-TOPO-budAB. Plasmid DNA was prepared from the TOPO clones and the sequence of the genes was verified with primers M13 Forward (SEQ ID NO:35), M13 Reverse (SEQ ID NO:36), N83 SeqF2 (SEQ ID NO:37), N83 SeqF3 (SEQ ID NO:38) and N84 SeqR4 (SEQ ID NO:39) (see Table 5).

The budC coding region was amplified from *K. pneumoniae* ATCC 25955 genomic DNA by PCR using primer pair BC Spe F and BC Xba R given as SEQ ID NOs:40 and 41, respectively, creating a 0.8 kbp product. The forward primer incorporated a SpeI restriction site, a RBS and modified the CDS by changing the second and third codons from AAA to AAG. The reverse primer incorporated an XbaI restriction site. The PCR product was cloned into pCR4 Blunt-TOPO creating pCR4 Blunt-TOPO-budC. Plasmid DNA was prepared from the TOPO clones and the sequence of the genes was verified with primers M13 Forward (SEQ ID NO:35) and M13 Reverse (SEQ ID NO:36).

To construct the budABC operon, pCR4 Blunt-TOPO-budC was digested with SnaBI and XbaI releasing a 1.0 kbp budC fragment. The vector pTrc99a (Amann et al., Gene 69(2):301-315 (1988)) was digested with SmaI and XbaI creating a 4.2 kbp linearized vector fragment. The vector and the budC fragment were ligated to create pTrc99a-budC and transformed into E. coli Top 10 cells (Invitrogen). Transformants were analyzed by PCR amplification with primers Trc F (SEQ ID NO:42) and Trc R (SEQ ID NO:43) for a 1.2 kbp product to confirm the presence of the budC insert. The budAB genes were subcloned from pCR4 Blunt-TOPO-budAB as a 2.5 kbp EcoRI/SpeI fragment. Vector pTrc99a-budC was digested with EcoRI and SpeI and the resulting 5.0 kbp vector fragment was gel-purified. The purified vector and budAB insert were ligated and transformed into E. coli Top 10 cells. Transformants were screened by PCR amplification with primers Trc F (SEQ ID NO:42) and N84 Seq R2 (SEQ ID NO:65) to confirm creation of pTrc99a-budABC. In this plasmid, the bud A, B, and C coding regions are adjacent to each other, in this order, and between the Trc promoter and the rrnB termination sequence.

Results:

Three independent isolates of E. coli Top 10/pTrc99a-budABC were examined for the production of butanediol, using E. coli Top 10/pCL1925-Kodd-ddr (described below) as a negative control. The strains were grown in LB medium containing 100 µg/mL carbenicillin. The resulting cells were used to inoculate shake flasks (approximately 175 mL total volume) containing 125 mL of TM3a/glucose medium with 100 µg/mL carbenicillin. In addition, the flasks inoculated with strains carrying pTrc99a-budABC contained 0.4 mM isopropyl β-D-1-thiogalactopyranoside (IPTG). TM3a/glucose medium contains (per liter): 10 g glucose, 13.6 g $KH_2PO_4$, 2.0 g citric acid monohydrate, 3.0 g $(NH_4)_2SO_4$, 2.0 g $MgSO_4.7H_2O$, 0.2 g $CaCl_2.2H_2O$, 0.33 g ferric ammonium citrate, 1.0 mg thiamine HCl, 0.50 g yeast extract, and 10 mL trace elements solution, adjusted to pH 6.8 with $NH_4OH$. The solution of trace elements contained: citric acid $H_2O$ (4.0 g/L), $MnSO_4.H_2O$ (3.0 g/L), NaCl (1.0 g/L), $FeSO_4.7H_2O$ (0.10 g/L), $CoCl_2.6H_2O$ (0.10 g/L), $ZnSO_4.7H_2O$ (0.10 g/L), $CuSO_4.5H_2O$ (0.010 g/L), $H_3BO_3$ (0.010 g/L), and $Na_2MoO_4$ $2H_2O$ (0.010 g/L). The flasks, capped with vented caps, were inoculated at a starting $OD_{600}$ of approximately 0.03 units and incubated at 34° C. with shaking at 300 rpm.

Approximately 23 h after induction, an aliquot of the broth was analyzed by HPLC (Shodex Sugar SH1011 column) and GC(HP-INNOWax), using the same methods described in the General Methods section for 2-butanol and 2-butanone. The results of the analysis are given in Table 14. The three E. coli clones converted glucose to acetoin and meso-2,3-butanediol, the desired intermediates of the pathway, with a molar selectivity of 14%. This selectivity was approximately 35-fold higher than that observed with the E. coli control strain lacking budABC.

TABLE 14

Production of Acetoin and meso-2,3-butanediol by E. coli Top 10/pTrc99a-budABC

| Strain | $OD_{600}$ | Acetoin, mM | Meso-2,3-Butanediol, mM | Molar Selectivity[a], % |
|---|---|---|---|---|
| Negative control | 1.4 | 0.07 | 0.03 | 0.4 |
| Isolate #1 | 1.5 | 0.64 | 1.3 | 14 |
| Isolate #2 | 1.4 | 0.70 | 1.2 | 14 |
| Isolate #3 | 1.4 | 0.74 | 1.3 | 15 |

[a]Molar selectivity is (acetoin + meso-2,3-butanediol)/(glucose consumed).

Construction of Vector pCL1925-KoDD-ddr:

The diol dehydratase (GenBank D45071, SEQ ID NO:69) and reactivating factor (GenBank AF017781, SEQ ID NO:70) operons were PCR amplified from Klebsiella oxytoca ATCC 8724 as a single unit with primers DDo For (SEQ ID NO: 44) and DDo Rev (SEQ ID NO:45). The forward primer incorporated an optimized E. coli RBS and a HindIII restriction site. The reverse primer included an XbaI restriction site. The 5318 bp PCR product was cloned into pCR4Blunt-TOPO and clones of the resulting pCR4Blunt-TOPO-Kodd-ddr were sequenced with primers M13 Forward (SEQ ID NO:35), M13 Reverse (SEQ ID NO:36), DDko seq F2 (SEQ ID NO:46), DDko seq F5 (SEQ ID NO:47), DDko seq F7 (SEQ ID NO:48), DDko seq F9 (SEQ ID NO:49), DDko seq R1 (SEQ ID NO:50), DDko seq R3 (SEQ ID NO:51), DDko seq R7 (SEQ ID NO:52), and DDko seq R10 (SEQ ID NO:53). A clone having the insert with the expected sequence was identified.

For expression, the diol dehydratase/reactivating factor genes were subcloned into pCL1925 (U.S. Pat. No. 7,074,608), a low copy plasmid carrying the glucose isomerase promoter from Streptomcyes. pCR4Blunt-TOPO-Kodd-ddr was digested with HindIII and XbaI and the resulting 5.3 kbp Kodd-ddr fragment was gel-purified. Vector pCL1925 was digested with HindIII and XbaI and the resulting 4539 bp vector fragment was gel purified. The vector and Kodd-ddr fragment were ligated and transformed into E. coli Top10. Transformants were screened by PCR with primers DDko Seq F7 (SEQ ID NO:48) and DDko Seq R7 (SEQ ID NO: 52). Amplification of the plasmid (pCL1925-Kodd-ddr) carrying the insert resulted in a product of approximately 797 bp.

Activity of diol dehydratase towards meso-2,3-butanediol was measured by incubating cell extract (total protein ~0.8 mg/mL) with 10 mM butanediol and 12 mM coenzyme $B_{12}$ in 80 mM HEPES (pH 8.2) for 17 h at room temperature. Formation of the expected product, 2-butanone, was determined by HPLC as described in the General Methods.

Construction of Vector pCL1925-KoDD-ddr::T5 chnA ter:

To provide a heterologous alcohol dehydrogenase activity, the chnA gene encoding cyclohexanol dehydrogenase from Acinetobacter sp. (Cheng et al., J. Bacteriol. 182:4744-4751 (2000)) was cloned into the pCL1925 vector with the diol dehydratase operon, pCL1925-Kodd-ddr. The chnA gene, given as SEQ ID NO:71 (Genbank No: AF282240, SEQ ID NO:73) was amplified from pDCQ2, a cosmid carrying the cyclohexanol gene cluster from Acinetobacter, with primers ChnA F (SEQ ID NO:54) and ChnA R (SEQ ID NO:55). The resulting 828 bp PCR product was cloned into pCR4Blunt-TOPO to create pCR4Blunt-TOPO-chnA and transformants were screened by colony PCR with primers M13 Forward (SEQ ID NO:35) and M13 Reverse (SEQ ID NO:36). Correct clones produced a PCR product of about 1 kbp and were sequenced with primers M13 Forward (SEQ ID NO:35) and M13 Reverse (SEQ ID NO:36).

After sequencing pCR4Blunt-TOPO-chnA to confirm the correct sequence, the chnA gene was subcloned from the plasmid as an 813 bp MfeI/SmaI fragment. The expression vector pQE30 (Qiagen) was digested with MfeI and SmaI and the resulting 3350 bp vector fragment was gel-purified. The chnA fragment and the purified vector were ligated and transformed into E. coli Top10 cells. Transformants were colony PCR screened with primers chnSeq F1 (SEQ ID NO:56) and chnseq R1 (SEQ ID NO:57) for a 494 bp PCR product. This cloning placed the chnA gene under the control of the T5 promoter in the plasmid, pQE30-chnA.

To prepare the pCL1925 vector to carry two operons, terminators were added to the vector. A tonB terminator-mcstrpA terminator fragment was prepared by oligonucleotide annealing with primers Top ter F1 (SEQ ID NO:58), Top ter F2 (SEQ ID NO:59), Bot ter R1 (SEQ ID NO:60) and Bot ter R2 (SEQ ID NO:61). The annealed DNA was gel-purified on a 6% PAGE gel (Embi-tec, San Diego, Calif.). Vector pCL1925 was digested with SacI and XbaI and gel-purified. The annealed DNA and vector fragment were ligated to create pCL1925-ter. Transformants were screened by colony PCR amplification with primers pCL1925 vec F (SEQ ID NO:62) and pCL1925 vec R1 (SEQ ID NO:63) for the presence of a PCR product of approximately 400 bp. Positive clones from the PCR screen were sequenced with the same primers.

Vector pCL1925-ter was digested with XhoI and PmeI and the resulting 4622 bp fragment was gel-purified. pQE30-chnA was digested with NcoI and the DNA was treated with Klenow DNA polymerase to blunt the ends. pQE30-chnA was then digested with XhoI and the resulting 1.2 kbp T5 promoter-chnA fragment was gel-purified. The pCL1925-ter vector and the chnA operon fragment were ligated together to give pCL1925-ter-T5chnA and transformed into *E. coli* Top10. Transformants were screened by colony PCR amplification with primers pCL1925 vec F (SEQ ID NO:64) and chnseq R1 (SEQ ID NO:59) for a product of approximately 1 kbp.

To finish building the pathway vector, the pCL1925-KoDD-ddr plasmid was digested with XbaI and SacI and the resulting 9504 bp vector fragment was gel-purified. The chnA operon flanked by terminators, with the trpA terminator (Koichi et al. (1997) Volume 272, Number 51, pp. 32034-32041) 3' to the chnA coding sequence, from pCL1925-ter-T5chnA was gel-purified as a 1271 bp XbaI/SacI fragment. After ligation of the fragments and transformation into *E. coli* Top10, transformants were screened by colony PCR. Primers chnseq F1 (SEQ ID NO:58) and pCL1925 vec R2 (SEQ ID NO:64) amplified the expected 1107 bp PCR product in the resulting plasmid, pCL1925-KoDD-ddr::ter-T5chnA.

Example 14

Expression of a 2-Butanol Biosynthetic Pathway in *E. coli* with Overexpressed Endogenous Alcohol Dehydrogenase The purpose of this Example was to express a 2-butanol biosynthetic pathway in several *E. coli* strains.

Construction of *E. coli* Strains Constitutively Expressing yqhD:

*E. coli* contains a native gene (yqhD) that was identified as a 1,3-propanediol dehydrogenase (U.S. Pat. No. 6,514,733). The yqhD gene, given as SEQ ID NO:74, has 40% identity to the gene adhB in *Clostridium*, a probable NADH-dependent butanol dehydrogenase. The yqhD gene was placed under the constitutive expression of a variant of the glucose isomerase promoter 1.6GI (SEQ ID NO:67) in *E. coli* strain MG1655 1.6yqhD::Cm (WO 2004/033646) using λ Red technology (Datsenko and Wanner, *Proc. Natl. Acad. Sci. U.S.A.* 97:6640 (2000)). Similarly, the native promoter was replaced by the 1.5GI promoter (WO 2003/089621) (SEQ ID NO:68), creating strain MG1655 1.5yqhD::Cm, thus, replacing the 1.6GI promoter of MG1655 1.6yqhD::Cm with the 1.5GI promoter. The 1.5GI and 1.6GI promoters differ by 1 bp in the −35 region, thereby altering the strength of the promoters (WO 2004/033646). While replacing the native yqhD promoter with either the 1.5GI or 1.6GI promoter, the yqhC gene encoding the putative transcriptional regulator for the yqh operon was deleted. Butanol dehydrogenase activity was confirmed by enzyme assay using methods that are well known in the art.

Transformation of *E. coli* Strains:

Pathway plasmids pCL1925-Kodd-ddr and pTrc99a-budABC, described in Example 13, were co-transformed into *E. coli* strains MG1655, MG1655 1.6yqhD, and MG1655 1.5yqhD. The two latter strains overexpress the 1,3-propanediol dehydrogenase, YqhD, which also has butanol dehydrogenase activity. Strains were examined for the production of 2-butanone and 2-butanol essentially as described above. Cells were inoculated into shake flasks (approximately 175 mL total volume) containing either 50 or 150 mL of TM3a/glucose medium (with 0.1 mg/L vitamin $B_{12}$, appropriate antibiotics and IPTG) to represent medium and low oxygen conditions, respectively. Spectinomycin (50 µg/mL) and carbenicillin (100 µg/mL) were used for plasmids pCL1925-Kodd-ddr and pTrc99a-budABC, respectively. The flasks were inoculated at a starting $OD_{600}$ of ≦0.04 units and incubated at 34° C. with shaking at 300 rpm. The flasks containing 50 mL of medium were capped with vented caps; the flasks containing 150 mL, were capped with non-vented caps to minimize air exchange. IPTG was present at time zero at a concentration of zero or 0.04 mM. Analytical results for 2-butanone and 2-butanol production are presented in Table 15. All the *E. coli* strains comprising a 2-butanol biosynthetic pathway produced 2-butanone under low and medium oxygen conditions and produced 2-butanol under low oxygen conditions.

TABLE 15

Production of 2-Butanone and 2-Butanol by *E. coli* MG1655 strains harboring pathway plasmids pCL1925-Kodd-ddr and pTrc99a-budABC

| Strain[a,b] | IPTG, mM | Volume of Medium, mL | 2-Butanone, mM | 2-Butanol, mM |
|---|---|---|---|---|
| MG1655 #1 | 0 | 50 | 0.08 | Not detected |
| MG1655 #2 | 0 | 50 | 0.11 | Not detected |
| MG1655 #1 | 0.04 | 50 | 0.12 | Not detected |
| MG1655 #2 | 0.04 | 50 | 0.11 | Not detected |
| MG1655 #1 | 0 | 150 | 0.15 | 0.047 |
| MG1655 #2 | 0 | 150 | 0.19 | 0.041 |
| MG1655 #1 | 0.04 | 150 | 0.10 | 0.015 |
| MG1655 #2 | 0.04 | 150 | 0.11 | 0.015 |
| MG1655 1.5yqhD #1 | 0 | 50 | 0.10 | Not detected |
| MG1655 1.5yqhD #2 | 0 | 50 | 0.07 | Not detected |
| MG1655 1.5yqhD #1 | 0.04 | 50 | 0.12 | Not detected |
| MG1655 1.5yqhD #2 | 0.04 | 50 | 0.18 | Not detected |
| MG1655 1.5yqhD #1 | 0 | 150 | 0.16 | 0.030 |
| MG1655 1.5yqhD #2 | 0 | 150 | 0.18 | 0.038 |
| MG1655 1.5yqhD #1 | 0.04 | 150 | 0.10 | 0.021 |
| MG1655 1.5yqhD #2 | 0.04 | 150 | 0.09 | 0.017 |
| MG1655 1.6yqhD #1 | 0 | 50 | 0.08 | Not detected |
| MG1655 1.6yqhD #2 | 0 | 50 | 0.07 | Not detected |
| MG1655 1.6yqhD #1 | 0.04 | 50 | 0.12 | Not detected |
| MG1655 1.6yqhD #2 | 0.04 | 50 | 0.15 | Not detected |
| MG1655 1.6yqhD #1 | 0 | 150 | 0.17 | 0.019 |
| MG1655 1.6yqhD #2 | 0 | 150 | 0.18 | 0.041 |

TABLE 15-continued

Production of 2-Butanone and 2-Butanol by *E. coli* MG1655 strains harboring pathway plasmids pCL1925-Kodd-ddr and pTrc99a-budABC

| Strain[a,b] | IPTG, mM | Volume of Medium, mL | 2-Butanone, mM | 2-Butanol, mM |
|---|---|---|---|---|
| MG1655 1.6yqhD #1 | 0.04 | 150 | 0.11 | 0.026 |
| MG1655 1.6yqhD #2 | 0.04 | 150 | 0.11 | 0.038 |
| Control (uninoculated medium) | | | Not detected | Not detected |

[a]#1 and #2 represent independent isolates.
[b]MG1655 is MG1655/pCL1925-Kodd-ddr/pTrc99a-budABC
MG1655 1.6yqhD is MG1655 1.6yqhD/pCL1925-Kodd-ddr/pTrc99a-budABC
MG1655 1.6yqhD is MG1655 1.5yqhD/pCL1925-Kodd-ddr/pTrc99a-budABC.

Example 15

Expression of a 2-Butanol Biosynthetic Pathway in *E. coli* with Heterologous Alcohol Dehydrogenase Plasmids pCL1925-KoDD-ddr::ter-T5chnA and pTrc99a-budABC, described in Example 13, were transformed into *E. coli* strains MG1655 and MG1655 ΔyqhCD for a demonstration of the production of 2-butanol.

MG1655 ΔyqhCD carries a yqhCD inactivation that was made using the method of Datsenko and Wanner (*Proc. Natl. Acad. Sci. U.S.A.* 97(12):6640-6645 (2000)). After replacement of the region with the FRT-CmR-FRT cassette of pKD3, the chloramphenicol resistance marker was removed using the FLP recombinase. The sequence of the deleted region is given as SEQ ID NO:66.

Strains MG1655/pTrc99a-budABC/pCL1925KoDD-ddr::ter-T5 chnA and MG1655 ΔyqhCD/pTrc99a-budABC/pCL1925KoDD-ddr::ter-T5 chnA were examined for the production of 2-butanone and 2-butanol essentially as described above. Strain MG1655 ΔyqhCD/pCL1925 was used as a negative control. Cells were inoculated into shake flasks (approximately 175 mL total volume) containing 50 or 150 mL of TM3a/glucose medium (with 0.1 mg/L vitamin $B_{12}$ and appropriate antibiotics) to represent medium and low oxygen conditions, respectively. Spectinomycin (50 μg/mL) and ampicillin (100 μg/mL) were used for selection of pCL1925 based plasmids and pTrc99a-budABC, respectively. Enzyme activity derived from pTrc99a-budABC was detected by enzyme assay in the absence of IPTG inducer, thus, IPTG was not added to the medium. The flasks were inoculated at a starting $OD_{600}$ of ≦0.01 units and incubated at 34° C. with shaking at 300 rpm for 24 h. The flasks containing 50 mL of medium were capped with vented caps; the flasks containing 150 mL, were capped with non-vented caps to minimize air exchange. Analytical results for 2-butanone and 2-butanol production are presented in Table 16. Both *E. coli* strains comprising a 2-butanol biosynthetic pathway produced 2-butanone under low and medium oxygen conditions and produced 2-butanol under low oxygen conditions, while the negative control strain did not produce detectable levels of either 2-butanone or 2-butanol.

TABLE 16

Production of 2-butanone and 2-butanol by *E. coli* strains

| Strain[a] | Volume, mL | 2-Butanone, mM | 2-Butanol, mM |
|---|---|---|---|
| Negative control, MG1655 ΔyqhCD/pCL1925 | 50 | Not detected | Not detected |
| MG1655/pTrc99a-budABC/pCL1925KoDD-ddr::T5 chnA ter | 50 | 0.33 | Not detected |
| MG1655 ΔyqhCD/pTrc99a-budABC/pCL1925KoDD-ddr::T5 chnA ter #1 | 50 | 0.23 | Not detected |
| MG1655 ΔyqhCD/pTrc99a-budABC/pCL1925KoDD-ddr::T5 chnA #2 | 50 | 0.19 | Not detected |
| Negative control, MG1655 ΔyqhCD/pCL1925 | 150 | Not detected | Not detected |
| MG1655/pTrc99a-budABC/pCL1925KoDD-ddr::T5 chnA ter | 150 | 0.41 | 0.12 |
| MG1655 ΔyqhCD/pTrc99a-budABC/pCL1925KoDD-ddr::T5 chnA #1 | 150 | 0.15 | 0.46 |
| MG1655 ΔyqhCD/pTrc99a-budABC/pCL1925KoDD-ddr::T5 chnA #2 | 150 | 0.44 | 0.14 |
| Medium | | Not detected | Not detected |

[a]#1 and #2 represent independent isolates.

Example 16

Cloning of Amino:Pyruvate Transaminase (APT)

An amino:pyruvate transaminase (APT) from *Vibrio fluvialis* JS17 was identified by Shin et al. (Appl. Microbiol. Biotechnol. (2003) 61:463-471). The amino acid sequence (SEQ ID NO:122) was found to have significant homology with ω-amino acid:pyruvate transaminases (Shin and Kim (*J. Org. Chem.* 67:2848-2853 (2002)). It was shown that the *Vibrio fluvialis* APT has transaminase activity towards acetoin.

For expression of the APT enzyme in *E. coli*, a codon optimized APT coding region (SEQ ID NO:144) was designed using the preferred *E. coli* codons with additional considerations such as codon balance and mRNA stability, and synthesized (by DNA2.0; Redwood City, Calif.). The coding region DNA fragment was subcloned into the pBAD.HisB vector (Invitrogen) between the NcoI and HindIII sites and the resulting plasmid, hereafter referred to as pBAD.APT1, was transformed into TOP10 cells.

Example 17

Characterization of *Vibrio fluvialis* APT Alanine:Acetoin Aminotransferase Activity A 5 mL volume of LB broth+100 µg/mL ampicillin was inoculated with a fresh colony of TOP10/pBAD:APT1 cells. The culture was incubated at 37° C. for approximately 16 h with shaking (225 rpm). A 300 µL aliquot of this culture was used to inoculate 300 mL of the same medium, which was incubated at 37° C. with shaking (225 rpm). When the culture reached an $OD_{600}$ of 0.8, L-arabinose was added to a final concentration of 0.2% (w/v). The culture was incubated for an additional 16 h, then harvested. The cells were washed once with 100 mM potassium phosphate buffer (pH 7.8) and then frozen and stored at −80° C.

To isolate the enzyme, the cell pellet was thawed and resuspended in 8 mL of 100 mM potassium phosphate buffer (pH 7) containing 0.2 mM ethylenediaminetetraacetate, 1 mM dithiothreitol and 1 tablet of protease inhibitor cocktail (Roche; Indianapolis, Ind.). The cells were lysed by two passes through a French pressure cell at 900 psi, and the resulting lysate was clarified by centrifugation for 30 min at 17000×g. Ammonium sulfate was added to 35% saturation, and the solution was stirred for 30 min at room temperature, at which point precipitated solids were removed by centrifugation (30 min, 17000×g). Additional ammonium sulfate was added to the supernatant to give 55% saturation, and the solution was again stirred for 30 min at room temperature. The precipitated solids were removed by centrifugation (30 min, 17000×g) and then resuspended in 5 mL of 100 mM potassium phosphate buffer (pH 7) containing 10 µM pyridoxal 5'-phosphate and 1 mM dithiothreitol. This solution was desalted by passage through a PD10 column equilibrated with Buffer A (50 mM bis-tris propane buffer (pH 6) containing 10 µM pyridoxal 5'-phosphate and 1 mM dithiothreitol). The desalted extract was then loaded onto a 20 mL Q-Fast Flow column pre-equilibrated with Buffer A. APT was eluted with a linear gradient of 0-0.1 M NaCl in Buffer A. The enzyme was detected in eluted fractions by the presence of a protein band of size ~50 kD when analyzed by SDS-polyacrylamide gel electrophoresis and by the characteristic absorbance at 418 nm. Fractions containing the enzyme eluted at ~0.3 M NaCl. These fractions were pooled to yield a total of 6 mL of a 5.45 mg/mL solution of enzyme, which was >90% pure, as judged by SDS-polyacrylamide gel electrophoresis.

The alanine:acetoin aminotransferase activity of APT was assayed using a lactic dehydrogenase coupled assay. Reaction mixtures contained 100 mM bis-tris propane (pH 9.0), 10 µM pyridoxal 5'-phosphate, 0-50 mM acetoin, 0-5 mM L-alanine, 0.14 or 0.28 mg/mL purified enzyme, 200 µM NADH and 20 U/mL lactic dehydrogenase (Sigma; St. Louis, Mo.). The reaction was followed by measuring the change in absorbance at 340 nm, indicative of the oxidation of NADH. Under these conditions, the $k_{cat}/K_m$ for acetoin was 10 $M^{-1}s^{-1}$ and that for L-alanine was 400 $M^{-1}s^{-1}$.

The identity of the expected product 3-amino-2-butanol was confirmed by comparison to a synthetic standard. A mixture of (R,R)- and (S,S)-3-amino-2-butanol was synthesized by the method of Dickey et al. [*J Amer Chem Soc* 74:944 (1952)]: 5 g of trans-2,3-epoxybutane were slowly stirred into 150 mL of cold (4° C.) $NH_4OH$. The reaction was slowly warmed to room temperature, sealed and stirred at room temperature for an additional 10 days. At this time, excess ammonia and water and residual epoxybutane were removed by rotary evaporation under vacuum at 40° C. The resulting clear oil (2.9 g) was resuspended in water to a concentration of 10% (w/v). Production of the desired product was confirmed by NMR analysis and comparison of the spectrum to that reported by Levy et al. [*Org. Magnetic Resonance* 14:214 (1980)]. A mixture of the corresponding (2R,3S)- and (2S,3R)-isomers was produced using the identical method with the exception that the starting material was the cis-isomer of 2,3-epoxybutane.

An analytical method for detection of 3-amino-2-butanol was developed based on the o-phthaldialdehyde derivatization method for amino acid determination reported by Roth [*Anal. Chem.* 43:880 (1971)]. A 200 µL aliquot of 1 mM 3-amino-2-butanol (mixture of isomers) was mixed with 200 µL of a 50 mM solution of borate (pH 9.5), to which was added 10 µL of 5 µL/mL 2-mercaptoethanol in ethanol and 10 µL of 10 mg/mL o-phthaldialdehye in ethanol. The solution was incubated at room temperature for 10 min, at which time the derivative was extracted into 200 µL hexane. The hexane was separated from the aqueous solution by decanting, and 10 µL were injected onto a Chiracel OD HPLC column (Daicel Chemical Industries; Fort Lee, N.J.). The column was run isocratically with a mobile phase of 90:10 hexane:isopropanol at a rate of 1 mL/min. The derivatized isomers of 3-amino-2-butanol were detected by absorbance at 340 nm with retention times of approximately 15.7 and 16.8 min [(2S,3S) and (2R,3R)], and 18.4 and 21.9 min [(2R,3S) and (2S,3R)]. To differentiate the enantiomers in the first mixture, the pure (2R,3R) isomer (Bridge Organics; Vicksburg, Mich.) was also run under the identical conditions and found to be the 16.8 min peak. To differentiate the enantiomers in the second mixture, the mixture was first kinetically resolved using the alanine:acetoin aminotransferase: 0.28 mg of purified enzyme was incubated with 10 mM pyruvate and 10 mM 3-amino-2-butanol [1:1 mixture of (2R,3S) and (2S,3R) isomers] in 1 mL of 100 mM bis-tris propane (pH 9.0). After 24 h at room temperature, an aliquot was removed and analyzed as described above. Analysis revealed that the 18.4 min peak was 95% depleted, while the 21.9 min peak was >90% retained. A 100 µL aliquot of the remaining reaction mixture was mixed with 50 µL of 20 mM NADH and 10 µL of extract from the TOP10/pTrc99a-BudC strain described in Example 13. The BudC enzyme is known to reduce (R)-acetoin to meso-2,3-butanediol and (S)-acetoin to (S,S)-2,3-butanediol [Ui et al. (2004) *Letters in Applied Microbiology* 39:533-

537]. After 3 h, samples were taken from the reaction and analyzed as described above for acetoin and butanediol. The analysis indicated that the primary product of the reduction was meso-2,3-butanediol, indicating that the product of the aminotransferase reaction was (R)-acetoin, and therefore the consumed 3-amino-2-butanol isomer was the (2R,3S) isomer. Thus the retention time of 18.4 min can be assigned to this isomer and 21.9 to the (2S,3R) isomer.

To confirm that the product of the APT-catalyzed alanine:acetoin aminotransferase reaction was 3-amino-2-butanol, 0.28 mg of purified enzyme was incubated with 10 mM acetoin, 10 mM L-alanine, 50 U lactic dehydrogenase and 200 μM NADH in 1 mL of 100 mM bis-tris propane (pH 9.0). The reaction mixture was incubated at room temperature for 20 h, after which a 200 μL aliquot was removed and derivatized as described above. The retention times of the derivatized products were 15.8 min (major product) and 18.5 min (minor product), matching that of the (2S,3S)- and (2R,3S)-3-amino-2-butanol standards.

Example 18

Identification and Cloning of *Erwinia carotovora* subsp. *atroseptica* Amino Alcohol Kinase and Amino Alcohol O-Phosphate Lyase The purpose of this example is to describe the identification and cloning of sequences encoding an amino alcohol kinase and amino alcohol O-phosphate lyase from the bacterium *Erwinia carotovora*. These two enzymes are part of Pathway 1 for the conversion of 3-amino-2-butanol to 2-butanone via the intermediate 3-amino-2-butanol phosphate as shown in FIG. 1.

Prediction of the *Erwinia* Amino Alcohol Kinase and the Amino Alcohol O-Phosphate Lyase ATP-dependent amino alcohol kinase and amino alcohol O-phosphate lyase activities have been detected in several *Pseudomonas* and *Erwinia* species, including *Pseudomonas* sp. P6 (NCIB10431), *Pseudomonas putida* NCIB 10558 (Jones et al. (1973) *Biochem. J.* 134:167-182), *Erwinia carotovora*, *Erwinia amanas*, *Erwina milletiae*, and *Erwinia atroseptica* (Jones et al. (1973) *Biochem. J.* 134:959-968). In these studies, the extracts of the above species were shown to have activity for the enzymatic conversion of aminopropanol through aminopropanol O-phosphate to propionaldehyde, and the conversion of ethanolamine through ethanolamine O-phosphate to acetaldehyde.

The genomic sequence of the *Erwinia atroseptica* strain in which these activities were reported to exist (now designated as *Erwinia* carotovora subsp. *atroseptica* strain SCR11043 (ATCC BAA-672)) has been determined at the Sanger Institute (Bell et al. *Proc. Natl. Acad. Sci. USA* 101 (30): 11105-11110). Analysis of the putative kinases in the *Erwinia carotovora* subsp. *atroseptica* genome revealed an operon sequence (SEQ ID NO:154) encoding a putative protein (ECA2059; SEQ ID NO:124) that is 39% identical to a *Rhizobium loti* homoserine kinase and a putative class-III pyridoxal phosphate (PLP)-dependent aminotransferase (ECA2060; SEQ ID NO:126) that is 58% identical to a putative aminotransferase from *Rhizobium meliloti*. We predicted that ECA2059 was an amino alcohol kinase and ECA2060 was an amino alcohol O-phosphate lyase which uses PLP as cofactor. Cloning of the Putative Amino Alcohol Kinase and Putative Amino Alcohol O-phosphase Lyase from *Erwinia carotovora* subsp. *atroseptica*

Genomic DNA of *Erwinia carotovora* subsp. *atroseptica* (ATCC #: BAA-672D) was obtained from American Type Culture Collection (ATCC). The operon encoding the putative amino alcohol kinase (KA) and amino alcohol O-phosphate lyase (AT) was named KA-AT (SEQ ID NO:154. This operon was amplified from the *Erwinia* genomic DNA by Phusion DNA polymerase (Finnzymes; via New England Biolabs; Ipswich, Mass.) using primers OT872 (SEQ. ID. No. 127) and OT873 (SEQ. ID. No128). A DNA fragment of 2.4 kb was obtained by the PCR reaction, which corresponds to the size of the KA-AT operon. The PCR product was digested with EcoRI and PstI restriction enzymes, and cloned into vector pKK223-3 (Amersham Biosciences; Piscataway, N.J.) which was digested with the same restriction enzymes. This produced plasmid pKK223.KA-AT, which contained the putative *Erwinia* amino alcohol kinase-lyase operon under control of the tac promoter. Similarly, plasmids pKK223.KA and pKK223.AT were made which placed the putative *Erwinia* kinase and the putative *Erwinia* lyase coding regions in separate vectors, each under the control of the tac promoter. For the PCR cloning of the KA coding region (SEQ ID NO:123), primers OT872 (SEQ. ID. No. 127) and OT879 (SEQ. ID. No. 129) were used; and for the PCR cloning of AT coding region (SEQ ID NO:125), primers OT873 (SEQ. ID. No. 128) and OT880 (SEQ. ID. No. 130) were used in the PCR amplifications, which generated PCR products of 1.1 kb and 1.3 kb respectively. The PCR products were each digested with EcoRI and PstI, and ligated into vector pKK223-3 to generate pKK223.KA and pKK223.AT.

In Vivo Activity of the Putative Amino Alcohol Kinase and Putative Amino Alcohol O-phosphate Lyase from *Erwinia carotovora* subsp. *atroseptica*

Plasmids pKK223.KA-AT, pKK223.KA, pKK223.AT and pKK223-3 were transformed into the *E. coli* MG1655 strain. The transformants were restreaked onto a MOPS minimal media plate containing 1% glucose, 0.5% aminopropanol as a sole nitrogen source, 1 mM IPTG and 100 μg/mL ampicillin. Expression of KA-AT, KA and AT genes were induced by the IPTG. A control plate had no IPTG included. The plates were incubated at 37° C. for 7 days. On the plate with IPTG, only the strain MG1655/pKK223.KA-AT grew, while all the other three strains did not grow. On the plate without added IPTG, the strain MG1655/pKK223.KA-AT grew, but the colonies were significantly smaller than those on the IPTG-containing plate, which corresponds to the lower expression levels of KA and AT in the uninduced cells. None of the other three strains grew on this plate. This indicates that the co-expression of the putative *Erwinia* KA and AT genes provided sufficient enzyme activities that allowed the *E. coli* strain MG1655/pKK223.KA-AT to utilize aminopropanol as a sole nitrogen source. Expression of each individual enzyme of either KA or AT was not sufficient to provide such enzyme activity in vivo.

Example 19

In vitro Activity of *Erwinia* Putative Amino Alcohol Kinase and Amino Alcohol O-Phosphate Lyase Subcloning of the *Erwinia* KA-AT Operon into the pBAD.HisB Vector and Induction of Protein Expression The protein expression levels of *Erwinia* putative KA and AT enzymes expressed in MG1655 cells from the pKK223.KA-AT vector were analyzed by SDS-PAGE analysis. The expression level of the *Erwinia* AT enzyme was relatively low, with a new protein band detected at the correct molecular weight of 46 kD in the soluble fraction of a cell extract, while no new protein band was detected at the size predicted for the KA enzyme.

In an effort to improve the expression of the *Erwinia* putative KA and AT genes, the KA-AT operon was subcloned into the EcoRI and HindIII sites of vector pBAD.HisB-EcoRI. pBAD.HisB-EcoRI was derived from the pBAD.HisB vector (Invitrogen), by replacing the NcoI site in pBAD.HisB with an EcoRI site via QuickChange site-directed mutagenesis (Stratagene, La Jolla, Calif.) using primers OT909 (SEQ ID.#131) & OT910 (SEQ ID.#132). In the constructed plasmid pBAD.KA-AT, the KA-AT operon was placed directly under control of the araB promoter (without His-tag).

The PBAD.KA-AT plasmid was transformed into the *E. coli* TOP10 strain. A 50 mL culture of TOP10/pBAD.KA-AT strain was grown to mid log phase ($OD_{600}$=0.6) in LB, 100 μg/mL ampicillin media at 37° C. with shaking at 250 rpm. The culture was induced by addition of L-arabinose to a final concentration of 0.1% (w/v), and it was further incubated at 37° C. for 5 h before harvesting by centrifugation. The cell pellet was resuspended in ice cold 50 mM Tris-HCl, pH 8.0, and disrupted by sonication on ice with a Fischer Sonic Model 300 Dismembrator (Fischer, Pittsburgh, Pa.) at 50% power, repeating four cycles of 30 seconds sonication with 60 seconds rest in-between each cycle. Each sonicated sample was centrifuged (15,000×g, 4 min, 4° C.). Clarified cell free extracts were analyzed for protein expression level and amino alcohol O-phosphate lyase activity.

Chemical Synthesis of Aminobutanol O-Phosphate and Aminopropanol O-Phosphate

The substrate (R,R)-3-amino-2-butanol O-phosphate was synthesized by a method based on that reported by Ferrari and Ferrari (U.S. Pat. No. 2,730,542 [1956]) for phosphoethanolamine: 10 mmol of $H_3PO_4$ in a 50% (w/v) aqueous solution was mixed with a 50% (w/v) solution of 3-amino-2-butanol (~20:1 (R,R):(S,S) isomers; Bridge Organics; Vicksburg, Mich.) while stirring on ice. After mixing, the solution was slowly warmed to room temperature and then stirred under vacuum and heated to 70° C. After 1 h at 70° C., the temperature was slowly increased to 185° C. and maintained there for an additional 2 h. At that time, the reaction was cooled to room temperature and the vacuum released. The remaining material was dissolved in water, and analysis by NMR indicated that 80% of the starting material was converted to product with 20% remaining unreacted. No additional products were observed.

The additional substrates (2R,3S)-3-amino-2-butanol O-phosphate and (2S,3R)-3-amino-2-butanol O-phosphate were synthesized by the same procedure using a 1:1 mixture of (2R,3S)-3-amino-2-butanol and (2S,3R)-3-amino-2-butanol (synthesized as described in Example 17) as the starting material. DL-1-amino-2-propanol O-phosphate, (S)-2-amino-1-propanol O-phosphate, and (R)-2-amino-1-propanol O-phosphate were synthesized by the same procedure using DL-1-amino-2-propanol, (R)-2-amino-1-propanol, or (S)-2-amino-1-propanol as the starting material.

Analysis of the Aminopropanol O-Phosphate Lyase Activity Encoded by the Putative *Erwinia* KA-AT Operon The aminopropanol O-phosphate lyase assay was performed as described by Jones et al. (1973, *Biochem. J.* 134: 167-182) and G. Gori et al. (1995, Chromatographia 40:336) The formation of propionaldehyde from aminopropanol O-phosphate was assayed calorimetrically with MBTH, which allows the detection of aldehyde formation. The reaction was performed as follows. In a 1 mL reaction, 100 μg cell free extract of *E. coli* TOP10/pBAD.KA-AT was added to 10 mM DL-1-amino-2-propanol O-phosphate in 100 mM Tris-HCl, pH 7.8, with 0.1 mM PLP. The reaction was incubated at 37° C. for 10 min and 30 min, with an aliquot of 100 μL reaction mixture removed at each time point and mixed with 100 μL of 6 mg/mL MBTH in 375 mM glycine-HCl, pH 2.7. This mixture was incubated at 100° C. for 3 min, cooled on ice for 15-30 s, and 1 mL of 3.3 mg/mL $FeCl_3.6H_2O$ (in 10 mM HCl) was added, followed by incubation for 30 min at room temperature. The absorbance of the reaction mixture which contains the aldehyde-MBTH adduct, was measured at 670 nm. The results of the assay are listed in Table 17. In the presence of the aminopropanol phosphate substrate, PLP and cell free extract, formation of aldehyde was detected, as indicated by an $Abs_{670}$ that was higher than the control background of up to 0.3. In the absence of either the substrate or the cell free extract, no aldehyde formation was detected. In the absence of added PLP, somewhat less amount aldehyde was detected, presumably due to the presence of PLP in the cell free extract. Cell free extract of the uninduced TOP10/pBAD.KA-AT-culture did not produce any detectable aldehyde in the reaction. These results indicated that the putative *Erwinia* amino alcohol O-phosphate lyase does catalyze the conversion of aminopropanol O-phosphate to propionaldehyde.

TABLE 17

Aminopropanol O-phosphate lyase assay. Sample 1 was the cell free extract of a non-induced control of *E. coli* TOP10/pBAD.KA-AT. Samples 2-5 contained the cell free extract of the induced culture *E. coli* TOP10/pBAD.KA-AT.

| Sample Number | Induction by 0.1% arabinose | Aminopropanol O-phosphate | PLP | Enzyme extract (100 μg/mL) | $OD_{670}$, 10 min | $OD_{670}$, 30 min |
|---|---|---|---|---|---|---|
| 1 | uninduced | (+) | (+) | (+) | 0.262 | 0.255 |
| 2 | induced | (+) | (+) | (+) | 1.229 | 2.264 |
| 3 | induced | (−) | (+) | (+) | 0.303 | 0.223 |
| 4 | induced | (+) | (−) | (+) | 0.855 | 1.454 |
| 5 | induced | (+) | (+) | (−) | 0.156 | 0.065 |

Analysis of the Activity of the *Erwinia* Amino Alcohol O-Phosphate Lyase Towards Aminobutanol O-Phosphate Substrate The activity of the amino alcohol O-phosphate lyase towards the aminobutanol O-phosphate substrates was studied under the same conditions as described above. The reaction was carried out at 37° C. overnight in a 1 mL reaction that contained 100 μg of cell free extract of *E. coli* TOP10/pBAD.KA-AT, 10 mM aminobutanol O-phosphate (either the mixture of (R,R)+(S,S) or the mixture of (R,S)+(S,R) isomers described in Example 19) in 100 mM Tris-HCl, pH 7.8, with 0.1 mM PLP. An aliquot of 100 μL reaction mixture was removed and the 2-butanone product was detected using the MBTH derivatization method described in the General Methods. The two peaks representing the derivatized 2-butanone isomers were observed. Therefore the *Erwinia* amino alcohol O-phosphate lyase is an aminobutanol phosphate phospholyase in addition to an aminopropanol phosphate phospholyase.

Analysis of the Activity of the *Erwinia* Amino Alcohol O-Phosphate Lyase Towards Stereoisomers of Aminopropanol O-Phosphate and Aminobutanol O-Phosphate The activity of the *Erwinia* amino alcohol O-phosphate lyase towards various stereoisomers of aminopropanol O-phosphate and aminobutanol O-phosphate was studied under the same conditions as described above. In the presence of the *Erwinia* amino alcohol O-phosphate lyase, both (R) and (S)-2-amino-1-propanol O-phosphate were converted to propanone by the enzyme, but the product yield was much higher with the (S) isomer. The enzyme also produced butanone from both mixtures of 3-amino-2-butanol O-phosphate isomers, with a higher product yield found in the reaction containing the (R,S) and (S,R) substrate isomers. Both propanone and butanone products were derivatized by MBTH, and detected by HPLC as described in General Methods.

Optimization of the Gene Expression Level for the *Erwinia* Amino Alcohol Kinase and Amino Alcohol O-Phosphate Lyase In order to improve the expression levels for the *Erwinia* amino alcohol kinase and the amino alcohol O-phosphate lyase in *E. coli*, codon optimized coding regions for both enzymes (named EKA: SEQ ID NO:155 and EAT: SEQ ID NO:156 respectively) were synthesized by DNA2.0 (Redwood City, Calif.). Each coding region was synthesized with 5' and 3' tails including restriction sites for cloning: EKA has 5' BbsI and 3' EcoRI, HindIII sites; EAT has 5' EcoRI and 3' HindIII sites. The EKA and EAT coding regions were provided from DNA2.0 as plasmids pEKA and pEAT, which were in the pJ51 vector of DNA2.0. The EKA optimized coding region was subcloned by ligating a BbsI and HindIII digested fragment of pEKA into the pBAD.HisB vector between the NcoI and HindIII sites, to generate plasmid PBAD.EKA. In the resulting plasmid the coding region is 5' to the His tag, so a coding region for an N-terminus $His_6$ tag fused to the *Erwinia* amino alcohol kinase was constructed by performing a QuickChange site-directed mutagenesis reaction using primers SEQ ID NO:157 and SEQ ID NO:158 to generate vector pBAD.His-EKA.

pBAD.His-EKA was transformed into *E. coli* strain BL21-AI (F⁻ ompt hsdSB (rB⁻ mB⁻) gal dcm araB::T7RNAP-tetA; Invitrogen) to produce strain BL21-AI/pBAD.HisA-EKA. A 50 mL culture of BL21-AI/pBAD.HisA-EKA was grown to mid-log stage ($OD_{600}$=0.6), induced with 0.1% arabinose, and further incubated at 30° C. overnight. Cell free extracts were prepared by sonication. The $His_6$-tagged fusion protein of *Erwinia* amino alcohol kinase was purified using the ProBond™ Purification System (Invitrogen) under non-denaturing purification conditions following the manufacturer's instructions.

The kinase activity of the $His_6$-tagged *Erwinia* amino alcohol kinase is analyzed by the ADP Quest Assay (DiscoveRx, Fremont, Calif.) following the manufacturer's instructions. This is a biochemical assay that measures the accumulation of ADP, a product of the amino alcohol kinase reaction using either aminopropanol or aminobutanol as substrate. 10 mM substrate is mixed with $His_6$-tagged *Erwinia* amino alcohol kinase, in 100 mM Tris-HCl, pH 7.8, 10 mM $MgCl_2$, 2 mM KCl, 0.1 mM ATP, and incubated at 37° C. for 1 h in a 0.2 mL reaction. ADP reagent A (100 µL) and ADP reagent B (200 µL) are added and the mixture is incubated at room temperature for 30 min. The fluorescence signal indicating activity is measured with excitation wavelength of 530 nm and emission wavelength of 590 nm.

Example 20

Expression of Entire Pathway 3

Construction of Vector pCLBudAB-ter-T5chnA

The vector pTrc99a::BudABC (described in Example 13) is digested with EcoRI, and the DNA is treated with Klenow DNA polymerase to blunt the ends. The blunted vector is subsequently digested with SpeI to yield a 2.5 kb fragment containing the budA and budB genes. The vector pCL1925-ter-T5chnA (described in Example 13) is digested with HindIII, and the DNA was treated with Klenow DNA polymerase to blunt the ends. The blunted vector is subsequently digested with XbaI to yield a 4.6 kb fragment which is then ligated to the budAB fragment from pTrc99a::BudABC. The resulting plasmid, designated pCLBudAB-ter-T5chnA, is used to transform *E. coli* Top10 cells, and single colonies are screened for proper plasmid structure by PCR using primers pCL1925vecF (SEQ ID NO:62) and N84seqR3 (SEQ ID NO:159). Plasmid is prepared from a single colony which yields a PCR product of the expected size of 1.4 kb.

Construction of Vector pKK223.KA-AT-APT

The APT gene is amplified from the vector PBAD.APT (described in Example 16) by PCR using primers APTfor (SEQ ID NO:162; 5' includes RBS and SmaI site) and APTrev (SEQ ID NO:163; 3' adds SmaI site). The product of expected size of 1.7 kbp is gel purified and digested with SmaI to yield blunt ends. The vector pKK223.KA-AT (described in Example 18) is digested with PstI, and the DNA is treated with Klenow DNA polymerase to blunt the ends. The resulting DNA fragment is ligated with the SmaI-digested PCR product, and the ligation product is used to transform *E. coli* Top10 cells. Individual ampicillin resistant colonies are screened by PCR using primers OT872 (SEQ ID NO:127) and APTrev (SEQ ID NO:163). The presence of a PCR product of the expected size of 4.1 kbp indicates that the gene encoding APT is present and oriented in the same direction as the genes encoding KA and AT. The sequence of the insert is verified using the primers APTseqRev (SEQ ID NO:160) and APTseqFor (SEQ ID NO:161). This plasmid is named pKK223.KA-AT-APT. Proper expression of all three genes is verified by growing a 5 mL culture of Top10/pKK223.KA-AT-APT in LB+100 µg/mL ampicillin at 37° C. with shaking. When the $OD_{600}$ reaches ~0.8, expression of the genes on the plasmid is induced by addition of IPTG to 0.4 mM. The expression is evaluated by SDS PAGE and activity assays as described above.

Construction of 2-butanol Production Strain and Production of 2-butanone and 2-butanol

*E. coli* strain MG1655 is transformed with both pKK223.KA-AT-APT and pCLBudAB-ter-T5chnA, and transformants selected for ampicillin and spectinomycin resistance, indicative of the presence of the plasmids. The cells are inoculated into shake flasks (approximately 175 mL total volume) containing 50 or 150 mL of TM3a/glucose medium (with appropriate antibiotics) to represent medium and low oxygen conditions, respectively. IPTG is added to 0.4 mM to induce expression of genes from pKK223.KA-AT-APT. As a negative control, MG1655 cells are grown in the same medium lacking antibiotics. The flasks are inoculated at a starting $OD_{600}$ of ≦0.01 and incubated at 34° C. with shaking at 300 rpm for 24 h. The flasks containing 50 mL of medium are capped with vented caps; the flasks containing 150 mL are capped with non-vented caps to minimize air exchange. The MG1655/pKK223.KA-AT-APT/pCLBudAB-ter-T5chnA strain comprising a 2-butanol biosynthetic pathway produces both 2-butanone and 2-butanol under low and medium oxygen conditions while the negative control strain does not produce detectable levels of either 2-butanone or 2-butanol.

Example 21

Characterization of Glycerol Dehydratase Butanediol Dehydratase Activity

Glycerol dehydratase (E.C. 4.2.1.30) and diol dehydratase (E.C. 4.2.1.28), while structurally related, are often distinguished in the art based on various differences that include substrate specificity. This example demonstrates that glycerol dehydratase converts meso-2,3-butanediol to 2-butanone. The recombinant *E. coli* strain KLP23/pSYCO12, comprising *Klebsiella pneumoniae* genes encoding the multiple subunits of glycerol dehydratase (alpha: SEQ ID NO:145 (coding region) and 146 (protein); beta: SEQ ID NO: 147 (coding region) and 148 (protein); and gamma: SEQ ID NO: 149 (coding region) and 150 (protein)) and *Klebsiella pneumoniae* genes encoding the multiple subunits of glycerol dehydratase reactivase (large subunit, SEQ ID NO: 151 (coding region) and 152 (protein); and small subunit, SEQ ID NO: 153 (coding region) and 154 (protein)), is described in Emptage et al. U.S. Pat. No. 6,514,733 and in WO 2003089621, which are herein incorporated by reference. A crude, cell free extract of KLP23/pSYCO12 was prepared by methods known to one skilled in the art. Enzyme assay was performed in the absence of light in 80 mM HEPES buffer, pH 8.2 at 37° C. with 12 µM coenzyme $B_{12}$ and 10 mM meso-2,3-butanediol. The formation of 2-butanone was monitored by HPLC (Shodex SH-1011 column and SH-G guard column with refractive index detection; 0.01 M $H_2SO_4$ as the mobile phase at a flow rate of 0.5 mL/min and a column temperature of 50° C.; 2-butanone retention time=40.2 min). The rate of 2-butanone formation by the glycerol dehydratase preparation was determined to be 0.4 nmol/min/mg of crude protein.

Example 22

Increased Tolerance of *Saccharomyces cerevisiae* to 2-butanol at Decreased Growth Temperatures Tolerance levels were determined for yeast strain *Saccharomyces cerevisiae* BY4741 (ATCC 201388) at 25° C. and 30° C. as follows. The strain was cultured in YPD medium. Overnight cultures in the absence of any test compound were started in 25 mL of YPD medium in 150 mL flasks with incubation at 30° C. or at 25° C. in shaking water baths. The next morning, each overnight culture was diluted into a 500 mL flask containing 300 mL of fresh medium to an initial $OD_{600}$ of about 0.1. The flasks were incubated in shaking water baths at 30° C. or 25° C., using the same temperature as used for each overnight culture. The large cultures were incubated for 3 hours and then were split into flasks in the absence (control) and in the presence of 2.5% or 3.5% of 2-butanol. Growth was followed by measuring $OD_{600}$ for six hours after addition of the 2-butanol. The $\Delta OD_{600}$ was calculated by subtracting the initial $OD_{600}$ from the final $OD_{600}$ at 6 hours. The percent growth inhibition relative to the control culture was calculated as follows: % Growth Inhibition=100−[100 (Sample $\Delta OD_{600}$/Control $\Delta OD_{600}$)]. The results are summarized in Table 18 below and indicate that growth of strain BY4741 was less inhibited by 2.5% and 3.5% 2-butanol at 25° C. than by 2.5% and 3.5% 2-butanol at 30° C.

TABLE 18

Growth of *Saccharomyces cerevisiae* Strain BY4741 at 25° C. and 30° C. with 2-Butanol.

| % 2-Butanol | Temperature ° C. | % Growth Inhibition |
| --- | --- | --- |
| 2.5 | 30 | 95 |
| 2.5 | 25 | 89 |
| 3.5 | 30 | 99 |
| 3.5 | 25 | 97 |

What is claimed is:

1. A method for the production of 2-butanol comprising:
  a) providing a recombinant microbial production host which produces 2-butanol, wherein the recombinant microbial production host comprises heterologous DNA molecules encoding polypeptides that catalyze each of the following substrate to product conversions:
    i) pyruvate to alpha-acetolactate,
    ii) alpha-acetolactate to acetoin,
    iii) acetoin to 2,3-butanediol,
    iv) 2,3-butanediol to 2-butanone, and
    v) 2-butanone to 2-butanol;
  b) seeding the production host of (a) into a fermentation medium comprising a fermentable carbon substrate to create a fermentation culture;
  c) growing the production host in the fermentation culture at a first temperature for a first period of time;
  d) lowering the temperature of the fermentation culture to a second temperature; and
  e) incubating the production host at the second temperature of step (d) for a second period of time;
  whereby 2-butanol is produced.

2. The method according to claim 1, wherein the fermentable carbon substrate is derived from a grain or sugar source selected from the group consisting of wheat, corn, barley, oats, rye, sugar cane, sugar beets, cassaya, sweet sorghum, and mixtures thereof.

3. The method according to claim 1, wherein the fermentable carbon substrate is derived from cellulosic or lignocellulosic biomass selected from the group consisting of corn cobs, crop residues, corn husks, corn stover, grasses, wheat straw, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

4. The method according to claim 1, wherein the fermentable carbon substrate is selected from the group consisting of monosaccharides, oligosaccharides, and polysaccharides.

5. The method according to claim 1, wherein the fermentation culture is maintained under conditions selected from the group consisting of anaerobic conditions and microaerobic conditions.

6. The method according to claim 1, wherein while growing the production host in (c) at a first temperature over a first period of time, a metabolic parameter of the fermentation culture is monitored.

7. The method according to claim 6, wherein the metabolic parameter that is monitored is selected from the group consisting of optical density, pH, respiratory quotient, fermentable carbon substrate utilization, $CO_2$ production, and 2-butanol production.

8. The method according to claim 1, wherein lowering the temperature of the fermentation culture of step (d) occurs at a predetermined time.

9. The method according to claim 1, wherein the lowering of the temperature of the fermentation culture of step (d) coincides with a change in a metabolic parameter.

10. The method according to claim 9, wherein the change in metabolic parameter is a decrease in the rate of 2-butanol production.

11. The method according to claim 1, wherein the first temperature is from about 25° C. to about 40° C.

12. The method according to claim 1, wherein the second temperature is from about 3° C. to about 25° C. lower than the first temperature.

13. The method according to claim 1, wherein steps (d) and (e) are repeated one or more times.

14. The method according to claim 1, wherein the recombinant microbial production host is selected from the group consisting of *Clostridium, Zymomonas, Escherichia, Salmonella, Rhodococcus, Pseudomonas, Bacillus, Lactobacillus, Enterococcus, Alcaligenes, Klebsiella, Paenibacillus, Arthrobacter, Corynebacterium, Brevibacterium, Saccharomyces*, and *Pichia*.

15. A method for the production of 2-butanol comprising,
 a) providing a recombinant microbial production host which produces 2-butanol, wherein the recombinant microbial production host comprises heterologous DNA molecules encoding a polypeptides that catalyze each of the following substrate to product conversions:
  i) pyruvate to alpha-acetolactate,
  ii) alpha-acetolactate to acetoin,
  iii) acetoin to 3-amino-2-butanol,
  iv) 3-amino-2-butanol to 3-amino-2-butanol phosphate,
  v) 3-amino-2-butanol phosphate to 2-butanone, and
  vi) 2-butanone to 2-butanol;
 b) seeding the production host of (a) into a fermentation medium comprising a fermentable carbon substrate to create a fermentation culture;
 c) growing the production host in the fermentation culture at a first temperature for a first period of time;
 d) lowering the temperature of the fermentation culture to a second temperature; and
 e) incubating the production host at the second temperature of step (d) for a second period of time;
 whereby 2-butanol is produced.

16. The method according to claim 15, wherein the polypeptide that catalyzes a substrate to product conversion of pyruvate to alpha-acetolactate is acetolactate synthase.

17. The method according to claim 15, wherein the polypeptide that catalyzes a substrate to product conversion of alpha-acetolactate to acetoin is acetolactate decarboxylase.

18. The method according to claim 15, wherein the polypeptide that catalyzes a substrate to product conversion of acetoin to 3-amino-2-butanol is acetoin aminase.

19. The method according to claim 15, wherein the polypeptide that catalyzes a substrate to product conversion of 3-amino-2-butanol to 3-amino-2-butanol phosphate is aminobutanol kinase.

20. The method according to claim 15, wherein the polypeptide that catalyzes a substrate to product conversion of 3-amino-2-butanol phosphate to 2-butanone is aminobutanol phosphate phospho-lyase.

21. The method according to claim 15, wherein the polypeptide that catalyzes a substrate to product conversion of 2-butanone to 2-butanol is butanol dehydrogenase.

22. The method according to claim 16, wherein the acetolactate synthase has an amino acid sequence having at least 95% identity to an amino acid sequence selected from the group consisting of SEQ ID NO:4, SEQ ID NO:77, and SEQ ID NO:79 based on the Clustal W method of alignment using the default parameters of GAP PENALTY=10, GAP LENGTH PENALTY=0.1, and Gonnet 250 series of protein weight matrix.

23. The method according to claim 17, wherein the acetolactate decarboxylase has an amino acid sequence having at least 95% identity to an amino acid sequence selected from the group consisting of SEQ ID NO:2, SEQ ID NO: 81, and SEQ ID NO:83 based on the Clustal W method of alignment using the default parameters of GAP PENALTY=10, GAP LENGTH PENALTY=0.1, and Gonnet 250 series of protein weight matrix.

24. The method according to claim 18, wherein the acetoin aminase has an amino acid sequence having at least 95% identity to an amino acid sequence as set forth in SEQ ID NO:122 based on the Clustal W method of alignment using the default parameters of GAP PENALTY=10, GAP LENGTH PENALTY=0.1, and Gonnet 250 series of protein weight matrix.

25. The method according to claim 19, wherein the aminobutanol kinase has an amino acid sequence having at least 95% identity to an amino acid sequence as set forth in SEQ ID NO:124 based on the Clustal W method of alignment using the default parameters of GAP PENALTY=10, GAP LENGTH PENALTY=0.1, and Gonnet 250 series of protein weight matrix.

26. The method according to claim 20, wherein the aminobutanol phosphate phospho-lyase has an amino acid sequence having at least 95% identity to an amino acid sequence as set forth in SEQ ID NO:126 based on the Clustal W method of alignment using the default parameters of GAP PENALTY=10, GAP LENGTH PENALTY=0.1, and Gonnet 250 series of protein weight matrix.

27. The method according to claim 21, wherein the butanol dehydrogenase has an amino acid sequence having at least 95% identity to an amino acid sequence selected from the group consisting of SEQ ID NO:14, SEQ ID NO:72, SEQ ID NO:75, and SEQ ID NO:91 based on the Clustal W method of alignment using the default parameters of GAP PENALTY=10, GAP LENGTH PENALTY=0.1, and Gonnet 250 series of protein weight matrix.

28. The method according to claim 1, wherein the polypeptide that catalyzes a substrate to product conversion of pyruvate to alpha-acetolactate is acetolactate synthase.

29. The method according to claim 1, wherein the polypeptide that catalyzes a substrate to product conversion of alpha-acetolactate to acetoin is acetolactate decarboxylase.

30. The method according to claim 1, wherein the polypeptide that catalyzes a substrate to product conversion of acetoin to 2,3-butanediol is butanediol dehydrogenase.

31. The method according to claim 1, wherein the polypeptide that catalyzes a substrate to product conversion of 2,3-butanediol to 2-butanone is diol dehydratase or glycerol dehydratase.

32. The method according to claim 1, wherein the polypeptide that catalyzes a substrate to product conversion of 2-butanone to 2-butanol is butanol dehydrogenase.

33. The method according to claim 28, wherein the acetolactate synthase has an amino acid sequence having at least 95% identity to an amino acid sequence selected from the group consisting of SEQ ID NO:4, SEQ ID NO:77, and SEQ ID NO:79 based on the Clustal W method of alignment using the default parameters of GAP PENALTY=10, GAP LENGTH PENALTY=0.1, and Gonnet 250 series of protein weight matrix.

34. The method according to claim 29, wherein the acetolactate decarboxylase has an amino acid sequence having at least 95% identity to an amino acid sequence selected from the group consisting of SEQ ID NO:2, SEQ ID NO: 81, and SEQ ID NO:83 based on the Clustal W method of alignment using the default parameters of GAP PENALTY=10, GAP LENGTH PENALTY=0.1, and Gonnet 250 series of protein weight matrix.

35. The method according to claim 30, wherein the butanediol dehydrogenase has an amino acid sequence having at least 95% identity to an amino acid sequence selected from the group consisting of SEQ ID NO:6, SEQ ID NO:85, SEQ ID NO:87, and SEQ ID NO:89 based on the Clustal W method of alignment using the default parameters of GAP PENALTY=10, GAP LENGTH PENALTY=0.1, and Gonnet 250 series of protein weight matrix.

36. The method according to claim 31, wherein the diol dehydratase or glycerol dehydratase comprises fused large, medium and small subunits and has at least 95% identity to an amino acid sequence comprising all three of the amino acid sequences encoding large, medium and small subunits, selected from the group consisting of:
   a) SEQ ID NO:8, SEQ ID NO:10, and SEQ ID NO:12;
   b) SEQ ID NO:93, SEQ ID NO:95, and SEQ ID NO:97;
   c) SEQ ID NO:99, SEQ ID NO:101, and SEQ ID NO:103;
   d) SEQ ID NO:105, SEQ ID NO:107, and SEQ ID NO:109;
   e) SEQ ID NO:135, SEQ ID NO:136, and SEQ ID NO:137;
   f) SEQ ID NO:138, SEQ ID NO:139, and SEQ ID NO:140;
   g) SEQ ID NO:146, SEQ ID NO:148, and SEQ ID NO:150;
   h) SEQ ID NO:141, SEQ ID NO:142, and SEQ ID NO:143; and
   i) SEQ ID NO:164, SEQ ID NO:165, and SEQ ID NO:166;
   based on the Clustal W method of alignment using the default parameters of GAP PENALTY=10, GAP LENGTH PENALTY=0.1, and Gonnet 250 series of protein weight matrix.

37. The method according to claim 32, wherein the butanol dehydrogenase has an amino acid sequence having at least 95% identity to an amino acid sequence selected from the group consisting of SEQ ID NO:14, SEQ ID NO:72, SEQ ID NO:75, and SEQ ID NO:91 based on the Clustal W method of alignment using the default parameters of GAP PENALTY=10, GAP LENGTH PENALTY=0.1, and Gonnet 250 series of protein weight matrix.

38. The method according to claim 15, wherein the fermentable carbon substrate is derived from a grain or sugar source selected from the group consisting of wheat, corn, barley, oats, rye, sugar cane, sugar beets, cassava, sweet sorghum, and mixtures thereof.

39. The method according to claim 15, wherein the fermentable carbon substrate is derived from cellulosic or lignocellulosic biomass selected from the group consisting of corn cobs, crop residues, corn husks, corn stover, grasses, wheat straw, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

40. The method according to claim 15, wherein the fermentable carbon substrate is selected from the group consisting of monosaccharides, oligosaccharides, and polysaccharides.

41. The method according to claim 15, wherein the fermentation culture is maintained under conditions selected from the group consisting of anaerobic conditions and microaerobic conditions.

42. The method according to claim 15, wherein while growing the production host in (c) at a first temperature over a first period of time, a metabolic parameter of the fermentation culture is monitored.

43. The method according to claim 42, wherein the metabolic parameter that is monitored is selected from the group consisting of optical density, pH, respiratory quotient, fermentable carbon substrate utilization, $CO_2$ production, and 2-butanol production.

44. The method according to claim 15, wherein lowering the temperature of the fermentation culture of step (d) occurs at a predetermined time.

45. The method according to claim 15, wherein the lowering of the temperature of the fermentation culture of step (d) coincides with a change in a metabolic parameter.

46. The method according to claim 45, wherein the change in metabolic parameter is a decrease in the rate of 2-butanol production.

47. The method according to claim 15, wherein the first temperature is from about 25° C. to about 40° C.

48. The method according to claim 15, wherein the second temperature is from about 3° C. to about 25° C. lower than the first temperature.

49. The method according to claim 15, wherein steps (d) and (e) are repeated one or more times.

50. The method according to claim 15, wherein the recombinant microbial production host is selected from the group consisting of *Clostridium, Zymomonas, Escherichia, Salmonella, Rhodococcus, Pseudomonas, Bacillus, Lactobacillus, Enterococcus, Alcaligenes, Klebsiella, Paenibacillus, Arthrobacter, Corynebacterium, Brevibacterium, Saccharomyces*, and *Pichia*.

* * * * *

SEQUENCE LISTING

```
<160> NUMBER OF SEQ ID NOS: 164

<210> SEQ ID NO 1
<211> LENGTH: 780
<212> TYPE: DNA
<213> ORGANISM: Klebsiella pneumoniae

<400> SEQUENCE: 1
atgaatcatt ctgctgaatg cacctgcgaa gagagtctat gcgaaaccct gcgggcgttt      60
tccgcgcagc atcccgagag cgtgctctat cagacatcgc tcatgagcgc cctgctgagc     120
ggggtttacg aaggcagcac caccatcgcg gacctgctga aacacggcga tttcggcctc     180
ggcaccttta tgagctgga cggggagctg atcgccttca gcagtcaggt ctatcagctg     240
cgcgccgacg gcagcgcgcg caaagcccag ccggagcaga aaacgccgtt cgcggtgatg     300
acctggttcc agccgcagta ccggaaaacc tttgaccatc cggtgagccg ccagcagctg     360
cacgaggtga tcgaccagca aatcccctct gacaacctgt tctgcgccct gcgcatcgac     420
ggccatttcc gccatgccca tacccgcacc gtgccgcgcc agacgccgcc gtaccgggcg     480
atgaccgacg tcctcgacga tcagccggtg ttccgcttta accagcgcga aggggtgctg     540
gtcggcttcc ggacccgca gcatatgcag gggatcaacg tcgccgggta tcacgagcac     600
tttattaccg atgaccgcaa aggcggcggt cacctgctgg attaccagct cgaccatggg     660
gtgctgacct tcggcgaaat tcacaagctg atgatcgacc tgcccgccga cagcgcgttc     720
ctgcaggcta atctgcatcc cgataatctc gatgccgcca tccgttccgt agaaagttaa     780
```

<210> SEQ ID NO 2
<211> LENGTH: 259
<212> TYPE: PRT
<213> ORGANISM: Klebsiella pneumoniae

<400> SEQUENCE: 2

Met Asn His Ser Ala Glu Cys Thr Cys Glu Glu Ser Leu Cys Glu Thr
1               5                   10                  15

Leu Arg Ala Phe Ser Ala Gln His Pro Glu Ser Val Leu Tyr Gln Thr
            20                  25                  30

Ser Leu Met Ser Ala Leu Leu Ser Gly Val Tyr Glu Gly Ser Thr Thr
        35                  40                  45

Ile Ala Asp Leu Leu Lys His Gly Asp Phe Gly Leu Gly Thr Phe Asn
    50                  55                  60

Glu Leu Asp Gly Glu Leu Ile Ala Phe Ser Ser Gln Val Tyr Gln Leu
65                  70                  75                  80

Arg Ala Asp Gly Ser Ala Arg Lys Ala Gln Pro Glu Gln Lys Thr Pro
                85                  90                  95

Phe Ala Val Met Thr Trp Phe Gln Pro Gln Tyr Arg Lys Thr Phe Asp
            100                 105                 110

His Pro Val Ser Arg Gln Gln Leu His Glu Val Ile Asp Gln Gln Ile
        115                 120                 125

Pro Ser Asp Asn Leu Phe Cys Ala Leu Arg Ile Asp Gly His Phe Arg
    130                 135                 140

His Ala His Thr Arg Thr Val Pro Arg Gln Thr Pro Pro Tyr Arg Ala
145                 150                 155                 160

Met Thr Asp Val Leu Asp Asp Gln Pro Val Phe Arg Phe Asn Gln Arg
                165                 170                 175

Glu Gly Val Leu Val Gly Phe Arg Thr Pro Gln His Met Gln Gly Ile
            180                 185                 190

Asn Val Ala Gly Tyr His Glu His Phe Ile Thr Asp Asp Arg Lys Gly
        195                 200                 205

Gly Gly His Leu Leu Asp Tyr Gln Leu Asp His Gly Val Leu Thr Phe
    210                 215                 220

Gly Glu Ile His Lys Leu Met Ile Asp Leu Pro Ala Asp Ser Ala Phe
225                 230                 235                 240

Leu Gln Ala Asn Leu His Pro Asp Asn Leu Asp Ala Ala Ile Arg Ser
                245                 250                 255

Val Glu Ser

<210> SEQ ID NO 3
<211> LENGTH: 1680
<212> TYPE: DNA
<213> ORGANISM: Klebsiella pneumoniae

<400> SEQUENCE: 3
atggacaaac agtatccggt acgccagtgg gcgcacggcg ccgatctcgt cgtcagtcag      60
ctggaagctc agggagtacg ccaggtgttc ggcatccccg cgccaaaat tgacaaggtc     120 ttcgactcac tgctggattc ctcgattcgc attattccgg tacgccacga agccaacgcc    180
gcgtttatgg ccgccgccgt cggacgcatt accggcaaag cgggcgtggc gctggtcacc    240
tccggtccgg gctgttccaa cctgatcacc ggcatggcca ccgcgaacag cgaaggcgac    300
ccggtggtgg ccctgggcgg cgcggtaaaa cgcgccgata agcgaagca ggtccaccag     360 agtatggata cggtggcgat gttcagcccg gtcaccaaat acgccgtcga ggtgacggcg    420

```
ccggatgcgc tggcggaagt ggtctccaac gccttccgcg ccgccgagca gggccggccg      480
ggcagcgcgt tcgttagcct gccgcaggat gtggtcgatg gcccggtcag cggcaaagtg      540
ctgccggcca gcggggcccc gcagatgggc gccgcgccgg atgatgccat cgaccaggtg      600
gcgaagctta tcgcccaggc gaagaacccg atcttcctgc tcggcctgat ggccagccag      660
ccggaaaaca gcaaggcgct cgccgtttg ctggagacca gccatattcc agtcaccagc       720
acctatcagg ccgccggagc ggtgaatcag gataacttct ctcgcttcgc cggccgggtt      780
gggctgttta acaaccaggc cggggaccgt ctgctgcagc tcgccgacct ggtgatctgc      840
atcggctaca gcccggtgga atacgaaccg gcgatgtgga cagcggcaa cgcgacgctg       900 gtgcacatcg acgtgctgcc cgcctatgaa gagcgcaact acaccccgga tgtcgagctg      960
gtgggcgata tcgccggcac tctcaacaag ctggcgcaaa atatcgatca tcggctggtg     1020
ctctccccgc aggcggcgga gatcctccgc gaccgccagc accagcgcga gctgctggac     1080
cgccgcggcg cgcagctgaa ccagtttgcc ctgcatccgc tgcgcatcgt tcgcgccatg     1140
caggacatcg tcaacagcga cgtcacgttg accgtggaca tgggcagctt ccatatctgg     1200
attgcccgct acctgtacag cttccgcgcc cgtcaggtga tgatctccaa cggccagcag     1260
accatgggcg tcgccctgcc ctgggctatc ggcgcctggc tggtcaatcc tgagcgaaaa     1320
gtggtctccg tctccggcga cggcggcttc ctgcagtcga gcatggagct ggagaccgcc     1380
gtccgcctga agccaacgt actgcacctg atctgggtcg ataacggcta caacatggtg      1440
gccattcagg aagagaaaaa ataccagcgc ctgtccggcg tcgagttcgg gccgatggat     1500
tttaaagcct atgccgaatc cttcggcgcg aaagggtttg ccgtggaaag cgccgaggcg     1560
ctggagccga ccctgcacgc ggcgatggac gtcgacggcc cggcggtggt ggccattccg     1620
gtggattatc gcgataaccc gctgctgatg ggccagctgc atctgagtca gattctgtaa     1680
```

<210> SEQ ID NO 4
<211> LENGTH: 559
<212> TYPE: PRT
<213> ORGANISM: Klebsiella pneumoniae

<400> SEQUENCE: 4

```
Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
                20                  25                  30

Pro Gly Ala Lys Ile Asp Lys Val Phe Asp Ser Leu Leu Asp Ser Ser
            35                  40                  45

Ile Arg Ile Ile Pro Val Arg His Glu Ala Asn Ala Ala Phe Met Ala
        50                  55                  60

Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110

Asp Lys Ala Lys Gln Val His Gln Ser Met Asp Thr Val Ala Met Phe
        115                 120                 125

Ser Pro Val Thr Lys Tyr Ala Val Glu Val Thr Ala Pro Asp Ala Leu
    130                 135                 140

Ala Glu Val Val Ser Asn Ala Phe Arg Ala Ala Glu Gln Gly Arg Pro
145                 150                 155                 160
```

Gly Ser Ala Phe Val Ser Leu Pro Gln Asp Val Val Gly Pro Val
                165                 170                 175

Ser Gly Lys Val Leu Pro Ala Ser Gly Ala Pro Gln Met Gly Ala Ala
            180                 185                 190

Pro Asp Asp Ala Ile Asp Gln Val Ala Lys Leu Ile Ala Gln Ala Lys
                195                 200                 205

Asn Pro Ile Phe Leu Leu Gly Leu Met Ala Ser Gln Pro Glu Asn Ser
            210                 215                 220

Lys Ala Leu Arg Arg Leu Leu Glu Thr Ser His Ile Pro Val Thr Ser
225                 230                 235                 240

Thr Tyr Gln Ala Ala Gly Ala Val Asn Gln Asp Asn Phe Ser Arg Phe
                245                 250                 255

Ala Gly Arg Val Gly Leu Phe Asn Asn Gln Ala Gly Asp Arg Leu Leu
            260                 265                 270

Gln Leu Ala Asp Leu Val Ile Cys Ile Gly Tyr Ser Pro Val Glu Tyr
            275                 280                 285

Glu Pro Ala Met Trp Asn Ser Gly Asn Ala Thr Leu Val His Ile Asp
            290                 295                 300

Val Leu Pro Ala Tyr Glu Arg Asn Tyr Thr Pro Asp Val Glu Leu
305                 310                 315                 320

Val Gly Asp Ile Ala Gly Thr Leu Asn Lys Leu Ala Gln Asn Ile Asp
            325                 330                 335

His Arg Leu Val Leu Ser Pro Gln Ala Ala Glu Ile Leu Arg Asp Arg
            340                 345                 350

Gln His Gln Arg Glu Leu Leu Asp Arg Arg Gly Ala Gln Leu Asn Gln
            355                 360                 365

Phe Ala Leu His Pro Leu Arg Ile Val Arg Ala Met Gln Asp Ile Val
            370                 375                 380

Asn Ser Asp Val Thr Leu Thr Val Asp Met Gly Ser Phe His Ile Trp
385                 390                 395                 400

Ile Ala Arg Tyr Leu Tyr Ser Phe Arg Ala Arg Gln Val Met Ile Ser
                405                 410                 415

Asn Gly Gln Gln Thr Met Gly Val Ala Leu Pro Trp Ala Ile Gly Ala
            420                 425                 430

Trp Leu Val Asn Pro Glu Arg Lys Val Val Ser Val Ser Gly Asp Gly
            435                 440                 445

Gly Phe Leu Gln Ser Ser Met Glu Leu Glu Thr Ala Val Arg Leu Lys
        450                 455                 460

Ala Asn Val Leu His Leu Ile Trp Val Asp Asn Gly Tyr Asn Met Val
465                 470                 475                 480

Ala Ile Gln Glu Glu Lys Lys Tyr Gln Arg Leu Ser Gly Val Glu Phe
                485                 490                 495

Gly Pro Met Asp Phe Lys Ala Tyr Ala Glu Ser Phe Gly Ala Lys Gly
            500                 505                 510

Phe Ala Val Glu Ser Ala Glu Ala Leu Glu Pro Thr Leu His Ala Ala
            515                 520                 525

Met Asp Val Asp Gly Pro Ala Val Ala Ile Pro Val Asp Tyr Arg
530                 535                 540

Asp Asn Pro Leu Leu Met Gly Gln Leu His Leu Ser Gln Ile Leu
545                 550                 555

<210> SEQ ID NO 5
<211> LENGTH: 771
<212> TYPE: DNA

<213> ORGANISM: Klebsiella pneumoniae

<400> SEQUENCE: 5

```
atgaaaaaag tcgcacttgt taccggcgcc ggccagggga ttggtaaagc tatcgccctt      60
cgtctggtga aggatggatt tgccgtggcc attgccgatt ataacgacgc caccgccaaa     120
gcggtcgcct cggaaatcaa ccaggccggc ggacacgccg tggcggtgaa agtggatgtc     180
tccgaccgcg atcaggtatt tgccgccgtt gaacaggcgc gcaaaacgct gggcggcttc     240
gacgtcatcg tcaataacgc cggtgtggca ccgtctacgc cgatcgagtc cattaccccg     300
gagattgtcg acaaagtcta caacatcaac gtcaaagggg tgatctgggg tattcaggcg     360
gcggtcgagg cctttaagaa agaggggcac ggcgggaaaa tcatcaacgc ctgttcccag     420
gccggccacg tcggcaaccc ggagctggcg gtgtatagct ccagtaaatt cgcggtacgc     480
ggcttaaccc agaccgccgc tcgcgacctc gcgccgctgg gcatcacggt caacggctac     540
tgcccgggga ttgtcaaaac gccaatgtgg gccgaaattg accgccaggt gtccgaagcc     600
gccggtaaac gctgggcta cggtaccgcc gagttcgcca aacgcatcac tctcggtcgt     660
ctgtccgagc cggaagatgt cgccgcctgc gtctcctatc ttgccagccc ggattctgat     720
tacatgaccg tcagtcgtt gctgatcgac ggcgggatgg tatttaacta a              771
```

<210> SEQ ID NO 6
<211> LENGTH: 256
<212> TYPE: PRT
<213> ORGANISM: Klebsiella pneumoniae

<400> SEQUENCE: 6

```
Met Lys Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
            20                  25                  30

Asp Tyr Asn Asp Ala Thr Ala Lys Ala Val Ala Ser Glu Ile Asn Gln
        35                  40                  45

Ala Gly Gly His Ala Val Ala Val Lys Val Asp Val Ser Asp Arg Asp
    50                  55                  60

Gln Val Phe Ala Ala Val Glu Gln Ala Arg Lys Thr Leu Gly Gly Phe
65                  70                  75                  80

Asp Val Ile Val Asn Asn Ala Gly Val Ala Pro Ser Thr Pro Ile Glu
                85                  90                  95

Ser Ile Thr Pro Glu Ile Val Asp Lys Val Tyr Asn Ile Asn Val Lys
            100                 105                 110

Gly Val Ile Trp Gly Ile Gln Ala Ala Val Glu Ala Phe Lys Lys Glu
        115                 120                 125

Gly His Gly Gly Lys Ile Ile Asn Ala Cys Ser Gln Ala Gly His Val
    130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Gly Tyr Cys Pro Gly Ile Val Lys Thr Pro Met Trp Ala Glu
            180                 185                 190

Ile Asp Arg Gln Val Ser Glu Ala Ala Gly Lys Pro Leu Gly Tyr Gly
        195                 200                 205

Thr Ala Glu Phe Ala Lys Arg Ile Thr Leu Gly Arg Leu Ser Glu Pro
    210                 215                 220
```

Glu Asp Val Ala Ala Cys Val Ser Tyr Leu Ala Ser Pro Asp Ser Asp
225                 230                 235                 240

Tyr Met Thr Gly Gln Ser Leu Leu Ile Asp Gly Gly Met Val Phe Asn
            245                 250                 255

<210> SEQ ID NO 7
<211> LENGTH: 1665
<212> TYPE: DNA
<213> ORGANISM: Klebsiella oxytoca

<400> SEQUENCE: 7
atgagatcga aaagatttga agcactggcg aaacgccctg tgaatcagga cggcttcgtt      60
aaggagtgga tcgaagaagg ctttatcgcg atggaaagcc cgaacgaccc aaaaccgtcg     120
attaaaatcg ttaacggcgc ggtgaccgag ctggacggga aaccggtaag cgattttgac     180
ctgatcgacc actttatcgc ccgctacggt atcaacctga accgcgccga agaagtgatg     240
gcgatggatt cggtcaagct ggccaacatg ctgtgcgatc gaacgttaa acgcagcgaa      300 atcgtcccgc tgaccaccgc gatgacgccg gcgaaaattg tcgaagtggt ttcgcatatg     360
aacgtcgtcg agatgatgat ggcgatgcag aaaatgcgcg cccgccgcac cccgtcccag     420
caggcgcacg tcaccaacgt caaagataac ccggtacaga ttgccgccga cgccgccgaa     480
ggggcatggc gcggatttga cgaacaggaa accaccgttg cggtagcgcg ctatgcgccg     540
ttcaacgcca tcgcgctgct ggtgggctcg caggtaggcc gtccgggcgt gctgacgcag     600
tgctcgctgg aagaagccac cgagctgaag ctcggcatgc tgggccacac ctgctacgcc     660
gaaaccatct ccgtctacgg caccgagccg gtctttaccg acggcgacga cacgccgtgg     720
tcgaagggct cctcgcctc gtcctacgcc tctcgcgggc tgaaaatgcg ctttacctcc      780
ggctccggct cggaagtgca gatgggctac gccgaaggca atccatgct ttatctggaa      840 gcgcgctgca tctacatcac caaagccgcg ggcgtacagg tctgcaaaa cggttccgta      900 agctgcatcg gcgtgccgtc tgcggtgcct tccggcattc gcgcggtgct ggcggaaaac     960
ctgatctgtt cgtcgctgga tctggagtgc gcctccagca acgaccagac cttcacccac    1020
tccgatatgc gtcgtaccgc gcgcctgctg atgcagttcc tgccgggcac cgactttatc    1080
tcctccggtt attccgcggt gccgaactac gacaacatgt cgccggctc caacgaagat     1140 gccgaagact tgacgactaa caacgtcatc agcgcgacc tgaaggtgga cggcggtttg     1200
cgtccggttc gcgaagagga cgtcatcgcc atccgtaaca aagccgcccg cgcgctgcag    1260
gccgtgtttg ccggaatggg gctgccgccg attaccgatg aagaagttga agccgcgacc    1320
tacgcccacg gttcgaaaga tatgccggag cgcaacatcg tcgaagacat caagttcgcc    1380
caggaaatca tcaataaaaa ccgcaacggt ctggaagtgg tgaaagcgct ggcgcagggc    1440
ggattcaccg acgtggccca ggacatgctc aacatccaga agctaagct gaccggggac     1500 tacctgcata cctccgcgat tatcgtcggc gacgggcagg tgctgtcagc cgtcaacgac    1560
gtcaacgact atgccggtcc ggcaacgggc tatcgcctgc agggcgaacg ctgggaagag    1620
attaaaaaca tccctggcgc tcttgatccc aacgagattg attaa                    1665

<210> SEQ ID NO 8
<211> LENGTH: 554
<212> TYPE: PRT
<213> ORGANISM: Klebsiella oxytoca

<400> SEQUENCE: 8

Met Arg Ser Lys Arg Phe Glu Ala Leu Ala Lys Arg Pro Val Asn Gln
1               5                   10                  15

-continued

Asp Gly Phe Val Lys Glu Trp Ile Glu Glu Gly Phe Ile Ala Met Glu
                20                  25                  30

Ser Pro Asn Asp Pro Lys Pro Ser Ile Lys Ile Val Asn Gly Ala Val
                35                  40                  45

Thr Glu Leu Asp Gly Lys Pro Val Ser Asp Phe Asp Leu Ile Asp His
 50                  55                  60

Phe Ile Ala Arg Tyr Gly Ile Asn Leu Asn Arg Ala Glu Glu Val Met
 65                  70                  75                  80

Ala Met Asp Ser Val Lys Leu Ala Asn Met Leu Cys Asp Pro Asn Val
                85                  90                  95

Lys Arg Ser Glu Ile Val Pro Leu Thr Thr Ala Met Thr Pro Ala Lys
                100                 105                 110

Ile Val Glu Val Val Ser His Met Asn Val Val Glu Met Met Met Ala
                115                 120                 125

Met Gln Lys Met Arg Ala Arg Arg Thr Pro Ser Gln Gln Ala His Val
 130                 135                 140

Thr Asn Val Lys Asp Asn Pro Val Gln Ile Ala Ala Asp Ala Ala Glu
145                 150                 155                 160

Gly Ala Trp Arg Gly Phe Asp Glu Gln Glu Thr Thr Val Ala Val Ala
                165                 170                 175

Arg Tyr Ala Pro Phe Asn Ala Ile Ala Leu Leu Val Gly Ser Gln Val
                180                 185                 190

Gly Arg Pro Gly Val Leu Thr Gln Cys Ser Leu Glu Glu Ala Thr Glu
                195                 200                 205

Leu Lys Leu Gly Met Leu Gly His Thr Cys Tyr Ala Glu Thr Ile Ser
 210                 215                 220

Val Tyr Gly Thr Glu Pro Val Phe Thr Asp Gly Asp Asp Thr Pro Trp
225                 230                 235                 240

Ser Lys Gly Phe Leu Ala Ser Ser Tyr Ala Ser Arg Gly Leu Lys Met
                245                 250                 255

Arg Phe Thr Ser Gly Ser Gly Ser Glu Val Gln Met Gly Tyr Ala Glu
                260                 265                 270

Gly Lys Ser Met Leu Tyr Leu Glu Ala Arg Cys Ile Tyr Ile Thr Lys
                275                 280                 285

Ala Ala Gly Val Gln Gly Leu Gln Asn Gly Ser Val Ser Cys Ile Gly
 290                 295                 300

Val Pro Ser Ala Val Pro Ser Gly Ile Arg Ala Val Leu Ala Glu Asn
305                 310                 315                 320

Leu Ile Cys Ser Ser Leu Asp Leu Glu Cys Ala Ser Ser Asn Asp Gln
                325                 330                 335

Thr Phe Thr His Ser Asp Met Arg Arg Thr Ala Arg Leu Leu Met Gln
                340                 345                 350

Phe Leu Pro Gly Thr Asp Phe Ile Ser Ser Gly Tyr Ser Ala Val Pro
                355                 360                 365

Asn Tyr Asp Asn Met Phe Ala Gly Ser Asn Glu Asp Ala Glu Asp Phe
 370                 375                 380

Asp Asp Tyr Asn Val Ile Gln Arg Asp Leu Lys Val Asp Gly Gly Leu
385                 390                 395                 400

Arg Pro Val Arg Glu Glu Asp Val Ile Ala Ile Arg Asn Lys Ala Ala
                405                 410                 415

Arg Ala Leu Gln Ala Val Phe Ala Gly Met Gly Leu Pro Pro Ile Thr
                420                 425                 430

Asp Glu Glu Val Glu Ala Ala Thr Tyr Ala His Gly Ser Lys Asp Met

```
                435                 440                 445
Pro Glu Arg Asn Ile Val Glu Asp Ile Lys Phe Ala Gln Glu Ile Ile
450                 455                 460
Asn Lys Asn Arg Asn Gly Leu Glu Val Val Lys Ala Leu Ala Gln Gly
465                 470                 475                 480
Gly Phe Thr Asp Val Ala Gln Asp Met Leu Asn Ile Gln Lys Ala Lys
                485                 490                 495
Leu Thr Gly Asp Tyr Leu His Thr Ser Ala Ile Val Gly Asp Gly
                500                 505                 510
Gln Val Leu Ser Ala Val Asn Asp Val Asn Asp Tyr Ala Gly Pro Ala
            515                 520                 525
Thr Gly Tyr Arg Leu Gln Gly Glu Arg Trp Glu Glu Ile Lys Asn Ile
530                 535                 540
Pro Gly Ala Leu Asp Pro Asn Glu Ile Asp
545                 550

<210> SEQ ID NO 9
<211> LENGTH: 675
<212> TYPE: DNA
<213> ORGANISM: Klebsiella oxytoca

<400> SEQUENCE: 9
atggaaatta tgaaaaatt gctgcgccag ataattgaag acgtgctcag cgagatgaag        60
ggcagcgata aaccggtctc gtttaatgcg ccggcggcct ccgcggcgcc ccaggccacg       120
ccgcccgccg cgacggcttc ctgacggaa gtgggcgaag cgcgtcaggg aacccagcag       180
gacgaagtga ttatcgccgt cggcccggct ttcggcctgg cgcagaccgt caatatcgtc       240
ggcatcccgc ataagagcat tttgcgcgaa gtcattgccg gtattgaaga agaaggcatt       300
aaggcgcgcg tgattcgctg ctttaaatcc tccgacgtgg ccttcgtcgc cgttgaaggt       360
aatcgcctga cgggctccgg catctctatc ggcatccagt cgaaaggcac cacggtgatc       420
caccagcagg ggctgccgcc gctctctaac ctggagctgt cccgcaggc gccgctgctg       480 accctggaaa cctatcgcca gatcggcaaa aacgccgccc gctatgcgaa cgcgaatcg       540 ccgcagccgg tcccgacgct gaatgaccag atggcgcggc cgaagtacca ggcgaaatcg       600 gccatttttgc acattaaaga gaccaagtac gtggtgacgg gcaaaaaccc gcaggaactg       660
cgcgtggcgc tttga                                                       675

<210> SEQ ID NO 10
<211> LENGTH: 224
<212> TYPE: PRT
<213> ORGANISM: Klebsiella oxytoca

<400> SEQUENCE: 10

Met Glu Ile Asn Glu Lys Leu Leu Arg Gln Ile Ile Glu Asp Val Leu
1               5                   10                  15

Ser Glu Met Lys Gly Ser Asp Lys Pro Val Ser Phe Asn Ala Pro Ala
            20                  25                  30

Ala Ser Ala Ala Pro Gln Ala Thr Pro Pro Ala Gly Asp Gly Phe Leu
        35                  40                  45

Thr Glu Val Gly Glu Ala Arg Gln Gly Thr Gln Gln Asp Glu Val Ile
    50                  55                  60

Ile Ala Val Gly Pro Ala Phe Gly Leu Ala Gln Thr Val Asn Ile Val
65                  70                  75                  80

Gly Ile Pro His Lys Ser Ile Leu Arg Glu Val Ile Ala Gly Ile Glu
                85                  90                  95
```

Glu Glu Gly Ile Lys Ala Arg Val Ile Arg Cys Phe Lys Ser Ser Asp
            100                 105                 110

Val Ala Phe Val Ala Val Glu Gly Asn Arg Leu Ser Gly Ser Gly Ile
        115                 120                 125

Ser Ile Gly Ile Gln Ser Lys Gly Thr Thr Val Ile His Gln Gln Gly
130                 135                 140

Leu Pro Pro Leu Ser Asn Leu Glu Leu Phe Pro Gln Ala Pro Leu Leu
145                 150                 155                 160

Thr Leu Glu Thr Tyr Arg Gln Ile Gly Lys Asn Ala Ala Arg Tyr Ala
                165                 170                 175

Lys Arg Glu Ser Pro Gln Pro Val Pro Thr Leu Asn Asp Gln Met Ala
            180                 185                 190

Arg Pro Lys Tyr Gln Ala Lys Ser Ala Ile Leu His Ile Lys Glu Thr
        195                 200                 205

Lys Tyr Val Val Thr Gly Lys Asn Pro Gln Glu Leu Arg Val Ala Leu
210                 215                 220

<210> SEQ ID NO 11
<211> LENGTH: 522
<212> TYPE: DNA
<213> ORGANISM: Klebsiella oxytoca

<400> SEQUENCE: 11

```
atgaataccg acgcaattga atcgatggta cgcgacgtat tgagccgcat gaacagcctg    60
cagggcgagg cgcctgcggc ggctccggcg gctggcggcg cgtcccgtag cgccagggtc   120
agcgactacc cgctggcgaa caagcacccg gaatgggtga aaaccgccac caataaaacg   180
ctggacgact ttacgctgga aaacgtgctg agcaataaag tcaccgccca ggatatgcgt   240
attaccccgg aaaccctgcg cttacaggct tctattgcca agacgcgggg ccgcgaccgg   300
ctggcgatga acttcgagcg cgccgccgag ctgaccgcgg taccggacga tcgcattctt   360
gaaatctaca cgccctccg cccctatcgc tcgacgaaag aggagctgct ggcgatcgcc   420
gacgatctcg aaagccgcta tcaggcgaag atttgcgccg ctttcgttcg cgaagcggcc   480
acgctgtacg tcgagcgtaa aaaactcaaa ggcgacgatt aa                     522
```

<210> SEQ ID NO 12
<211> LENGTH: 173
<212> TYPE: PRT
<213> ORGANISM: Klebsiella oxytoca

<400> SEQUENCE: 12

Met Asn Thr Asp Ala Ile Glu Ser Met Val Arg Asp Val Leu Ser Arg
1               5                   10                  15

Met Asn Ser Leu Gln Gly Glu Ala Pro Ala Ala Pro Ala Ala Gly
            20                  25                  30

Gly Ala Ser Arg Ser Ala Arg Val Ser Asp Tyr Pro Leu Ala Asn Lys
        35                  40                  45

His Pro Glu Trp Val Lys Thr Ala Thr Asn Lys Thr Leu Asp Asp Phe
    50                  55                  60

Thr Leu Glu Asn Val Leu Ser Asn Lys Val Thr Ala Gln Asp Met Arg
65                  70                  75                  80

Ile Thr Pro Glu Thr Leu Arg Leu Gln Ala Ser Ile Ala Lys Asp Ala
                85                  90                  95

Gly Arg Asp Arg Leu Ala Met Asn Phe Glu Arg Ala Ala Glu Leu Thr
            100                 105                 110

```
Ala Val Pro Asp Asp Arg Ile Leu Glu Ile Tyr Asn Ala Leu Arg Pro
            115                 120                 125

Tyr Arg Ser Thr Lys Glu Glu Leu Leu Ala Ile Ala Asp Asp Leu Glu
        130                 135                 140

Ser Arg Tyr Gln Ala Lys Ile Cys Ala Ala Phe Val Arg Glu Ala Ala
145                 150                 155                 160

Thr Leu Tyr Val Glu Arg Lys Lys Leu Lys Gly Asp Asp
                165                 170

<210> SEQ ID NO 13
<211> LENGTH: 1041
<212> TYPE: DNA
<213> ORGANISM: Rhodococcus ruber

<400> SEQUENCE: 13
atgaaagccc tccagtacac cgagatcggc tccgagccgg tcgtcgtcga cgtccccacc      60
ccggcgcccg ggccgggtga gatcctgctg aaggtcaccg cggccggctt gtgccactcg     120
gacatcttcg tgatggacat gccggcagag cagtacatct acggtcttcc cctcacccta     180
ggccacgagg gcgtcggcac cgtcgccgaa ctcggcgccg cgtcaccgg attcgagacg      240 ggggacgccg tcgccgtgta cgggccgtgg ggtgcggtg cgtgccacgc gtgcgcgcgc     300
ggccgggaga actactgcac ccgcgccgcc gagctgggca tcaccccgcc cggtctcggc     360
tcgcccgggt cgatggccga gtacatgatc gtcgactcgg cgcgccacct cgtcccgatc     420
ggggacctcg accccgtcgc ggcggttccg ctcaccgacg cgggcctgac gccgtaccac     480
gcgatctcgc gggtcctgcc cctgctggga cccggctcga ccgcggtcgt catcggggtc     540
ggcggactcg gcacgtcgg catccagatc ctgcgcgccg tcagcgcggc ccgcgtgatc     600
gccgtcgatc tcgacgacga ccgactcgcg ctcgcccgcg aggtcggcgc cgacgcggcg     660
gtgaagtcgg cgccggggc ggcggacgcg atccgggagc tgaccggcgg tgagggcgcg     720
acggcggtgt cgacttcgt cggcgcccag tcgacgatcg acacggcgca gcaggtggtc     780
gcgatcgacg ggcacatctc ggtggtcggc atccatgccg gcgcccacgc caaggtcggc     840
ttcttcatga tcccgttcgg cgcgtccgtc gtgacgccgt actggggcac gcggtccgag     900
ctgatggacg tcgtggacct ggcccgtgcc ggccggctcg acatccacac cgagacgttc     960
accctcgacg agggacccac ggcctaccgg cggctacgcg agggcagcat ccgcggccgc    1020
ggggtggtcg tcccgggctg a                                              1041

<210> SEQ ID NO 14
<211> LENGTH: 346
<212> TYPE: PRT
<213> ORGANISM: Klebsiella oxytoca

<400> SEQUENCE: 14

Met Lys Ala Leu Gln Tyr Thr Glu Ile Gly Ser Glu Pro Val Val Val
1               5                   10                  15

Asp Val Pro Thr Pro Ala Pro Gly Pro Gly Glu Ile Leu Leu Lys Val
            20                  25                  30

Thr Ala Ala Gly Leu Cys His Ser Asp Ile Phe Val Met Asp Met Pro
        35                  40                  45

Ala Glu Gln Tyr Ile Tyr Gly Leu Pro Leu Thr Leu Gly His Glu Gly
    50                  55                  60

Val Gly Thr Val Ala Glu Leu Gly Ala Gly Val Thr Gly Phe Glu Thr
65                  70                  75                  80

Gly Asp Ala Val Ala Val Tyr Gly Pro Trp Gly Cys Gly Ala Cys His
```

85              90              95
Ala Cys Ala Arg Gly Arg Glu Asn Tyr Cys Thr Arg Ala Ala Glu Leu
                100                 105                 110
Gly Ile Thr Pro Pro Gly Leu Gly Ser Pro Gly Ser Met Ala Glu Tyr
            115                 120                 125
Met Ile Val Asp Ser Ala Arg His Leu Val Pro Ile Gly Asp Leu Asp
        130                 135                 140
Pro Val Ala Ala Val Pro Leu Thr Asp Ala Gly Leu Thr Pro Tyr His
145                 150                 155                 160
Ala Ile Ser Arg Val Leu Pro Leu Leu Gly Pro Gly Ser Thr Ala Val
                165                 170                 175
Val Ile Gly Val Gly Gly Leu Gly His Val Gly Ile Gln Ile Leu Arg
            180                 185                 190
Ala Val Ser Ala Ala Arg Val Ile Ala Val Asp Leu Asp Asp Asp Arg
        195                 200                 205
Leu Ala Leu Ala Arg Glu Val Gly Ala Asp Ala Val Lys Ser Gly
210                 215                 220
Ala Gly Ala Ala Asp Ala Ile Arg Glu Leu Thr Gly Gly Glu Gly Ala
225                 230                 235                 240
Thr Ala Val Phe Asp Phe Val Gly Ala Gln Ser Thr Ile Asp Thr Ala
                245                 250                 255
Gln Gln Val Val Ala Ile Asp Gly His Ile Ser Val Val Gly Ile His
            260                 265                 270
Ala Gly Ala His Ala Lys Val Gly Phe Phe Met Ile Pro Phe Gly Ala
        275                 280                 285
Ser Val Val Thr Pro Tyr Trp Gly Thr Arg Ser Glu Leu Met Asp Val
290                 295                 300
Val Asp Leu Ala Arg Ala Gly Arg Leu Asp Ile His Thr Glu Thr Phe
305                 310                 315                 320
Thr Leu Asp Glu Gly Pro Thr Ala Tyr Arg Arg Leu Arg Glu Gly Ser
                325                 330                 335
Ile Arg Gly Arg Gly Val Val Val Pro Gly
            340                 345

<210> SEQ ID NO 15
<211> LENGTH: 29
<212> TYPE: DNA
<213> ORGANISM: Artificial Sequence
<220> FEATURE:
<223> OTHER INFORMATION: Primer

<400> SEQUENCE: 15
caccatggac aaacagtatc cggtacgcc                                       29

<210> SEQ ID NO 16
<211> LENGTH: 25
<212> TYPE: DNA
<213> ORGANISM: Artificial Sequence
<220> FEATURE:
<223> OTHER INFORMATION: Primer

<400> SEQUENCE: 16
cgaagggcga tagctttacc aatcc                                           25

<210> SEQ ID NO 17
<211> LENGTH: 32
<212> TYPE: DNA
<213> ORGANISM: Artificial Sequence
<220> FEATURE:

<223> OTHER INFORMATION: Primer

<400> SEQUENCE: 17
caccatgaat cattctgctg aatgcacctg cg                32

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
gatactgttt gtccatgtga cc                           22

<210> SEQ ID NO 19
<211> LENGTH: 28
<212> TYPE: DNA
<213> ORGANISM: Artificial Sequence
<220> FEATURE:
<223> OTHER INFORMATION: Primer

<400> SEQUENCE: 19
caccatgaaa aaagtcgcac ttgttacc                     28

<210> SEQ ID NO 20
<211> LENGTH: 15
<212> TYPE: DNA
<213> ORGANISM: Artificial Sequence
<220> FEATURE:
<223> OTHER INFORMATION: Primer

<400> SEQUENCE: 20
ttagttaaat accat                                   15

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
caccatgaga tcgaaaagat ttg                          23

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
cttagagaag ttaatcgtcg cc                           22

<210> SEQ ID NO 23
<211> LENGTH: 25
<212> TYPE: DNA
<213> ORGANISM: Artificial Sequence
<220> FEATURE:
<223> OTHER INFORMATION: Primer

<400> SEQUENCE: 23
caccatgaaa gccctccagt acacc                        25

<210> SEQ ID NO 24

```
<211> LENGTH: 18
<212> TYPE: DNA
<213> ORGANISM: Artificial Sequence
<220> FEATURE:
<223> OTHER INFORMATION: Primer

<400> SEQUENCE: 24
cgtcgtgtca tgcccggg                                                       18

<210> SEQ ID NO 25
<211> LENGTH: 36
<212> TYPE: DNA
<213> ORGANISM: Artificial Sequence
<220> FEATURE:
<223> OTHER INFORMATION: Primer

<400> SEQUENCE: 25
gatcgaattc gtttaaactt agttttctac cgcacg                                   36

<210> SEQ ID NO 26
<211> LENGTH: 34
<212> TYPE: DNA
<213> ORGANISM: Artificial Sequence
<220> FEATURE:
<223> OTHER INFORMATION: Primer

<400> SEQUENCE: 26
gatcgcatgc aagctttcat atagtcggaa ttcc                                     34

<210> SEQ ID NO 27
<211> LENGTH: 43
<212> TYPE: DNA
<213> ORGANISM: Artificial Sequence
<220> FEATURE:
<223> OTHER INFORMATION: Primer

<400> SEQUENCE: 27
gatcgaattc gtttaaacaa aggaggtctg attcatgaga tcg                           43

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
gatcggattc ttaatcgtcg cc                                                  22

<210> SEQ ID NO 29
<211> LENGTH: 36
<212> TYPE: DNA
<213> ORGANISM: Artificial Sequence
<220> FEATURE:
<223> OTHER INFORMATION: Primer

<400> SEQUENCE: 29
gatcggatcc aaaggaggtc gggcgcatga aagccc                                   36

<210> SEQ ID NO 30
<211> LENGTH: 32
<212> TYPE: DNA
<213> ORGANISM: Artificial Sequence
<220> FEATURE:
<223> OTHER INFORMATION: Primer

<400> SEQUENCE: 30
```

```
gatctctaga aagctttcag cccgggacga cc                                    32
```

<210> SEQ ID NO 31
<211> LENGTH: 21
<212> TYPE: DNA
<213> ORGANISM: Artificial Sequence
<220> FEATURE:
<223> OTHER INFORMATION: Primer

<400> SEQUENCE: 31

```
actttctttc gcctgtttca c                                                21
```

<210> SEQ ID NO 32
<211> LENGTH: 79
<212> TYPE: DNA
<213> ORGANISM: Artificial Sequence
<220> FEATURE:
<223> OTHER INFORMATION: Primer

<400> SEQUENCE: 32

```
catgaagctt gtttaaactc ggtgaccttg aaaataatga aaacttatat tgttttgaaa      60
ataatgaaaa cttatattg                                                   79
```

<210> SEQ ID NO 33
<211> LENGTH: 39
<212> TYPE: DNA
<213> ORGANISM: Artificial Sequence
<220> FEATURE:
<223> OTHER INFORMATION: Primer BABC F

<400> SEQUENCE: 33

```
gagctcgaat tcaaaggagg aagtgtatat gaatcattc                             39
```

<210> SEQ ID NO 34
<211> LENGTH: 35
<212> TYPE: DNA
<213> ORGANISM: Artificial Sequence
<220> FEATURE:
<223> OTHER INFORMATION: Primer BAB R

<400> SEQUENCE: 34

```
ggatcctcta gaattagtta ataccatcc cgccg                                  35
```

<210> SEQ ID NO 35
<211> LENGTH: 17
<212> TYPE: DNA
<213> ORGANISM: Artificial Sequence
<220> FEATURE:
<223> OTHER INFORMATION: Primer M13 Forward

<400> SEQUENCE: 35

```
gtaaaacgac ggccagt                                                     17
```

<210> SEQ ID NO 36
<211> LENGTH: 16
<212> TYPE: DNA
<213> ORGANISM: Artificial Sequence
<220> FEATURE:
<223> OTHER INFORMATION: Primer M13 Reverse

<400> SEQUENCE: 36

```
aacagctatg accatg                                                      16
```

<210> SEQ ID NO 37
<211> LENGTH: 20
<212> TYPE: DNA

```
<213> ORGANISM: Artificial Sequence
<220> FEATURE:
<223> OTHER INFORMATION: Primer N83 SeqF2

<400> SEQUENCE: 37
gctggattac cagctcgacc                                          20

<210> SEQ ID NO 38
<211> LENGTH: 20
<212> TYPE: DNA
<213> ORGANISM: Artificial Sequence
<220> FEATURE:
<223> OTHER INFORMATION: Primer N83SeqF3

<400> SEQUENCE: 38
cggacgcatt accggcaaag                                          20

<210> SEQ ID NO 39
<211> LENGTH: 20
<212> TYPE: DNA
<213> ORGANISM: Artificial Sequence
<220> FEATURE:
<223> OTHER INFORMATION: Primer N84 SeqR4

<400> SEQUENCE: 39
cgaagcgaga gaagttatcc                                          20

<210> SEQ ID NO 40
<211> LENGTH: 38
<212> TYPE: DNA
<213> ORGANISM: Artificial Sequence
<220> FEATURE:
<223> OTHER INFORMATION: Primer BC Spe F

<400> SEQUENCE: 40
actagtaaag gaggaaagag tatgaagaag gtcgcact                      38

<210> SEQ ID NO 41
<211> LENGTH: 26
<212> TYPE: DNA
<213> ORGANISM: Artificial Sequence
<220> FEATURE:
<223> OTHER INFORMATION: Primer BC Xba R

<400> SEQUENCE: 41
tctagaaagc aggggcaagc catgtc                                   26

<210> SEQ ID NO 42
<211> LENGTH: 20
<212> TYPE: DNA
<213> ORGANISM: Artificial Sequence
<220> FEATURE:
<223> OTHER INFORMATION: Primer Trc F

<400> SEQUENCE: 42
ttgacaatta atcatccggc                                          20

<210> SEQ ID NO 43
<211> LENGTH: 20
<212> TYPE: DNA
<213> ORGANISM: Artificial Sequence
<220> FEATURE:
<223> OTHER INFORMATION: Primer Trc R

<400> SEQUENCE: 43
cttctctcat ccgccaaaac                                          20
```

<210> SEQ ID NO 44
<211> LENGTH: 38
<212> TYPE: DNA
<213> ORGANISM: Artificial Sequence
<220> FEATURE:
<223> OTHER INFORMATION: Primer DDo For

<400> SEQUENCE: 44
aagcttaaag gaggctgatt catgagatcg aaaagatt                         38

<210> SEQ ID NO 45
<211> LENGTH: 27
<212> TYPE: DNA
<213> ORGANISM: Artificial Sequence
<220> FEATURE:
<223> OTHER INFORMATION: Primer DDo Rev

<400> SEQUENCE: 45
tctagattat tcatcctgct gttctcc                                     27

<210> SEQ ID NO 46
<211> LENGTH: 22
<212> TYPE: DNA
<213> ORGANISM: Artificial Sequence
<220> FEATURE:
<223> OTHER INFORMATION: Primer DDko seq F2

<400> SEQUENCE: 46
gcatggcgcg gatttgacga ac                                          22

<210> SEQ ID NO 47
<211> LENGTH: 22
<212> TYPE: DNA
<213> ORGANISM: Artificial Sequence
<220> FEATURE:
<223> OTHER INFORMATION: Primer DDko seq F5

<400> SEQUENCE: 47
cattaaagag accaagtacg tg                                          22

<210> SEQ ID NO 48
<211> LENGTH: 24
<212> TYPE: DNA
<213> ORGANISM: Artificial Sequence
<220> FEATURE:
<223> OTHER INFORMATION: Primer DDko seq F7

<400> SEQUENCE: 48
atatcctggt ggtgtcgtcg gcgt                                        24

<210> SEQ ID NO 49
<211> LENGTH: 22
<212> TYPE: DNA
<213> ORGANISM: Artificial Sequence
<220> FEATURE:
<223> OTHER INFORMATION: Primer DDko seq F9

<400> SEQUENCE: 49
tctttgtcac caacgccctg cg                                          22

<210> SEQ ID NO 50
<211> LENGTH: 22
<212> TYPE: DNA
<213> ORGANISM: Artificial Sequence
<220> FEATURE:
<223> OTHER INFORMATION: Primer DDko seq R1

```
<400> SEQUENCE: 50
gcccaccgcg ctcgccgccg cg                                              22

<210> SEQ ID NO 51
<211> LENGTH: 22
<212> TYPE: DNA
<213> ORGANISM: Artificial Sequence
<220> FEATURE:
<223> OTHER INFORMATION: Primer DDko seq R3

<400> SEQUENCE: 51
cccccaggat ggcggcttcg gc                                              22

<210> SEQ ID NO 52
<211> LENGTH: 22
<212> TYPE: DNA
<213> ORGANISM: Artificial Sequence
<220> FEATURE:
<223> OTHER INFORMATION: Primer DDko seq R7

<400> SEQUENCE: 52
gggccgacgg cgataatcac tt                                              22

<210> SEQ ID NO 53
<211> LENGTH: 22
<212> TYPE: DNA
<213> ORGANISM: Artificial Sequence
<220> FEATURE:
<223> OTHER INFORMATION: Primer DDko seq R10

<400> SEQUENCE: 53
ttcttcgatc cactccttaa cg                                              22

<210> SEQ ID NO 54
<211> LENGTH: 56
<212> TYPE: DNA
<213> ORGANISM: Artificial Sequence
<220> FEATURE:
<223> OTHER INFORMATION: Primer ChnA F

<400> SEQUENCE: 54
catcaattga ctacgtagtc gtacgtgtaa ggaggtttga aatggaaaaa attatg         56

<210> SEQ ID NO 55
<211> LENGTH: 40
<212> TYPE: DNA
<213> ORGANISM: Artificial Sequence
<220> FEATURE:
<223> OTHER INFORMATION: Primer ChnA R

<400> SEQUENCE: 55
catgctagcc ccgggtatct tctactcatt ttttatttcg                           40

<210> SEQ ID NO 56
<211> LENGTH: 22
<212> TYPE: DNA
<213> ORGANISM: Artificial Squence
<220> FEATURE:
<223> OTHER INFORMATION: Primer chnSeq F1

<400> SEQUENCE: 56
ctcaacaggg tgtaagtgta gt                                              22

<210> SEQ ID NO 57
<211> LENGTH: 22
<212> TYPE: DNA
```

```
<213> ORGANISM: Artificial Sequence
<220> FEATURE:
<223> OTHER INFORMATION: Primer chnSeq R1

<400> SEQUENCE: 57
cgttttgata tagccaggat gt                                              22

<210> SEQ ID NO 58
<211> LENGTH: 35
<212> TYPE: DNA
<213> ORGANISM: Artificial Sequence
<220> FEATURE:
<223> OTHER INFORMATION: Primer Top ter F1

<400> SEQUENCE: 58
ctagaagtca aaagcctccg accggaggct tttga                                35

<210> SEQ ID NO 59
<211> LENGTH: 60
<212> TYPE: DNA
<213> ORGANISM: Artificial Sequence
<220> FEATURE:
<223> OTHER INFORMATION: Primer Top ter F2

<400> SEQUENCE: 59
ctgctcgagt tgctagcaag tttaaacaaa aaaagcccg ctcattaggc gggctgagct      60

<210> SEQ ID NO 60
<211> LENGTH: 37
<212> TYPE: DNA
<213> ORGANISM: Artificial Sequence
<220> FEATURE:
<223> OTHER INFORMATION: Primer Bot ter R1

<400> SEQUENCE: 60
cagcccgcct aatgagcggg cttttttttg tttaaac                              37

<210> SEQ ID NO 61
<211> LENGTH: 50
<212> TYPE: DNA
<213> ORGANISM: Artificial Sequence
<220> FEATURE:
<223> OTHER INFORMATION: Primer Bot ter R2

<400> SEQUENCE: 61
ttgctagcaa ctcgagcagt caaaagcctc cggtcggagg cttttgactt                50

<210> SEQ ID NO 62
<211> LENGTH: 22
<212> TYPE: DNA
<213> ORGANISM: Artificial Sequence
<220> FEATURE:
<223> OTHER INFORMATION: Primer pCL1925 vec F

<400> SEQUENCE: 62
cggtatcatc aacaggctta cc                                              22

<210> SEQ ID NO 63
<211> LENGTH: 22
<212> TYPE: DNA
<213> ORGANISM: Artificial Sequence
<220> FEATURE:
<223> OTHER INFORMATION: Primer pCL1925 vec R1

<400> SEQUENCE: 63
agggttttcc cagtcacgac gt                                              22
```

```
<210> SEQ ID NO 64
<211> LENGTH: 22
<212> TYPE: DNA
<213> ORGANISM: Artificial Sequence
<220> FEATURE:
<223> OTHER INFORMATION: Primer pCL1925 vec R2

<400> SEQUENCE: 64
cgcaatagtt ggcgaagtaa tc                                              22

<210> SEQ ID NO 65
<211> LENGTH: 20
<212> TYPE: DNA
<213> ORGANISM: Artificial Sequence
<220> FEATURE:
<223> OTHER INFORMATION: Primer N84 Seq R2

<400> SEQUENCE: 65
gcatcgagat tatcgggatg                                                 20

<210> SEQ ID NO 66
<211> LENGTH: 208
<212> TYPE: DNA
<213> ORGANISM: Escherichia coli

<400> SEQUENCE: 66
atcgcccgca ttcttgccgc atcttccccc ggcgtcacac cgaagtaacg tttaaactca     60
cggctgtgta ggctggagct gcttcgaagt tcctatactt tctagagaat aggaacttcg   120
gaataggaac taaggaggat attcatatga ttacgttgga tgtcagccgc cgtatatacg   180
aagccgcccg ctaagctttt tacgcctc                                      208

<210> SEQ ID NO 67
<211> LENGTH: 42
<212> TYPE: DNA
<213> ORGANISM: Artificial Squence
<220> FEATURE:
<223> OTHER INFORMATION: Promoter 1.6GI Variant

<400> SEQUENCE: 67
gcccttgaca atgccacatc ctgagcaaat aattcaacca ct                       42

<210> SEQ ID NO 68
<211> LENGTH: 42
<212> TYPE: DNA
<213> ORGANISM: Artificial Sequence
<220> FEATURE:
<223> OTHER INFORMATION: Promoter 1.5 GI

<400> SEQUENCE: 68
gcccttgact atgccacatc ctgagcaaat aattcaacca ct                       42

<210> SEQ ID NO 69
<211> LENGTH: 3240
<212> TYPE: DNA
<213> ORGANISM: Klebsiella oxytoca

<400> SEQUENCE: 69
ggcgcggtcc gccaggcggt cacctccgcg cgcgaaatcg gcaaaaccgt ccttgcgacc     60
ctcggtgctg aaccgaaaaa cgatcgcccg tcctacatct gatacccacg aggctgattc   120
atgagatcga aaagatttga agcactggcg aaacgccctg tgaatcagga cggcttcgtt   180
aaggagtgga tcgaagaagg ctttatcgcg atggaaagcc cgaacgaccc aaaaccgtcg   240
```

```
attaaaatcg ttaacggcgc ggtgaccgag ctggacggga aaccggtaag cgattttgac      300
ctgatcgacc actttatcgc ccgctacggt atcaacctga accgcgccga agaagtgatg      360
gcgatggatt cggtcaagct ggccaacatg ctgtgcgatc cgaacgttaa acgcagcgaa      420
atcgtcccgc tgaccaccgc gatgacgccg gcgaaaattg tcgaagtggt ttcgcatatg      480
aacgtcgtcg agatgatgat ggcgatgcag aaaatgcgcg cccgccgcac cccgtcccag      540
caggcgcacg tcaccaacgt caaagataac ccggtacaga ttgccgccga cgccgccgaa      600
ggggcatggc gcggatttga cgaacaggaa accaccgttg cggtagcgcg ctatgcgccg      660
ttcaacgcca tcgcgctgct ggtgggctcg caggtaggcc gtccgggcgt gctgacgcag      720
tgctcgctgg aagaagccac cgagctgaag ctcggcatgc tgggccacac ctgctacgcc      780
gaaaccatct ccgtctacgg caccgagccg gtctttaccg acggcgacga cacgccgtgg      840
tcgaagggct tcctcgcctc gtcctacgcc tctcgcgggc tgaaaatgcg ctttacctcc      900
ggctccggct cggaagtgca gatgggctac gccgaaggca aatccatgct ttatctggaa      960
gcgcgctgca tctacatcac caaagccgcg ggcgtacagg gtctgcaaaa cggttccgta     1020
agctgcatcg gcgtgccgtc tgcggtgcct tccggcattc gcgcggtgct ggcggaaaac     1080
ctgatctgtt cgtcgctgga tctggagtgc gcctccagca acgaccagac cttcacccac     1140
tccgatatgc gtcgtaccgc gcgcctgctg atgcagttcc tgccgggcac cgactttatc     1200
tcctccggtt attccgcggt gccgaactac gacaacatgt tcgccggctc caacgaagat     1260
gccgaagact ttgacgacta caacgtcatc cagcgcgacc tgaaggtgga cggcggtttg     1320
cgtccggttc gcgaagagga cgtcatcgcc atccgtaaca aagccgcccg cgcgctgcag     1380
gccgtgtttg ccggaatggg gctgccgccg attaccgatg aagaagttga agccgcgacc     1440
tacgcccacg gttcgaaaga tatgccggag cgcaacatcg tcgaagacat caagttcgcc     1500
caggaaatca tcaataaaaa ccgcaacggt ctggaagtgg tgaaagcgct ggcgcagggc     1560
ggattcaccg acgtggccca ggacatgctc aacatccaga aagctaagct gaccggggac     1620
tacctgcata cctccgcgat tatcgtcggc gacgggcagg tgctgtcagc cgtcaacgac     1680
gtcaacgact atgccggtcc ggcaacgggc tatcgcctgc agggcgaacg ctgggaagag     1740
attaaaaaca tccctggcgc tcttgatccc aacgagattg attaaggggt gagaaatgga     1800
aattaatgaa aaattgctgc gccagataat tgaagacgtg ctcagcgaga tgaagggcag     1860
cgataaaccg gtctcgttta atgcgccggc ggcctccgcg gcgccccagg ccacgccgcc     1920
cgccggcgac ggcttcctga cggaagtggg cgaagcgcgt cagggaaccc agcaggacga     1980
agtgattatc gccgtcggcc cggctttcgg cctggcgcag accgtcaata tcgtcggcat     2040
cccgcataag agcattttgc gcgaagtcat tgccggtatt gaagaagaag cattaaggc      2100 gcgcgtgatt cgctgcttta atcctccga cgtggccttc gtcgccgttg aaggtaatcg      2160
cctgagcggc tccggcatct ctatcggcat ccagtcgaaa ggcaccacgg tgatccacca     2220 gcagggctg ccgccgctct ctaacctgga gctgttcccg caggcgccgc tgctgaccct      2280
ggaaacctat cgccagatcg gcaaaaacgc cgcccgctat gcgaaacgcg aatcgccgca     2340
gccggtcccg acgctgaatg accagatggc gcggccgaag taccaggcga atcggccat      2400 tttgcacatt aaagagacca agtacgtggt gacgggcaaa aacccgcagg aactgcgcgt     2460
ggcgctttga taaaggataa ctccatgaat accgacgcaa ttgaatcgat ggtacgcgac     2520
gtattgagcc gcatgaacag cctgcagggc gaggcgcctg cggcggctcc ggcggctggc     2580
ggcgcgtccc gtagcgccag ggtcagcgac tacccgctgg cgaacaagca cccggaatgg     2640
```

```
gtgaaaaccg ccaccaataa aacgctggac gactttacgc tggaaaacgt gctgagcaat    2700
aaagtcaccg cccaggatat gcgtattacc ccggaaaccc tgcgcttaca ggcttctatt    2760
gccaaagacg cgggccgcga ccggctggcg atgaacttcg agcgcgccgc cgagctgacc    2820
gcggtaccgg acgatcgcat tcttgaaatc tacaacgccc tccgcccta tcgctcgacg     2880 aaagaggagc tgctggcgat cgccgacgat ctcgaaagcc gctatcaggc gaagatttgc    2940
gccgctttcg ttcgcgaagc ggccacgctg tacgtcgagc gtaaaaaact caaaggcgac    3000
gattaacttc tctaagtaat tcgagatgca ttgaggcggc aagtgagtga caaattcgtc    3060
tggaacgaat ttgaacagcc ataggctggc tttagtgagg gacagggatg tccctcataa    3120
ccccgatgag cttactgtag taagtgattc gggtgaaaga acgcagccaa caaaaaggca    3180
gtttgaagta cgacgagaaa aggggcatgt gatgcgatat atagctggca ttgatatcgg    3240

<210> SEQ ID NO 70
<211> LENGTH: 2640
<212> TYPE: DNA
<213> ORGANISM: Klebsiella oxytoca

<400> SEQUENCE: 70
acgtcgagcg taaaaaactc aaaggcgacg attaacttct ctaagtaatt cgagatgcat      60
tgaggcggca agtgagtgac aaattcgtct ggaacgaatt tgaacagcca taggctggct     120
ttagtgaggg acagggatgt ccctcataac cccgatgagc ttactgtagt aagtgattcg     180
ggtgaaagaa cgcagccaac aaaaaggcag tttgaagtac gacgagaaaa ggggcatgtg     240
atgcgatata tagctggcat tgatatcggc aactcatcga cggaagtcgc cctggcgacc     300
ctggatgagg ctggcgcgct gacgatcacc cacagcgcgc tggcggaaac caccggaatc     360
aaaggcacgt tgcgtaacgt gttcgggatt caggaggcgc tcgccctcgt cgccagaggc     420
gccgggatcg ccgtcagcga tatttcgctc atccgcatca acgaagcgac gccggtgatt     480
ggcgatgtgg cgatggaaac cattaccgaa accatcatca ccgaatcgac catgatcggc     540
cataacccga aaacgcccgg cggcgcgggg cttggcacag gcatcaccat tacgccgcag     600
gagctgctaa cccgccggc ggacgcgccc tatatcctgg tggtgtcgtc ggcgttcgat     660
tttgccgata tcgccagcgt gattaacgct tccctgcgcg ccgggtatca gattaccggc     720 gtcatttac agcgcgacga tggcgtgctg gtcagcaacc ggctggaaaa accgctgccg     780
atcgttgacg aagtgctgta catcgaccgc attccgctgg ggatgctggc ggcgattgag     840
gtcgccgttc cggggaaggt catcgaaacc ctctctaacc cttacggcat cgccaccgtc     900
tttaacctca gccccgagga gacgaagaac atcgtcccga tggcccgggc gctgattggc     960
aaccgttccg ccgtggtggt caaaacgcca tccggcgacg tcaaagcgcg cgcgataccc    1020
gccggtaatc ttgagctgct ggcccagggc cgtagcgtgc gcgtggatgt ggccgccggc    1080
gccgaagcca tcatgaaagc ggtcgacggc tgcggcaggc tcgataacgt caccggcgaa    1140
tccggcacca atatcggcgg catgctggaa cacgtgcgcc agaccatggc cgagctgacc    1200
aacaagccga gcagcgaaat atttattcag gacctgctgg ccgttgatac ctcggtaccg    1260
gtgagcgtta ccggcggtct ggccggggag ttctcgctgg agcaggccgt gggcatcgcc    1320
tcgatggtga atcggatcg cctgcagatg gcaatgatcg cccgcgaaat cgagcagaag    1380
ctcaatatcg acgtgcagat cggcggcgca gaggccgaag ccgccatcct gggggcgctg    1440
accacgccgg gcaccacccg accgctggcg atcctcgacc tcggcgcggg ctccaccgat    1500
gcctccatca tcaaccccaa aggcgacatc atcgccaccc atctcgccgg cgcaggcgac    1560
```

```
atggtgacga tgattattgc ccgcgagctg gggctggaag accgctatct ggcggaagag    1620
atcaagaagt acccgctggc taaggtggaa agcctgttcc atttacgcca cgaggacggc    1680
agcgtgcagt tcttctccac gccgctgccg cccgccgtgt cgcccgcgt ctgcgtggtg     1740 aaagcggacg aactggtgcc gctgcccggc gatttagcgc tggaaaaagt gcgcgccatt    1800
cgccgcagcg ccaaagagcg ggtctttgtc accaacgccc tgcgcgcgct cgtcaggtc     1860 agccccaccg gcaacattcg cgatattccg ttcgtggtgc tggtcggcgg ttcgtcgctg    1920
gatttcgaag tcccgcagct ggtcaccgat gcgctggcgc actaccgcct ggttgccgga    1980
cggggaaata ttcgcggcag cgagggcccc gaaacgcgg tggccaccgg cctgattctc      2040
tcctggcata aggagtttgc gcatgaacgg taatcacagc gccccggcca tcgcgatcgc    2100
cgtcatcgac ggctgcgacg gcctgtggcg cgaagtgctg ctgggtatcg aagaggaagg    2160 tatcccttc cggctccagc atcacccggc cggagaggtc gtggacagcg cctggcaggc     2220
ggcgcgcagc tcgccgctgc tggtgggcat cgcctgcgac cgccatatgc tggtcgtgca    2280
ctacaagaat ttacccgcat cggcgccgct ttttacgctg atgcatcatc aggacagtca    2340
ggcccatcgc aacaccggta ataacgcggc acggctggtc aagggggatcc ctttccggga   2400 tctgaatagc gaagcaacag gagaacagca ggatgaataa cgcactggga ctggttgaaa    2460
caaaagggtt agtgggcgcc attgaggccg ccgatgcgat ggtgaaatcc gccaacgtgc    2520
agctggtcgg ctacgaaaaa attggctcgg gcctcgtcac cgtgatggtg cgcggcgacg    2580
tcggcgcggt caaagcggcg gtagacgcgg gcagcgcggc ggcgagcgcg gtgggcgaag    2640

<210> SEQ ID NO 71
<211> LENGTH: 756
<212> TYPE: DNA
<213> ORGANISM: Acinetobacter sp.

<400> SEQUENCE: 71
atggaaaaaa ttatgtcaaa taaattcaac aataaagtcg ctttaattac tggcgctggt     60
tcaggtattg gtaaaagcac cgcactgctt ttggctcaac agggtgtaag tgtagtggtt    120
tcagatatta acctggaagc agcacagaaa gttgtgacga aaattgtcgc tttaggcggg    180
aaagcggctg cgaataaggc caatactgct gagcctgaag acatgaaagc tgcagtcgag    240
tttgcggtca gcacttttgg tgcactgcat ttggccttca ataatgcggg aattctgggt    300
gaagttaact ccaccgaaga attgagcatt gaaggatggc gtcgtgtgat tgatgtgaac    360
ttgaatgcgt ttttctacag catgcattat gaagttcctg caatcttggc cgcagggggc    420
ggagcgattg tcaataccgc ttctattgca ggcttgatcg ggattcaaaa tatttcaggc    480
tatgtcgctg caaacatgg cgtaacgggt ctaacgaaag cggcggcatt ggaatatgca    540
gataaaggga ttcgcattaa ttcagtacat cctggctata tcaaaacgcc tttgattgca    600
gaatttgaag aagcagaaat ggtaaaacta catccgattg gtcgtttggg acagccggaa    660
gaagttgctc aggttgttgc cttcctactt tctgatgatg cttcatttgt gaccggtagt    720
cagtatgtgg tcgatggtgc atatacctcg aaataa                              756

<210> SEQ ID NO 72
<211> LENGTH: 251
<212> TYPE: PRT
<213> ORGANISM: Acinetobacter sp.

<400> SEQUENCE: 72

Met Glu Lys Ile Met Ser Asn Lys Phe Asn Asn Lys Val Ala Leu Ile
 1               5                  10                  15
```

Thr Gly Ala Gly Ser Gly Ile Gly Lys Ser Thr Ala Leu Leu Leu Ala
              20                  25                  30

Gln Gln Gly Val Ser Val Val Ser Asp Ile Asn Leu Glu Ala Ala
         35                  40                  45

Gln Lys Val Val Asp Glu Ile Val Ala Leu Gly Gly Lys Ala Ala Ala
 50                  55                  60

Asn Lys Ala Asn Thr Ala Glu Pro Glu Asp Met Lys Ala Ala Val Glu
65                  70                  75                  80

Phe Ala Val Ser Thr Phe Gly Ala Leu His Leu Ala Phe Asn Asn Ala
                 85                  90                  95

Gly Ile Leu Gly Glu Val Asn Ser Thr Glu Leu Ser Ile Glu Gly
            100                 105                 110

Trp Arg Arg Val Ile Asp Val Asn Leu Asn Ala Val Phe Tyr Ser Met
            115                 120                 125

His Tyr Glu Val Pro Ala Ile Leu Ala Ala Gly Gly Ala Ile Val
        130                 135                 140

Asn Thr Ala Ser Ile Ala Gly Leu Ile Gly Ile Gln Asn Ile Ser Gly
145                 150                 155                 160

Tyr Val Ala Ala Lys His Gly Val Thr Gly Leu Thr Lys Ala Ala Ala
                165                 170                 175

Leu Glu Tyr Ala Asp Lys Gly Ile Arg Ile Asn Ser Val His Pro Gly
            180                 185                 190

Tyr Ile Lys Thr Pro Leu Ile Ala Glu Phe Glu Glu Ala Glu Met Val
            195                 200                 205

Lys Leu His Pro Ile Gly Arg Leu Gly Gln Pro Glu Glu Val Ala Gln
        210                 215                 220

Val Val Ala Phe Leu Leu Ser Asp Asp Ala Ser Phe Val Thr Gly Ser
225                 230                 235                 240

Gln Tyr Val Val Asp Gly Ala Tyr Thr Ser Lys
            245                 250

<210> SEQ ID NO 73
<211> LENGTH: 17417
<212> TYPE: DNA
<213> ORGANISM: Acinetobacter sp.

<400> SEQUENCE: 73

```
ctagcattta cgcgtgaggt aggtgggtag gtctgtaatg tgaagatcta cgaggaaatc     60
ggcgtcatga cgtgaggtcc agcgaaccgt cttgcgtaat ccgtcattca tggtgagtaa    120
cattgcccgt atttcgcgtt cagtatatag cagaccagca tgattaacga gatcctgggt    180
attttagtcc ggacacccaa agtcccatgc ggtcgccaga tccagtaagt cgactacgac    240
ttgctcatct gtagccaacc ccgcaatcac ttccacaatt ttcatcagtg gaaccggatt    300
gaagaaatgg aaacctgcga tacggccctg atgctgacac gcagatgcaa ttgaggtcac    360
agatagtgag gatgtatttg aaaccagaat agtttcttca gccacaatcc tttcaagctg    420
tttaaacaaa gtttgcttga tttccagatt tcaataatt gcttctacga ccagatcaac    480
gccagcaacc tcttcaatgc tttccaagat aatcaatcgg gctaaggtat ccacaagctg    540
ctgttcggtt aactttcctt tagcagctag tttgtgcaag ttactttta atttttccaa    600
gccttgctca gcagcgccgg gtttagcatc aaataaacgg acctcaacac cgcctgtgc    660
tgcaatttgc gcaataccca ttcccattac gcctgtgcca atcaaggcca ttttttgaat    720
cgtcatgact tattttcctt gatattgagg gcttcgcttt tcgaaaaagg cattgacgcc    780
```

```
ttcttttttga tcttgtgtat caaataaaat ttggaaggct ttacgctcta atgccaaagc    840
accatcgagt ggcatattgg cacctagtgt tgtgacttct ttgatctgtt caacggcaat    900
cggtgagagt tgggcaatct gtgtcgcaat ttcaaccgct ttagcaaggg tttgatcatc    960
ctcaaccact tcgaaaacca accccatttt gtcagcttct tctgcagaaa agatcttttcc  1020 tgttaacact atttgcatgg ctttaaactt ccctaccgca cgcagtaagc gttgggtacc   1080
accagcacct ggcatcagcc ccaatttgac ttcaggctga ccaaactggg ctgattttcc   1140
ggcaataatg atgtctgcat gcattgcaag ttcacaccca ccacccaatg catatccatt   1200
cacagcagcc acaatcggtt tagggcaatc aataatggcc cgccagtact gttccgtatg   1260
gcgtaaatac atgtctacgg ttttgcagt ggtgaagtcc cggatatccg cacctgctgc    1320
aaatactttt tcaccaccag taatgacaat tgcgcggact gtatcagatg cagcgagctg   1380
ctcaaacatt gctgcgagct gttggcgcag ttccagattc aatgcatttc tagtatctgg   1440
acgatgtagt tcaacaatgg ccacaccatt actttgaata tctaaattca atatttcatt   1500
ttccataaca acctacatgt ttcgcatagc ggtttattta aaccaaatat acctgttttt   1560
ttgcaacaat aaagcccaca ggaacatagt tttaaattaa aaattggcta aaaatattta   1620
aaaaacacaa ataaaatacc gcacagcggt atttgatatc aatattattg catttatttt   1680
tccattctgt catattattt tcattccaaa gcattagatc accctgcat gaagcagaga    1740 tggctaaatt tacctatcta atacaagggc ttaaaaatga ttcgcgatca agacacatta   1800
aatcagctgg ttgacatgat ccgtcagttt gtcgatggcg ttcttattcc caatgaagaa   1860
attgttgcgg aaaccgatga aattccagct gaaatcgtgc agcaaatgaa agaactgggt   1920 cttttttggtc tcaccattcc tgaggaatat gagggtcttg gcctgaccat ggaggaagag   1980
gtttacattg catttgaact gggacgtacc tctcctgctt tccgttcact gatcggcact   2040
aacaatggga tcggttcatc aggcttaatt attgatggct ccgaagagca gaaacagtat   2100 ttttttgccac gtctggcaag tggtgaaatt attggttcat tctgtttaac tgaacctgat   2160
tccggttcag atgctgcctc tttaaaaacc acagcggtga agatggtga tcattacatt    2220 ttaaatggca ctaagcgtta catcaccaat gcaccgcatg cgggtgtctt tactgtcatg   2280
gcacgtacca gtaccgaaat taaaggtaca ggtggaattt cagcctttat cgtggacagt   2340
aaaactcctg gtatttcctt gggtaaacgt gataagaaga tgggccaaaa aggtgcacat   2400
acctgtgatg tgattttga aaactgtcgt attcctgcat ctgcactcat tggtggtgtt    2460
gaaggtgtag gttttaaaac tgcaatgaag gtacttgata aaggccgtat tcatattgct   2520
gcattaagtg taggtgctgc tacgcgtatg ctggaagatt ccctacaata tgccgttgag   2580
cgcaaacagt ttggtcaagc gattgcgaac ttccagttga ttcaaggtat gttagccgat   2640
tctaaagctg aaatttacgc agcaaaatgt atggtattag atgctgcccg acttcgtgat   2700
gctggacaga atgtcagcac ggaagcatct tgtgccaaga tgtttgccac tgaaatgtgt   2760
ggccgtgtcg cagatcgtgg cgtacagatc catggtggtg cgggttatat cagtgaatat   2820
gctattgagc gttttttaccg tgatgtacgt ttattccgtt tgtatgaagg tacaacgcaa   2880
atccaacagg tcattattgc ccgcaatatg atccgtgaag cgactcaata attgtataac   2940
aggtattgag tgtatctaaa aggacgggat tagtgattta agctataact tgaatactaa   3000
tcctgacttt ttgatggcaa ggctataaaa cctcctagct cattttatct ctaagctaat   3060
cacagctgaa agatattttc agtcttcatc cttaccagac agttcacaat acaaaattgg   3120
attttatgaa tatgcaagaa caagaaatcg aacgcgaatc aatggagttt gacgtcgtga   3180
```

```
ttgtcggcgc aggaccggcc ggtctttctg cagcgatcaa gatccgtcaa cttgcaattg    3240
aaaacaacct gaacgatctg tcggtttgtg tggtggaaaa aggctctgaa gtcggtgcgc    3300
acatcttgtc cggtgcggta ctggaaccac gtgccatgaa tgagctgttc ccgaactgga    3360
aggaagaagg tgcacctttta aatgttccag tgaccgaaga caagacctat ttcctgctct    3420
cggatgaaaa atcacaagaa gcgccacact ggatggtgcc taaaaccatg cataacgatg    3480
gcaactatgt tatctcgctc ggcaacgtag tgcgctggtt gggtcaaaaa gcggaagagc    3540
tggaagtatc tattttcccg ggctttgccg ctgctgaaat tctgtaccat gcagatggtt    3600
cggtgaaagg cattcaaacc ggtgacatgg gcattggcaa ggatggcgaa ccgacccata    3660
actttactcc gggctatgaa ctgcatgcca aatacaccct gtttgctgaa ggctgccgtg    3720
gccacctcgg caagcgtttta attgccaaat acaacctcga taaagattca gatccacaac    3780
attacggtat cggtatcaaa gagctgtggg aaatcgaccc ggcgaaacac aagccaggtc    3840
tggtgatgca cggtgccggc tggccattgt ctgaaaccgg ttcttcaggc ggctggtggt    3900
tgtatcatgc ggaaaacaat caggtgactt tgggcatgat cgtcgatctg tcttacacca    3960
acccgcatat gtatccgttt atggaaatgc agcgctggaa aacccatccg ctgatcaagc    4020
agtatctgga aggtggcaaa cgtatttctt atggcgcgcg tgcggtaacc aaaggcggct    4080
ttaactcgct accgaaattt accttcccgg gcggatcgct gattggtgac gatgccggct    4140
tcctgaactt tgccaaaatc aagggctcac ataccgcgat gaaatccggc atgctctgcg    4200
gtgaagcagt gtttgaagcc attgctgccg gtgtggaaaa aggtggtgac cttgcggttg    4260
cgcgtgtgac ggaaggcgaa gacttgtttg ccaaaaaact gacttcttac accgacaagt    4320
tcaataatag ctggctgaaa gaagagctgt acaactcgcg taactttggc ccggccatgc    4380
acaagtttgg tcagtggctc ggtggtgcgt ttaactttat cgaccagaac gtgtttaagg    4440
tgccgtttac cctgcatgac ctggtgacgg atttcggtgc gctgaaaacc gtcgatgcgg    4500
tgaacttcaa gccgaattat ccaaaaccgg atggcaaact gacctttgac cgtctgtctt    4560
cggtgtttgt atccaacacg gtgcatgaag aaaaccagcc agcgcattta aaactgactg    4620
acacttcgat tccggtgaat gtcaacctgc caaaatggga tgaaccggcg cagcgctact    4680
gccccgcggg tgtatacgaa atcatggaaa atgatgacgg ttcgaaacgc ttccagatca    4740
atgcagccaa ctgtgtgcac tgcaagacct gtgacatcaa ggatccttca cagaacatca    4800
cctgggtaac accggaaggt ggtggtggtc caaactatcc gaatatgtaa gtctaatcac    4860
ttcaaggaag aggtttccca tttcccttct ttctagcaga tgaagaagct tgcaactaaa    4920
agagattgtt tggatcagtt acccaaaatc gttgaaaaga ttttaactct tcgattttta    4980 tttttttaggt aatcctagcc ctctcggggg ctaggattaa aaattttaag ttattccaac    5040
acgaatgaca aattgttcaa tgcaaaataa aaacatacaa tatataaata tatttttttaa    5100 ttaaaacata agattacaat aaaataagaa tttttatttg gagtttgttt tttttctaca    5160
atgatcatta tgtacaattt ttaggttcac cccatccaag ccttgtgatt gcattcctgc    5220
gattctttat tcaatgaata agcaatgcta ttaatcagca atgaataacc agcactgcag    5280
attttgaata aattcacatg tcgtaatgga gattatcatg tcacaaaaaa tggatttttga   5340 tgctatcgtg attggtggtg gttttggcgg actttatgca gtcaaaaaat taagagacga    5400
gctcgaactt aaggttcagg cttttgataa agccacggat gtcgcaggta cttggtactg    5460
gaaccgttac ccaggtgcat tgtcggatac agaaacccac ctctactgct attcttggga    5520
taaagaatta ctacaatcgc tagaaatcaa gaaaaaatat gtgcaaggcc ctgatgtacg    5580
```

```
caagtattta cagcaagtgg ctgaaaagca tgatttaaag aagagctatc aattcaatac    5640
cgcggttcaa tcggctcatt acaacgaagc agatgccttg tgggaagtca ccactgaata    5700
tggtgataag tacacggcgc gtttcctcat cactgcttta ggcttattgt ctgcgcctaa    5760
cttgccaaac atcaaaggca ttaatcagtt taaaggtgag ctgcatcata ccagccgctg    5820
gccagatgac gtaagttttg aaggtaaacg tgtcggcgtg attggtacgg gttccaccgg    5880
tgttcaggtt attacggctg tggcacctct ggctaaacac ctcactgtct tccagcgttc    5940
tgcacaatac agcgttccaa ttggcaatga tccactgtct gaagaagatg ttaaaaagat    6000
caaagacaat tatgacaaaa tttgggatgg tgtatggaat tcagcccttg cctttggcct    6060
gaatgaaagc acagtgccag caatgagcgt atcagctgaa gaacgcaagg cagtttttga    6120
aaaggcatgg caaacaggtg gcggtttccg tttcatgttt gaaactttcg gtgatattgc    6180
caccaatatg gaagccaata tcgaagcgca aaatttcatt aagggtaaaa ttgctgaaat    6240
cgtcaaagat ccagccattg cacagaagct tatgccacag gatttgtatg caaaacgtcc    6300
gttgtgtgac agtggttact acaacacctt taaccgtgac aatgtccgtt tagaagatgt    6360
gaaagccaat ccgattgttg aaattaccga aaacggtgtg aaactcgaaa atggcgattt    6420
cgttgaatta gacatgctga tatgtgccac aggttttgat gccgtcgatg caactatgt    6480
gcgcatggac attcaaggta aaaacggctt ggccatgaaa gactactgga agaaggtcc    6540
gtcgagctat atgggtgtca ccgtaaataa ctatccaaac atgttcatgg tgcttggacc    6600
gaatggcccg tttaccaacc tgccgccatc aattgaatca caggtggaat ggatcagtga    6660
taccattcaa tacacggttg aaaacaatgt tgaatccatt gaagcgacaa agaagcgga    6720
agaacaatgg actcaaactt gcgccaatat tgcggaaatg accttattcc ctaaagcgca    6780
atcctggatt tttggtgcga atatcccggg caagaaaaac acggtttact tctatctcgg    6840
tggtttaaaa gaatatcgca gtgcgctagc caactgcaaa aaccatgcct atgaaggttt    6900
tgatattcaa ttacaacgtt cagatatcaa gcaacctgcc aatgcctaaa tatatggggg    6960
gcatccccca tattccattt tgtttaacat cagtcatatg ccagggatgt cttatcatga    7020
actatccaaa tataccttta tatatcaacg gtgagtttct agatcatacc aatagagacg    7080
tcaaagaagt ttttaatcca gtgaaccatg aatgtattgg actcatggcc tgtgcatcac    7140
aagcagacct ggactacgca cttgaaagtt cacaacaggc ttttctaagg tggaaaaaaa    7200
cttctcctat cacccgtagt gaaatcctca gaacctttgc gaaactagcg cgtgaaaaag    7260
cagcagaaat cgggcgcaat attcccttg atcaaggtaa gccctgaaa gaagccattg    7320
cagaagtcac tgtctgtgca gaacatgcag aatggcatgc agaagaatgc cgacgcattt    7380
atggccgtgt tattccaccg cgtaacccaa atgtacagca actagtagtc agagaaccgc    7440
tgggcgtatg tctggcattt tcaccgtgga atttcccgtt taatcaggca attcgtaaaa    7500
tttctgctgc aattgctgcc ggctgcacca tcattgtgaa aggttctggc gacacaccaa    7560
gcgcggtata tgcgattgcc cagctatttc atgaggcggg tttgccgaat ggtgtgctga    7620
atgtgatttg gggtgactca aacttcattt ctgattacat gatcaaatcg ccgatcatcc    7680
aaaagatttc attcacaggc tcaaccccgg tgggtaaaaa attagcctcg caagcgagtc    7740
tgtatatgaa gccttgcacc atggaattgg gtggtcatgc accggtcatc gtctgtgatg    7800
atgctgatat tgatgccgct gttgaacatc tggtcggtta taaattccgt aatgcaggac    7860
aggtctgtgt atcaccaacc cgttttatg tgcaggaagg tatttataag gaattttctg    7920
agaaagtggt gttaagagcc aaacagatca agtgggttg tggcttagac gcatcctcag    7980
```

```
atatgggacc attggctcaa gctcgccgca tgcatgcaat gcaacaaatt gttgaagatg    8040
cggttcataa aggctcaaaa ttactgcttg gcggaaataa aatttctgac aaaggcaatt    8100
tttttgaacc aacggtactc ggtgacttgt gcaatgacac ccagtttatg aatgacgagc    8160
catttggtcc gatcattggt ttgatacctt ttgacacaat agaccatgtc ctggaagaag    8220
caaatcgatt accatttgga ttagcctctt acgcttttac cacatccagc aaaaatgcgc    8280
atcaaatctc atacgactg gaggctggca tggtttcgat taaccacatg ggattggcgc     8340
tcgctgaaac accttttggt ggtattaagg atagcggttt tggtagtgaa gggggtatcg    8400
aaacctttga cggttacctc agaaccaaat ttattacgca actcaattag aaatggatct    8460
tggtgtgcgt aggcacacca attctctttt gactttaagg atgaaagtta aatgagcaca    8520
gacaaagcaa atacgctgat caaacccgaa gatgtcgtgt tatggattcc gggtaatgtc    8580
acaattgaca gcatgaatgc cggttgggaa acattgcaa tcagagggta cgaatatacc     8640
aacctcgatg tgcatattcc tgccatgcgt gactacatga tcgtcaacta taaaaaaagt    8700
gcggcggaaa tgcgtagaaa aggcgatgcc tcttgggata cccaagtggt taagccgggt    8760
tatgtctcct tgttgacctg tggtgaagat tcccgctggg cgtggaatga ccatattgcc    8820
gtcacccatg tctacatttc gcatgactcc atcacctcaa tggcgaataa ggtgtttgat    8880
tatgatatcg cttcgatccg aatcagagac gaagtcggtg tggaagatca tgttttacct    8940
gctctgactt cacttttaga actagaatta aagcaaggtg gtttaggtgg aaacctgtat    9000
ttagagagca ttaaaaaacca gatcgccctg catttactcc gtcagtatgc caaattagat    9060
tttaaggaag acagtgccg ttctggtttt actcccctac aacgcagact gttattagaa     9120
tttatcaatg aaaacatgag cattaaaaatt accctcgaag attttagcggg attagtcaag   9180 atgagcgtgc ctcatttaat gagaaaattt aaagtcgatt ttggtaattc ccctgctgcc    9240
tacatcatga atctcaggt gcaatttgct aaacgttttgc tcacttcaaa aaaagaaatt    9300
ccactgaaag tgattgccag tgaagccggt ttttgcgatc agagccatat gacccgagta    9360
tttcaaaaat tttttgggaa aacacccatc gaaatcagac aggaacacac caatctcgtg    9420
tctgaaaatt cagtctcctc tattgttttt tgagtactaa gagccacgca agaacctgat    9480
tttcaataaa gcatccactg aaaaccagtg tggacttaca tgcattattt atgcaaaata    9540
acaaatgtca tgtgagtatc aagatatact ttctatcgct atcaagaact tgccagtaca    9600
ggcaatatgg atgcactcat caaccagagt cgcagaactc caaatttaaa aaaccgagtg    9660
gatgagcaaa ctgaataagc tgttgttgat tttgcaatcc aatatccagc ttatggtcag    9720
catcggacca gtaatgagct acgtcagatt ggcatcttcg tatctggcag cggtgtgcgc    9780
tctatctggc ttagacacaa tcttgagaat ttcaaaaagc gattaaaggc acttgaaatt    9840
aaagttgctc aagaaggcat tcagttgaat gatcagcaga ttgccgcatt agaacgtaaa    9900
catgaagatg atgttgcttg tggtgaaatt gaaacacatc atccaggtta ccttggagca    9960
caagatactt tttatgtcgg aaatctaaaa ggtgttgggc atatttatca gcaaactttt   10020
attgatactt atagcaaagt ggttcactgc aagctgtaca caaccaagac accaatcaca   10080
gccgcagatt tattgaatga ccgcgtgtta ccattctatg agtcacaagg attgccaatg   10140
cttcgcattt tgaccgacag aggcaccgaa tattgcggta agttgaaca tcacgattat    10200 gagctttatt tggctctgaa tgatattgat cacactaaaa ctaaagcagc atcaccacaa   10260
acaaatggga tctgtgagcg cttccataag acgatcttgc aggagtttta tcagattact   10320
tttcgaaaga aactctatag ctcattagaa gagttacagc ttgatctaga cggttggctg   10380
```

```
aaattctata atactgaacg aacccatcag ggtaaggtgt gtaatggcag atgagcagca    10440
ttgctgcgca agattgcaac attacttgat ggaaaacgta tttgggctga aaagaattta    10500
gttcaaattt aacctgacag tcttaagcaa atatcggtaa ctatcagatc aggtttgaga    10560
taccgtctga aacgtcaagt aaatgattga gaattcatgc tcaataatct gcttgataag    10620
gctgttggtg tttgagcaca ccataacaaa gatgaatcaa cttcctcatc gcggctccaa    10680
tcgctatcat cttggtttta ccattcgcca ataaacgttc attcattgcc ctgatgtgag    10740
ggttatgccg agttgcgaca atggctgcca tatataaacc agcacgtatt ttggaagagc    10800
ccgctttgga taaacggctt ctgccatgaa tggaactacc cgattgcttt tgaatgggga    10860
ccaaaccgac aaaggcagcc gcttgactag ccctttcaaa agtatggctg cgcaagaaac    10920
tgagcattaa taaactggtt cgatctgcaa tggctggaat actgctgagc agttctttat    10980 catttttttaa atcaggattc tgattaatgt gatcatcaat ttgctggtcg ataccctgaa    11040
tgtgtttgtt taactgttca atactcttgt ggatagactg aagtacaggt tccatcgtga    11100
aggtcgactc tgctttttcc aaacgattct tttcacgttg taaatcttca caagaatag     11160 ctcttctatc cagcaaagca ttcagcaatt gaatatgttt aggtaaaggt tgccaaaaat    11220
gtagatcggc agtcatcgca aatcgagcta ggacctcact atccaccttg tctgttttat    11280
tcagcttaga catactctga gcaaaatatc gagctctggc aggattggtt acacagactt    11340
gatagcccgc atcaaataaa tatttaacca agagttcatg ataaatagat gttgcttcca    11400
ttaaaataat ggtctgcgta gaagttgcag catgctgctt tagccaggtt tgaagttgct    11460
caaaaccttt tggtgtattt gaaaaagttt tggttttctt tttatttgca gaattttcta    11520
aaattaaaca gcaatcaatt ttagctttag caacatcaat accaagataa aacataatct    11580
ttacctgctt tatttatcca attattgttt tagcataacc accgtctttt cttgtgaatg    11640
cagcatcaaa gtgcttgtta ccgtccagag ttgtgcaagt ggttagggca aattacaggt    11700
tttatctcaa actctaactt tatgttttgc tagtacacga aactctgcaa tttgcaatat    11760
agtgatagct aatcactatg aatggtaaga tacaagctag tacacataag aagatattac    11820
ttcttctcag gcagattcgc agcaaagaaa aattttccct tacaacaata gataaaagaa    11880
aagagggtat caccccctctt tcctcttttat atgggggtat cttctactca ttttttattt    11940
cgaggtatat gcaccatcga ccacatactg actaccggtc acaaatgaag catcatcaga    12000
aagtaggaag gcaacaacct gagcaacttc ttccggctgt cccaaacgac caatcggatg    12060
tagttttacc atttctgctt cttcaaattc tgcaatcaaa ggcgttttga tatagccagg    12120
atgtactgaa ttaatgcgaa tcccttttatc tgcatattcc aatgccgccg ctttcgttag    12180
acccgttacg ccatgttttg cagcgacata gcctgaaata ttttgaatcc cgatcaagcc    12240
tgcaatagaa gcggtattga caatcgctcc gcccccctgcg gccaagattg caggaacttc    12300
ataatgcatg ctgtagaaaa ccgcattcaa gttcacatca atcacacgac gccatccttc    12360
aatgctcaat tcttcggtgg agttaacttc acccagaatt cccgcattat tgaaggccaa    12420
atgcagtgca ccaaaagtgc tgaccgcaaa ctcgactgca gctttcatgt cttcaggctc    12480
agcagtattg gccttattcg cagccgcttt cccgcctaaa gcgacaattt cgtccacaac    12540
tttctgtgct gcttccaggt taatatctga aaccactaca cttacaccct gttgagccaa    12600
aagcagtgcg gtgcttttac caataccctga accagcgcca gtaattaaag cgactttatt    12660
gttgaattta tttgacataa ttttttccat ttcaaatttt aagcatcaaa gcttgtttca    12720
tattttaaga ttcaagaaac cagatccggt agatgactcg tctgccaagc gacaacccgt    12780
```

```
ctgatatcag gcttgcgatt caccctgtag acggttttca ttcctaaatt ctgtatttcc   12840
aagttatata aacaaaagtg ctaatctatg gggaattccc aggatccaaa caaatagaat   12900
gccatgaaag catcttttgc caagcgctgt gctgtatgtt tcctagacaa accaccaacg   12960
ataactgcaa cttttgaac tccttacaat ttccttattt tctttcccct tcatcgcata   13020
aaaatagttt ttgcattcac aacaaaatca gcatgaatag ttttaaaact cactgtacat   13080
attttctata ttgatgacca agctggatat tgaattgcaa aattctatac agcctgttca   13140
acatgatcga tttagaaggc atacagtaaa cgtgactgaa gtccagaaat tccaagcca   13200 ttttcaacat tcacatcttg tcgccattgt aataatagct gcagattcgg cttgatattg   13260
gtagaagcag aaacgacaaa ggtatctttt ctatcactgc cacgttcagt gacaccattc   13320
accttttctt taccgccatc ggtatgtctc caggtgacag ccaaattgga tttatcggtc   13380
actttataga gtgcggagaa atctgtctgg aaaaaaacct ctttctcaat gttggtatat   13440
ttttgctcgc tataaagttc aaactgcccc accccctcaa gcgcaaattt atcagttaaa   13500
gcatggtaat aaccggcctg aacattatat tgatagcgat cattactgat ggcaaaaccc   13560
ttcgtttcat tactgccggt aggtacggtc aaaaaaccac cgaaaccaaa atagcgccct   13620
ttttcagcat catgcaatgg ccaggcgata ccacccacaa ttaaatcacc gacacccgag   13680
atatcatcag cgccattcat cttttgcttg gcaaaaggca agaggaattg aggatctaca   13740
atccaatccc ctacttcaat aaaacgaacg taacgcaata ttcccaaatc aatgcttaaa   13800
tcgagatcat cagcgacttt atcaccattt gcatacgcct tatccgcttc cgtatgctgg   13860
taataggcaa ccgctaagtt ggttcccct ggaagtgctt gataatcccc ggcatcagaa   13920
ctcacccctg cggcttgcag gtccaaagcg gcagttaaag caaagaccaa agcagctatt   13980
ttttgatttg aacgatgata gaaatagttt ttcatttgtt tcattttaa ctctccgttg   14040 ttttgactca ttttttaaa atgagtcttc ctagcacaaa gaccactcag gtctttgcgc   14100
aatttcttga ttttgatttg ggtattaaat atggaaaaac gttgggtgat cagttttcgt   14160
gcataagcac aatacgcccg atgacgttgc catctttcaa gtctccaaat gcggaattga   14220
tctgcgaaat tggcagtttt ttcacgggaa tggctgacat gtgggtttct ttcaccagct   14280
ccaccagctc tcttaattcc tctaccgtcc ctacataact gccctggatt gtgagtggtc   14340
tcattggaat caccggaatg gaaagcttaa tttctcccc catcaatccg cagatcacaa   14400
tatgcccacc acgtgcagca ctcgccaagg caaggctcaa tgttggatta ctgccaacca   14460
gatcaaggat cagacgtgca ccaccgtcag ttgcctgaat cagctgttga gcagcatcct   14520
cacttcggct attgatgacc gataatgcac cggcagcacg tgctgcttcc agtttgctgt   14580
catcaatatc aactacgatt gcgccttggg cttgcatagc tttgagcaac tcgagtgcca   14640
tcagccctaa accaccggca ccaatgatca ccaccggctc gctttgaatc aaatcaccga   14700
attttttcag tgcactgtat gttgtcacgc ctgcacatgc caaaggtgca gcttcagcca   14760
gatccagacc tgcaatatcc accagatatc gtggatgcgg cacgatgata tattcggcaa   14820
aaccacccgg cttggcgatg cctaactgtt gcggtttggc acacaggttt tcttcgccac   14880
gtttacagta gttgcattca ccgcaaccaa tccatggatg aaccaagctg accatgccga   14940
ccttgactga ttccgcatct ggaccgacag caaccacctg acctgtaatt tcatgactta   15000
aggttaaggg tggcttcagc ccacgatctg caagggataa acgcttgccc ccacctagat   15060
cataataacc ttcccataag tgtaaatccg tatggcatag acctgcggct tttacatgga   15120
gtaaaacttc agtacctttc ggttgcggaa tttctttctc aacgtcttcg agtggttgtc   15180
```

-continued

```
catgatgcgt cacgcagtaa cagtgcatga atctctcctt tgaaacaata aaatagacgg    15240
ccttgtagtg aacaaagtct tttattcact aagtttttata cgccgtgtgg gcactgattt    15300
atgctttaaa ccactgcgca attttcgcta attcttgatc agcttcactt gcacgcccag    15360
ctaggaaagg aaaaacgtgc tgcatgttgt ccaccacaga taaagtcaca tcaacaccct    15420
cttttttttgc aatatcagca agacgtgttg cattgtctac aagtgattca actgatccgg    15480
cattgatata caaacgtggg aaaacctgat aattggcttt taacggattc gccaatggat    15540
ttgccggatc accatgttca cccaagaaca tttgtgacat gcctttaagc agatccactg    15600
taatcaaggc atcagtggca tcgttgctga tcagggtttc acctttgtgc tccatatcca    15660
gccaaggaga gaatgcaatc actgctcctg gcaactcaat cccttcattt cgtagattga    15720
gtacggttga tatcgccaga ttccccccccg cagaatcccc tgcggtcagc atattttttg    15780
cagtaaagcc acgctggagt agttctttat atactgctgt cacgtcctga atttgtgccg    15840
ggaagacatg ttctggtgaa cgtcggtaat caaccacaaa tgcggatacc cctaaatact    15900
tggccaaatg ccccaccagc ttacggtgac tggccgaaga accgaccgca atccaccgc    15960
catgggtata aatgatgact ttggataagt cagcatcttt cggataaatc caaagacctt    16020
ctacacctgc cacaacatcg aatttataag acacttcttc cggttccaat gtaggttgat    16080
gccattcatc aaacatactg cgaaagtctt caatggtcat attcggatttt tcctgcatcc    16140
gtcttgacca gttcgcatat aaatcgaaaa gaaattgagt attgctttgt gtgctattca    16200
ttttaaaaatc cttgatttga tatttaagga ataaatccta gttttattcc atgaagatat    16260
aaaaacttga gtgccatcac tcatggctag acactcagaa gatccaaatc taaagagtgg    16320
ctttgcatca ctggtttgat acaattttttt gcatgactaa gtaatctacg gataatctaa    16380
ccgtttcaaa ttagtatttt aaaatgtaaa aaatacatac cagcgaatgt tttctgcaaa    16440
atcgcatcct gttcaatata gcttttgatc ctacttattc tcttttctat tccagtccgt    16500
tataaaaaag ctttcattca ttttcatgca atcatgagct atgaatgttc ttaaacatta    16560
aacgattgtg tgtatggctg acttgtacat tcttgtactt attttttgtat aaaatgatca    16620
ggctcatcaa tttatgggaa aaattacaat tcgggtacaa tatctttcct gtttcatgaa    16680
tctattcaac tcattaaact tacgacccctc aactgcccaa aatcataggaa tctgccgatc    16740
cacttgcaga attagcaatg ctaaaacatg aactccaaag agttactaaa aaagagcat    16800
attaaaaaaa agccgtggca tatttcgcaa gccagttcaa gtcaggtatg tctttattca    16860
gtacctcagt taaactttag attttcataa cgatggttat tctgcatggc taaatacgct    16920
aatcagcaaa aaactctcca aaagataggc acagaaacac atatcaacca taaaaaccat    16980
ctcagacagt atatttacaa gcctctaatt caccgcactc acacttctct gcaagccttt    17040
ttaaatacccc tgtacaaagt tctcagcctg atgaagcttc accttggact tagctttcag    17100
ttcagcctgt acttggtcag tttctgaatt ttcatttgca taaaactcct ccaccacatc    17160
catacccctcc tcaatgtcag tttcaaaatg tgcattgtca tagccttgcc gtgccatttg    17220
aatggcttat tgaagattaa tggcatcacg taaagttaaa tccacgtaat acacaggtgt    17280
tcgatagctt tgcgtcgtag actttctcga agagtcaatt gcagcggtag gcatgacagc    17340
aagccattca atgccgcatg gtaataactc agccgtgcgg ccaacgttcg tatgctgtta    17400
aaacccggtt attctaa                                                   17417
```

<210> SEQ ID NO 74
<211> LENGTH: 1164
<212> TYPE: DNA

-continued

```
<213> ORGANISM: Escherichia coli

<400> SEQUENCE: 74
atgaacaact ttaatctgca caccccaacc cgcattctgt ttggtaaagg cgcaatcgct      60
ggtttacgcg aacaaattcc tcacgatgct cgcgtattga ttacctacgg cggcggcagc     120
gtgaaaaaaa ccggcgttct cgatcaagtt ctggatgccc tgaaaggcat ggacgtgctg     180
gaatttggcg gtattgagcc aaacccggct tatgaaacgc tgatgaacgc cgtgaaactg     240
gttcgcgaac agaaagtgac tttcctgctg gcggttggcg gcggttctgt actggacggc     300
accaaattta tcgccgcagc ggctaactat ccggaaaata tcgatccgtg gcacattctg     360
caaacgggcg gtaaagagat taaaagcgcc atcccgatgg gctgtgtgct gacgctgcca     420
gcaaccggtt cagaatccaa cgcaggcgcg gtgatctccc gtaaaaccac aggcgacaag     480
caggcgttcc attctgccca tgttcagccg gtatttgccg tgctcgatcc ggtttatacc     540
tacaccctgc cgccgcgtca ggtggctaac ggcgtagtgg acgcctttgt acacaccgtg     600
aacagtatg ttaccaaacc ggttgatgcc aaaattcagg accgtttcgc agaaggcatt      660
ttgctgacgc taatcgaaga tggtccgaaa gccctgaaag agccagaaaa ctacgatgtg     720
cgcgccaacg tcatgtgggc ggcgactcag gcgctgaacg gtttgattgg cgctggcgta     780
ccgcaggact gggcaacgca tatgctgggc acgaactga ctgcgatgca cggtctggat      840
cacgcgcaaa cactggctat cgtcctgcct gcactgtgga atgaaaaacg cgataccaag     900
cgcgctaagc tgctgcaata tgctgaacgc gtctggaaca tcactgaagg ttccgatgat     960
gagcgtattg acgccgcgat tgccgcaacc cgcaatttct ttgagcaatt aggcgtgccg    1020
acccacctct ccgactacgg tctggacggc agctccatcc cggctttgct gaaaaaactg    1080
gaagagcacg gcatgaccca actgggcgaa aatcatgaca ttacgttgga tgtcagccgc    1140
cgtatatacg aagccgcccg ctaa                                           1164

<210> SEQ ID NO 75
<211> LENGTH: 387
<212> TYPE: PRT
<213> ORGANISM: Escherichia coli

<400> SEQUENCE: 75

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
```

```
        145                 150                 155                 160
Gln Ala Phe His Ser Ala His Val Gln Pro Val Phe Ala Val Leu Asp
                165                 170                 175
Pro Val Tyr Thr Tyr Thr Leu Pro Pro Arg Gln Val Ala Asn Gly Val
                180                 185                 190
Val Asp Ala Phe Val His Thr Val Glu Gln Tyr Val Thr Lys Pro Val
                195                 200                 205
Asp Ala Lys Ile Gln Asp Arg Phe Ala Glu Gly Ile Leu Leu Thr Leu
        210                 215                 220
Ile Glu Asp Gly Pro Lys Ala Leu Lys Glu Pro Glu Asn Tyr Asp Val
225                 230                 235                 240
Arg Ala Asn Val Met Trp Ala Ala Thr Gln Ala Leu Asn Gly Leu Ile
                245                 250                 255
Gly Ala Gly Val Pro Gln Asp Trp Ala Thr His Met Leu Gly His Glu
                260                 265                 270
Leu Thr Ala Met His Gly Leu Asp His Ala Gln Thr Leu Ala Ile Val
                275                 280                 285
Leu Pro Ala Leu Trp Asn Glu Lys Arg Asp Thr Lys Arg Ala Lys Leu
        290                 295                 300
Leu Gln Tyr Ala Glu Arg Val Trp Asn Ile Thr Gly Ser Asp Asp
305                 310                 315                 320
Glu Arg Ile Asp Ala Ala Ile Ala Ala Thr Arg Asn Phe Phe Glu Gln
                325                 330                 335
Leu Gly Val Pro Thr His Leu Ser Asp Tyr Gly Leu Asp Gly Ser Ser
                340                 345                 350
Ile Pro Ala Leu Leu Lys Lys Leu Glu Glu His Gly Met Thr Gln Leu
                355                 360                 365
Gly Glu Asn His Asp Ile Thr Leu Asp Val Ser Arg Arg Ile Tyr Glu
        370                 375                 380
Ala Ala Arg
385

<210> SEQ ID NO 76
<211> LENGTH: 1623
<212> TYPE: DNA
<213> ORGANISM: Bacillus subtilis

<400> SEQUENCE: 76
atgtatttgg cattccaggt gcaaaaattg atgcggtatt tgacgcttta caagataaag      60
gacctgaaat tatcgttgcc cggcacgaac aaaacgcagc aattcatggc ccaagcagtc     120
ggccgtttaa ctggaaaacc gggagtcgtg ttagtcacat caggaccggg tgcctctaac     180
ttggcaacag gcctgctgac agcgaacact gaaggagacc ctgtcgttgc gcttgctgga     240
aacgtgatcc gtgcatatcg tttaaaacgg acacatcaat cttttggataa tgcggcgcta     300 ttccagccga ttacaaaata cagtgtagaa gttcaagatg taaaaaatat accggaagct     360
gttacaaatg catttaggat agcgtcagca gggcaggctg gggccgcttt tgtgagcttt     420
ccgcaagatg ttgtgaatga agtcacaaat acgaaaaacg tgcgtgctgt tgcagcgcca     480
aaactcggtc ctgcagcaga tgatgcaatc agtgcggcca tagcaaaaat ccaaacagca     540
aaacttcctg tcgttttggt cggcatgaaa ggcggaagac cggaagcaat taagcggtt     600 cgcaagcttt tgaaaaaggt tcagcttcca tttgttgaaa catatcaagc tgccggtacc     660
ctttctagag atttagagga tcaatatttt ggccgtatcg gtttgttccg caaccagcct     720
ggcgatttac tgctagagca ggcagatgtt gttctgacga tcggctatga cccgattgaa     780
```

```
tatgatccga aattctggaa tatcaatgga gaccggacaa ttatccattt agacgagatt      840
atcgctgaca ttgatcatgc ttaccagcct gatcttgaat tgatcggtga cattccgtcc      900
acgatcaatc atatcgaaca cgatgctgtg aaagtggaat ttgcagagcg tgagcagaaa      960
atcctttctg atttaaaaca atatatgcat gaaggtgagc aggtgcctgc agattggaaa     1020
tcagacagag cgcaccctct tgaaatcgtt aaagagttgc gtaatgcagt cgatgatcat     1080
gttacagtaa cttgcgatat cggttcgcac tccatttgga tgtcacgtta tttccgcagc     1140
tacgagccgt taacattaat gatcagtaac ggtatgcaaa cactcggcgt tgcgcttcct     1200
tgggcaatcg gcgcttcatt ggtgaaaccg ggagaaaaag tggtttctgt ctctggtgac     1260
ggcggtttct tattctcagc aatggaatta gagacagcag ttcgactaaa agcaccaatt     1320
gtacacattg tatggaacga cagcacatat gacatggtgc atttccagca attgaaaaaa     1380
tataaccgta catctgcggt cgatttcgga aatatcgata tcgtgaaata tgcggaaagc     1440
ttcggagcaa ctgcgttgcg cgtagaatca ccagaccagc tggcagatgt tctgcgtcaa     1500
ggcatgaacg ctgaaggtcc tgtcatcatc gatgtcccgg ttgactacag tgataacatt     1560
aatttagcaa gtgacaagct tccgaaagaa ttcggggaac tcatgaaaac gaaagctctc     1620
tag                                                                   1623
```

<210> SEQ ID NO 77
<211> LENGTH: 540
<212> TYPE: PRT
<213> ORGANISM: Bacillus subtilis

<400> SEQUENCE: 77

```
Met Tyr Leu Ala Phe Gln Val Gln Lys Leu Met Arg Tyr Leu Thr Leu
1               5                   10                  15

Tyr Lys Ile Lys Asp Leu Lys Leu Ser Leu Pro Gly Thr Asn Lys Thr
            20                  25                  30

Gln Gln Phe Met Ala Gln Ala Val Gly Arg Leu Thr Gly Lys Pro Gly
        35                  40                  45

Val Val Leu Val Thr Ser Gly Pro Gly Ala Ser Asn Leu Ala Thr Gly
    50                  55                  60

Leu Leu Thr Ala Asn Thr Glu Gly Asp Pro Val Val Ala Leu Ala Gly
65                  70                  75                  80

Asn Val Ile Arg Ala Tyr Arg Leu Lys Arg Thr His Gln Ser Leu Asp
                85                  90                  95

Asn Ala Ala Leu Phe Gln Pro Ile Thr Lys Tyr Ser Val Glu Val Gln
            100                 105                 110

Asp Val Lys Asn Ile Pro Glu Ala Val Thr Asn Ala Phe Arg Ile Ala
        115                 120                 125

Ser Ala Gly Gln Ala Gly Ala Ala Phe Val Ser Phe Pro Gln Asp Val
    130                 135                 140

Val Asn Glu Val Thr Asn Thr Lys Asn Val Arg Ala Val Ala Ala Pro
145                 150                 155                 160

Lys Leu Gly Pro Ala Ala Asp Asp Ala Ile Ser Ala Ala Ile Ala Lys
                165                 170                 175

Ile Gln Thr Ala Lys Leu Pro Val Val Leu Val Gly Met Lys Gly Gly
            180                 185                 190

Arg Pro Glu Ala Ile Lys Ala Val Arg Lys Leu Leu Lys Lys Val Gln
        195                 200                 205

Leu Pro Phe Val Glu Thr Tyr Gln Ala Ala Gly Thr Leu Ser Arg Asp
    210                 215                 220
```

| | | | | | | | | | | | | | | |
|---|---|---|---|---|---|---|---|---|---|---|---|---|---|---|
| Leu | Glu | Asp | Gln | Tyr | Phe | Gly | Arg | Ile | Gly | Leu | Phe | Arg | Asn | Gln | Pro |
| 225 | | | | 230 | | | | | 235 | | | | | 240 | |

Leu Glu Asp Gln Tyr Phe Gly Arg Ile Gly Leu Phe Arg Asn Gln Pro
225                 230                 235                 240

Gly Asp Leu Leu Leu Glu Gln Ala Asp Val Val Leu Thr Ile Gly Tyr
                245                 250                 255

Asp Pro Ile Glu Tyr Asp Pro Lys Phe Trp Asn Ile Asn Gly Asp Arg
            260                 265                 270

Thr Ile Ile His Leu Asp Glu Ile Ile Ala Asp Ile Asp His Ala Tyr
        275                 280                 285

Gln Pro Asp Leu Glu Leu Ile Gly Asp Ile Pro Ser Thr Ile Asn His
    290                 295                 300

Ile Glu His Asp Ala Val Lys Val Glu Phe Ala Glu Arg Glu Gln Lys
305                 310                 315                 320

Ile Leu Ser Asp Leu Lys Gln Tyr Met His Glu Gly Glu Gln Val Pro
                325                 330                 335

Ala Asp Trp Lys Ser Asp Arg Ala His Pro Leu Glu Ile Val Lys Glu
            340                 345                 350

Leu Arg Asn Ala Val Asp Asp His Val Thr Val Thr Cys Asp Ile Gly
        355                 360                 365

Ser His Ser Ile Trp Met Ser Arg Tyr Phe Arg Ser Tyr Glu Pro Leu
    370                 375                 380

Thr Leu Met Ile Ser Asn Gly Met Gln Thr Leu Gly Val Ala Leu Pro
385                 390                 395                 400

Trp Ala Ile Gly Ala Ser Leu Val Lys Pro Gly Glu Lys Val Val Ser
                405                 410                 415

Val Ser Gly Asp Gly Gly Phe Leu Phe Ser Ala Met Glu Leu Glu Thr
            420                 425                 430

Ala Val Arg Leu Lys Ala Pro Ile Val His Ile Val Trp Asn Asp Ser
        435                 440                 445

Thr Tyr Asp Met Val His Phe Gln Gln Leu Lys Lys Tyr Asn Arg Thr
    450                 455                 460

Ser Ala Val Asp Phe Gly Asn Ile Asp Ile Val Lys Tyr Ala Glu Ser
465                 470                 475                 480

Phe Gly Ala Thr Ala Leu Arg Val Glu Ser Pro Asp Gln Leu Ala Asp
                485                 490                 495

Val Leu Arg Gln Gly Met Asn Ala Glu Gly Pro Val Ile Ile Asp Val
            500                 505                 510

Pro Val Asp Tyr Ser Asp Asn Ile Asn Leu Ala Ser Asp Lys Leu Pro
        515                 520                 525

Lys Glu Phe Gly Glu Leu Met Lys Thr Lys Ala Leu
    530                 535                 540

<210> SEQ ID NO 78
<211> LENGTH: 1680
<212> TYPE: DNA
<213> ORGANISM: Klebsiella terrigena

<400> SEQUENCE: 78
atggacaaac cgcgtcacga acgtcaatgg gcccacggtg ccgacttaat cgtcagccag      60
cttgaggccc agggcgtacg ccaggtcttc ggcatccccg gtgccaaaat cgacaaggtg     120
tttgattccc tcctcgactc ctcaatccgc attattccgg tgcgcacga ggctaacgcc      180 gcctttatgg ccgcggcggt cgggcggatt accggtaaag cgggcgtcgc gctggtgacc     240 tccggtccg ctgctcaaa cctgattacc ggcatggcca ccgccaatag cgaaggcgac       300
ccggtggtgg cgctgggcgg cgcggtgaag cgcgcggata aggccaagct ggttcaccaa     360

-continued

```
agcatggaca ccgtggcgat gttcagcccg gtcaccaaat acgccgtcga ggtgaccgcc      420
tccgacgcgc tggccgaggt ggtctccaac gcctttcgcg ccgccgaaca ggggcgtccg      480
gggagcgcgt ttgtcagcct gccgcaggat atcgttgacg gccccgccag cggcagcacg      540
ctgcccgcca gcagagcgcc gcagatgggc gccgcgccgg atggcgccgt tgacagcgtg      600
gcgcaggcga tcgccgcggc gaagaaccct atcttcctgc tcgggctgat ggccagccag      660
ccggaaaaca gccgcgccct gcaccgccat gctggaaaaa agccatattc cggtcaccag      720
cacctatcag gcgccggggc ggtaaatcag gataacttcg cccgcttcgc cggccgggta      780
ggcctgttta ataaccaggc gggcgatcgc ctgctgcgtc aggcggacct gatcatctgc      840
atcggctata gcccggttga gtacgaaccg gcgatgtgga acagcggcac ggcaaccctg      900
gtgcatatcg acgtgctgcc ggcctatgaa gagcggaact acgtcccgga tatcgagctg      960
gtgggcgaca tcgccgccac cctcgagaag ctggcccagc gcattgaaca tcggctggtg     1020
ttaactccgc aggcggcgga catcctcgcc gaccgccagc gccagcggga gctgcttgac     1080
cgccgcgggg cgcagctgaa tcagtttgcg ctccacccgc tgcgcatcgt gcgggcgatg     1140
caggatatcg tcaatagcga cgtcaccttg accgtcgata tgggcagttt ccatatctgg     1200
attgcccgct acctctacag cttccgcgcc cgccaggtga tgatctccaa cggtcagcaa     1260
acgatgggcg tcgcgctgcc gtgggcaatc ggcgcgtggc tggtcaatcc gcagcgcaag     1320
gtggtctcgg tatccggcga tggcggcttc ctgcagtcga gcatggagct ggagaccgcc     1380
gtgcgcctgc acgccaatat tctgcacatc atctgggtcg ataacggcta caacatggtg     1440
gcgattcagg aacagaagaa atatcagcgc ctctccggcg tggagttcgg cccggtcgat     1500
ttcaaagtct acgccgaagc gttcggggcc tgcgggtttg cggtagagag cgccgaggcc     1560
ctggagccga ccctgcgcgc ggcgatggat gtcgacggcc cggcggtggt cgccattccg     1620
gtcgattacc gcgataaccc tctgctgatg ggccagctcc atctcagcca aatactgtga    1680
```

<210> SEQ ID NO 79
<211> LENGTH: 559
<212> TYPE: PRT
<213> ORGANISM: Klebsiella terrigena

<400> SEQUENCE: 79

```
Met Asp Lys Pro Arg His Glu Arg Gln Trp Ala His Gly Ala Asp Leu
1               5                   10                  15

Ile Val Ser Gln Leu Glu Ala Gln Gly Val Arg Gln Val Phe Gly Ile
            20                  25                  30

Pro Gly Ala Lys Ile Asp Lys Val Phe Asp Ser Leu Leu Asp Ser Ser
        35                  40                  45

Ile Arg Ile Ile Pro Val Arg His Glu Ala Asn Ala Ala Phe Met Ala
    50                  55                  60

Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110

Asp Lys Ala Lys Leu Val His Gln Ser Met Asp Thr Val Ala Met Phe
        115                 120                 125

Ser Pro Val Thr Lys Tyr Ala Val Glu Val Thr Ala Ser Asp Ala Leu
    130                 135                 140
```

```
Ala Glu Val Val Ser Asn Ala Phe Arg Ala Ala Glu Gln Gly Arg Pro
145                 150                 155                 160

Gly Ser Ala Phe Val Ser Leu Pro Gln Asp Ile Val Asp Gly Pro Ala
                165                 170                 175

Ser Gly Ser Thr Leu Pro Ala Ser Arg Ala Pro Gln Met Gly Ala Ala
            180                 185                 190

Pro Asp Gly Ala Val Asp Ser Val Ala Gln Ala Ile Ala Ala Ala Lys
            195                 200                 205

Asn Pro Ile Phe Leu Leu Gly Leu Met Ala Ser Gln Pro Glu Asn Ser
210                 215                 220

Arg Ala Leu His Arg His Ala Gly Lys Lys Pro Tyr Ser Gly His Gln
225                 230                 235                 240

His Leu Ser Gly Ala Gly Ala Val Asn Gln Asp Asn Phe Ala Arg Phe
                245                 250                 255

Ala Gly Arg Val Gly Leu Phe Asn Asn Gln Ala Gly Asp Arg Leu Leu
            260                 265                 270

Arg Gln Ala Asp Leu Ile Ile Cys Ile Gly Tyr Ser Pro Val Glu Tyr
            275                 280                 285

Glu Pro Ala Met Trp Asn Ser Gly Thr Ala Thr Leu Val His Ile Asp
290                 295                 300

Val Leu Pro Ala Tyr Glu Glu Arg Asn Tyr Val Pro Asp Ile Glu Leu
305                 310                 315                 320

Val Gly Asp Ile Ala Ala Thr Leu Glu Lys Leu Ala Gln Arg Ile Glu
                325                 330                 335

His Arg Leu Val Leu Thr Pro Gln Ala Ala Asp Ile Leu Ala Asp Arg
            340                 345                 350

Gln Arg Gln Arg Glu Leu Leu Asp Arg Arg Gly Ala Gln Leu Asn Gln
            355                 360                 365

Phe Ala Leu His Pro Leu Arg Ile Val Arg Ala Met Gln Asp Ile Val
370                 375                 380

Asn Ser Asp Val Thr Leu Thr Val Asp Met Gly Ser Phe His Ile Trp
385                 390                 395                 400

Ile Ala Arg Tyr Leu Tyr Ser Phe Arg Ala Arg Gln Val Met Ile Ser
                405                 410                 415

Asn Gly Gln Gln Thr Met Gly Val Ala Leu Pro Trp Ala Ile Gly Ala
            420                 425                 430

Trp Leu Val Asn Pro Gln Arg Lys Val Val Ser Val Ser Gly Asp Gly
            435                 440                 445

Gly Phe Leu Gln Ser Ser Met Glu Leu Glu Thr Ala Val Arg Leu His
450                 455                 460

Ala Asn Ile Leu His Ile Ile Trp Val Asp Asn Gly Tyr Asn Met Val
465                 470                 475                 480

Ala Ile Gln Glu Gln Lys Lys Tyr Gln Arg Leu Ser Gly Val Glu Phe
                485                 490                 495

Gly Pro Val Asp Phe Lys Val Tyr Ala Glu Ala Phe Gly Ala Cys Gly
            500                 505                 510

Phe Ala Val Glu Ser Ala Glu Ala Leu Glu Pro Thr Leu Arg Ala Ala
            515                 520                 525

Met Asp Val Asp Gly Pro Ala Val Val Ala Ile Pro Val Asp Tyr Arg
530                 535                 540

Asp Asn Pro Leu Leu Met Gly Gln Leu His Leu Ser Gln Ile Leu
545                 550                 555

<210> SEQ ID NO 80
```

```
<211> LENGTH: 768
<212> TYPE: DNA
<213> ORGANISM: Bacillus subtilis

<400> SEQUENCE: 80
atgaaacgag aaagcaacat tcaagtgctc agccgtggtc aaaaagatca gcctgtgagc      60
cagatttatc aagtatcaac aatgacttct ctattagacg gagtatatga cggagatttt     120
gaactgtcag agattccgaa atatggagac ttcggtatcg gaacctttaa caagcttgac     180
ggagagctga ttgggtttga cggcgaattt taccgtcttc gctcagacgg aaccgcgaca     240
ccggtccaaa atggagaccg ttcaccgttc tgttcattta cgttctttac accggacatg     300
acgcacaaaa ttgatgcgaa aatgacacgc gaagactttg aaaaagagat caacagcatg     360
ctgccaagca gaaacttatt ttatgcaatt cgcattgacg gattgtttaa aaaggtgcag     420
acaagaacag tagaacttca agaaaaacct tacgtgccaa tggttgaagc ggtcaaaaca     480
cagccgattt tcaacttcga caacgtgaga ggaacgattg taggtttctt gacaccagct     540
tatgcaaacg gaatcgccgt ttctggctat cacctgcact tcattgacga aggacgcaat     600
tcaggcggac acgttttga ctatgtgctt gaggattgca cggttacgat ttctcaaaaa     660
atgaacatga atctcagact tccgaacaca gcggatttct ttaatgcgaa tctggataac     720
cctgattttg cgaaagatat cgaaacaact gaaggaagcc ctgaataa               768

<210> SEQ ID NO 81
<211> LENGTH: 255
<212> TYPE: PRT
<213> ORGANISM: Bacillus subtilis

<400> SEQUENCE: 81

Met Lys Arg Glu Ser Asn Ile Gln Val Leu Ser Arg Gly Gln Lys Asp
1               5                   10                  15

Gln Pro Val Ser Gln Ile Tyr Gln Val Ser Thr Met Thr Ser Leu Leu
            20                  25                  30

Asp Gly Val Tyr Asp Gly Asp Phe Glu Leu Ser Glu Ile Pro Lys Tyr
        35                  40                  45

Gly Asp Phe Gly Ile Gly Thr Phe Asn Lys Leu Asp Gly Glu Leu Ile
    50                  55                  60

Gly Phe Asp Gly Glu Phe Tyr Arg Leu Arg Ser Asp Gly Thr Ala Thr
65                  70                  75                  80

Pro Val Gln Asn Gly Asp Arg Ser Pro Phe Cys Ser Phe Thr Phe Phe
                85                  90                  95

Thr Pro Asp Met Thr His Lys Ile Asp Ala Lys Met Thr Arg Glu Asp
            100                 105                 110

Phe Glu Lys Glu Ile Asn Ser Met Leu Pro Ser Arg Asn Leu Phe Tyr
        115                 120                 125

Ala Ile Arg Ile Asp Gly Leu Phe Lys Lys Val Gln Thr Arg Thr Val
    130                 135                 140

Glu Leu Gln Glu Lys Pro Tyr Val Pro Met Val Glu Ala Val Lys Thr
145                 150                 155                 160

Gln Pro Ile Phe Asn Phe Asp Asn Val Arg Gly Thr Ile Val Gly Phe
                165                 170                 175

Leu Thr Pro Ala Tyr Ala Asn Gly Ile Ala Val Ser Gly Tyr His Leu
            180                 185                 190

His Phe Ile Asp Glu Gly Arg Asn Ser Gly Gly His Val Phe Asp Tyr
        195                 200                 205

Val Leu Glu Asp Cys Thr Val Thr Ile Ser Gln Lys Met Asn Met Asn
```

```
                210                 215                 220
Leu Arg Leu Pro Asn Thr Ala Asp Phe Phe Asn Ala Asn Leu Asp Asn
225                 230                 235                 240

Pro Asp Phe Ala Lys Asp Ile Glu Thr Thr Glu Gly Ser Pro Glu
                245                 250                 255
```

<210> SEQ ID NO 82
<211> LENGTH: 780
<212> TYPE: DNA
<213> ORGANISM: Klebsiella terrigena

<400> SEQUENCE: 82

```
gtgaatcatt atcctgaatg cacctgccag agagcctgt gcgaaaccgt acgcggcttc      60
tccgcccacc accctgatag cgttatctat cagacctctc tgatgagcgc gctgctgagc   120
ggggtctatg agggtagcac caccatcgcc gacctgctga cccacggcga cttcggtctc   180
ggcacctta acgaactcga tggcgaactg attgccttta gcagcgaggt ctaccagctg   240
cgcgctgacg gcagcgcgcg taaagcccgg gcggatcaaa aaacgccctt cgcggtgatg   300
acctggttca gaccgcagta ccgtaaaacc tttgaccacc cggtcagccg ccagcagctg   360
cacgacgtta tcgaccagca aatcccctcc gataacctgt tctgcgccct gcatattgat   420
ggtcactttc gccacgccca cacccgcacc gtgccgcggc agacgccgcc ctatcgggcg   480
atgaccgacg tgctcgatga ccagccggtt ttccgcttca accagcgcaa ggggacgctg   540
gtcggctttc gcaccccgca gcatatgcag ggccttaacg ttgccggcta ccacgagcac   600
tttattaccg acgatcgcca gggcggcggc catctgctgg actaccagct cgatagcggc   660
gtgctgacct tcggcgagat ccacaagctg atgattgacc tcccggccga cagcgctttc   720
ctgcaggccg acctgcatcc tgacaatctc gatgccgcta ttcgtgcggt agaaaactaa   780
```

<210> SEQ ID NO 83
<211> LENGTH: 259
<212> TYPE: PRT
<213> ORGANISM: Klebsiella terrigena

<400> SEQUENCE: 83

```
Met Asn His Tyr Pro Glu Cys Thr Cys Gln Glu Ser Leu Cys Glu Thr
1               5                   10                  15

Val Arg Gly Phe Ser Ala His His Pro Asp Ser Val Ile Tyr Gln Thr
                20                  25                  30

Ser Leu Met Ser Ala Leu Leu Ser Gly Val Tyr Glu Gly Ser Thr Thr
            35                  40                  45

Ile Ala Asp Leu Leu Thr His Gly Asp Phe Gly Leu Gly Thr Phe Asn
        50                  55                  60

Glu Leu Asp Gly Glu Leu Ile Ala Phe Ser Ser Glu Val Tyr Gln Leu
65                  70                  75                  80

Arg Ala Asp Gly Ser Ala Arg Lys Ala Arg Ala Asp Gln Lys Thr Pro
                85                  90                  95

Phe Ala Val Met Thr Trp Phe Arg Pro Gln Tyr Arg Lys Thr Phe Asp
                100                 105                 110

His Pro Val Ser Arg Gln Gln Leu His Asp Val Ile Asp Gln Gln Ile
            115                 120                 125

Pro Ser Asp Asn Leu Phe Cys Ala Leu His Ile Asp Gly His Phe Arg
        130                 135                 140

His Ala His Thr Arg Thr Val Pro Arg Gln Thr Pro Pro Tyr Arg Ala
145                 150                 155                 160
```

```
Met Thr Asp Val Leu Asp Asp Gln Pro Val Phe Arg Phe Asn Gln Arg
                165                 170                 175
Lys Gly Thr Leu Val Gly Phe Arg Thr Pro Gln His Met Gln Gly Leu
            180                 185                 190
Asn Val Ala Gly Tyr His Glu His Phe Ile Thr Asp Asp Arg Gln Gly
        195                 200                 205
Gly Gly His Leu Leu Asp Tyr Gln Leu Asp Ser Gly Val Leu Thr Phe
    210                 215                 220
Gly Glu Ile His Lys Leu Met Ile Asp Leu Pro Ala Asp Ser Ala Phe
225                 230                 235                 240
Leu Gln Ala Asp Leu His Pro Asp Asn Leu Asp Ala Ala Ile Arg Ala
                245                 250                 255
Val Glu Asn

<210> SEQ ID NO 84
<211> LENGTH: 1053
<212> TYPE: DNA
<213> ORGANISM: Bacillus cereus

<400> SEQUENCE: 84
atgaaagcac tactttggca taatcaacgt gatgtacgag tagaagaagt accagaacca      60
acagtaaaac caggaacagt gaaaatcaaa gttaaatggt gtggtatttg tgggacagac     120
ttgcatgaat atttagcagg gcctattttt attccaacag aagaacatcc attaacacat     180
gtgaaagcac ctgttatttt aggtcatgag tttagtggtg aggtaataga gattggtgaa     240
ggagttacat ctcataaagt gggagaccgc gttgttgtag agccaattta ttcttgtggt     300
aaatgtgaag cttgtaaaca tggacattac aatgtttgtg aacaacttgt tttccacggt     360
cttggcggag aaggcggcgg tttctctgaa tatacagtag taccagaaga tatggttcat     420
cacattccag atgaaatgac gtatgaacaa ggtgcgcttg tagaaccagc agcagtagca     480
gttcatgcag tacgtcaaag taaattaaaa gaaggggaag ctgtagcggt atttggttgc     540
ggtccaattg gacttcttgt tatccaagca gctaaagcag caggagcaac tcctgttatt     600
gcagttgaac tttctaaaga acgtcaagag ttagcgaaat tagcaggtgc ggattatgta     660
ttaaatccag caactcaaga tgtgttagct gaaattcgta acttaacaaa tggtttaggt     720
gtaaatgtta gctttgaagt aacaggtgtt gaagttgtac tacgccaagc gattgaaagt     780
acaagcttcg aaggacaaac tgtaattgtt agtgtatggg aaaaagacgc aacaattact     840
ccaaataact agtattaaaa agaaaaagaa gttattggta ttttaggata ccgtcacatc     900
ttcccagctg ttattaaatt gattagctcc ggtcaaattc aagcagagaa attaattacg     960
aaaaaaatta cagtggatca agttgttgaa gaaggatttg aagcacttgt aaaagataaa    1020
acacaagtga aaattcttgt ttcacctaaa taa                                 1053

<210> SEQ ID NO 85
<211> LENGTH: 350
<212> TYPE: PRT
<213> ORGANISM: Bacillus cereus

<400> SEQUENCE: 85

Met Lys Ala Leu Leu Trp His Asn Gln Arg Asp Val Arg Val Glu Glu
1               5                   10                  15

Val Pro Glu Pro Thr Val Lys Pro Gly Thr Val Lys Ile Lys Val Lys
                20                  25                  30

Trp Cys Gly Ile Cys Gly Thr Asp Leu His Glu Tyr Leu Ala Gly Pro
            35                  40                  45
```

```
Ile Phe Ile Pro Thr Glu Glu His Pro Leu Thr His Val Lys Ala Pro
    50                  55                  60

Val Ile Leu Gly His Glu Phe Ser Gly Glu Val Ile Glu Ile Gly Glu
65                  70                  75                  80

Gly Val Thr Ser His Lys Val Gly Asp Arg Val Val Val Glu Pro Ile
                85                  90                  95

Tyr Ser Cys Gly Lys Cys Glu Ala Cys Lys His Gly His Tyr Asn Val
            100                 105                 110

Cys Glu Gln Leu Val Phe His Gly Leu Gly Gly Glu Gly Gly Gly Phe
        115                 120                 125

Ser Glu Tyr Thr Val Val Pro Glu Asp Met Val His His Ile Pro Asp
    130                 135                 140

Glu Met Thr Tyr Glu Gln Gly Ala Leu Val Glu Pro Ala Ala Val Ala
145                 150                 155                 160

Val His Ala Val Arg Gln Ser Lys Leu Lys Glu Gly Glu Ala Val Ala
                165                 170                 175

Val Phe Gly Cys Gly Pro Ile Gly Leu Leu Val Ile Gln Ala Ala Lys
            180                 185                 190

Ala Ala Gly Ala Thr Pro Val Ile Ala Val Glu Leu Ser Lys Glu Arg
        195                 200                 205

Gln Glu Leu Ala Lys Leu Ala Gly Ala Asp Tyr Val Leu Asn Pro Ala
    210                 215                 220

Thr Gln Asp Val Leu Ala Glu Ile Arg Asn Leu Thr Asn Gly Leu Gly
225                 230                 235                 240

Val Asn Val Ser Phe Glu Val Thr Gly Val Glu Val Val Leu Arg Gln
                245                 250                 255

Ala Ile Glu Ser Thr Ser Phe Glu Gly Gln Thr Val Ile Val Ser Val
            260                 265                 270

Trp Glu Lys Asp Ala Thr Ile Thr Pro Asn Asn Leu Val Leu Lys Glu
        275                 280                 285

Lys Glu Val Ile Gly Ile Leu Gly Tyr Arg His Ile Phe Pro Ala Val
    290                 295                 300

Ile Lys Leu Ile Ser Ser Gly Gln Ile Gln Ala Glu Lys Leu Ile Thr
305                 310                 315                 320

Lys Lys Ile Thr Val Asp Gln Val Val Glu Glu Gly Phe Glu Ala Leu
                325                 330                 335

Val Lys Asp Lys Thr Gln Val Lys Ile Leu Val Ser Pro Lys
            340                 345                 350
```

```
<210> SEQ ID NO 86
<211> LENGTH: 1053
<212> TYPE: DNA
<213> ORGANISM: Bacillus cereus

<400> SEQUENCE: 86
atgaaagcac tactttggca taatcaacgt gatgtacgag tagaagaagt accagaacca      60
acagtaaaac caggaacagt gaaaatcaaa gttaaatggt gtggtatttg tgggacagac     120
ttgcatgaat atttagcagg gcctattttt attccaacag aagaacatcc attaacacat     180
gtgaaagcac ctgttatttt aggtcatgag tttagtggtg aggtaataga gattggtgaa     240
ggagttacat ctcataaagt gggagaccgc gttgttgtag agccaattta ttcttgtggt     300
aaatgtgaag cttgtaaaca tggacattac aatgtttgtg aacaacttgt tttccacggt     360
cttggcggag aaggcggcgg tttctctgaa tatacagtag taccagaaga tatggttcat     420
```

-continued

```
cacattccag atgaaatgac gtatgaacaa ggtgcgcttg tagaaccagc agcagtagca    480
gttcatgcag tacgtcaaag taaattaaaa gaagggaag ctgtagcggt atttggttgc     540
ggtccaattg gacttcttgt tatccaagca gctaaagcag caggagcaac tcctgttatt    600
gcagttgaac tttctaaaga acgtcaagag ttagcgaaat tagcaggtgc ggattatgta    660
ttaaatccag caactcaaga tgtgttagct gaaattcgta acttaacaaa tggtttaggt    720
gtaaatgtta gctttgaagt aacaggtgtt gaagttgtac tacgccaagc gattgaaagt    780
acaagcttcg aaggacaaac tgtaattgtt agtgtatggg aaaaagacgc aacaattact    840
ccaaataact tagtattaaa agaaaaagaa gttattggta ttttaggata ccgtcacatc    900
ttcccagctg ttattaaatt gattagctcc ggtcaaattc aagcagagaa attaattacg    960
aaaaaaatta cagtggatca agttgttgaa gaaggatttg aagcacttgt aaaagataaa    1020
acacaagtga aaattcttgt ttcacctaaa taa                                 1053
```

<210> SEQ ID NO 87
<211> LENGTH: 350
<212> TYPE: PRT
<213> ORGANISM: Bacillus cereus

<400> SEQUENCE: 87

```
Met Lys Ala Leu Leu Trp His Asn Gln Arg Asp Val Arg Val Glu Glu
1               5                   10                  15

Val Pro Glu Pro Thr Val Lys Pro Gly Thr Val Lys Ile Lys Val Lys
            20                  25                  30

Trp Cys Gly Ile Cys Gly Thr Asp Leu His Gl

Trp Glu Lys Asp Ala Thr Ile Thr Pro Asn Asn Leu Val Leu Lys Glu
            275                 280                 285

Lys Glu Val Ile Gly Ile Leu Gly Tyr Arg His Ile Phe Pro Ala Val
        290                 295                 300

Ile Lys Leu Ile Ser Ser Gly Gln Ile Gln Ala Lys Leu Ile Thr
305                 310                 315                 320

Lys Lys Ile Thr Val Asp Gln Val Val Glu Glu Gly Phe Glu Ala Leu
            325                 330                 335

Val Lys Asp Lys Thr Gln Val Lys Ile Leu Val Ser Pro Lys
            340                 345                 350

<210> SEQ ID NO 88
<211> LENGTH: 1113
<212> TYPE: DNA
<213> ORGANISM: Lactococcus lactis

<400> SEQUENCE: 88
ttgcctgaaa cgacaaccat cctatataga ggaggcgttt ttatgcgcgc agcacgtttt     60
tacgaccgcg gggatatccg cattgatgaa attaatgaac caatagtaaa agctggccaa    120
gttggcattg atgtggcttg tgtgtggaatt tgtggaacag atctccatga attttttagat   180 ggcccaattt tttgtccgtc agcagaacat cctaatccaa ttactggaga agtaccacca    240
gtcactcttg acatgaaaat gtctggggtt gtaaatttta taggtgaagg agtaagcgga    300
cttaaagtag gtgaccatgt cgttgtcgaa ccttatatcg ttcccgaagg gactgataca    360
agtgaaactg acattataaa cctctcagaa ggctcaaact ttattggttt gggcggaaat    420
ggtggaggtt tggctgaaaa aatttctgtt gatgaacgtt gggttcacaa aattcctgat    480
aacttaccat tggatgaagc tgctctaatt gagccactat cagtcggcta tcacgctgtt    540
gaacgagcaa atttaagtga aaagagtacg gtattagttg ttggtgctgg accaattgga    600
ctattaactg ctgccgttgc aaaagcgcaa ggacatactg ttatcatcag tgaacctagt    660
ggacttcgtc gtaaaaaagc acaagaagca caagttgctg attatttctt caatccaatt    720
gaagatgaca ttcaagctaa agttcatgaa attaatgaaa aaggagtgga cgcagccttt    780
gaatgtacct ctgtccaacc gggatttgac gcttgtctag atgcgattcg tatgggtgga    840
acagttgtca ttgtcgcaat ttggggcaag cctgctagtg ttgatatggc aaaattagta    900
atcaaagaag ctaaccttttt aggaacgatt gcttataata acactcatcc aaaaacaatt    960
gatttagtat caacaggtaa aataaaattg gaccaattca tcacagctaa aatcggtttg   1020
gatgatttga ttgataaagg attcgatacg ctgattcatc ataatgaaac agctgttaaa   1080 atttttagttt caccaactgg taaaggtcta taa                              1113

<210> SEQ ID NO 89
<211> LENGTH: 370
<212> TYPE: PRT
<213> ORGANISM: Lactococcus lactis

<400> SEQUENCE: 89

Met Pro Glu Thr Thr Thr Ile Leu Tyr Arg Gly Gly Val Phe Met Arg
1               5                   10                  15

Ala Ala Arg Phe Tyr Asp Arg Gly Asp Ile Arg Ile Asp Glu Ile Asn
            20                  25                  30

Glu Pro Ile Val Lys Ala Gly Gln Val Gly Ile Asp Val Ala Trp Cys
        35                  40                  45

Gly Ile Cys Gly Thr Asp Leu His Glu Phe Leu Asp Gly Pro Ile Phe

```
                50                  55                  60
Cys Pro Ser Ala Glu His Pro Asn Pro Ile Thr Gly Glu Val Pro Pro
 65                  70                  75                  80

Val Thr Leu Gly His Glu Met Ser Gly Val Val Asn Phe Ile Gly Glu
                 85                  90                  95

Gly Val Ser Gly Leu Lys Val Gly Asp His Val Val Glu Pro Tyr
            100                 105                 110

Ile Val Pro Glu Gly Thr Asp Thr Ser Glu Thr Gly His Tyr Asn Leu
            115                 120                 125

Ser Glu Gly Ser Asn Phe Ile Gly Leu Gly Gly Asn Gly Gly Gly Leu
145                 135                 140

Ala Glu Lys Ile Ser Val Asp Glu Arg Trp Val His Lys Ile Pro Asp
145                 150                 155                 160

Asn Leu Pro Leu Asp Glu Ala Ala Leu Ile Glu Pro Leu Ser Val Gly
                165                 170                 175

Tyr His Ala Val Glu Arg Ala Asn Leu Ser Glu Lys Ser Thr Val Leu
            180                 185                 190

Val Val Gly Ala Gly Pro Ile Gly Leu Leu Thr Ala Ala Val Ala Lys
            195                 200                 205

Ala Gln Gly His Thr Val Ile Ile Ser Glu Pro Ser Gly Leu Arg Arg
210                 215                 220

Lys Lys Ala Gln Glu Ala Gln Val Ala Asp Tyr Phe Phe Asn Pro Ile
225                 230                 235                 240

Glu Asp Asp Ile Gln Ala Lys Val His Glu Ile Asn Glu Lys Gly Val
                245                 250                 255

Asp Ala Ala Phe Glu Cys Thr Ser Val Gln Pro Gly Phe Asp Ala Cys
            260                 265                 270

Leu Asp Ala Ile Arg Met Gly Gly Thr Val Val Ile Val Ala Ile Trp
            275                 280                 285

Gly Lys Pro Ala Ser Val Asp Met Ala Lys Leu Val Ile Lys Glu Ala
290                 295                 300

Asn Leu Leu Gly Thr Ile Ala Tyr Asn Asn Thr His Pro Lys Thr Ile
305                 310                 315                 320

Asp Leu Val Ser Thr Gly Lys Ile Lys Leu Asp Gln Phe Ile Thr Ala
                325                 330                 335

Lys Ile Gly Leu Asp Asp Leu Ile Asp Lys Gly Phe Asp Thr Leu Ile
            340                 345                 350

His His Asn Glu Thr Ala Val Lys Ile Leu Val Ser Pro Thr Gly Lys
            355                 360                 365

Gly Leu
    370

<210> SEQ ID NO 90
<211> LENGTH: 705
<212> TYPE: DNA
<213> ORGANISM: Pyrococcus furiosus

<400> SEQUENCE: 90
atgaaggttg ccgtaattac tggggcatcc cgtggaatcg gggaagctat agcaaaggcc    60
cttgctgaag atggatattc ccttgcctta gggctagaa gtgttgatag gttagagaag    120
attgccaagg aactcagcga aaacatgggg gtggaggtat tttacgacta cctcgatgta    180
tcaaaaccag aaagcgttga agagtttgca aggaaaacgc tagctcactt tggagatgtg    240
gacgttgttg tggccaatgc ggggcttggt tactttggta ggcttgaaga gcttacagaa    300
```

-continued

| | |
|---|---|
| gagcagttcc acgaaatgat tgaagtaaac cttttgggag tttggagaac aataaaagct | 360 |
| ttcttaaact ccttaaagcg gactggagga gtggctattg ttgttacttc agatgtttct | 420 |
| gcaaggctac ttccatacgg tggaggttat gtggcaacta aatgggctgc aagagcattg | 480 |
| gtaaggacct tccagattga gaatccagat gtgaggttct tcgagctaag acctggagca | 540 |
| gtagatacat attttggagg gagcaaagct gggaagccaa aggagcaagg gtatttaaaa | 600 |
| cctgaggaag ttgctgaggc agtaaaatac ctcctaagac ttccaaagga tgttagggtt | 660 |
| gaggaattaa tgttgcgctc aatttatcaa aaacctgagt attga | 705 |

<210> SEQ ID NO 91
<211> LENGTH: 234
<212> TYPE: PRT
<213> ORGANISM: Pyrococcus furiosus

<400> SEQUENCE: 91

```
Met Lys Val Ala Val Ile Thr Gly Ala Ser Arg Gly Ile Gly Glu Ala
1               5                   10                  15

Ile Ala Lys Ala Leu Ala Glu Asp Gly Tyr Ser Leu Ala Leu Gly Ala
            20                  25                  30

Arg Ser Val Asp Arg Leu Glu Lys Ile Ala Lys Glu Leu Ser Glu Lys
        35                  40                  45

His Gly Val Glu Val Phe Tyr Asp Tyr Leu Asp Val Ser Lys Pro Glu
    50                  55                  60

Ser Val Glu Glu Phe Ala Arg Lys Thr Leu Ala His Phe Gly Asp Val
65                  70                  75                  80

Asp Val Val Ala Asn Ala Gly Leu Gly Tyr Phe Gly Arg Leu Glu
                85                  90                  95

Glu Leu Thr Glu Glu Gln Phe His Glu Met Ile Glu Val Asn Leu Leu
            100                 105                 110

Gly Val Trp Arg Thr Ile Lys Ala Phe Leu Asn Ser Leu Lys Arg Thr
        115                 120                 125

Gly Gly Val Ala Ile Val Val Thr Ser Asp Val Ser Ala Arg Leu Leu
    130                 135                 140

Pro Tyr Gly Gly Gly Tyr Val Ala Thr Lys Trp Ala Ala Arg Ala Leu
145                 150                 155                 160

Val Arg Thr Phe Gln Ile Glu Asn Pro Asp Val Arg Phe Phe Glu Leu
                165                 170                 175

Arg Pro Gly Ala Val Asp Thr Tyr Phe Gly Gly Ser Lys Ala Gly Lys
            180                 185                 190

Pro Lys Glu Gln Gly Tyr Leu Lys Pro Glu Glu Val Ala Glu Ala Val
        195                 200                 205

Lys Tyr Leu Leu Arg Leu Pro Lys Asp Val Arg Val Glu Glu Leu Met
    210                 215                 220

Leu Arg Ser Ile Tyr Gln Lys Pro Glu Tyr
225                 230
```

<210> SEQ ID NO 92
<211> LENGTH: 1665
<212> TYPE: DNA
<213> ORGANISM: Salmonella typhimurium

<400> SEQUENCE: 92

| | |
|---|---|
| atgagatcga aaagattgga agcactggcg aaacgccctg tgaatcagga cggctttgtt | 60 |
| aaggagtgga tcgaagaagg ctttatcgcg atggaaagcc cgaacgaccc aaaaccgtcg | 120 |
| ataaaaatcg ttaacggcgc ggtaaccgag ctggacggaa aaccggttag cgaattcgac | 180 |

```
ctgatcgacc actttatcgc ccgctacggc atcaacctga accgcgccga agaagtgatg    240
gcgatggatt cggtcaagct ggctaacatg ctgtgcgatc cgaacgtcaa agcgcagcgaa   300 atcgttccgc taaccaccgc gatgacccca gcgaaaattg tcgaagtggt ttcgcatatg   360
aacgtggttg agatgatgat ggcgatgcag aaaatgcgcg cccgccgtac tccatctcaa   420
caggcgcacg tcaccaacgt taaagacaac ccggtgcaaa ttgccgccga tgccgccgaa   480
ggcgcatggc gcgggtttga cgaacaagag acgacggttg cggtagcgcg ctatgcgccg   540
ttcaacgcca tcgcgctgct ggttggttct caggtaggtc gtccgggggt actgactcaa   600
tgctcgctgg aagaagccac cgagctgaag ctcggcatgc tgggccacac ctgctacgcc   660
gaaaccatct ccgtttacgg caccgagccg tcttcaccg acggtgacga tacccccatgg   720 tcgaagggct tcttagcctc ttcctacgcc tctcgcggcc tgaaaatgcg cttcacctcc   780
ggctccggct ccgaagtgca gatgggctac gccgaaggca aatccatgct gtatctggaa   840
gcgcgctgca tctatatcac caaagccgcg ggcgttcagg gctgcaaaa cggctccgta   900 agcagcatcg gcgtaccgtc tgccgtgccg tcaggcattc gtgccgtgct ggcggaaaac   960
ctgatctgct cttcgctgga tctggaatgc gcctccagta acgaccagac cttcacccac  1020
tccgatatgc gtcgtaccgc tcgcctgctg atgcagttcc tgccgggtac cgactttatc  1080
tcctccggtt attccgcggt gccgaactac gacaacatgt cgccggttc caacgaagat  1140 gcggaagact ttgacgacta caacgttatc cagcgtgacc tgaaagtgga cggcggtctg  1200
cgcccggttc gcgaagagga cgttatcgcc atccgtaaca aagccgcccg cgcgctgcag  1260
gccgtgtttg ccggaatggg actgccgccg attaccgatg aagaagttga agccgcgacc  1320
tatgcccacg gttcgaaaga tatgccggag cgcaacatcg tcgaagacat caagttcgcc  1380
caggaaatca tcaataaaaa ccgcaacggt ctggaagttg tgaaagcgct ggctcagggc  1440
gggtttaccg acgtggccca ggacatgctc aacatccaga aagccaagct aaccggcgac  1500
tatttgcaca cctccgccat atcgtcggc gacggacaag tgctctctgc ggttaatgac  1560
gtcaatgact atgccggtcc ggcaacaggt tatcgcctgc agggagaacg ctgggaagag  1620
attaaaaaca tccctggcgc tcttgatccc aacgagattg attaa            1665
```

<210> SEQ ID NO 93
<211> LENGTH: 554
<212> TYPE: PRT
<213> ORGANISM: Salmonella typhimurium

<400> SEQUENCE: 93

Met Arg Ser Lys Arg Phe Glu Ala Leu Ala Lys Arg Pro Val Asn Gln
1               5                   10                  15

Asp Gly Phe Val Lys Glu Trp Ile Glu Gly Phe Ile Ala Met Glu
            20                  25                  30

Ser Pro Asn Asp Pro Lys Pro Ser Ile Lys Ile Val Asn Gly Ala Val
        35                  40                  45

Thr Glu Leu Asp Gly Lys Pro Val Ser Glu Phe Asp Leu Ile Asp His
    50                  55                  60

Phe Ile Ala Arg Tyr Gly Ile Asn Leu Asn Arg Ala Glu Glu Val Met
65                  70                  75                  80

Ala Met Asp Ser Val Lys Leu Ala Asn Met Leu Cys Asp Pro Asn Val
                85                  90                  95

Lys Arg Ser Glu Ile Val Pro Leu Thr Thr Ala Met Thr Pro Ala Lys
            100                 105                 110

-continued

```
Ile Val Glu Val Val Ser His Met Asn Val Val Glu Met Met Met Ala
            115                 120                 125
Met Gln Lys Met Arg Ala Arg Arg Thr Pro Ser Gln Gln Ala His Val
130                 135                 140
Thr Asn Val Lys Asp Asn Pro Val Gln Ile Ala Ala Asp Ala Ala Glu
145                 150                 155                 160
Gly Ala Trp Arg Gly Phe Asp Glu Gln Glu Thr Thr Val Ala Val Ala
                165                 170                 175
Arg Tyr Ala Pro Phe Asn Ala Ile Ala Leu Leu Val Gly Ser Gln Val
            180                 185                 190
Gly Arg Pro Gly Val Leu Thr Gln Cys Ser Leu Glu Glu Ala Thr Glu
        195                 200                 205
Leu Lys Leu Gly Met Leu Gly His Thr Cys Tyr Ala Glu Thr Ile Ser
    210                 215                 220
Val Tyr Gly Thr Glu Pro Val Phe Thr Asp Gly Asp Thr Pro Trp
225                 230                 235                 240
Ser Lys Gly Phe Leu Ala Ser Ser Tyr Ala Ser Arg Gly Leu Lys Met
                245                 250                 255
Arg Phe Thr Ser Gly Ser Gly Ser Glu Val Gln Met Gly Tyr Ala Glu
            260                 265                 270
Gly Lys Ser Met Leu Tyr Leu Glu Ala Arg Cys Ile Tyr Ile Thr Lys
        275                 280                 285
Ala Ala Gly Val Gln Gly Leu Gln Asn Gly Ser Val Ser Ser Ile Gly
    290                 295                 300
Val Pro Ser Ala Val Pro Ser Gly Ile Arg Ala Val Leu Ala Glu Asn
305                 310                 315                 320
Leu Ile Cys Ser Ser Leu Asp Leu Glu Cys Ala Ser Ser Asn Asp Gln
                325                 330                 335
Thr Phe Thr His Ser Asp Met Arg Arg Thr Ala Arg Leu Leu Met Gln
            340                 345                 350
Phe Leu Pro Gly Thr Asp Phe Ile Ser Ser Gly Tyr Ser Ala Val Pro
        355                 360                 365
Asn Tyr Asp Asn Met Phe Ala Gly Ser Asn Glu Asp Ala Glu Asp Phe
    370                 375                 380
Asp Asp Tyr Asn Val Ile Gln Arg Asp Leu Lys Val Asp Gly Gly Leu
385                 390                 395                 400
Arg Pro Val Arg Glu Glu Asp Val Ile Ala Ile Arg Asn Lys Ala Ala
                405                 410                 415
Arg Ala Leu Gln Ala Val Phe Ala Gly Met Gly Leu Pro Pro Ile Thr
            420                 425                 430
Asp Glu Glu Val Glu Ala Ala Thr Tyr Ala His Gly Ser Lys Asp Met
        435                 440                 445
Pro Glu Arg Asn Ile Val Glu Asp Ile Lys Phe Ala Gln Glu Ile Ile
    450                 455                 460
Asn Lys Asn Arg Asn Gly Leu Glu Val Val Lys Ala Leu Ala Gln Gly
465                 470                 475                 480
Gly Phe Thr Asp Val Ala Gln Asp Met Leu Asn Ile Gln Lys Ala Lys
                485                 490                 495
Leu Thr Gly Asp Tyr Leu His Thr Ser Ala Ile Ile Val Gly Asp Gly
            500                 505                 510
Gln Val Leu Ser Ala Val Asn Asp Val Asn Asp Tyr Ala Gly Pro Ala
        515                 520                 525
Thr Gly Tyr Arg Leu Gln Gly Glu Arg Trp Glu Glu Ile Lys Asn Ile
    530                 535                 540
```

Pro Gly Ala Leu Asp Pro Asn Glu Ile Asp
545                 550

<210> SEQ ID NO 94
<211> LENGTH: 675
<212> TYPE: DNA
<213> ORGANISM: Salmonella typhimurium

<400> SEQUENCE: 94

```
atggaaatta atgaaaaatt gctgcgccag ataattgaag acgtactccg cgatatgaag      60
ggcagcgata aacccgtctc gtttaatgcg cctgcggcat ccacagcacc acagaccgct     120
gcgcctgcgg gcgacggctt tctgaccgaa gtgggcgaag cgcgccaggg cactcagcag     180
gacgaagtca ttatcgccgt cggcccggca tttggcctgg cgcaaaccgt caatatcgtc     240
ggcttaccgc ataagagcat tctgcgcgaa gtcattgccg gtattgaaga agaaggcatc     300
aaggcgcgcg tgattcgctg ctttaaatct tccgacgtgg cgttcgtcgc cgttgaaggt     360
aaccgcctga gcggatccgg catctccatc ggcatccagt cgaaaggtac tacggttatc     420
caccagcagg ggctaccgcc gctctccaac ctggagctgt tcccgcaggc accgctgctg     480
acgctggaaa cctaccgtca gattggtaaa aacgccgccc gctatgcgaa cgagaatca     540
ccgcagccgg tccctacgct caatgaccag atggcacgcc cgaagtacca ggcaaagtcg     600
gccattttgc atattaaaga gaccaagtac gtcgtgacgg gcaaaaaccc gcaggaactg     660
cgcgtggcgc tttga                                                      675
```

<210> SEQ ID NO 95
<211> LENGTH: 224
<212> TYPE: PRT
<213> ORGANISM: Salmonella typhimurium

<400> SEQUENCE: 95

Met Glu Ile Asn Glu Lys Leu Leu Arg Gln Ile Ile Glu Asp Val Leu
1               5                   10                  15

Arg Asp Met Lys Gly Ser Asp Lys Pro Val Ser Phe Asn Ala Pro Ala
            20                  25                  30

Ala Ser Thr Ala Pro Gln Thr Ala Ala Pro Ala Gly Asp Gly Phe Leu
        35                  40                  45

Thr Glu Val Gly Glu Ala Arg Gln Gly Thr Gln Gln Asp Glu Val Ile
    50                  55                  60

Ile Ala Val Gly Pro Ala Phe Gly Leu Ala Gln Thr Val Asn Ile Val
65                  70                  75                  80

Gly Leu Pro His Lys Ser Ile Leu Arg Glu Val Ile Ala Gly Ile Glu
                85                  90                  95

Glu Glu Gly Ile Lys Ala Arg Val Ile Arg Cys Phe Lys Ser Ser Asp
            100                 105                 110

Val Ala Phe Val Ala Val Glu Gly Asn Arg Leu Ser Gly Ser Gly Ile
        115                 120                 125

Ser Ile Gly Ile Gln Ser Lys Gly Thr Thr Val Ile His Gln Gln Gly
    130                 135                 140

Leu Pro Pro Leu Ser Asn Leu Glu Leu Phe Pro Gln Ala Pro Leu Leu
145                 150                 155                 160

Thr Leu Glu Thr Tyr Arg Gln Ile Gly Lys Asn Ala Ala Arg Tyr Ala
                165                 170                 175

Lys Arg Glu Ser Pro Gln Pro Val Pro Thr Leu Asn Asp Gln Met Ala
            180                 185                 190

```
Arg Pro Lys Tyr Gln Ala Lys Ser Ala Ile Leu His Ile Lys Glu Thr
        195                 200                 205

Lys Tyr Val Val Thr Gly Lys Asn Pro Gln Glu Leu Arg Val Ala Leu
    210                 215                 220
```

<210> SEQ ID NO 96
<211> LENGTH: 522
<212> TYPE: DNA
<213> ORGANISM: Salmonella typhimurium

<400> SEQUENCE: 96

```
atgaataccg acgcaattga atcgatggtc cgggacgtat tgagccgcat gaacagcctg      60
cagggcgatg cgccagcagc ggctcctgcg gcaggcggca cgtcccgcag cgcaaaggtc     120
agcgactacc cgctggcgaa caaacacccg gaatgggtga aaaccgccac caataaaacg     180
ctggacgact ttacgctgga aaacgtgctg agcaataaag tcaccgctca ggatatgcgt     240
attaccccgg aaaccctgcg cttacaggcc tctatcgcca agatgcgggt cgcgaccgg      300
ctggcgatga acttcgaacg cgccgccgaa ctgaccgcgg taccggacga tcgcattctt     360
gaaatctaca acgcccttcg tccgtatcgt tcaacgaaag aagagctgct cgctatcgcc     420
gacgatctcg aaaaccgtta tcaggcaaag atttgcgcag ctttcgttcg tgaagcggca     480
gggctgtacg ttgagcgtaa aaaactcaaa ggcgacgatt aa                        522
```

<210> SEQ ID NO 97
<211> LENGTH: 173
<212> TYPE: PRT
<213> ORGANISM: Salmonella typhimurium

<400> SEQUENCE: 97

```
Met Asn Thr Asp Ala Ile Glu Ser Met Val Arg Asp Val Leu Ser Arg
1               5                   10                  15

Met Asn Ser Leu Gln Gly Asp Ala Pro Ala Ala Pro Ala Ala Gly
            20                  25                  30

Gly Thr Ser Arg Ser Ala Lys Val Ser Asp Tyr Pro Leu Ala Asn Lys
        35                  40                  45

His Pro Glu Trp Val Lys Thr Ala Thr Asn Lys Thr Leu Asp Asp Phe
    50                  55                  60

Thr Leu Glu Asn Val Leu Ser Asn Lys Val Thr Ala Gln Asp Met Arg
65                  70                  75                  80

Ile Thr Pro Glu Thr Leu Arg Leu Gln Ala Ser Ile Ala Lys Asp Ala
                85                  90                  95

Gly Arg Asp Arg Leu Ala Met Asn Phe Glu Arg Ala Ala Glu Leu Thr
            100                 105                 110

Ala Val Pro Asp Asp Arg Ile Leu Glu Ile Tyr Asn Ala Leu Arg Pro
        115                 120                 125

Tyr Arg Ser Thr Lys Glu Glu Leu Leu Ala Ile Ala Asp Asp Leu Glu
    130                 135                 140

Asn Arg Tyr Gln Ala Lys Ile Cys Ala Ala Phe Val Arg Glu Ala Ala
145                 150                 155                 160

Gly Leu Tyr Val Glu Arg Lys Lys Leu Lys Gly Asp Asp
                165                 170
```

<210> SEQ ID NO 98
<211> LENGTH: 1677
<212> TYPE: DNA
<213> ORGANISM: Lactobacillus collinoides

<400> SEQUENCE: 98

```
ttggaacgtc aaaaaagatt tgaaaaatta gagaaacgtc cagtgcattt agatgggttc    60
gttaagaact gggacgacga aggtttagtt gcccttaacg gtaagaacga tccaaagcca   120
agcattacga tcgaaaacgg tgttgttact gaaatggatg gtaagaagaa ggcagacttc   180
gaccttatcg acaagtacat cgctgaatac gggatcaact tggacaatgc tgaaaagact   240
ttaaacacag attcagttaa gatcgccaac atgatgtgtg atcctaacgt ctcccgtgct   300
gaaattattg aatatacaac tgctatgaca ccagccaagg ctgctgaagt tatcagccag   360
ttaaacttcg ctgaaatgat catggcaact caaaagatgc ggccacgtcg acccctatg    420 actcaagtcc acgctaccaa cactttggat aacccagttg aaatcgctgc tgatgctgcc   480
gaagctgcat acgtggggt tcctgaagaa gaaaccacca ctgccattgc tcggtatgcg   540
ccaatgaacg ctatttcaat catggttggg gcccaagcag gccgtcctgg tgttatcacc   600
caatgttcag ttgaagaagc tgacgaattg agtttgggga tgcgtggggtt tactgcctat   660 gctgaaacca tttcagttta tgggactgac cgggtcttca ctgatggtga tataccccct   720
tggtcaaaag gtttcttagc ttcttgctac gcttcacgtg gtttgaagat gcggtttact   780
tcaggtgccg gttcagaagc tatgatgggc tacactgaag gtaaatcaat gctttaccttg   840 gaagctcgtt gtatctacat taccaaggcg tcaggtgttc aaggtctgca aaacggtggt   900
gttagttgta tcgggatgcc aggtgccgtc gttggtggta tccgtgaagt cttaggtgaa   960
aacttactat gtatgtcact tgatgttgaa tgtgcttctg gttgtgacca agccttctct  1020
cactctgaca ttcgtcggac tggccggatg attggccaat tcatcgctgg tactgattac  1080
ctgtcatcag gttacgctgc gaagaaaaac atggataaca ccttcgctgg ttcaaacatg  1140
gatgttctgg actacgatga ttacatcact ttggaacgtg atatggctat taacggtggt  1200
atcatgccaa ttaccgaaga ggaatctatt aagattcgtc acaaggctgc ggttgctatc  1260
caagctgtct ttgatggctt aggcctacca cagatcactg atgaagaagt tgaagccgca  1320
acttatggca gcaattcaaa cgacatgcca aaacgtgaca tggttcaaga tatgaaagct  1380
gctcaaggtc tgatgactcg tggcattact gttgttgacg ttatcaaggc cttatatgac  1440
catgatatta agacgtcgc tgaggctgtg cttaagttag cgcaacaaaa ggtttgtggt  1500
gattacctgc aaacatctgc tgtcttcttg gatggttgga agtgtacttc agctattaac  1560
aacgctaacg attacaaagg cccaggtact ggttaccgtc tatgggaaga caaagacaaa  1620
tgggatcgtc tagaaaacgt tccgtgggct ttggatcctc agaagttgga attctaa     1677
```

<210> SEQ ID NO 99
<211> LENGTH: 558
<212> TYPE: PRT
<213> ORGANISM: Lactobacillus collinoides

<400> SEQUENCE: 99

```
Met Glu Arg Gln Lys Arg Phe Glu Lys Leu Glu Lys Arg Pro Val His
1               5                   10                  15

Leu Asp Gly Phe Val Lys Asn Trp Asp Asp Glu Gly Leu Val Ala Leu
            20                  25                  30

Asn Gly Lys Asn Asp Pro Lys Pro Ser Ile Thr Ile Glu Asn Gly Val
        35                  40                  45

Val Thr Glu Met Asp Gly Lys Lys Ala Asp Phe Asp Leu Ile Asp
    50                  55                  60

Lys Tyr Ile Ala Glu Tyr Gly Ile Asn Leu Asp Asn Ala Glu Lys Thr
65                  70                  75                  80
```

```
Leu Asn Thr Asp Ser Val Lys Ile Ala Asn Met Met Cys Asp Pro Asn
                85                  90                  95

Val Ser Arg Ala Glu Ile Ile Glu Tyr Thr Thr Ala Met Thr Pro Ala
            100                 105                 110

Lys Ala Ala Glu Val Ile Ser Gln Leu Asn Phe Ala Glu Met Ile Met
            115                 120                 125

Ala Thr Gln Lys Met Arg Pro Arg Thr Pro Met Thr Gln Val His
130                 135                 140

Ala Thr Asn Thr Leu Asp Asn Pro Val Glu Ile Ala Ala Asp Ala Ala
145                 150                 155                 160

Glu Ala Ala Leu Arg Gly Val Pro Glu Glu Thr Thr Ala Ile
                165                 170                 175

Ala Arg Tyr Ala Pro Met Asn Ala Ile Ser Ile Met Val Gly Ala Gln
            180                 185                 190

Ala Gly Arg Pro Gly Val Ile Thr Gln Cys Ser Val Glu Glu Ala Asp
            195                 200                 205

Glu Leu Ser Leu Gly Met Arg Gly Phe Thr Ala Tyr Ala Glu Thr Ile
210                 215                 220

Ser Val Tyr Gly Thr Asp Arg Val Phe Thr Asp Gly Asp Thr Pro
225                 230                 235                 240

Trp Ser Lys Gly Phe Leu Ala Ser Cys Tyr Ala Ser Arg Gly Leu Lys
            245                 250                 255

Met Arg Phe Thr Ser Gly Ala Gly Ser Glu Ala Met Met Gly Tyr Thr
            260                 265                 270

Glu Gly Lys Ser Met Leu Tyr Leu Glu Ala Arg Cys Ile Tyr Ile Thr
            275                 280                 285

Lys Ala Ser Gly Val Gln Gly Leu Gln Asn Gly Gly Val Ser Cys Ile
290                 295                 300

Gly Met Pro Gly Ala Val Val Gly Gly Ile Arg Glu Val Leu Gly Glu
305                 310                 315                 320

Asn Leu Leu Cys Met Ser Leu Asp Val Glu Cys Ala Ser Gly Cys Asp
                325                 330                 335

Gln Ala Phe Ser His Ser Asp Ile Arg Arg Thr Gly Arg Met Ile Gly
            340                 345                 350

Gln Phe Ile Ala Gly Thr Asp Tyr Leu Ser Ser Gly Tyr Ala Ala Glu
            355                 360                 365

Glu Asn Met Asp Asn Thr Phe Ala Gly Ser Asn Met Asp Val Leu Asp
            370                 375                 380

Tyr Asp Asp Tyr Ile Thr Leu Glu Arg Asp Met Ala Ile Asn Gly Gly
385                 390                 395                 400

Ile Met Pro Ile Thr Glu Glu Ser Ile Lys Ile Arg His Lys Ala
                405                 410                 415

Ala Val Ala Ile Gln Ala Val Phe Asp Gly Leu Gly Leu Pro Gln Ile
            420                 425                 430

Thr Asp Glu Glu Val Glu Ala Ala Thr Tyr Gly Ser Asn Ser Asn Asp
            435                 440                 445

Met Pro Lys Arg Asp Met Val Gln Asp Met Lys Ala Ala Gln Gly Leu
450                 455                 460

Met Thr Arg Gly Ile Thr Val Val Asp Val Ile Lys Ala Leu Tyr Asp
465                 470                 475                 480

His Asp Ile Lys Asp Val Ala Glu Ala Val Leu Lys Leu Ala Gln Gln
                485                 490                 495

Lys Val Cys Gly Asp Tyr Leu Gln Thr Ser Ala Val Phe Leu Asp Gly
            500                 505                 510
```

Trp Lys Cys Thr Ser Ala Ile Asn Asn Ala Asn Asp Tyr Lys Gly Pro
            515                 520                 525

Gly Thr Gly Tyr Arg Leu Trp Glu Asp Lys Asp Lys Trp Asp Arg Leu
        530                 535                 540

Glu Asn Val Pro Trp Ala Leu Asp Pro Gln Lys Leu Glu Phe
545                 550                 555

<210> SEQ ID NO 100
<211> LENGTH: 693
<212> TYPE: DNA
<213> ORGANISM: Lactobacillus collinoides

<400> SEQUENCE: 100

```
gtgagttcag aaatcgatga acattgctt agaaatatca ttaaaggcgt tttaaatgaa       60
gttcaaaact ctgatacgcc aatttccttt ggtggccaag atgcagcccc agttgccggt      120
gccaaggaag gtgccgcacc agaaaagaag ttggattggt tccaacacgt tggaatcgcc      180
aaaccaggtt tgtcaaagga tgaagttgta attggtgttg ccccagcatt tgctgaagtg      240
ttgacgcaaa ctatgacgaa gatccaacac aaagacatcc tgcgtcaaat cattgccgga      300
gttgaagaag aaggtctcaa ggcccgtgtc gttaaggttt atcggacttc agacgtttcc      360
ttcgttccg ctgatgttga caagttgtca ggttcaggaa tttcagttgc cgttcaatca       420
aaggggacaa cgattattca ccaaaaggat caagcaccgt tgtcaaacct tgaattgttc      480
ccacaggctc cagttttgac attggacgct taccgtcaaa tcggtaagaa cgctgcccag      540
tatgctaagg gtatgtcacc aaccccagtg ccaacaatta cgaccagat ggcacgtgtg       600
caatatcaag cactttctgc tttgatgcac atcaaggaaa caaaacaggt tgttgttggg      660
aagcctgctg aagaaattaa ggtaaccttt tag                                    693
```

<210> SEQ ID NO 101
<211> LENGTH: 230
<212> TYPE: PRT
<213> ORGANISM: Lactobacillus collinoides

<400> SEQUENCE: 101

Met Ser Ser Glu Ile Asp Glu Thr Leu Leu Arg Asn Ile Ile Lys Gly
1               5                   10                  15

Val Leu Asn Glu Val Gln Asn Ser Asp Thr Pro Ile Ser Phe Gly Gly
            20                  25                  30

Gln Asp Ala Ala Pro Val Ala Gly Ala Lys Glu Gly Ala Ala Pro Glu
        35                  40                  45

Lys Lys Leu Asp Trp Phe Gln His Val Gly Ile Ala Lys Pro Gly Leu
    50                  55                  60

Ser Lys Asp Glu Val Val Ile Gly Val Ala Pro Ala Phe Ala Glu Val
65                  70                  75                  80

Leu Thr Gln Thr Met Thr Lys Ile Gln His Lys Asp Ile Leu Arg Gln
                85                  90                  95

Ile Ile Ala Gly Val Glu Glu Glu Gly Leu Lys Ala Arg Val Val Lys
            100                 105                 110

Val Tyr Arg Thr Ser Asp Val Ser Phe Val Ser Ala Asp Val Asp Lys
        115                 120                 125

Leu Ser Gly Ser Gly Ile Ser Val Ala Val Gln Ser Lys Gly Thr Thr
    130                 135                 140

Ile Ile His Gln Lys Asp Gln Ala Pro Leu Ser Asn Leu Glu Leu Phe
145                 150                 155                 160

```
Pro Gln Ala Pro Val Leu Thr Leu Asp Ala Tyr Arg Gln Ile Gly Lys
                165                 170                 175

Asn Ala Ala Gln Tyr Ala Lys Gly Met Ser Pro Thr Pro Val Pro Thr
            180                 185                 190

Ile Asn Asp Gln Met Ala Arg Val Gln Tyr Gln Ala Leu Ser Ala Leu
        195                 200                 205

Met His Ile Lys Glu Thr Lys Gln Val Val Gly Lys Pro Ala Glu
    210                 215                 220

Glu Ile Lys Val Thr Phe
225                 230

<210> SEQ ID NO 102
<211> LENGTH: 522
<212> TYPE: DNA
<213> ORGANISM: Lactobacillus collinoides

<400> SEQUENCE: 102
atgagtgaag tagatgactt agtagctaga attgctgctc agctacaaca aagtggaaac      60
gcttctagtg cctcaactag tgccggtact tctgctggtt ccgagaaaga attaggcgca     120
gcagattacc cactatttga aaagcaccca gatcaaatca agacgccatc aggtaaaaat     180
gttgaagaaa tcaccttgga aaatgttatt aacggcaagg tagacgcaaa ggatatgcgg     240
attacgcccg caaccctgaa gttacaaggt gaaattgctg ccaacgcagg tcggccagca     300
atccaacgga acttccagcg ggcttctgaa ttaacttcag ttcccgatga tgttgttttg     360
gacttatata attcattacg gccattccgt tcaaccaagc aagaattatt ggataccgcc     420
aaggagcttc gtgacaagta tcacgcacct atctgtgccg gctggttcga agaagcagcc     480
gaaaactacg aagtcaacaa gaagttgaag ggcgataact ag                        522

<210> SEQ ID NO 103
<211> LENGTH: 173
<212> TYPE: PRT
<213> ORGANISM: Lactobacillus collinoides

<400> SEQUENCE: 103

Met Ser Glu Val Asp Asp Leu Val Ala Arg Ile Ala Ala Gln Leu Gln
1               5                  10                  15

Gln Ser Gly Asn Ala Ser Ser Ala Ser Thr Ser Ala Gly Thr Ser Ala
            20                  25                  30

Gly Ser Glu Lys Glu Leu Gly Ala Ala Asp Tyr Pro Leu Phe Glu Lys
        35                  40                  45

His Pro Asp Gln Ile Lys Thr Pro Ser Gly Lys Asn Val Glu Glu Ile
    50                  55                  60

Thr Leu Glu Asn Val Ile Asn Gly Lys Val Asp Ala Lys Asp Met Arg
65                  70                  75                  80

Ile Thr Pro Ala Thr Leu Lys Leu Gln Gly Glu Ile Ala Ala Asn Ala
                85                  90                  95

Gly Arg Pro Ala Ile Gln Arg Asn Phe Gln Arg Ala Ser Glu Leu Thr
            100                 105                 110

Ser Val Pro Asp Asp Val Val Leu Asp Leu Tyr Asn Ser Leu Arg Pro
        115                 120                 125

Phe Arg Ser Thr Lys Gln Glu Leu Leu Asp Thr Ala Lys Glu Leu Arg
    130                 135                 140

Asp Lys Tyr His Ala Pro Ile Cys Ala Gly Trp Phe Glu Glu Ala Ala
145                 150                 155                 160

Glu Asn Tyr Glu Val Asn Lys Lys Leu Lys Gly Asp Asn
```

<210> SEQ ID NO 104
<211> LENGTH: 1665
<212> TYPE: DNA
<213> ORGANISM: Klebsiella pneumoniae

<400> SEQUENCE: 104

```
atgagatcga aagatttga agcactggcg aaacgccctg tgaatcagga tggtttcgtt      60
aaggagtgga ttgaagaggg ctttatcgcg atggaaagtc ctaacgatcc caaaccttct    120
atccgcatcg tcaacggcgc ggtgaccgaa ctcgacggta aaccggttga cgagttcgac    180
ctgattgacc actttatcgc gcgctacggc attaatctcg cccgggccga agaagtgatg    240
gccatggatt cggttaagct cgccaacatg ctctgcgacc cgaacgttaa acgcagcgac    300
atcgtgccgc tcactaccgc gatgaccccg gcgaaaatcg tggaagtggt gtcgcatatg    360
aacgtggtcg agatgatgat ggcgatgcaa aaaatgcgcg cccgccgcac gccgtcccag    420
caggcgcatg tcactaatat caaagataat ccggtacaga ttgccgccga cgccgctgaa    480
ggcgcatggc gcggctttga cgaacaggag accaccgtcg ccgtggcgcg ctacgcgcgg    540
ttcaacgcca tcgccctgct ggtgggttca caggttggcc gccccggcgt cctcacccag    600
tgttcgctgg aagaagccac cgagctgaaa ctgggcatgc tgggccacac ctgctatgcc    660
gaaaccattt cggtatacgg tacgaaccg gtgtttaccg atggcgatga cactccatgg     720
tcgaaaggct cctcgcctc ctcctacgcc tcgcgcggcc tgaaaatgcg ctttacctcc      780
ggttccggtt ctgaagtaca gatgggctat gccgaaggca aatcgatgct ttatctcgaa    840
gcgcgctgca tctacatcac caaagccgcc ggggtgcaag gcctgcagaa tggctccgtc    900
agctgtatcg gcgtaccgtc cgccgtgccg tccgggatcc gcgccgtact ggcggaaaac    960
ctgatctgct cagcgctgga tctggagtgc gcctccagca acgatcaaac ctttacccac   1020
tcggatatgc ggcgtaccgc gcgtctgctg atgcagttcc tgccaggcac cgacttcatc   1080
tcctccggtt actcggcggt gcccaactac gacaacatgt cgccggttc caacgaagat    1140
gccgaagact tcgatgacta caacgtgatc cagcgcgacc tgaaggtcga tggggtctg    1200
cggccggtgc gtgaagagga cgtgatcgcc attcgcaaca agccgcccg cgcgctgcag    1260
gcggtatttg ccggcatggg tttgccgcct attacggatg aagaggtaga agccgccacc   1320
tacgcccacg gttcaaaaga tatgcctgag cgcaatatcg tcgaggacat caagtttgct   1380
caggagatca tcaacaagaa ccgcaacggc ctggaggtgg tgaaagccct ggcgaaaggc   1440
ggcttccccg atgtcgccca ggacatgctc aatattcaga aagccaagct caccggcgac   1500
tacctgcata cctccgccat cattgttggc gagggccagg tgctctcggc cgtgaatgac   1560
gtgaacgatt atgccggtcc ggcaacaggc taccgcctgc aaggcgagcg ctgggaagag   1620
attaaaaata tcccgggcgc gctcgatccc aatgaacttg ctaa                    1665
```

<210> SEQ ID NO 105
<211> LENGTH: 554
<212> TYPE: PRT
<213> ORGANISM: Klebsiella pneumoniae

<400> SEQUENCE: 105

```
Met Arg Ser Lys Arg Phe Glu Ala Leu Ala Lys Arg Pro Val Asn Gln
1               5                   10                  15

Asp Gly Phe Val Lys Glu Trp Ile Glu Glu Gly Phe Ile Ala Met Glu
            20                  25                  30
```

```
Ser Pro Asn Asp Pro Lys Pro Ser Ile Arg Ile Val Asn Gly Ala Val
    35                  40                  45
Thr Glu Leu Asp Gly Lys Pro Val Asp Glu Phe Asp Leu Ile Asp His
50                  55                  60
Phe Ile Ala Arg Tyr Gly Ile Asn Leu Ala Arg Ala Glu Glu Val Met
65                  70                  75                  80
Ala Met Asp Ser Val Lys Leu Ala Asn Met Leu Cys Asp Pro Asn Val
                85                  90                  95
Lys Arg Ser Asp Ile Val Pro Leu Thr Thr Ala Met Thr Pro Ala Lys
            100                 105                 110
Ile Val Glu Val Val Ser His Met Asn Val Val Glu Met Met Met Ala
        115                 120                 125
Met Gln Lys Met Arg Ala Arg Arg Thr Pro Ser Gln Gln Ala His Val
    130                 135                 140
Thr Asn Ile Lys Asp Asn Pro Val Gln Ile Ala Ala Asp Ala Ala Glu
145                 150                 155                 160
Gly Ala Trp Arg Gly Phe Asp Glu Gln Glu Thr Thr Val Ala Val Ala
                165                 170                 175
Arg Tyr Ala Arg Phe Asn Ala Ile Ala Leu Leu Val Gly Ser Gln Val
            180                 185                 190
Gly Arg Pro Gly Val Leu Thr Gln Cys Ser Leu Glu Glu Ala Thr Glu
        195                 200                 205
Leu Lys Leu Gly Met Leu Gly His Thr Cys Tyr Ala Glu Thr Ile Ser
    210                 215                 220
Val Tyr Gly Thr Glu Pro Val Phe Thr Asp Gly Asp Thr Pro Trp
225                 230                 235                 240
Ser Lys Gly Phe Leu Ala Ser Ser Tyr Ala Ser Arg Gly Leu Lys Met
                245                 250                 255
Arg Phe Thr Ser Gly Ser Gly Ser Glu Val Gln Met Gly Tyr Ala Glu
            260                 265                 270
Gly Lys Ser Met Leu Tyr Leu Glu Ala Arg Cys Ile Tyr Ile Thr Lys
        275                 280                 285
Ala Ala Gly Val Gln Gly Leu Gln Asn Gly Ser Val Ser Cys Ile Gly
    290                 295                 300
Val Pro Ser Ala Val Pro Ser Gly Ile Arg Ala Val Leu Ala Glu Asn
305                 310                 315                 320
Leu Ile Cys Ser Ala Leu Asp Leu Glu Cys Ala Ser Ser Asn Asp Gln
                325                 330                 335
Thr Phe Thr His Ser Asp Met Arg Thr Ala Arg Leu Leu Met Gln
            340                 345                 350
Phe Leu Pro Gly Thr Asp Phe Ile Ser Ser Gly Tyr Ser Ala Val Pro
        355                 360                 365
Asn Tyr Asp Asn Met Phe Ala Gly Ser Asn Glu Asp Ala Glu Asp Phe
    370                 375                 380
Asp Asp Tyr Asn Val Ile Gln Arg Asp Leu Lys Val Asp Gly Gly Leu
385                 390                 395                 400
Arg Pro Val Arg Glu Glu Asp Val Ile Ala Ile Arg Asn Lys Ala Ala
                405                 410                 415
Arg Ala Leu Gln Ala Val Phe Ala Gly Met Gly Leu Pro Pro Ile Thr
            420                 425                 430
Asp Glu Glu Val Glu Ala Ala Thr Tyr Ala His Gly Ser Lys Asp Met
        435                 440                 445
Pro Glu Arg Asn Ile Val Glu Asp Ile Lys Phe Ala Gln Glu Ile Ile
    450                 455                 460
```

Asn Lys Asn Arg Asn Gly Leu Glu Val Val Lys Ala Leu Ala Lys Gly
465                 470                 475                 480

Gly Phe Pro Asp Val Ala Gln Asp Met Leu Asn Ile Gln Lys Ala Lys
                485                 490                 495

Leu Thr Gly Asp Tyr Leu His Thr Ser Ala Ile Ile Val Gly Glu Gly
            500                 505                 510

Gln Val Leu Ser Ala Val Asn Asp Val Asn Asp Tyr Ala Gly Pro Ala
        515                 520                 525

Thr Gly Tyr Arg Leu Gln Gly Glu Arg Trp Glu Glu Ile Lys Asn Ile
    530                 535                 540

Pro Gly Ala Leu Asp Pro Asn Glu Leu Gly
545                 550

<210> SEQ ID NO 106
<211> LENGTH: 687
<212> TYPE: DNA
<213> ORGANISM: Klebsiella pneumoniae

<400> SEQUENCE: 106

```
atggaaatta acgaaacgct gctgcgccag attatcgaag aggtgctgtc ggagatgaaa      60
tcaggcgcag ataagccggt ctcctttagc gcgccggcgt ctgtcgcctc tgccgcgccg     120
gtcgccgttg cgcctgtgtc cggcgacagc ttcctgacgg aaatcggcga agccaaaccc     180
ggcacgcagc aggatgaagt cattattgcc gtcgggccag cgtttggtct ggcgcaaacc     240
gccaatatcg tcggcattcc gcataaaaat attctgcgcg aagtgatcgc cggcattgag     300
gaagaaggca tcaaagcccg ggtgatccgc tgctttaagt catctgacgt cgccttcgtg     360
gcagtggaag caaccgcct gagcggctcc ggcatctcga tcggtattca gtcgaaaggc     420
accaccgtca tccaccagcg cggcctgccg ccgctttcca atctggaact cttcccgcag     480
gcgccgctgt taacgctgga aacctaccgt cagattggca aaaacgccgc gcgctacgcc     540
aaacgcgagt cgccgcagcc ggtgccgacg cttaacgatc agatggctcg tcccaaatac     600
caggcgaagt cggccatttt gcacattaaa gagaccaaat acgtggtgac gggcaaaaac     660
ccgcaggaac tgcgcgtggc gctttaa                                         687
```

<210> SEQ ID NO 107
<211> LENGTH: 228
<212> TYPE: PRT
<213> ORGANISM: Klebsiella pneumoniae

<400> SEQUENCE: 107

Met Glu Ile Asn Glu Thr Leu Leu Arg Gln Ile Ile Glu Glu Val Leu
1               5                   10                  15

Ser Glu Met Lys Ser Gly Ala Asp Lys Pro Val Ser Phe Ser Ala Pro
            20                  25                  30

Ala Ser Val Ala Ser Ala Ala Pro Val Ala Val Ala Pro Val Ser Gly
        35                  40                  45

Asp Ser Phe Leu Thr Glu Ile Gly Glu Ala Lys Pro Gly Thr Gln Gln
    50                  55                  60

Asp Glu Val Ile Ile Ala Val Gly Pro Ala Phe Gly Leu Ala Gln Thr
65                  70                  75                  80

Ala Asn Ile Val Gly Ile Pro His Lys Asn Ile Leu Arg Glu Val Ile
                85                  90                  95

Ala Gly Ile Glu Glu Glu Gly Ile Lys Ala Arg Val Ile Arg Cys Phe
            100                 105                 110

Lys Ser Ser Asp Val Ala Phe Val Ala Val Glu Gly Asn Arg Leu Ser
        115                 120                 125

Gly Ser Gly Ile Ser Ile Gly Ile Gln Ser Lys Gly Thr Thr Val Ile
    130                 135                 140

His Gln Arg Gly Leu Pro Pro Leu Ser Asn Leu Glu Leu Phe Pro Gln
145                 150                 155                 160

Ala Pro Leu Leu Thr Leu Glu Thr Tyr Arg Gln Ile Gly Lys Asn Ala
                165                 170                 175

Ala Arg Tyr Ala Lys Arg Glu Ser Pro Gln Pro Val Pro Thr Leu Asn
            180                 185                 190

Asp Gln Met Ala Arg Pro Lys Tyr Gln Ala Lys Ser Ala Ile Leu His
        195                 200                 205

Ile Lys Glu Thr Lys Tyr Val Val Thr Gly Lys Asn Pro Gln Glu Leu
    210                 215                 220

Arg Val Ala Leu
225

<210> SEQ ID NO 108
<211> LENGTH: 525
<212> TYPE: DNA
<213> ORGANISM: Klebsiella pneumoniae

<400> SEQUENCE: 108
atgaataccg acgcaattga atccatggta cgcgacgtgc tgagccggat gaacagccta      60
caggacgggg taacgcccgc gccagccgcg ccgacaaacg acaccgttcg ccagccaaaa     120
gttagcgact acccgttagc gacctgccat ccggagtggg tcaaaaccgc taccaataaa     180
acgctcgatg acctgacgct ggagaacgta ttaagcgatc gcgttacggg caggacatg      240 cgcatcactc cggaaacgct gcgtatgcag gcggcgatcg cccaggatgc cggacgcgat     300
cggctggcga tgaactttga gcgggccgca gagctcaccg cggttcccga cgaccgaatc     360
cttgagatct acaacgccct cgcccatac cgttccaccc aggcggagct actggcgatc     420
gctgatgacc tcgagcatcg ctaccaggca cgactctgtg ccgcctttgt tcgggaagcg     480
gccgggctgt acatcgagcg taagaagctg aaaggcgacg attaa                    525

<210> SEQ ID NO 109
<211> LENGTH: 174
<212> TYPE: PRT
<213> ORGANISM: Klebsiella pneumoniae

<400> SEQUENCE: 109

Met Asn Thr Asp Ala Ile Glu Ser Met Val Arg Asp Val Leu Ser Arg
1               5                   10                  15

Met Asn Ser Leu Gln Asp Gly Val Thr Pro Ala Pro Ala Ala Pro Thr
            20                  25                  30

Asn Asp Thr Val Arg Gln Pro Lys Val Ser Asp Tyr Pro Leu Ala Thr
        35                  40                  45

Cys His Pro Glu Trp Val Lys Thr Ala Thr Asn Lys Thr Leu Asp Asp
    50                  55                  60

Leu Thr Leu Glu Asn Val Leu Ser Asp Arg Val Thr Ala Gln Asp Met
65                  70                  75                  80

Arg Ile Thr Pro Glu Thr Leu Arg Met Gln Ala Ala Ile Ala Gln Asp
                85                  90                  95

Ala Gly Arg Asp Arg Leu Ala Met Asn Phe Glu Arg Ala Ala Glu Leu
            100                 105                 110

Thr Ala Val Pro Asp Asp Arg Ile Leu Glu Ile Tyr Asn Ala Leu Arg

```
                 115                 120                 125
Pro Tyr Arg Ser Thr Gln Ala Glu Leu Leu Ala Ile Ala Asp Asp Leu
    130                 135                 140

Glu His Arg Tyr Gln Ala Arg Leu Cys Ala Ala Phe Val Arg Glu Ala
145                 150                 155                 160

Ala Gly Leu Tyr Ile Glu Arg Lys Lys Leu Lys Gly Asp Asp
                165                 170

<210> SEQ ID NO 110
<211> LENGTH: 1833
<212> TYPE: DNA
<213> ORGANISM: Klebsiella oxytoca

<400> SEQUENCE: 110
atgcgatata tagctggcat tgatatcggc aactcatcga cggaagtcgc cctggcgacc     60
ctggatgagg ctggcgcgct gacgatcacc cacagcgcgc tggcggaaac caccggaatc    120
aaaggcacgt tgcgtaacgt gttcgggatt caggaggcgc tcgccctcgt cgccagaggc    180
gccgggatcg ccgtcagcga tatttcgctc atccgcatca acgaagcgac gccggtgatt    240
ggcgatgtgg cgatggaaac cattaccgaa accatcatca ccgaatcgac catgatcggc    300
cataacccga aaacgcccgg cggcgcgggg cttggcacag gcatcaccat tacgccgcag    360
gagctgctaa cccgcccggc ggacgcgccc tatatcctgg tggtgtcgtc ggcgttcgat    420
tttgccgata tcgccagcgt gattaacgct tccctgcgcg ccgggtatca gattaccggc    480 gtcatttta c agcgcgacga tggcgtgctg gtcagcaacc ggctggaaaa accgctgccg    540
atcgttgacg aagtgctgta catcgaccgc attccgctgg ggatgctggc ggcgattgag    600
gtcgccgttc cggggaaggt catcgaaacc ctctctaacc cttacggcat cgccaccgtc    660
tttaacctca gccccgagga gacgaagaac atcgtcccga tggcccgggc gctgattggc    720
aaccgttccg ccgtggtggt caaaacgcca tccggcgacg tcaaagcgcg cgcgataccc    780
gccggtaatc ttgagctgct ggcccagggc cgtagcgtgc gcgtggatgt ggccgccggc    840
gccgaagcca tcatgaaagc ggtcgacggc tgcggcaggc tcgataacgt caccggcgaa    900
tccggcacca atatcggcgg catgctggaa cacgtgcgcc agaccatggc cgagctgacc    960
aacaagccga gcagcgaaat atttattcag gacctgctgg ccgttgatac ctcggtaccg   1020
gtgagcgtta ccggcggtct ggccggggag ttctcgctgg agcaggccgt gggcatcgcc   1080
tcgatggtga atcggatcg cctgcagatg gcaatgatcg cccgcgaaat cgagcagaag   1140
ctcaatatcg acgtgcagat cggcggcgca gaggccgaag ccgccatcct gggggcgctg   1200
accacgccgg gcaccacccg accgctggcg atcctcgacc tcggcgcggg ctccaccgat   1260
gcctccatca tcaaccccaa aggcgacatc atcgccaccc atctcgccgg cgcaggcgac   1320
atggtgacga tgattattgc ccgcgagctg gggctggaag accgctatct ggcggaagag   1380
atcaagaagt acccgctggc taaggtggaa agcctgttcc atttacgcca cgaggacggc   1440
agcgtgcagt tcttctccac gccgctgccg ccgccgtgt cgccgcgt ctgcgtggtg   1500 aaagcggaca aactggtgcc gctgcccggc gatttagcgc tggaaaaagt gcgcgccatt   1560
cgccgcagcg ccaaagagcg ggtctttgtc accaacgccc tgcgcgcgct cgtcaggtc   1620 agccccaccg gcaacattcg cgatattccg ttcgtggtgc tggtcggcgg ttcgtcgctg   1680 gattttcgaag tcccgcagct ggtcaccgat gcgctggcgc actaccgcct ggttgccgga   1740
cggggaaata ttcgcggcag cgagggcccc cgaaacgcgg tggccaccgg cctgattctc   1800
tcctggcata aggagtttgc gcatgaacgg taa                                1833
```

<210> SEQ ID NO 111
<211> LENGTH: 610
<212> TYPE: PRT
<213> ORGANISM: Klebsiella oxytoca

<400> SEQUENCE: 111

```
Met Arg Tyr Ile Ala Gly Ile Asp Ile Gly Asn Ser Ser Thr Glu Val
1               5                   10                  15

Ala Leu Ala Thr Leu Asp Glu Ala Gly Ala Leu Thr Ile Thr His Ser
            20                  25                  30

Ala Leu Ala Glu Thr Thr Gly Ile Lys Gly Thr Leu Arg Asn Val Phe
        35                  40                  45

Gly Ile Gln Glu Ala Leu Ala Leu Val Ala Arg Gly Ala Gly Ile Ala
    50                  55                  60

Val Ser Asp Ile Ser Leu Ile Arg Ile Asn Glu Ala Thr Pro Val Ile
65                  70                  75                  80

Gly Asp Val Ala Met Glu Thr Ile Thr Glu Thr Ile Ile Thr Glu Ser
                85                  90                  95

Thr Met Ile Gly His Asn Pro Lys Thr Pro Gly Gly Ala Gly Leu Gly
            100                 105                 110

Thr Gly Ile Thr Ile Thr Pro Gln Glu Leu Leu Thr Arg Pro Ala Asp
        115                 120                 125

Ala Pro Tyr Ile Leu Val Val Ser Ala Phe Asp Phe Ala Asp Ile
    130                 135                 140

Ala Ser Val Ile Asn Ala Ser Leu Arg Ala Gly Tyr Gln Ile Thr Gly
145                 150                 155                 160

Val Ile Leu Gln Arg Asp Asp Gly Val Leu Val Ser Asn Arg Leu Glu
                165                 170                 175

Lys Pro Leu Pro Ile Val Asp Glu Val Leu Tyr Ile Asp Arg Ile Pro
            180                 185                 190

Leu Gly Met Leu Ala Ala Ile Glu Val Ala Val Pro Gly Lys Val Ile
        195                 200                 205

Glu Thr Leu Ser Asn Pro Tyr Gly Ile Ala Thr Val Phe Asn Leu Ser
    210                 215                 220

Pro Glu Glu Thr Lys Asn Ile Val Pro Met Ala Arg Ala Leu Ile Gly
225                 230                 235                 240

Asn Arg Ser Ala Val Val Lys Thr Pro Ser Gly Asp Val Lys Ala
                245                 250                 255

Arg Ala Ile Pro Ala Gly Asn Leu Glu Leu Leu Ala Gln Gly Arg Ser
            260                 265                 270

Val Arg Val Asp Val Ala Ala Gly Ala Glu Ala Ile Met Lys Ala Val
        275                 280                 285

Asp Gly Cys Gly Arg Leu Asp Asn Val Thr Gly Glu Ser Gly Thr Asn
    290                 295                 300

Ile Gly Gly Met Leu Glu His Val Arg Gln Thr Met Ala Glu Leu Thr
305                 310                 315                 320

Asn Lys Pro Ser Ser Glu Ile Phe Ile Gln Asp Leu Leu Ala Val Asp
                325                 330                 335

Thr Ser Val Pro Val Ser Val Thr Gly Gly Leu Ala Gly Glu Phe Ser
            340                 345                 350

Leu Glu Gln Ala Val Gly Ile Ala Ser Met Val Lys Ser Asp Arg Leu
        355                 360                 365

Gln Met Ala Met Ile Ala Arg Glu Ile Glu Gln Lys Leu Asn Ile Asp
    370                 375                 380
```

Val Gln Ile Gly Gly Ala Glu Ala Ala Ile Leu Gly Ala Leu
385                 390                 395                 400

Thr Thr Pro Gly Thr Thr Arg Pro Leu Ala Ile Leu Asp Leu Gly Ala
            405                 410                 415

Gly Ser Thr Asp Ala Ser Ile Ile Asn Pro Lys Gly Asp Ile Ile Ala
            420                 425                 430

Thr His Leu Ala Gly Ala Gly Asp Met Val Thr Met Ile Ile Ala Arg
            435                 440                 445

Glu Leu Gly Leu Glu Asp Arg Tyr Leu Ala Glu Ile Lys Lys Tyr
450                 455                 460

Pro Leu Ala Lys Val Glu Ser Leu Phe His Leu Arg His Glu Asp Gly
465                 470                 475                 480

Ser Val Gln Phe Phe Ser Thr Pro Leu Pro Pro Ala Val Phe Ala Arg
            485                 490                 495

Val Cys Val Val Lys Ala Asp Glu Leu Val Pro Leu Pro Gly Asp Leu
            500                 505                 510

Ala Leu Glu Lys Val Arg Ala Ile Arg Arg Ser Ala Lys Glu Arg Val
            515                 520                 525

Phe Val Thr Asn Ala Leu Arg Ala Leu Arg Gln Val Ser Pro Thr Gly
530                 535                 540

Asn Ile Arg Asp Ile Pro Phe Val Val Leu Val Gly Gly Ser Ser Leu
545                 550                 555                 560

Asp Phe Glu Val Pro Gln Leu Val Thr Asp Ala Leu Ala His Tyr Arg
            565                 570                 575

Leu Val Ala Gly Arg Gly Asn Ile Arg Gly Ser Glu Gly Pro Arg Asn
            580                 585                 590

Ala Val Ala Thr Gly Leu Ile Leu Ser Trp His Lys Glu Phe Ala His
            595                 600                 605

Glu Arg
    610

<210> SEQ ID NO 112
<211> LENGTH: 378
<212> TYPE: DNA
<213> ORGANISM: Klebsiella oxytoca

<400> SEQUENCE: 112
atgaacggta atcacagcgc cccggccatc gcgatcgccg tcatcgacgg ctgcgacggc      60
ctgtggcgcg aagtgctgct gggtatcgaa gaggaaggta tccctttccg gctccagcat     120 caccggccg agaggtcgt ggacagcgcc tggcaggcgg cgcgcagctc gccgctgctg      180
gtgggcatcg cctgcgaccg ccatatgctg gtcgtgcact acaagaattt acccgcatcg     240
gcgccgcttt ttacgctgat gcatcatcag gacagtcagg cccatcgcaa caccggtaat     300
aacgcggcac ggctggtcaa ggggatccct ttccgggatc tgaatagcga agcaacagga     360
gaacagcagg atgaataa                                                    378

<210> SEQ ID NO 113
<211> LENGTH: 125
<212> TYPE: PRT
<213> ORGANISM: Klebsiella oxytoca

<400> SEQUENCE: 113

Met Asn Gly Asn His Ser Ala Pro Ala Ile Ala Ile Ala Val Ile Asp
1               5                   10                  15

Gly Cys Asp Gly Leu Trp Arg Glu Val Leu Leu Gly Ile Glu Glu Glu

|  | 20 |  |  | 25 |  |  |  | 30 |  |  |  |
|---|---|---|---|---|---|---|---|---|---|---|---|

Gly Ile Pro Phe Arg Leu Gln His His Pro Ala Gly Glu Val Val Asp
                35                      40                      45

Ser Ala Trp Gln Ala Ala Arg Ser Ser Pro Leu Leu Val Gly Ile Ala
        50                      55                      60

Cys Asp Arg His Met Leu Val Val His Tyr Lys Asn Leu Pro Ala Ser
65                      70                      75                      80

Ala Pro Leu Phe Thr Leu Met His His Gln Asp Ser Gln Ala His Arg
                85                      90                      95

Asn Thr Gly Asn Asn Ala Ala Arg Leu Val Lys Gly Ile Pro Phe Arg
                100                     105                     110

Asp Leu Asn Ser Glu Ala Thr Gly Glu Gln Gln Asp Glu
                115                     120                     125

<210> SEQ ID NO 114
<211> LENGTH: 1833
<212> TYPE: DNA
<213> ORGANISM: Salmonella typhimurium

<400> SEQUENCE: 114

```
atgcgatata tagctggcat tgacatcggt aactcatcaa cggaagtcgc actggcgcgg      60
caagatgaga ctggcgcact gacgattaca cacagcgcgc tggcggaaac caccgggatc     120
aaaggcacgt tgcgtaacgt gttcggcatt caggaagcgc tcgccctcgt cgcaaagcgc     180
gcggggatca atgtcagaga tatttcgctc atccgcatta cgaagccac gccggtgatt      240
ggcgatgtgg cgatggaaac cattaccgaa accatcatca ccgaatcgac aatgatcggc     300
cataacccaa aaacgccggg cggagcaggc cttggtgtgg gtatcacgat tacgccggag     360
gagctgttaa cccgcccggc ggactcgtcc tatattctgg tggtatcgtc agcctttgat     420
tttgctgata tcgccaatgt tatcaacgcc tcaatgcgcg ccggatacca gattaccggc     480
gtcattttgc agcgcgacga tggcgtactg gtcagcaacc ggctggaaaa atcgctaccg     540
attgtcgatg aagttctgta catcgaccgc attccgctgg ggatgctggc ggcgattgaa     600
gtcgccgtgc cgggaaaggt tatcgaaacc ctctctaacc cttacggcat cgccaccgta     660
tttaatctca cgccgatga acaaaaaaac atcgtcccga tggcgcgcgc gctgattggc     720
aaccgttccg ccgtggtggt aaaaacgcca tccggcgacg tcaaagcgcg cgcaatacc     780
gccggtaacc tggagctgca ggctcagggt cgtaccgtgc gcgtggatgt gccgccggt     840
gccgaagcca tcatgaaagc ggtggacggt tgcggcaagc tcgacaacgt caccggcgag     900
gccgggacca atatcggcgg catgctggag cacgtgcgcc agaccatggc cgaactgacc     960
aacaagccga gcagtgagat tttcattcag gatctactgg ccgttgacac ctcggttccg    1020
gtgagcgtca ccggcggtct ggccggggag ttctcgctgg agcaggccgt cggcatcgcc    1080
tcgatggtga atcagaccg tctgcagatg gcgatgattg cccgtgaaat tgagcagaag    1140
cttaatatcg acgtgcagat cggcggcgct gaggctgaag ccgccattct gggcgcgctg    1200
accacgccgg gtaccaccg accgctggcg atcctcgacc tcggcgcggg ctccaccgat    1260
gcctccatca tcaaccctaa aggcgaaatc atcgccaccc atctcgccgg gcaggcgac    1320
atggtcacga tgattattgc cgcgaactg gggctgaag accgctatct ggcggaagag    1380
atcaaaaaat acccgctggc taaggtcgaa agcctgttcc acttacgcca cgaggacggc    1440
agcgtccagt tcttcccgac gccgctgcct ccgccgtgt tcgcccgcgt ctgcgtggtg    1500
aaaccggacg aactggtgcc gcttcccggc gacttagcgc tggaaaaagt gcgcgccatt    1560
```

-continued

```
cgccgcagcg ctaaagaacg cgtctttgtc accaacgccc tgcgcgcgct gcgccaggtc    1620
agtccaaccg gcaacattcg cgatattccg ttcgtggtgc tggtcggcgg ctcgtcgctg    1680
gatttcgaag ttccgcagct ggtcaccgat gcgctggcgc actaccgcct ggtcgccggg    1740
cgaggaaata ttcgcggcag cgaaggccca agaaacgcgg tggccaccgg cctgattctc    1800
tcctggcata aggagtttgc gcatggacag taa                                 1833
```

<210> SEQ ID NO 115
<211> LENGTH: 610
<212> TYPE: PRT
<213> ORGANISM: Salmonella typhimurium

<400> SEQUENCE: 115

```
Met Arg Tyr Ile Ala Gly Ile Asp Ile Gly Asn Ser Ser Thr Glu Val
1               5                   10                  15

Ala Leu Ala Arg Gln Asp Glu Thr Gly Ala Leu Thr Ile Thr His Ser
            20                  25                  30

Ala Leu Ala Glu Thr Thr Gly Ile Lys Gly Thr Leu Arg Asn Val Phe
        35                  40                  45

Gly Ile Gln Glu Ala Leu Ala Leu Val Ala Lys Arg Ala Gly Ile Asn
    50                  55                  60

Val Arg Asp Ile Ser Leu Ile Arg Ile Asn Glu Ala Thr Pro Val Ile
65                  70                  75                  80

Gly Asp Val Ala Met Glu Thr Ile Thr Glu Thr Ile Ile Thr Glu Ser
                85                  90                  95

Thr Met Ile Gly His Asn Pro Lys Thr Pro Gly Gly Ala Gly Leu Gly
            100                 105                 110

Val Gly Ile Thr Ile Thr Pro Glu Glu Leu Leu Thr Arg Pro Ala Asp
        115                 120                 125

Ser Ser Tyr Ile Leu Val Val Ser Ser Ala Phe Asp Phe Ala Asp Ile
    130                 135                 140

Ala Asn Val Ile Asn Ala Ser Met Arg Ala Gly Tyr Gln Ile Thr Gly
145                 150                 155                 160

Val Ile Leu Gln Arg Asp Asp Gly Val Leu Val Ser Asn Arg Leu Glu
                165                 170                 175

Lys Ser Leu Pro Ile Val Asp Glu Val Leu Tyr Ile Asp Arg Ile Pro
            180                 185                 190

Leu Gly Met Leu Ala Ala Ile Glu Val Ala Val Pro Gly Lys Val Ile
        195                 200                 205

Glu Thr Leu Ser Asn Pro Tyr Gly Ile Ala Thr Val Phe Asn Leu Asn
    210                 215                 220

Ala Asp Glu Thr Lys Asn Ile Val Pro Met Ala Arg Ala Leu Ile Gly
225                 230                 235                 240

Asn Arg Ser Ala Val Val Lys Thr Pro Ser Gly Asp Val Lys Ala
                245                 250                 255

Arg Ala Ile Pro Ala Gly Asn Leu Glu Leu Gln Ala Gln Gly Arg Thr
            260                 265                 270

Val Arg Val Asp Val Ala Ala Gly Ala Glu Ala Ile Met Lys Ala Val
        275                 280                 285

Asp Gly Cys Gly Lys Leu Asp Asn Val Thr Gly Glu Ala Gly Thr Asn
    290                 295                 300

Ile Gly Gly Met Leu Glu His Val Arg Gln Thr Met Ala Glu Leu Thr
305                 310                 315                 320

Asn Lys Pro Ser Ser Glu Ile Phe Ile Gln Asp Leu Leu Ala Val Asp
                325                 330                 335
```

```
Thr Ser Val Pro Val Ser Val Thr Gly Gly Leu Ala Gly Glu Phe Ser
            340                 345                 350

Leu Glu Gln Ala Val Gly Ile Ala Ser Met Val Lys Ser Asp Arg Leu
            355                 360                 365

Gln Met Ala Met Ile Ala Arg Glu Ile Glu Gln Lys Leu Asn Ile Asp
    370                 375                 380

Val Gln Ile Gly Gly Ala Glu Ala Glu Ala Ile Leu Gly Ala Leu
385                 390                 395                 400

Thr Thr Pro Gly Thr Thr Arg Pro Leu Ala Ile Leu Asp Leu Gly Ala
                405                 410                 415

Gly Ser Thr Asp Ala Ser Ile Ile Asn Pro Lys Gly Glu Ile Ile Ala
                420                 425                 430

Thr His Leu Ala Gly Ala Gly Asp Met Val Thr Met Ile Ile Ala Arg
            435                 440                 445

Glu Leu Gly Leu Glu Asp Arg Tyr Leu Ala Glu Ile Lys Lys Tyr
    450                 455                 460

Pro Leu Ala Lys Val Glu Ser Leu Phe His Leu Arg His Glu Asp Gly
465                 470                 475                 480

Ser Val Gln Phe Phe Pro Thr Pro Leu Pro Pro Ala Val Phe Ala Arg
                485                 490                 495

Val Cys Val Val Lys Pro Asp Glu Leu Val Pro Leu Pro Gly Asp Leu
                500                 505                 510

Ala Leu Glu Lys Val Arg Ala Ile Arg Arg Ser Ala Lys Glu Arg Val
            515                 520                 525

Phe Val Thr Asn Ala Leu Arg Ala Leu Arg Gln Val Ser Pro Thr Gly
    530                 535                 540

Asn Ile Arg Asp Ile Pro Phe Val Leu Val Gly Gly Ser Ser Leu
545                 550                 555                 560

Asp Phe Glu Val Pro Gln Leu Val Thr Asp Ala Leu Ala His Tyr Arg
                565                 570                 575

Leu Val Ala Gly Arg Gly Asn Ile Arg Gly Ser Glu Gly Pro Arg Asn
            580                 585                 590

Ala Val Ala Thr Gly Leu Ile Leu Ser Trp His Lys Glu Phe Ala His
            595                 600                 605

Gly Gln
    610

<210> SEQ ID NO 116
<211> LENGTH: 372
<212> TYPE: DNA
<213> ORGANISM: Salmonella typhimurium

<400> SEQUENCE: 116
atggacagta atcacagcgc cccggctatc gtcattaccg ttatcaacga ctgcgccagc      60
ctctggcacg aagtgctgct gggcattgaa gaggaaggca tccctttcct gcttcagcat     120 caccggctg gagatatcgt tgacagcgcc tggcaggcgg cgcgcagctc gccgctgctg      180
gtcggcattg cctgcgatcg acactcgctg gtcgtgcatt acaagaattt acccgcatcg     240
gcgccgcttt ttacgctgat gcatcatcag gacagtcagg cccaacgcaa caccggtaat     300
aacgcggcac ggctggtcaa agggatccct ttcgggatct ccatgcttaa tcacaggaga     360
acggcagtat ga                                                         372

<210> SEQ ID NO 117
<211> LENGTH: 123
```

-continued

```
<212> TYPE: PRT
<213> ORGANISM: Salmonella typhimurium

<400> SEQUENCE: 117

Met Asp Ser Asn His Ser Ala Pro Ala Ile Val Ile Thr Val Ile Asn
1               5                   10                  15

Asp Cys Ala Ser Leu Trp His Glu Val Leu Leu Gly Ile Glu Glu Glu
            20                  25                  30

Gly Ile Pro Phe Leu Leu Gln His His Pro Ala Gly Asp Ile Val Asp
        35                  40                  45

Ser Ala Trp Gln Ala Ala Arg Ser Ser Pro Leu Leu Val Gly Ile Ala
    50                  55                  60

Cys Asp Arg His Ser Leu Val Val His Tyr Lys Asn Leu Pro Ala Ser
65                  70                  75                  80

Ala Pro Leu Phe Thr Leu Met His His Gln Asp Ser Gln Ala Gln Arg
                85                  90                  95

Asn Thr Gly Asn Asn Ala Ala Arg Leu Val Lys Gly Ile Pro Phe Gly
            100                 105                 110

Ile Ser Met Leu Asn His Arg Arg Thr Ala Val
        115                 120

<210> SEQ ID NO 118
<211> LENGTH: 1833
<212> TYPE: DNA
<213> ORGANISM: Lactobacillus collinoides

<400> SEQUENCE: 118
atgacacgtg taattggtgt tgatatcggg aattcctcta cagaagttgc gcttgctgat      60
gtgtctgaca gtggtgaagt aaatttcatt aattctggaa tttccgatac aactggcatt     120
aaaggtacta acaaaattt gatcggggtg cgtaaatcca tccagatcgt tttgaaaaag      180
tcgaatatgc aaatttccga tgttgacctg attcggatca acgaagcaac gcccgttatc    240
ggtgatgttg ccatggagac catcaccgaa acggtgatta ctgaatcgac gatgatcggc    300
cacaacccag ggactcctgg gggtgtcggt actggttctg gttacacggt gaatttgctt    360
gatttgttga gccaaacgga taaggatcgt ccttatatcg ttatcatctc gaaagaaatc    420
gattttgctg acgcagctaa gctgatcaac gctatgtgg cttctggtta taatattacc     480
gctgccattc tgcaaagtga tgatggggtg ctgatcaata atcggttgac ccataagatt    540
cccatcgtgg atgaagtctc acagatcgac aaggtaccgt tgaacatgct tgccgcagtg    600
gaagttgcac cgcctggcaa agtaattgct caactttcca acccgtatgg cattgccaca    660
ctgttcgaac tttcctctga gaaaccaag aacattgtgc cagttgcccg agccttaatc     720
ggaaaccggt cagcggttgt tattaaaacc cctgccggtg atgttaaagc tcgtgttatc    780
ccagccggga aaatcttgat caatggccaa ccgaatggtc atggtgaagt taacgttgcg    840
gctggtgccg atgccatcat gaaaaaggtg aacgagttcg atagtgtcga tgacattacc    900
ggtgaatcgg gcactaacgt tggtgggatg cttgaaaaag tcgtcaaac atggctgag      960 ttgaccgaca agcaaaatag cgacattgcc attcaagatt tattagctgt caatacgtcc   1020
gttccagtaa cggtgcgtgg tggtctggct ggtgaattct caatggaaca agccgttggg   1080
attgctgcta tggtcaaatc tgatcacttg caaatgcaag cgattgcaga cctgatgaaa   1140
gatgaatttc acgttcaagt cgaaatcggc ggtgctgaag ctgaatcagc catcctcggt   1200
gcgctaacaa cgccagggac gacaaaacca attgccatcc ttgatttggg ggctggttca   1260
acggatgcat caattatcaa ccaaaaggac gaaaaggtcg ctattcactt ggctggtgcc   1320
```

```
ggtgatatgg ttaccatgat catcaattct gaacttgggt tggaagaccc atatttagct    1380
gaggatatta agaaatatcc gctggctaaa gttgataatc tattccagct acggcatgaa    1440
gatggtgccg ttcaattctt tgaagatcca ttacctgctg atttatttgc cagagttgtg    1500
gctgttaaac cagatggtta cgaaccactt cctggtaatt tgagtatcga gaaagttaaa    1560
atcgtccgtc aaactgctaa gaagcgggtg ttcgtaacga acgcaattcg tgccttacac    1620
cacgttagcc caacaggtaa tatccgagat atcccatttg tggtcattgt cggcggctca    1680
gccctcgatt ttgaaattcc acaattggtc accgatgaat tatcacactt taacttagtt    1740
gcaggtcgtg gtaatattcg gggaattgaa ggtccacgga acgccgtggc aactggtttg    1800
attctttcat acgcgagtga agagggga tag                                   1833
```

<210> SEQ ID NO 119
<211> LENGTH: 610
<212> TYPE: PRT
<213> ORGANISM: Lactobacillus collinoides

<400> SEQUENCE: 119

```
Met Thr Arg Val Ile Gly Val Asp Ile Gly Asn Ser Ser Thr Glu Val
1               5                   10                  15

Ala Leu Ala Asp Val Ser Asp Ser Gly Glu Val Asn Phe Ile Asn Ser
            20                  25                  30

Gly Ile Ser Asp Thr Thr Gly Ile Lys Gly Thr Lys Gln Asn Leu Ile
        35                  40                  45

Gly Val Arg Lys Ser Ile Gln Ile Val Leu Lys Lys Ser Asn Met Gln
    50                  55                  60

Ile Ser Asp Val Asp Leu Ile Arg Ile Asn Glu Ala Thr Pro Val Ile
65                  70                  75                  80

Gly Asp Val Ala Met Glu Thr Ile Thr Glu Thr Val Ile Thr Glu Ser
                85                  90                  95

Thr Met Ile Gly His Asn Pro Gly Thr Pro Gly Gly Val Gly Thr Gly
            100                 105                 110

Ser Gly Tyr Thr Val Asn Leu Leu Asp Leu Leu Ser Gln Thr Asp Lys
        115                 120                 125

Asp Arg Pro Tyr Ile Val Ile Ile Ser Lys Glu Ile Asp Phe Ala Asp
    130                 135                 140

Ala Ala Lys Leu Ile Asn Ala Tyr Val Ala Ser Gly Tyr Asn Ile Thr
145                 150                 155                 160

Ala Ala Ile Leu Gln Ser Asp Asp Gly Val Leu Ile Asn Asn Arg Leu
                165                 170                 175

Thr His Lys Ile Pro Ile Val Asp Glu Val Ser Gln Ile Asp Lys Val
            180                 185                 190

Pro Leu Asn Met Leu Ala Ala Val Glu Val Ala Pro Pro Gly Lys Val
        195                 200                 205

Ile Ala Gln Leu Ser Asn Pro Tyr Gly Ile Ala Thr Leu Phe Glu Leu
    210                 215                 220

Ser Ser Glu Glu Thr Lys Asn Ile Val Pro Val Ala Arg Ala Leu Ile
225                 230                 235                 240

Gly Asn Arg Ser Ala Val Val Ile Lys Thr Pro Ala Gly Asp Val Lys
                245                 250                 255

Ala Arg Val Ile Pro Ala Gly Lys Ile Leu Ile Asn Gly Gln Pro Asn
            260                 265                 270

Gly His Gly Glu Val Asn Val Ala Ala Gly Ala Asp Ala Ile Met Lys
        275                 280                 285
```

Lys Val Asn Glu Phe Asp Ser Val Asp Asp Ile Thr Gly Glu Ser Gly
    290                 295                 300

Thr Asn Val Gly Gly Met Leu Glu Lys Val Arg Gln Thr Met Ala Glu
305                 310                 315                 320

Leu Thr Asp Lys Gln Asn Ser Asp Ile Ala Ile Gln Asp Leu Leu Ala
                325                 330                 335

Val Asn Thr Ser Val Pro Val Thr Val Arg Gly Gly Leu Ala Gly Glu
            340                 345                 350

Phe Ser Met Glu Gln Ala Val Gly Ile Ala Ala Met Val Lys Ser Asp
        355                 360                 365

His Leu Gln Met Gln Ala Ile Ala Asp Leu Met Lys Asp Glu Phe His
    370                 375                 380

Val Gln Val Glu Ile Gly Gly Ala Glu Ala Glu Ser Ala Ile Leu Gly
385                 390                 395                 400

Ala Leu Thr Thr Pro Gly Thr Thr Lys Pro Ile Ala Ile Leu Asp Leu
                405                 410                 415

Gly Ala Gly Ser Thr Asp Ala Ser Ile Ile Asn Gln Lys Asp Glu Lys
            420                 425                 430

Val Ala Ile His Leu Ala Gly Ala Gly Asp Met Val Thr Met Ile Ile
        435                 440                 445

Asn Ser Glu Leu Gly Leu Glu Asp Pro Tyr Leu Ala Glu Asp Ile Lys
    450                 455                 460

Lys Tyr Pro Leu Ala Lys Val Asp Asn Leu Phe Gln Leu Arg His Glu
465                 470                 475                 480

Asp Gly Ala Val Gln Phe Phe Glu Asp Pro Leu Pro Ala Asp Leu Phe
                485                 490                 495

Ala Arg Val Val Ala Val Lys Pro Asp Gly Tyr Glu Pro Leu Pro Gly
            500                 505                 510

Asn Leu Ser Ile Glu Lys Val Lys Ile Val Arg Gln Thr Ala Lys Lys
        515                 520                 525

Arg Val Phe Val Thr Asn Ala Ile Arg Ala Leu His His Val Ser Pro
    530                 535                 540

Thr Gly Asn Ile Arg Asp Ile Pro Phe Val Val Ile Val Gly Gly Ser
545                 550                 555                 560

Ala Leu Asp Phe Glu Ile Pro Gln Leu Val Thr Asp Glu Leu Ser His
                565                 570                 575

Phe Asn Leu Val Ala Gly Arg Gly Asn Ile Arg Gly Ile Glu Gly Pro
            580                 585                 590

Arg Asn Ala Val Ala Thr Gly Leu Ile Leu Ser Tyr Ala Ser Glu Lys
        595                 600                 605

Arg Gly
    610

<210> SEQ ID NO 120
<211> LENGTH: 351
<212> TYPE: DNA
<213> ORGANISM: Lactobacillus collinoides

<400> SEQUENCE: 120
atggcatttg attctgaacg tccgtcaatt ctattggcga caccaacggg ttctaatggc      60
caacttccag aagttctaaa accaatgctc aatggtattg aagaagaaca gattcctttt     120
cagattctcg atatggaagg cggttcagca gttgagcggg cttataacgc gtcagttgct     180
tcacgattat cagtgggcgt tgggtttgat gatgcacata tcattgtgca ttataaaaac     240

```
ttgaaaccag aaaaaccgct gtttgatgtt gccatcactg atgcagcatc cattcgtaaa    300
gttggcgcaa acgccgctcg acttgtaaag ggagttccat tcaagaagta a             351
```

<210> SEQ ID NO 121
<211> LENGTH: 116
<212> TYPE: PRT
<213> ORGANISM: Lactobacillus collinoides

<400> SEQUENCE: 121

Met Ala Phe Asp Ser Glu Arg Pro Ser Ile Leu Leu Ala Thr Pro Thr
1               5                   10                  15

Gly Ser Asn Gly Gln Leu Pro Glu Val Leu Lys Pro Met Leu Asn Gly
            20                  25                  30

Ile Glu Glu Gln Ile Pro Phe Gln Ile Leu Asp Met Glu Gly Gly
        35                  40                  45

Ser Ala Val Glu Arg Ala Tyr Asn Ala Ser Val Ala Ser Arg Leu Ser
    50                  55                  60

Val Gly Val Gly Phe Asp Asp Ala His Ile Ile Val His Tyr Lys Asn
65                  70                  75                  80

Leu Lys Pro Glu Lys Pro Leu Phe Asp Val Ala Ile Thr Asp Ala Ala
                85                  90                  95

Ser Ile Arg Lys Val Gly Ala Asn Ala Ala Arg Leu Val Lys Gly Val
            100                 105                 110

Pro Phe Lys Lys
        115

<210> SEQ ID NO 122
<211> LENGTH: 453
<212> TYPE: PRT
<213> ORGANISM: Vibrio fluvialis

<400> SEQUENCE: 122

Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

```
Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Met Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 123
<211> LENGTH: 1122
<212> TYPE: DNA
<213> ORGANISM: Erwinia caratovora subsp. atroseptica

<400> SEQUENCE: 123
atgtctgacg gacgactcac cgcacttttt cctgcattcc cacacccggc gtccaatcag      60
cccgtatttg ccgaggcttc accgcacgac gacgagttaa tgacgcaggc cgtaccgcag     120
gtttcctgtc agcaggcgtt ggcgattgcg cagcaagaat atggcttgtc tgggcagatg     180
tcgctgcttc agggcgagcg tgatgtgaat ttctgtctga cggtgacgcc agatgaacgc     240
tacatgctga aagtcatcaa tgcggcagaa cctgccgacg tcagcaattt ccaaaccgcg     300
ctgctgctgc atcttgcccg tcaggcacct gaactgcccg taccgcgtat caggtcgaca     360
aaagcgggtc agtcggaaac aggcgttgag atcgatggtg tactgctgcg tgtgcggctt     420
gtgagctatc tggcaggaat gccgcagtat ctggcctcac cgtcaacggc gctgatgccg     480
cagttggggg gaacgctggc gcagttggat aacgcgcttc acagctttac gcatccggcg     540
gcaaaccgtg cgctgctgtg ggatatcagc cgggcagagc aggtgcgtcc ttacctcgat     600
ttcgtttctg aaccgcagca gtatcagcat cttcagcgta tttttgaccg ttatgacagt     660
```

-continued

```
aacgttgctc ctctgttgac gacgctacgt cgtcaggtca ttcataacga tctgaatccg    720
cataacgtgc tggtggatgg atcgtcgccg acgcgggtta ctggcattat cgattttggc    780
gatgccgtat ttgccccgtt aatttgcgaa gtcgcgacgg cactggcgta tcagatcggc    840
gatggaaccg atttgttgga gcatgttgtg ccgtttgttg cggcctatca ccaacgcatt    900
ccgttagcac cggaggagat tgcgctgtta cccgatctga tagcgacccg tatggcgctg    960
accctgacca ttgcgcagtg gcgagcatcg cgttatcccg acaatcggga gtatctgctg   1020
cgtaacgtgc cgcgctgttg gcacagtttg cagcgcattg cgacctattc ccatgcgcaa   1080
tttttgactc gcctacagca ggtttgcccg gagaatgcgc ga                      1122
```

<210> SEQ ID NO 124
<211> LENGTH: 374
<212> TYPE: PRT
<213> ORGANISM: Erwinia caratovora subsp. atroseptica

<400> SEQUENCE: 124

```
Met Ser Asp Gly Arg Leu Thr Ala Leu Phe Pro Ala Phe Pro His Pro
1               5                   10                  15

Ala Ser Asn Gln Pro Val Phe Ala Glu Ala Ser Pro His Asp Asp Glu
            20                  25                  30

Leu Met Thr Gln Ala Val Pro Gln Val Ser Cys Gln Gln Ala Leu Ala
        35                  40                  45

Ile Ala Gln Gln Glu Tyr Gly Leu Ser Gly Gln Met Ser Leu Leu Gln
    50                  55                  60

Gly Glu Arg Asp Val Asn Phe Cys Leu Thr Val Thr Pro Asp Glu Arg
65                  70                  75                  80

Tyr Met Leu Lys Val Ile Asn Ala Ala Glu Pro Ala Asp Val Ser Asn
                85                  90                  95

Phe Gln Thr Ala Leu Leu Leu His Leu Ala Arg Gln Ala Pro Glu Leu
            100                 105                 110

Pro Val Pro Arg Ile Arg Ser Thr Lys Ala Gly Gln Ser Glu Thr Gly
        115                 120                 125

Val Glu Ile Asp Gly Val Leu Leu Arg Val Arg Leu Val Ser Tyr Leu
    130                 135                 140

Ala Gly Met Pro Gln Tyr Leu Ala Ser Pro Ser Thr Ala Leu Met Pro
145                 150                 155                 160

Gln Leu Gly Gly Thr Leu Ala Gln Leu Asp Asn Ala Leu His Ser Phe
                165                 170                 175

Thr His Pro Ala Ala Asn Arg Ala Leu Leu Trp Asp Ile Ser Arg Ala
            180                 185                 190

Glu Gln Val Arg Pro Tyr Leu Asp Phe Val Ser Glu Pro Gln Gln Tyr
        195                 200                 205

Gln His Leu Gln Arg Ile Phe Asp Arg Tyr Asp Ser Asn Val Ala Pro
    210                 215                 220

Leu Leu Thr Thr Leu Arg Arg Gln Val Ile His Asn Asp Leu Asn Pro
225                 230                 235                 240

His Asn Val Leu Val Asp Gly Ser Ser Pro Thr Arg Val Thr Gly Ile
                245                 250                 255

Ile Asp Phe Gly Asp Ala Val Phe Ala Pro Leu Ile Cys Glu Val Ala
            260                 265                 270

Thr Ala Leu Ala Tyr Gln Ile Gly Asp Gly Thr Asp Leu Leu Glu His
        275                 280                 285

Val Val Pro Phe Val Ala Ala Tyr His Gln Arg Ile Pro Leu Ala Pro
```

```
            290                 295                 300
Glu Glu Ile Ala Leu Leu Pro Asp Leu Ile Ala Thr Arg Met Ala Leu
305                 310                 315                 320

Thr Leu Thr Ile Ala Gln Trp Arg Ala Ser Arg Tyr Pro Asp Asn Arg
                325                 330                 335

Glu Tyr Leu Leu Arg Asn Val Pro Arg Cys Trp His Ser Leu Gln Arg
            340                 345                 350

Ile Ala Thr Tyr Ser His Ala Gln Phe Leu Thr Arg Leu Gln Gln Val
        355                 360                 365

Cys Pro Glu Asn Ala Arg
    370

<210> SEQ ID NO 125
<211> LENGTH: 1272
<212> TYPE: DNA
<213> ORGANISM: Erwinia caratovora subsp. atroseptica

<400> SEQUENCE: 125
atgacagcga cagaagcttt gctggcgcgc cgtcagcgag tgttgggcgg cggttatcgc      60
ctgtttatg aagagccgct gcatgtcgcg cgcggcgagg gcgtgtggct gttcgatcac     120
caagggaaac gttatctgga tgtctacaat aatgtggctt cggtcggaca ttgccacccc     180
gcggtggttg aagccgtggc gcgacagagc gcacaactca ataccacac gcgctatttg      240
caccacgcga ttgtcgattt tgcggaagat ttgctgagcg aatttcccgc cgaattgaac     300
aatgtaatgc tgacctgtac cggcagtgag gctaacgatc tggcgctgcg tatcgcccga     360
catgtcacgg gcgggacggg gatgttggtg acgcgctggg cgtatcacgg cgtgaccagc     420
gcgctggcg aactgtctcc gtcgctgggg gatggcgttg tgcgcggtag ccatgtgaag      480
ctgatcgacg cgccagacac ttatcgtcag cccggtgcat tcttaccag cattcgtgaa     540
gcgctggcg agatgcaacg ggaaggtatt cgtcctgcgg cgctgctggt agataccatt      600
tttccagcg atggcgtgtt ctgtgcgccg gaaggcgaaa tggcacaggc ggcggcgttg      660
atccgtcagg cgggcgggct gtttattgcg gatgaagtgc agccgggctt cgggcgcacc     720
ggggaatcac tgtgggctt tgcgcgccac aatgtcgtcc ctgatttggt gagtctaggg     780
aaaccgatgg caacggaca tcccatcgct ggattggtgg gcgttccgc tctgttcgac      840
gcatttgggc gcgatgtgcg ctatttcaat acctttggcg gcaatccggt ttcctgtcag     900
gcggcgcacg cggtgctgcg ggtgattcgg gaagagcagt tgcagcagaa tgcccagcgg     960
gtcggtgatt atctgcggca agggttgcag caactggcgc agcatttccc gctgattggt    1020
gatattcggg cttacggcct gtttattggt gcggagctgg tcagcgatcg cgaaagtaaa    1080
acgccggcaa gtgaatccgc gttgcaggtg gtgaatgcga tgcgccaacg tggtgtgctc    1140
atcagcgcga cggggccagc ggcgaacata ctgaaaattc gcccgccgct ggtgtttctg    1200
gaagaacacg ccgatgtgtt cttaaccacg ctgagtgacg ttttagcgct catcggcact    1260
cgtgcacaga ga                                                         1272

<210> SEQ ID NO 126
<211> LENGTH: 424
<212> TYPE: PRT
<213> ORGANISM: Erwinia caratovora subsp. atroseptica

<400> SEQUENCE: 126

Met Thr Ala Thr Glu Ala Leu Leu Ala Arg Arg Gln Arg Val Leu Gly
1               5                   10                  15
```

Gly Gly Tyr Arg Leu Phe Tyr Glu Glu Pro Leu His Val Ala Arg Gly
            20                  25                  30

Glu Gly Val Trp Leu Phe Asp His Gln Gly Lys Arg Tyr Leu Asp Val
        35                  40                  45

Tyr Asn Asn Val Ala Ser Val Gly His Cys His Pro Ala Val Val Glu
 50                  55                  60

Ala Val Ala Arg Gln Ser Ala Gln Leu Asn Thr His Thr Arg Tyr Leu
 65                  70                  75                  80

His His Ala Ile Val Asp Phe Ala Glu Asp Leu Leu Ser Glu Phe Pro
                85                  90                  95

Ala Glu Leu Asn Asn Val Met Leu Thr Cys Thr Gly Ser Glu Ala Asn
            100                 105                 110

Asp Leu Ala Leu Arg Ile Ala Arg His Val Thr Gly Gly Thr Gly Met
        115                 120                 125

Leu Val Thr Arg Trp Ala Tyr His Gly Val Thr Ser Ala Leu Ala Glu
    130                 135                 140

Leu Ser Pro Ser Leu Gly Asp Gly Val Val Arg Gly Ser His Val Lys
145                 150                 155                 160

Leu Ile Asp Ala Pro Asp Thr Tyr Arg Gln Pro Gly Ala Phe Leu Thr
                165                 170                 175

Ser Ile Arg Glu Ala Leu Ala Gln Met Gln Arg Glu Gly Ile Arg Pro
            180                 185                 190

Ala Ala Leu Leu Val Asp Thr Ile Phe Ser Ser Asp Gly Val Phe Cys
        195                 200                 205

Ala Pro Glu Gly Glu Met Ala Gln Ala Ala Leu Ile Arg Gln Ala
    210                 215                 220

Gly Gly Leu Phe Ile Ala Asp Glu Val Gln Pro Gly Phe Gly Arg Thr
225                 230                 235                 240

Gly Glu Ser Leu Trp Gly Phe Ala Arg His Asn Val Val Pro Asp Leu
                245                 250                 255

Val Ser Leu Gly Lys Pro Met Gly Asn Gly His Pro Ile Ala Gly Leu
            260                 265                 270

Val Gly Arg Ser Ala Leu Phe Asp Ala Phe Gly Arg Ala Val Arg Tyr
        275                 280                 285

Phe Asn Thr Phe Gly Gly Asn Pro Val Ser Cys Gln Ala Ala His Ala
    290                 295                 300

Val Leu Arg Val Ile Arg Glu Glu Gln Leu Gln Gln Asn Ala Gln Arg
305                 310                 315                 320

Val Gly Asp Tyr Leu Arg Gln Gly Leu Gln Gln Leu Ala Gln His Phe
                325                 330                 335

Pro Leu Ile Gly Asp Ile Arg Ala Tyr Gly Leu Phe Ile Gly Ala Glu
            340                 345                 350

Leu Val Ser Asp Arg Glu Ser Lys Thr Pro Ala Ser Glu Ser Ala Leu
        355                 360                 365

Gln Val Val Asn Ala Met Arg Gln Arg Gly Val Leu Ile Ser Ala Thr
    370                 375                 380

Gly Pro Ala Ala Asn Ile Leu Lys Ile Arg Pro Pro Leu Val Phe Leu
385                 390                 395                 400

Glu Glu His Ala Asp Val Phe Leu Thr Thr Leu Ser Asp Val Leu Ala
                405                 410                 415

Leu Ile Gly Thr Arg Ala Gln Arg
            420

<210> SEQ ID NO 127

```
<211> LENGTH: 35
<212> TYPE: DNA
<213> ORGANISM: Artificial Seqquence
<220> FEATURE:
<223> OTHER INFORMATION: Primer

<400> SEQUENCE: 127
ctccggaatt catgtctgac ggacgactca ccgca                        35

<210> SEQ ID NO 128
<211> LENGTH: 46
<212> TYPE: DNA
<213> ORGANISM: Artificial Seqquence
<220> FEATURE:
<223> OTHER INFORMATION: Primer

<400> SEQUENCE: 128
ttccaatgca ttggctgcag ttatctctgt gcacgagtgc cgatga            46

<210> SEQ ID NO 129
<211> LENGTH: 40
<212> TYPE: DNA
<213> ORGANISM: Artificial Seqquence
<220> FEATURE:
<223> OTHER INFORMATION: Primer

<400> SEQUENCE: 129
aacagccaag cttggctgca gtcatcgcgc attctccggg                   40

<210> SEQ ID NO 130
<211> LENGTH: 40
<212> TYPE: DNA
<213> ORGANISM: Artificial Seqquence
<220> FEATURE:
<223> OTHER INFORMATION: Primer

<400> SEQUENCE: 130
tctccggaat tcatgacgtc tgaaatgaca gcgacagaag                   40

<210> SEQ ID NO 131
<211> LENGTH: 33
<212> TYPE: DNA
<213> ORGANISM: Artificial Sequence
<220> FEATURE:
<223> OTHER INFORMATION: Primer

<400> SEQUENCE: 131
gctaacagga ggagaattc atgggggtt ctc                            33

<210> SEQ ID NO 132
<211> LENGTH: 33
<212> TYPE: DNA
<213> ORGANISM: Artificial Sequence
<220> FEATURE:
<223> OTHER INFORMATION: Primer

<400> SEQUENCE: 132 gagaacccc catgaattct cctcctgtt agc                            33

<210> SEQ ID NO 133
<211> LENGTH: 723
<212> TYPE: DNA
<213> ORGANISM: Klebsiella terrigena

<400> SEQUENCE: 133
atgcaaaaag tcgcacttgt caccggcgcc ggtcagggca tcggtaaagc tatcgccctg   60
```

```
cgtctggtga aggatggatt tgccgtggca atcgccgatt acaacgacgc tacggccaca    120
gcggtagccg ctgaaatcaa ccaggccggc ggccgcgcgg tggccattaa ggtcgacgtc    180
tcgcgccggg accaggtttt cgccgccgtt gagcaggcgc gtaaagccct gggcggattc    240
aacgttatcg tcaacaacgc cggcatcgcg ccgtcaacgc cgatcgagtc catcaccgag    300
gagatcgtcg accgggtcta taacatcaac gttaagggcg tcatctgggg gatgcaggcg    360
gcggtggagg ccttcaaaaa agaggggcac ggcgggaaga tcgtcaacgc ctgctcccag    420
gccggccacg tcggcaaccc ggagctggcg gtctacagtt cgagtaaatt cgccgtgcgc    480
ggcctgacgc aaaccgccgc ccgcgatctg gcgccgctgg gcatcaccgt taacggcttc    540
tgcccaggga tcgttaagac gccaatgtgg gcggagattg accgtcagtg tcggaagcgg    600
cgggcaaacc gctgggctac ggcacggctg aatttgccaa acgcatcacc cttggccgcc    660
tgtcggagcc tgaagacgtc gccgcctgcg tgtcgttcct cgccagcccg gattccgact    720
ata                                                                  723
```

<210> SEQ ID NO 134
<211> LENGTH: 241
<212> TYPE: PRT
<213> ORGANISM: Klebsiella terrigena

<400> SEQUENCE: 134

```
Met Gln Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
            20                  25                  30

Asp Tyr Asn Asp Ala Thr Ala Thr Ala Val Ala Ala Glu Ile Asn Gln
        35                  40                  45

Ala Gly Gly Arg Ala Val Ala Ile Lys Val Asp Val Ser Arg Arg Asp
    50                  55                  60

Gln Val Phe Ala Ala Val Glu Gln Ala Arg Lys Ala Leu Gly Gly Phe
65                  70                  75                  80

Asn Val Ile Val Asn Asn Ala Gly Ile Ala Pro Ser Thr Pro Ile Glu
                85                  90                  95

Ser Ile Thr Glu Glu Ile Val Asp Arg Val Tyr Asn Ile Asn Val Lys
            100                 105                 110

Gly Val Ile Trp Gly Met Gln Ala Val Glu Ala Phe Lys Lys Glu
        115                 120                 125

Gly His Gly Gly Lys Ile Val Asn Ala Cys Ser Gln Ala Gly His Val
    130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Gly Phe Cys Pro Gly Ile Val Lys Thr Pro Met Trp Ala Glu
            180                 185                 190

Ile Asp Arg Gln Cys Arg Lys Arg Arg Ala Asn Arg Trp Ala Thr Ala
        195                 200                 205

Arg Leu Asn Leu Pro Asn Ala Ser Pro Leu Ala Ala Cys Arg Ser Leu
    210                 215                 220

Lys Thr Ser Pro Pro Ala Cys Arg Ser Ser Pro Ala Arg Ile Pro Thr
225                 230                 235                 240

Ile
```

-continued

```
<210> SEQ ID NO 135
<211> LENGTH: 554
<212> TYPE: PRT
<213> ORGANISM: Clostridium pasteurianum

<400> SEQUENCE: 135

Met Lys Ser Lys Arg Phe Gln Val Leu Ser Glu Arg Pro Val Asn Lys
1               5                   10                  15

Asp Gly Phe Ile Gly Glu Trp Pro Glu Glu Gly Leu Ile Ala Met Ser
            20                  25                  30

Ser Pro Asn Asp Pro Lys Pro Ser Ile Lys Ile Lys Glu Gly Lys Val
        35                  40                  45

Ile Glu Leu Asp Gly Lys Asn Arg Glu Asp Phe Asp Met Ile Asp Arg
    50                  55                  60

Phe Ile Ala Asn Tyr Gly Ile Asn Leu Asn Arg Ala Glu Asp Val Ile
65                  70                  75                  80

Lys Met Asp Ser Val Lys Leu Ala Lys Met Leu Val Asp Ile Asn Val
                85                  90                  95

Asp Arg Lys Thr Ile Val Glu Leu Thr Thr Ala Met Thr Pro Ala Lys
            100                 105                 110

Ile Val Glu Val Val Gly Asn Met Asn Val Val Glu Met Met Met Ala
        115                 120                 125

Leu Gln Lys Met Arg Ala Arg Lys Thr Pro Ser Asn Gln Cys His Val
    130                 135                 140

Thr Asn Leu Lys Asp Asn Pro Val Gln Ile Ala Ala Asp Ala Ala Glu
145                 150                 155                 160

Ala Ala Ile Arg Gly Phe Asp Gln Glu Thr Thr Val Gly Ile Val
                165                 170                 175

Arg Tyr Ala Pro Phe Asn Ala Leu Ala Leu Val Gly Ala Gln Val
            180                 185                 190

Gly Arg Gly Gly Val Leu Thr Gln Cys Ala Ile Glu Glu Ala Thr Glu
    195                 200                 205

Leu Glu Leu Gly Met Arg Gly Leu Thr Ser Tyr Ala Glu Thr Val Ser
    210                 215                 220

Val Tyr Gly Thr Glu Asn Val Phe Thr Asp Gly Asp Asp Thr Pro Trp
225                 230                 235                 240

Ser Lys Ala Phe Leu Ala Ser Ala Tyr Ala Ser Arg Gly Leu Lys Met
                245                 250                 255

Arg Phe Thr Ser Gly Ser Gly Ser Glu Ala Leu Met Gly Tyr Ala Glu
            260                 265                 270

Gly Lys Ser Met Leu Tyr Leu Glu Ala Arg Cys Ile Tyr Ile Thr Lys
        275                 280                 285

Ala Ala Gly Val Gln Gly Leu Gln Asn Gly Ser Val Ser Cys Ile Gly
    290                 295                 300

Met Thr Gly Ala Leu Pro Ser Gly Ile Arg Ala Val Leu Gly Glu Asn
305                 310                 315                 320

Leu Ile Thr Thr Met Leu Asp Ile Glu Val Ala Ser Ala Asn Asp Gln
                325                 330                 335

Thr Phe Ser His Ser Asp Ile Arg Arg Thr Ala Arg Met Leu Met Gln
            340                 345                 350

Met Leu Pro Gly Thr Asp Phe Ile Phe Ser Gly Tyr Ser Ser Val Pro
        355                 360                 365

Asn Tyr Asp Asn Met Phe Ala Gly Ser Asn Phe Asp Ala Glu Asp Phe
    370                 375                 380

Asp Asp Tyr Asn Val Ile Gln Arg Asp Leu Met Val Asp Gly Gly Leu
```

```
            385                 390                 395                 400
Arg Pro Val Ser Glu Glu Val Ile Thr Ile Arg Asn Lys Ala Ala
                    405                 410                 415

Arg Ala Ile Gln Ala Val Phe Glu Gly Leu Lys Leu Pro Ala Ile Thr
                420                 425                 430

Asp Glu Glu Val Glu Ala Val Thr Tyr Ser His Gly Ser Lys Asp Val
            435                 440                 445

Pro Glu Arg Asn Val Val Glu Asp Leu Lys Ala Glu Glu Met Ile
        450                 455                 460

Asn Arg Gly Ile Thr Gly Ile Asp Val Val Lys Ala Leu Ser Lys His
465                 470                 475                 480

Gly Phe Asp Asp Ile Ala Glu Asn Ile Leu Asn Met Leu Lys Gln Arg
                485                 490                 495

Ile Ser Gly Asp Tyr Leu Gln Thr Ser Ala Ile Ile Asp Lys Asn Phe
                500                 505                 510

Asn Val Val Ser Ala Val Asn Asp Cys Asn Asp Tyr Met Gly Pro Gly
                515                 520                 525

Thr Gly Tyr Arg Leu Ser Lys Glu Arg Trp Asp Glu Ile Lys Asn Ile
        530                 535                 540

Pro Asn Ala Met Lys Pro Glu Asp Ile Lys
545                 550

<210> SEQ ID NO 136
<211> LENGTH: 179
<212> TYPE: PRT
<213> ORGANISM: Clostridium pasteurianum

<400> SEQUENCE: 136

Met Glu Leu Lys Glu Lys Asp Ile Ala Leu Ser Gly Asn Gln Ser Asn
1               5                   10                  15

Glu Val Val Ile Gly Ile Ala Pro Ala Phe Gly Lys Tyr Gln His Gln
                20                  25                  30

Ser Ile Val Gly Val Pro His Asp Lys Ile Leu Arg Glu Leu Ile Ala
            35                  40                  45

Gly Ile Glu Glu Gly Leu Lys Ser Arg Val Val Arg Ile Ile Arg
        50                  55                  60

Thr Ser Asp Val Ser Phe Ile Ala His Asp Ala Ala Val Leu Ser Gly
65                  70                  75                  80

Ser Gly Ile Gly Ile Gly Ile Gln Ser Lys Gly Thr Thr Val Ile His
                85                  90                  95

Gln Lys Asp Leu Leu Pro Leu Asn Asn Leu Glu Leu Phe Pro Gln Ala
                100                 105                 110

Pro Leu Leu Asp Leu Asp Ile Phe Arg Leu Ile Gly Lys Asn Ala Ala
            115                 120                 125

Lys Tyr Ala Lys Gly Glu Ser Pro Asn Pro Val Pro Thr Arg Asn Asp
130                 135                 140

Gln Met Val Arg Pro Lys Phe Gln Ala Lys Ala Ala Leu Leu His Ile
145                 150                 155                 160

Lys Glu Thr Lys His Val Val Gln Asn Ala Lys Pro Ile Glu Leu Glu
                165                 170                 175

Ile Ile Ser

<210> SEQ ID NO 137
<211> LENGTH: 146
<212> TYPE: PRT
<213> ORGANISM: Clostridium pasteurianum
```

<400> SEQUENCE: 137

```
Met Ser Asp Ile Thr Asn Asn Ile Lys Val Asp Tyr Glu Asn Asp Tyr
1               5                   10                  15

Pro Leu Ala Ala Lys Arg Ser Glu Trp Ile Lys Thr Pro Thr Gly Lys
            20                  25                  30

Asn Leu Lys Asp Ile Thr Leu Glu Ala Val Ile Asp Glu Asn Val Lys
        35                  40                  45

Ala Glu Asp Val Arg Ile Ser Arg Asp Thr Leu Glu Leu Gln Ala Gln
    50                  55                  60

Val Ala Glu Gly Ser Gly Arg Cys Ala Ile Ala Arg Asn Phe Arg Arg
65                  70                  75                  80

Ala Ala Glu Leu Ile Ser Ile Ser Asp Glu Arg Ile Leu Glu Ile Tyr
                85                  90                  95

Asn Ala Leu Arg Pro Tyr Arg Ser Thr Lys Asn Glu Leu Leu Ala Ile
            100                 105                 110

Ala Asp Glu Leu Glu Glu Lys Tyr Asp Ala Lys Val Asn Ala Asp Phe
        115                 120                 125

Ile Arg Glu Ala Ala Glu Val Tyr Ser Lys Arg Asn Lys Val Arg Ile
    130                 135                 140

Glu Asp
145
```

<210> SEQ ID NO 138
<211> LENGTH: 555
<212> TYPE: PRT
<213> ORGANISM: Escherichia blattae

<400> SEQUENCE: 138

```
Met Arg Arg Ser Lys Arg Phe Glu Val Leu Glu Lys Arg Pro Val Asn
1               5                   10                  15

Gln Asp Gly Leu Ile Gly Glu Trp Pro Glu Gly Leu Ile Ala Met
            20                  25                  30

Gly Ser Pro Trp Asp Pro Pro Ser Ser Val Lys Val Glu Gln Gly Arg
        35                  40                  45

Ile Val Glu Leu Asp Gly Lys Ala Arg Ala Asp Phe Asp Met Ile Asp
    50                  55                  60

Arg Phe Ile Ala Asp Tyr Ala Ile Asn Ile Glu Thr Glu His Ala
65                  70                  75                  80

Met Gly Leu Asp Ala Leu Thr Ile Ala Arg Met Leu Val Asp Ile Asn
                85                  90                  95

Val Ser Arg Ala Glu Ile Ile Lys Val Thr Thr Ala Ile Thr Pro Ala
            100                 105                 110

Lys Ala Val Glu Val Met Ser His Met Asn Val Val Glu Met Met Met
        115                 120                 125

Ala Leu Gln Lys Met Arg Ala Arg Arg Thr Pro Ser Asn Gln Cys His
    130                 135                 140

Val Thr Asn Leu Lys Asp Asn Pro Val Gln Ile Ala Ala Asp Ala Ala
145                 150                 155                 160

Glu Ala Gly Ile Arg Gly Phe Ser Glu Gln Glu Thr Val Gly Ile
            165                 170                 175

Ala Arg Tyr Ala Pro Phe Asn Ala Leu Ala Leu Ile Gly Ser Gln
        180                 185                 190

Ser Gly Arg Pro Gly Val Leu Thr Gln Cys Ser Val Glu Glu Ala Thr
            195                 200                 205
```

```
Glu Leu Glu Leu Gly Met Arg Gly Phe Thr Ser Tyr Ala Glu Thr Val
210                 215                 220

Ser Val Tyr Gly Thr Glu Ala Val Phe Thr Asp Gly Asp Asp Thr Pro
225                 230                 235                 240

Trp Ser Lys Ala Phe Leu Ala Ser Ala Tyr Ala Ser Arg Gly Leu Lys
                245                 250                 255

Met Arg Tyr Thr Ser Gly Thr Gly Ser Glu Ala Leu Met Gly Tyr Ala
            260                 265                 270

Glu Ser Lys Ser Met Leu Tyr Leu Glu Ser Arg Cys Ile Phe Ile Thr
        275                 280                 285

Lys Gly Ala Gly Val Gln Gly Leu Gln Asn Gly Ala Val Ser Cys Ile
290                 295                 300

Gly Met Thr Gly Ala Val Pro Ser Gly Ile Arg Ala Val Leu Ala Glu
305                 310                 315                 320

Asn Leu Ile Ala Ser Met Leu Asp Leu Glu Val Ala Ser Ala Asn Asp
                325                 330                 335

Gln Thr Phe Ser His Ser Asp Ile Arg Arg Thr Ala Arg Thr Leu Met
            340                 345                 350

Gln Met Leu Pro Gly Thr Asp Phe Ile Phe Ser Gly Tyr Ser Ala Val
        355                 360                 365

Pro Asn Tyr Asp Asn Met Phe Ala Gly Ser Asn Phe Asp Ala Glu Asp
370                 375                 380

Phe Asp Asp Tyr Asn Ile Leu Gln Arg Asp Leu Met Val Asp Gly Gly
385                 390                 395                 400

Leu Arg Pro Val Ser Glu Glu Thr Ile Ala Ile Arg Asn Lys Ala
                405                 410                 415

Ala Arg Ala Val Gln Ala Val Phe Arg Glu Leu Gly Leu Pro Pro Val
            420                 425                 430

Thr Asp Glu Glu Val Thr Ala Ala Thr Tyr Ala His Gly Ser Lys Asp
        435                 440                 445

Met Pro Pro Arg Asn Val Val Glu Asp Leu Ser Ala Val Glu Glu Met
450                 455                 460

Met Lys Arg Asn Ile Thr Gly Leu Asp Ile Val Arg Ala Leu Ser Val
465                 470                 475                 480

Asn Gly Phe Asp Asp Val Ala Asn Asn Ile Leu Asn Met Leu Arg Gln
                485                 490                 495

Arg Val Thr Gly Asp Tyr Leu Gln Thr Ser Ala Ile Leu Asp Arg Glu
            500                 505                 510

Phe Glu Val Val Ser Ala Val Asn Asp Ile Asn Asp Tyr Gln Gly Pro
        515                 520                 525

Gly Thr Gly Tyr Arg Ile Ser Pro Gln Arg Trp Glu Glu Ile Lys Asn
530                 535                 540

Ile Ala Thr Val Ile Gln Pro Asp Ser Ile Glu
545                 550                 555

<210> SEQ ID NO 139
<211> LENGTH: 196
<212> TYPE: PRT
<213> ORGANISM: Escherichia blattae

<400> SEQUENCE: 139

Met Glu Thr Thr Gln Lys Lys Ala Pro Val Phe Thr Leu Asn Leu Val
1               5                   10                  15

Glu Ser Gly Val Ala Lys Pro Gly Glu Arg Ser Asp Glu Val Val Ile
                20                  25                  30
```

```
Gly Val Gly Pro Ala Phe Asp Lys Tyr Gln His Lys Thr Leu Ile Asp
         35                  40                  45

Met Pro His Lys Ala Ile Ile Lys Glu Leu Val Ala Gly Val Glu Glu
 50                  55                  60

Glu Gly Leu His Ala Arg Val Arg Ile Leu Arg Thr Ser Asp Val
 65                  70                  75                  80

Ser Phe Met Ala Trp Asp Ala Ala Asn Leu Ser Gly Ser Gly Ile Gly
                 85                  90                  95

Ile Gly Ile Gln Ser Lys Gly Thr Thr Val Ile His Gln Arg Asp Leu
            100                 105                 110

Leu Pro Leu Ser Asn Leu Glu Leu Phe Ser Gln Ala Pro Leu Leu Thr
            115                 120                 125

Leu Glu Thr Tyr Arg Gln Ile Gly Lys Asn Ala Ala Arg Tyr Ala Arg
130                 135                 140

Lys Glu Ser Pro Ser Pro Val Pro Val Val Asn Asp Gln Met Val Arg
145                 150                 155                 160

Pro Lys Phe Met Ala Lys Ala Leu Phe His Ile Lys Glu Thr Lys
                165                 170                 175

His Val Val Ala Asp Ala Lys Pro Val Thr Leu Asn Ile Glu Ile Thr
            180                 185                 190

Arg Glu Glu Ala
        195

<210> SEQ ID NO 140
<211> LENGTH: 141
<212> TYPE: PRT
<213> ORGANISM: Escherichia blattae

<400> SEQUENCE: 140

Met Thr Thr Thr Lys Met Ser Ala Ala Asp Tyr Pro Leu Ala Ser Arg
 1               5                  10                  15

Cys Pro Glu Arg Ile Gln Thr Pro Thr Gly Lys Pro Leu Thr Asp Ile
             20                  25                  30

Thr Leu Glu Asn Val Leu Ala Gly Lys Val Gly Pro Gln Asp Val Arg
         35                  40                  45

Ile Ser Arg Glu Thr Leu Glu Tyr Gln Ala Gln Ile Ala Glu Gln Met
 50                  55                  60

His Arg His Ala Ile Ala Arg Asn Leu Arg Arg Ala Gly Glu Leu Ile
 65                  70                  75                  80

Ala Ile Pro Asp Ala Arg Ile Leu Glu Ile Tyr Asn Ala Leu Arg Pro
                 85                  90                  95

Tyr Arg Ser Ser Val Glu Glu Leu Leu Ala Ile Ala Asp Glu Leu Glu
            100                 105                 110

Thr Arg Tyr Gln Ala Thr Val Asn Ala Ala Phe Ile Arg Glu Ala Ala
            115                 120                 125

Glu Val Tyr Arg Gln Arg Asp Lys Leu Arg Lys Glu Ala
130                 135                 140

<210> SEQ ID NO 141
<211> LENGTH: 555
<212> TYPE: PRT
<213> ORGANISM: Citrobacter freundii

<400> SEQUENCE: 141

Met Arg Arg Ser Lys Arg Phe Glu Val Leu Ala Gln Arg Pro Val Asn
 1               5                  10                  15

Gln Asp Gly Leu Ile Gly Glu Trp Pro Glu Glu Gly Leu Ile Ala Met
```

```
                    20                  25                  30
Glu Ser Pro Tyr Asp Pro Ala Ser Ser Val Lys Val Glu Asn Gly Arg
                35                  40                  45

Ile Val Glu Leu Asp Gly Lys Ser Arg Ala Glu Phe Asp Met Ile Asp
 50                  55                  60

Arg Phe Ile Ala Asp Tyr Ala Ile Asn Val Pro Glu Ala Glu Arg Ala
 65                  70                  75                  80

Met Gln Leu Asp Ala Leu Glu Ile Ala Arg Met Leu Val Asp Ile His
                85                  90                  95

Val Ser Arg Glu Glu Ile Ile Ala Ile Thr Thr Ala Ile Thr Pro Ala
                100                 105                 110

Lys Arg Leu Glu Val Met Ala Gln Met Asn Val Val Glu Met Met Met
                115                 120                 125

Ala Leu Gln Lys Met Arg Ala Arg Arg Thr Pro Ser Asn Gln Cys His
                130                 135                 140

Val Thr Asn Leu Lys Asp Asn Pro Val Gln Ile Ala Ala Asp Ala Ala
145                 150                 155                 160

Glu Ala Gly Ile Arg Gly Phe Ser Glu Gln Glu Thr Thr Val Gly Ile
                165                 170                 175

Ala Arg Tyr Ala Pro Phe Asn Ala Leu Ala Leu Leu Val Gly Ser Gln
                180                 185                 190

Cys Gly Ala Pro Gly Val Leu Thr Gln Cys Ser Val Glu Glu Ala Thr
                195                 200                 205

Glu Leu Glu Leu Gly Met Arg Gly Leu Thr Ser Tyr Ala Glu Thr Val
                210                 215                 220

Ser Val Tyr Gly Thr Glu Ser Val Phe Thr Asp Gly Asp Asp Thr Pro
225                 230                 235                 240

Trp Ser Lys Ala Phe Leu Ala Ser Ala Tyr Ala Ser Arg Gly Leu Lys
                245                 250                 255

Met Arg Tyr Thr Ser Gly Thr Gly Ser Glu Ala Leu Met Gly Tyr Ser
                260                 265                 270

Glu Ser Lys Ser Met Leu Tyr Leu Glu Ser Arg Cys Ile Phe Ile Thr
                275                 280                 285

Lys Gly Ala Gly Val Gln Gly Leu Gln Asn Gly Ala Val Ser Cys Ile
                290                 295                 300

Gly Met Thr Gly Ala Val Pro Ser Gly Ile Arg Ala Val Leu Ala Glu
305                 310                 315                 320

Asn Leu Ile Ala Ser Met Leu Asp Leu Glu Val Ala Ser Ala Asn Asp
                325                 330                 335

Gln Thr Phe Ser His Ser Asp Ile Arg Arg Thr Ala Arg Thr Leu Met
                340                 345                 350

Gln Met Leu Pro Gly Thr Asp Phe Ile Phe Ser Gly Tyr Ser Ala Val
                355                 360                 365

Pro Asn Tyr Asp Asn Met Phe Ala Gly Ser Asn Phe Asp Ala Glu Asp
                370                 375                 380

Phe Asp Asp Tyr Asn Ile Leu Gln Arg Asp Leu Met Val Asp Gly Gly
385                 390                 395                 400

Leu Arg Pro Val Thr Glu Glu Thr Ile Ala Ile Arg Asn Lys Ala
                405                 410                 415

Ala Arg Ala Ile Gln Ala Val Phe Arg Glu Leu Gly Leu Pro Leu Ile
                420                 425                 430

Ser Asp Glu Glu Val Asp Ala Ala Thr Tyr Ala His Gly Ser Lys Asp
                435                 440                 445
```

Met Pro Ala Arg Asn Val Val Glu Asp Leu Ala Ala Val Glu Glu Met
450                 455                 460

Met Lys Arg Asn Ile Thr Gly Leu Asp Ile Val Gly Ala Leu Ser Ser
465                 470                 475                 480

Ser Gly Phe Glu Asp Ile Ala Ser Asn Ile Leu Asn Met Leu Arg Gln
                485                 490                 495

Arg Val Thr Gly Asp Tyr Leu Gln Thr Ser Ala Ile Leu Asp Arg Gln
            500                 505                 510

Phe Asp Val Val Ser Ala Val Asn Asp Ile Asn Asp Tyr Gln Gly Pro
        515                 520                 525

Gly Thr Gly Tyr Arg Ile Ser Ala Glu Arg Trp Ala Glu Ile Lys Asn
    530                 535                 540

Ile Ala Gly Val Val Gln Pro Gly Ser Ile Glu
545                 550                 555

<210> SEQ ID NO 142
<211> LENGTH: 194
<212> TYPE: PRT
<213> ORGANISM: Citrobacter freundii

<400> SEQUENCE: 142

Met Glu Cys Thr Thr Glu Arg Lys Pro Val Phe Thr Leu Gln Val Ser
1               5                   10                  15

Glu Gly Glu Ala Ala Lys Ala Asp Glu Arg Val Asp Glu Val Val Ile
            20                  25                  30

Gly Val Gly Pro Ala Phe Asp Lys Tyr Gln His Lys Thr Leu Ile Asp
        35                  40                  45

Met Pro His Lys Ala Ile Leu Lys Glu Leu Val Ala Gly Ile Glu Glu
    50                  55                  60

Glu Gly Leu His Ala Arg Val Val Arg Ile Leu Arg Thr Ser Asp Val
65                  70                  75                  80

Ser Phe Met Ala Trp Asp Ala Ala Asn Leu Ser Gly Ser Gly Ile Gly
                85                  90                  95

Ile Gly Ile Gln Ser Lys Gly Thr Thr Val Ile His Gln Arg Asp Leu
            100                 105                 110

Leu Pro Leu Ser Asn Leu Glu Leu Phe Ser Gln Ala Pro Leu Leu Thr
        115                 120                 125

Leu Glu Thr Tyr Arg Gln Ile Gly Lys Asn Ala Ala Arg Tyr Ala Arg
    130                 135                 140

Lys Glu Ser Pro Ser Pro Val Pro Val Asn Asp Gln Met Val Arg
145                 150                 155                 160

Pro Lys Phe Met Ala Lys Ala Leu Phe His Ile Lys Glu Thr Lys
                165                 170                 175

His Val Val Gln Asp Arg Ala Pro Val Thr Leu His Ile Ala Leu Val
            180                 185                 190

Arg Glu

<210> SEQ ID NO 143
<211> LENGTH: 142
<212> TYPE: PRT
<213> ORGANISM: Citrobacter freundii

<400> SEQUENCE: 143

Met Asn Asp Asn Ile Met Thr Ala Gln Asp Tyr Pro Leu Ala Thr Arg
1               5                   10                  15

Cys Pro Glu Lys Ile Gln Thr Pro Thr Gly Lys Pro Leu Thr Glu Ile
            20                  25                  30

```
Thr Leu Glu Asn Val Leu Ala Gly Arg Val Gly Pro Gln Asp Val Arg
         35                  40                  45

Ile Ser Gln Gln Thr Leu Glu Tyr Gln Ala Gln Ile Ala Glu Gln Met
 50                  55                  60

Gln Arg His Ala Val Ala Arg Asn Phe Arg Ala Ala Glu Leu Ile
 65                  70                  75                  80

Ala Ile Pro Asp Ala Arg Ile Leu Glu Ile Tyr Asn Ala Leu Arg Pro
                 85                  90                  95

Phe Arg Ser Ser Phe Ala Glu Leu Gln Ala Ile Ala Asp Glu Leu Glu
                100                 105                 110

His Thr Trp His Ala Thr Val Asn Ala Gly Phe Val Arg Glu Ser Ala
            115                 120                 125

Glu Val Tyr Leu Gln Arg Asn Lys Leu Arg Lys Gly Ser Gln
        130                 135                 140
```

<210> SEQ ID NO 144
<211> LENGTH: 1359
<212> TYPE: DNA
<213> ORGANISM: Artificial sequence
<220> FEATURE:
<223> OTHER INFORMATION: Codon optimized Vibrio fluvialis amine:pyruvate transaminase

<400> SEQUENCE: 144

```
atgaacaaac cacagtcttg ggaagctcgt gcagaaacct attctctgta cggcttcact      60
gacatgccgt ccctgcacca gcgtggtact gttgttgtca cgcacggcga aggtccgtac     120
attgttgacg tcaatggtcg ccgttatctg gacgctaatt ctggcctgtg aatatggtt     180
gcaggttttg accataaggg tctgatcgac gcagctaagg ctcagtacga gcgttttccg     240
ggctaccatg cgttcttcgg tcgtatgagc gatcagacgg tgatgctgtc gaaaaactg     300
gtagaagtct ctccgttcga cagcggccgt gtgttctata cgaacagcgg tagcgaagca     360
aacgacacta tggttaagat gctgtggttc ctgcatgcgg cggaaggtaa gccacaaaag     420
cgcaaaattc tgacccgttg gaacgcgtat acggcgtta ctgcagttag cgcctccatg     480
accggtaaac cgtacaacag cgttttcggt ctgccgctgc aggtttcgt tcacctgact     540
tgccctcact actggcgtta cggtgaagaa ggcgagacgg aagaacaatt cgttgcacgc     600
ctggcacgcg aactggaaga gactatccag cgtgagggtg ctgacactat cgctggcttc     660
tttgctgagc cggttatggg tgcaggtggt gttattccgc tgctaaagg ttattttcag     720
gctattctgc caatcctgcg taaatatgac atcccggtta tctctgacga agttatctgt     780
ggttttggtc gcactggcaa cacctggggt gcgtaactt atgatttac tccggatgct     840
atcatctcta gcaaaaacct gaccgccggt ttcttcccga tgggcgcagt gatcctgggt     900
ccagaactga gcaagcgcct ggaaaccgca attgaagcaa tcgaggaatt ccgcacggc     960
tttaccgcgt ccggccatcc ggtaggctgt gcaatcgcgc tgaaagcgat cgatgttgtt    1020
atgaacgaag gctggcgga aaacgttcgc gtctggcac cgcgcttcga agaacgtctg    1080
aaacatatcg cggaacgtcc gaacattggt gaatatcgtg gtatcggttt tatgtgggct    1140
ctggaggcag tcaaagacaa agcgtctaaa actccgttcg atggcaatct gagcgtgagc    1200
gaacgtatcg ccaacacttg caccgacctg gtctgatct gccgtccact gggccaaagc    1260
gtagtgctgt gtccgccgtt tatcctgacc gaagcgcaaa tggacgaaat gttcgacaaa    1320
ctggagaaag cactggataa agtgttcgca gaggtggca                          1359
```

<210> SEQ ID NO 145
<211> LENGTH: 1668
<212> TYPE: DNA
<213> ORGANISM: Klebsiella pneumoniae

<400> SEQUENCE: 145

```
atgaaaagat caaaacgatt tgcagtactg gcccagcgcc ccgtcaatca ggacgggctg      60
attggcgagt ggcctgaaga ggggctgatc gccatggaca gccccctttga cccggtctct    120
tcagtaaaag tggacaacgg tctgatcgtc gaactggacg gcaaacgccg ggaccagttt    180
gacatgatcg accgattttat cgccgattac gcgatcaacg ttgagcgcac agagcaggca    240
atgcgcctgg aggcggtgga aatagcccgt atgctggtgg atattcacgt cagccgggag    300
gagatcattg ccatcactac cgccatcacg ccggccaaag cggtcgaggt gatggcgcag    360
atgaacgtgg tggagatgat gatggcgctg cagaagatgc gtgcccgccg acccccctcc    420
aaccagtgcc acgtcaccaa tctcaaagat aatccggtgc agattgccgc tgacgccgcc    480
gaggccggga tccgcggctt ctcagaacag agagaccacg tcggtatcgc gcgctacgcg    540
ccgtttaacg ccctggcgct gttggtcggt tcgcagtgcg gccgccccgg cgtgttgacg    600
cagtgctcgg tggaagaggc caccgagctg agctgggca tgcgtggctt aaccagctac    660
gccgagacgg tgtcggtcta cggcaccgaa gcggtattta ccgacggcga tgatacgccg    720
tggtcaaagg cgttcctcgc ctcggcctac gcctcccgcg ggttgaaaat gcgctacacc    780
tccggcaccg atccgaagc gctgatgggc tattcggaga gcaagtcgat gctctacctc    840
gaatcgcgct gcatcttcat tactaaaggc gccggggttc agggactgca aaacggcgcg    900
gtgagctgta tcggcatgac cggcgctgtg ccgtcgggca ttcgggcggt gctggcggaa    960
aacctgatcg cctctatgct cgacctcgaa gtggcgtccg ccaacgacca gactttctcc    1020
cactcggata ttcgccgcac cgcgcgcacc ctgatgcaga tgctgccggg caccgacttt    1080
attttctccg gctacagcgc ggtgccgaac tacgacaaca tgttcgccgg ctcgaacttc    1140
gatgcggaag attttgatga ttacaacatc ctgcagcgtg acctgatggt tgacggcggc    1200
ctgcgtccgg tgaccgaggc ggaaaccatt gccattcgcc agaaagcggc gcgggcgatc    1260
caggcggttt tccgcgagct ggggctgccg ccaatcgccg acgaggaggt ggaggccgcc    1320
acctacgcgc acggcagcaa cgagatgccg ccgcgtaacg tggtggagga tctgagtgcg    1380
gtggaagaga tgatgaagcg caacatcacc ggcctcgata ttgtcggcgc gctgagccgc    1440
agcggctttg aggatatcgc cagcaatatt ctcaatatgc tgcgccagcg ggtcaccggc    1500
gattacctgc agacctcggc cattctcgat cggcagttcg aggtggtgag tgcggtcaac    1560
gacatcaatg actatcaggg gccgggcacc ggctatcgca tctctgccga acgctgggcg    1620
gagatcaaaa atattccggg cgtggttcag cccgacacca ttgaataa               1668
```

<210> SEQ ID NO 146
<211> LENGTH: 555
<212> TYPE: PRT
<213> ORGANISM: Klebsiella pneumoniae

<400> SEQUENCE: 146

```
Met Lys Arg Ser Lys Arg Phe Ala Val Leu Ala Gln Arg Pro Val Asn
1               5                   10                  15

Gln Asp Gly Leu Ile Gly Glu Trp Pro Glu Glu Gly Leu Ile Ala Met
            20                  25                  30

Asp Ser Pro Phe Asp Pro Val Ser Ser Val Lys Val Asp Asn Gly Leu
        35                  40                  45
```

```
Ile Val Glu Leu Asp Gly Lys Arg Asp Gln Phe Asp Met Ile Asp
 50                  55                  60

Arg Phe Ile Ala Asp Tyr Ala Ile Asn Val Glu Arg Thr Glu Gln Ala
 65                  70                  75                  80

Met Arg Leu Glu Ala Val Glu Ile Ala Arg Met Leu Val Asp Ile His
                 85                  90                  95

Val Ser Arg Glu Glu Ile Ile Ala Ile Thr Thr Ala Ile Thr Pro Ala
                100                 105                 110

Lys Ala Val Glu Val Met Ala Gln Met Asn Val Val Glu Met Met Met
                115                 120                 125

Ala Leu Gln Lys Met Arg Ala Arg Arg Thr Pro Ser Asn Gln Cys His
130                 135                 140

Val Thr Asn Leu Lys Asp Asn Pro Val Gln Ile Ala Ala Asp Ala Ala
145                 150                 155                 160

Glu Ala Gly Ile Arg Gly Phe Ser Gln Glu Thr Thr Val Gly Ile
                165                 170                 175

Ala Arg Tyr Ala Pro Phe Asn Ala Leu Ala Leu Val Gly Ser Gln
                180                 185                 190

Cys Gly Arg Pro Gly Val Leu Thr Gln Cys Ser Val Glu Glu Ala Thr
                195                 200                 205

Glu Leu Glu Leu Gly Met Arg Gly Leu Thr Ser Tyr Ala Glu Thr Val
210                 215                 220

Ser Val Tyr Gly Thr Glu Ala Val Phe Thr Asp Gly Asp Asp Thr Pro
225                 230                 235                 240

Trp Ser Lys Ala Phe Leu Ala Ser Ala Tyr Ala Ser Arg Gly Leu Lys
                245                 250                 255

Met Arg Tyr Thr Ser Gly Thr Gly Ser Glu Ala Leu Met Gly Tyr Ser
                260                 265                 270

Glu Ser Lys Ser Met Leu Tyr Leu Glu Ser Arg Cys Ile Phe Ile Thr
                275                 280                 285

Lys Gly Ala Gly Val Gln Gly Leu Gln Asn Gly Ala Val Ser Cys Ile
                290                 295                 300

Gly Met Thr Gly Ala Val Pro Ser Gly Ile Arg Ala Val Leu Ala Glu
305                 310                 315                 320

Asn Leu Ile Ala Ser Met Leu Asp Leu Glu Val Ala Ser Ala Asn Asp
                325                 330                 335

Gln Thr Phe Ser His Ser Asp Ile Arg Arg Thr Ala Arg Thr Leu Met
                340                 345                 350

Gln Met Leu Pro Gly Thr Asp Phe Ile Phe Ser Gly Tyr Ser Ala Val
                355                 360                 365

Pro Asn Tyr Asp Asn Met Phe Ala Gly Ser Asn Phe Asp Ala Glu Asp
370                 375                 380

Phe Asp Asp Tyr Asn Ile Leu Gln Arg Asp Leu Met Val Asp Gly Gly
385                 390                 395                 400

Leu Arg Pro Val Thr Glu Ala Glu Thr Ile Ala Ile Arg Gln Lys Ala
                405                 410                 415

Ala Arg Ala Ile Gln Ala Val Phe Arg Glu Leu Gly Leu Pro Pro Ile
                420                 425                 430

Ala Asp Glu Glu Val Glu Ala Ala Thr Tyr Ala His Gly Ser Asn Glu
                435                 440                 445

Met Pro Pro Arg Asn Val Val Glu Asp Leu Ser Ala Val Glu Glu Met
                450                 455                 460

Met Lys Arg Asn Ile Thr Gly Leu Asp Ile Val Gly Ala Leu Ser Arg
465                 470                 475                 480
```

```
Ser Gly Phe Glu Asp Ile Ala Ser Asn Ile Leu Asn Met Leu Arg Gln
            485                 490                 495

Arg Val Thr Gly Asp Tyr Leu Gln Thr Ser Ala Ile Leu Asp Arg Gln
            500                 505                 510

Phe Glu Val Val Ser Ala Val Asn Asp Ile Asn Asp Tyr Gln Gly Pro
            515                 520                 525

Gly Thr Gly Tyr Arg Ile Ser Ala Glu Arg Trp Ala Glu Ile Lys Asn
            530                 535                 540

Ile Pro Gly Val Val Gln Pro Asp Thr Ile Glu
545                 550                 555

<210> SEQ ID NO 147
<211> LENGTH: 585
<212> TYPE: DNA
<213> ORGANISM: Klebsiella pneumoniae

<400> SEQUENCE: 147
gtgcaacaga caacccaaat tcagccctct tttaccctga aaacccgcga gggcggggta      60
gcttctgccg atgaacgcgc cgatgaagtg gtgatcggcg tcggccctgc cttcgataaa     120
caccagcatc acactctgat cgatatgccc catggcgcga tcctcaaaga gctgattgcc     180
ggggtggaag aagagggggct tcacgcccgg gtggtgcgca ttctgcgcac gtccgacgtc     240
tcctttatgg cctgggatgc ggccaacctg agcggctcgg ggatcggcat cggtatccag     300
tcgaagggga ccacggtcat ccatcagcgc gatctgctgc cgctcagcaa cctggagctg     360
ttctcccagg cgccgctgct gacgctggag acctaccggc agattggcaa aaacgctgcg     420
cgctatgcgc gcaaagagtc accttcgccg gtgccggtgg tgaacgatca gatggtgcgg     480
ccgaaattta tggccaaagc cgcgctattt catatcaaag agaccaaaca tgtggtgcag     540
gacgccgagc ccgtcaccct gcacatcgac ttagtaaggg agtga                    585

<210> SEQ ID NO 148
<211> LENGTH: 194
<212> TYPE: PRT
<213> ORGANISM: Klebsiella pneumoniae

<400> SEQUENCE: 148

Met Gln Gln Thr Thr Gln Ile Gln Pro Ser Phe Thr Leu Lys Thr Arg
1               5                   10                  15

Glu Gly Gly Val Ala Ser Ala Asp Glu Arg Ala Asp Glu Val Val Ile
            20                  25                  30

Gly Val Gly Pro Ala Phe Asp Lys His Gln His His Thr Leu Ile Asp
        35                  40                  45

Met Pro His Gly Ala Ile Leu Lys Glu Leu Ile Ala Gly Val Glu Glu
    50                  55                  60

Glu Gly Leu His Ala Arg Val Val Arg Ile Leu Arg Thr Ser Asp Val
65                  70                  75                  80

Ser Phe Met Ala Trp Asp Ala Ala Asn Leu Ser Gly Ser Gly Ile Gly
                85                  90                  95

Ile Gly Ile Gln Ser Lys Gly Thr Thr Val Ile His Gln Arg Asp Leu
            100                 105                 110

Leu Pro Leu Ser Asn Leu Glu Leu Phe Ser Gln Ala Pro Leu Leu Thr
        115                 120                 125

Leu Glu Thr Tyr Arg Gln Ile Gly Lys Asn Ala Ala Arg Tyr Ala Arg
    130                 135                 140

Lys Glu Ser Pro Ser Pro Val Pro Val Val Asn Asp Gln Met Val Arg
```

```
                145                 150                 155                 160
Pro Lys Phe Met Ala Lys Ala Ala Leu Phe His Ile Lys Glu Thr Lys
                    165                 170                 175

His Val Val Gln Asp Ala Glu Pro Val Thr Leu His Ile Asp Leu Val
                180                 185                 190

Arg Glu

<210> SEQ ID NO 149
<211> LENGTH: 426
<212> TYPE: DNA
<213> ORGANISM: Klebsiella pneumoniae

<400> SEQUENCE: 149
atgagcgaga aaaccatgcg cgtgcaggat tatccgttag ccacccgctg cccggagcat      60
atcctgacgc ctaccggcaa accattgacc gatattaccc tcgagaaggt gctctctggc    120
gaggtgggcc cgcaggatgt gcggatctcc cgccagaccc ttgagtacca ggcgcagatt    180
gccgagcaga tgcagcgcca tgcggtggcg cgcaatttcc gccgcgcggc ggagcttatc    240
gccattcctg acgagcgcat tctggctatc tataacgcgc tgcgcccgtt ccgctcctcg    300
caggcggagc tgctggcgat cgccgacgag ctggagcaca cctggcatgc gacagtgaat    360
gccgcctttg tccgggagtc ggcggaagtg tatcagcagc ggcataagct gcgtaaagga    420
agctaa                                                               426

<210> SEQ ID NO 150
<211> LENGTH: 141
<212> TYPE: PRT
<213> ORGANISM: Klebsiella pneumoniae

<400> SEQUENCE: 150

Met Ser Glu Lys Thr Met Arg Val Gln Asp Tyr Pro Leu Ala Thr Arg
1               5                  10                  15

Cys Pro Glu His Ile Leu Thr Pro Thr Gly Lys Pro Leu Thr Asp Ile
                20                  25                  30

Thr Leu Glu Lys Val Leu Ser Gly Glu Val Gly Pro Gln Asp Val Arg
            35                  40                  45

Ile Ser Arg Gln Thr Leu Glu Tyr Gln Ala Gln Ile Ala Glu Gln Met
        50                  55                  60

Gln Arg His Ala Val Ala Arg Asn Phe Arg Arg Ala Ala Glu Leu Ile
65                  70                  75                  80

Ala Ile Pro Asp Glu Arg Ile Leu Ala Ile Tyr Asn Ala Leu Arg Pro
                85                  90                  95

Phe Arg Ser Ser Gln Ala Glu Leu Leu Ala Ile Ala Asp Glu Leu Glu
                    100                 105                 110

His Thr Trp His Ala Thr Val Asn Ala Ala Phe Val Arg Glu Ser Ala
            115                 120                 125

Glu Val Tyr Gln Gln Arg His Lys Leu Arg Lys Gly Ser
        130                 135                 140

<210> SEQ ID NO 151
<211> LENGTH: 1824
<212> TYPE: DNA
<213> ORGANISM: Klebsiella pneumoniae

<400> SEQUENCE: 151
atgccgttaa tagccgggat tgatatcggc aacgccacca ccgaggtggc gctggcgtcc       60
gactacccgc aggcgagggc gtttgttgcc agcgggatcg tcgcgacgac gggcatgaaa     120
```

```
gggacgcggg acaatatcgc cgggaccctc gccgcgctgg agcaggccct ggcgaaaaca    180
ccgtggtcga tgagcgatgt ctctcgcatc tatcttaacg aagccgcgcc ggtgattggc    240
gatgtggcga tggagaccat caccgagacc attatcaccg aatcgaccat gatcggtcat    300
aacccgcaga cgccgggcgg ggtgggcgtt ggcgtgggga cgactatcgc cctcgggcgg    360
ctggcgacgc tgccggcggc gcagtatgcc gaggggtgga tcgtactgat tgacgacgcc    420
gtcgatttcc ttgacgccgt gtggtggctc aatgaggcgc tcgaccgggg gatcaacgtg    480
gtggcggcga tcctcaaaaa ggacgacggc gtgctggtga acaaccgcct gcgtaaaacc    540
ctgccggtgg tggatgaagt gacgctgctg gagcaggtcc ccgaggggt aatggcggcg    600 gtggaagtgg ccgcgccggg ccaggtggtg cggatcctgt cgaatcccta cgggatcgcc    660
accttcttcg ggctaagccc ggaagagacc caggccatcg tccccatcgc ccgcgccctg    720
attggcaacc gttccgcggt ggtgctcaag accccgcagg gggatgtgca gtcgcgggtg    780
atcccggcgg gcaacctcta cattagcggc gaaaagcgcc gcggagaggc cgatgtcgcc    840
gagggcgcgg aagccatcat gcaggcgatg agcgcctgcg ctccggtacg cgacatccgc    900
ggcgaaccgg gcacccacgc cggcggcatg cttgagcggg tgcgcaaggt aatggcgtcc    960
ctgaccggcc atgagatgag cgcgatatac atccaggatc tgctggcggt ggatacgttt   1020
attccgcgca aggtgcaggg cgggatggcc ggcgagtgcg ccatggagaa tgccgtcggg   1080
atggcggcga tggtgaaagc ggatcgtctg caaatgcagg ttatcgcccg cgaactgagc   1140
gcccgactgc agaccgaggt ggtggtgggc ggcgtggagg ccaacatggc catcgccggg   1200
gcgttaacca ctcccggctg tgcggcgccg ctggcgatcc tcgacctcgg cgccggctcg   1260
acggatgcgg cgatcgtcaa cgcggagggg cagataacgg cggtccatct cgccggggcg   1320
gggaatatgg tcagcctgtt gattaaaacc gagctgggcc tcgaggatct ttcgctggcg   1380
gaagcgataa aaaatacccc gctggccaaa gtggaaagcc tgttcagtat tcgtcacgag   1440
aatggcgcgg tggagttctt tcgggaagcc ctcagcccgg cggtgttcgc caaagtggtg   1500
tacatcaagg agggcgaact ggtgccgatc gataacgcca gcccgctgga aaaaattcgt   1560
ctcgtgcgcc ggcaggcgaa agagaaagtg tttgtcacca actgcctgcg cgcgctgcgc   1620
caggtctcac ccgcggttc cattcgcgat atcgcctttg tggtgctggt gggcggctca   1680
tcgctggact ttgagatccc gcagcttatc acggaagcct tgtcgcacta tggcgtggtc   1740
gccgggcagg gcaatattcg gggaacagaa gggccgcgca atgcggtcgc caccgggctg   1800
ctactggccg gtcaggcgaa ttaa                                          1824
```

<210> SEQ ID NO 152
<211> LENGTH: 607
<212> TYPE: PRT
<213> ORGANISM: Klebsiella pneumoniae

<400> SEQUENCE: 152

```
Met Pro Leu Ile Ala Gly Ile Asp Ile Gly Asn Ala Thr Thr Glu Val
1               5                   10                  15

Ala Leu Ala Ser Asp Tyr Pro Gln Ala Arg Ala Phe Val Ala Ser Gly
                20                  25                  30

Ile Val Ala Thr Thr Gly Met Lys Gly Thr Arg Asp Asn Ile Ala Gly
            35                  40                  45

Thr Leu Ala Ala Leu Glu Gln Ala Leu Ala Lys Thr Pro Trp Ser Met
        50                  55                  60

Ser Asp Val Ser Arg Ile Tyr Leu Asn Glu Ala Ala Pro Val Ile Gly
```

```
                65                  70                  75                  80
            Asp Val Ala Met Glu Thr Ile Thr Glu Thr Ile Ile Thr Glu Ser Thr
                                85                  90                  95

Met Ile Gly His Asn Pro Gln Thr Pro Gly Gly Val Gly Val Gly Val
                            100                 105                 110

Gly Thr Thr Ile Ala Leu Gly Arg Leu Ala Thr Leu Pro Ala Ala Gln
                        115                 120                 125

Tyr Ala Glu Gly Trp Ile Val Leu Ile Asp Ala Val Asp Phe Leu
                    130                 135                 140

Asp Ala Val Trp Trp Leu Asn Glu Ala Leu Asp Arg Gly Ile Asn Val
            145                 150                 155                 160

Val Ala Ala Ile Leu Lys Lys Asp Asp Gly Val Leu Val Asn Asn Arg
                            165                 170                 175

Leu Arg Lys Thr Leu Pro Val Val Asp Glu Val Thr Leu Leu Glu Gln
                        180                 185                 190

Val Pro Glu Gly Val Met Ala Ala Val Glu Val Ala Ala Pro Gly Gln
                    195                 200                 205

Val Val Arg Ile Leu Ser Asn Pro Tyr Gly Ile Ala Thr Phe Phe Gly
                    210                 215                 220

Leu Ser Pro Glu Glu Thr Gln Ala Ile Val Pro Ile Ala Arg Ala Leu
            225                 230                 235                 240

Ile Gly Asn Arg Ser Ala Val Val Leu Lys Thr Pro Gln Gly Asp Val
                            245                 250                 255

Gln Ser Arg Val Ile Pro Ala Gly Asn Leu Tyr Ile Ser Gly Glu Lys
                        260                 265                 270

Arg Arg Gly Glu Ala Asp Val Ala Glu Gly Ala Glu Ala Ile Met Gln
                    275                 280                 285

Ala Met Ser Ala Cys Ala Pro Val Arg Asp Ile Arg Gly Glu Pro Gly
                    290                 295                 300

Thr His Ala Gly Gly Met Leu Glu Arg Val Arg Lys Val Met Ala Ser
            305                 310                 315                 320

Leu Thr Gly His Glu Met Ser Ala Ile Tyr Ile Gln Asp Leu Leu Ala
                            325                 330                 335

Val Asp Thr Phe Ile Pro Arg Lys Val Gln Gly Gly Met Ala Gly Glu
                        340                 345                 350

Cys Ala Met Glu Asn Ala Val Gly Met Ala Ala Met Val Lys Ala Asp
                    355                 360                 365

Arg Leu Gln Met Gln Val Ile Ala Arg Glu Leu Ser Ala Arg Leu Gln
                    370                 375                 380

Thr Glu Val Val Gly Gly Val Glu Ala Asn Met Ala Ile Ala Gly
            385                 390                 395                 400

Ala Leu Thr Thr Pro Gly Cys Ala Ala Pro Leu Ala Ile Leu Asp Leu
                            405                 410                 415

Gly Ala Gly Ser Thr Asp Ala Ala Ile Val Asn Ala Glu Gly Gln Ile
                        420                 425                 430

Thr Ala Val His Leu Ala Gly Ala Gly Asn Met Val Ser Leu Leu Ile
                    435                 440                 445

Lys Thr Glu Leu Gly Leu Glu Asp Leu Ser Leu Ala Glu Ala Ile Lys
                    450                 455                 460

Lys Tyr Pro Leu Ala Lys Val Glu Ser Leu Phe Ser Ile Arg His Glu
            465                 470                 475                 480

Asn Gly Ala Val Glu Phe Phe Arg Glu Ala Leu Ser Pro Ala Val Phe
                            485                 490                 495
```

-continued

```
Ala Lys Val Val Tyr Ile Lys Glu Gly Glu Leu Val Pro Ile Asp Asn
            500                 505                 510

Ala Ser Pro Leu Glu Lys Ile Arg Leu Val Arg Gln Ala Lys Glu
        515                 520                 525

Lys Val Phe Val Thr Asn Cys Leu Arg Ala Leu Arg Gln Val Ser Pro
    530                 535                 540

Gly Gly Ser Ile Arg Asp Ile Ala Phe Val Val Leu Val Gly Gly Ser
545                 550                 555                 560

Ser Leu Asp Phe Glu Ile Pro Gln Leu Ile Thr Glu Ala Leu Ser His
                565                 570                 575

Tyr Gly Val Val Ala Gly Gln Gly Asn Ile Arg Gly Thr Glu Gly Pro
            580                 585                 590

Arg Asn Ala Val Ala Thr Gly Leu Leu Leu Ala Gly Gln Ala Asn
        595                 600                 605

<210> SEQ ID NO 153
<211> LENGTH: 354
<212> TYPE: DNA
<213> ORGANISM: Klebsiella pneumoniae

<400> SEQUENCE: 153
atgtcgcttt caccgccagg cgtacgcctg ttttacgatc cgcgcgggca ccatgccggc      60
gccatcaatg agctgtgctg ggggctggag gagcagggg tcccctgcca gaccataacc     120
tatgacggag gcggtgacgc cgctgcgctg gcgccctgg cggccagaag ctcgcccctg      180
cgggtgggta tcgggctcag cgcgtccggc gagatagccc tcactcatgc ccagctgccg     240
gcggacgcgc cgctggctac cggacacgtc accgatagcg acgatcaact gcgtacgctc     300
ggcgccaacg ccgggcagct ggttaaagtc ctgccgttaa gtgagagaaa ctga           354

<210> SEQ ID NO 154
<211> LENGTH: 117
<212> TYPE: PRT
<213> ORGANISM: Klebsiella pneumoniae

<400> SEQUENCE: 154

Met Ser Leu Ser Pro Pro Gly Val Arg Leu Phe Tyr Asp Pro Arg Gly
1               5                   10                  15

His His Ala Gly Ala Ile Asn Glu Leu Cys Trp Gly Leu Glu Glu Gln
            20                  25                  30

Gly Val Pro Cys Gln Thr Ile Thr Tyr Asp Gly Gly Asp Ala Ala
        35                  40                  45

Ala Leu Gly Ala Leu Ala Ala Arg Ser Ser Pro Leu Arg Val Gly Ile
    50                  55                  60

Gly Leu Ser Ala Ser Gly Glu Ile Ala Leu Thr His Ala Gln Leu Pro
65                  70                  75                  80

Ala Asp Ala Pro Leu Ala Thr Gly His Val Thr Asp Ser Asp Asp Gln
                85                  90                  95

Leu Arg Thr Leu Gly Ala Asn Ala Gly Gln Leu Val Lys Val Leu Pro
            100                 105                 110

Leu Ser Glu Arg Asn
        115

<210> SEQ ID NO 155
<211> LENGTH: 1125
<212> TYPE: DNA
<213> ORGANISM: artificial sequence
<220> FEATURE:
<223> OTHER INFORMATION: Codon optimized amino alcohol kinase from
```

Erwinia caratovora subsp. atroseptica

<400> SEQUENCE: 155

```
atgagcgatg

```
gcttttggtc gtgatgttcg ctactttaat actttcggcg gtaacccagt atcctgccag      900
gcggcacatg ctgttctgcg cgttatccgt gaagaacagc tgcagcagaa cgcgcagcgt      960
gttggtgatt atctgcgcca aggtctgcag cagctggcac aacacttccc gctgatcggt     1020
gacattcgtg catatggtct gtttatcggt gctgaactgg tttccgaccg tgaatccaaa     1080
accccagcga gcgagtctgc actgcaggtt gttaacgcga tgcgtcagcg tggtgtactg     1140
atctccgcaa ccggcccggc ggcgaacatt ctgaagatcc gtcctccgct ggtattcctg     1200
gaggaacacg cggacgtgtt cctgactacc ctgtccgacg tgctggcgct gatcggtact     1260
cgtgcacagc gttaa                                                      1275
```

<210> SEQ ID NO 157
<211> LENGTH: 77
<212> TYPE: DNA
<213> ORGANISM: artificial sequence
<220> FEATURE:
<223> OTHER INFORMATION: Primer

<400> SEQUENCE: 157

```
caggaggaat taaccatggg gggttctcat catcatcatc atcatggtga cgatgacgat       60
aagatgagcg atggccg                                                     77
```

<210> SEQ ID NO 158
<211> LENGTH: 77
<212> TYPE: DNA
<213> ORGANISM: artificial sequence
<220> FEATURE:
<223> OTHER INFORMATION: Primer

<400> SEQUENCE: 158

```
cggccatcgc tcatcttatc gtcatcgtca ccatgatgat gatgatgatg agaaccccc       60 atggttaatt cctcctg                                                    77
```

<210> SEQ ID NO 159
<211> LENGTH: 20
<212> TYPE: DNA
<213> ORGANISM: artificial sequence
<220> FEATURE:
<223> OTHER INFORMATION: Primer

<400> SEQUENCE: 159

```
ggacctgctt cgctttatcg                                                  20
```

<210> SEQ ID NO 160
<211> LENGTH: 15
<212> TYPE: DNA
<213> ORGANISM: artificial sequence
<220> FEATURE:
<223> OTHER INFORMATION: Primer

<400> SEQUENCE: 160

```
gctagagatg atagc                                                       15
```

<210> SEQ ID NO 161
<211> LENGTH: 18
<212> TYPE: DNA
<213> ORGANISM: artificial sequence
<220> FEATURE:
<223> OTHER INFORMATION: Primer

<400> SEQUENCE: 161

```
ggaagagact atccagcg                                                    18
```

<210> SEQ ID NO 162
<211> LENGTH: 50
<212> TYPE: DNA
<213> ORGANISM: artificial sequence
<220> FEATURE:
<223> OTHER INFORMATION: Primer

<400> SEQUENCE: 162

```
gcgcgcccgg gaagaaggag ctcttcacca tgaacaaacc acagtcttgg          50
```

<210> SEQ ID NO 163
<211> LENGTH: 28
<212> TYPE: DNA
<213> ORGANISM: artificial sequence
<220> FEATURE:
<223> OTHER INFORMATION: Primer

<400> SEQUENCE: 163

```
gcgcgcccgg gttcatgcca cctctgcg                                  28
```

<210> SEQ ID NO 164
<211> LENGTH: 2432
<212> TYPE: DNA
<213> ORGANISM: Erwinia caratovora subsp. atroseptica

<400> SEQUENCE: 164

```
atgtctgacg gacgactcac cgcactttt cctgcattcc cacacccggc gtccaatcag    60
cccgtatttg ccgaggcttc accgcacgac gacgagttaa tgacgcaggc cgtaccgcag   120
gtttcctgtc agcaggcgtt ggcgattgcg cagcaagaat atggcttgtc tgggcagatg   180
tcgctgcttc agggcgagcg tgatgtgaat ttctgtctga cggtgacgcc agatgaacgc   240
tacatgctga aagtcatcaa tgcggcagaa cctgccgacg tcagcaattt ccaaaccgcg   300
ctgctgctgc atcttgcccg tcaggcacct gaactgcccg taccgcgtat caggtcgaca   360
aaagcgggtc agtcggaaac aggcgttgag atcgatggtg tactgctgcg tgtgcggctt   420
gtgagctatc tggcaggaat gccgcagtat ctggcctcac cgtcaacggc gctgatgccg   480
cagttggggg gaacgctggc gcagttggat aacgcgcttc acagctttac gcatccggcg   540
gcaaaccgtg cgctgctgtg ggatatcagc cgggcagagc aggtgcgtcc ttacctcgat   600
ttcgtttctg aaccgcagca gtatcagcat cttcagcgta ttttttgaccg ttatgacagt   660
aacgttgctc ctctgttgac gacgctacgt cgtcaggtca ttcataacga tctgaatccg   720
cataacgtgc tggtggatgg atcgtcgccg acgcgggtta ctggcattat cgattttggc   780
gatgccgtat ttgccccgtt aatttgcgaa gtcgcgacgg cactggcgta tcagatcggc   840
gatggaaccg atttgttgga gcatgttgtg ccgtttgttg cggcctatca ccaacgcatt   900
ccgttagcac cggaggagat tgcgctgtta cccgatctga tagcgacccg tatggcgctg   960
accctgacca ttgcgcagtg gcgagcatcg cgttatcccg acaatcggga gtatctgctg  1020
cgtaacgtgc cgcgctgttg gcacagtttg cagcgcattg cgacctattc ccatgcgcaa  1080
ttttgactc gcctacagca ggtttgcccg gagaatgcgc gatgaaccag aaaggaatga  1140
cgtctatgac gtctgaaatg acagcgacag aagctttgct ggcgcgccgt cagcgagtgt  1200
tgggcggcgg ttatcgcctg ttttatgaag agccgctgca tgtcgcgcgc ggcgagggcg  1260
tgtggctgtt cgatcaccaa gggaaacgtt atctggatgt ctacaataat gtggcttcgg  1320
tcggacattg ccaccccgcg gtggttgaag ccgtggcgcg acagagcgca caactcaata  1380
cccacacgcg ctatttgcac cacgcgattg tcgatttttgc ggaagatttg ctgagcgaat  1440
```

```
ttcccgccga attgaacaat gtaatgctga cctgtaccgg cagtgaggct aacgatctgg    1500
cgctgcgtat cgcccgacat gtcacgggcg ggacggggat gttggtgacg cgctgggcgt    1560
atcacggcgt gaccagcgcg ctggcggaac tgtctccgtc gctgggggat ggcgttgtgc    1620
gcggtagcca tgtgaagctg atcgacgcgc cagacactta tcgtcagccc ggtgcatttc    1680
ttaccagcat tcgtgaagcg ctggcgcaga tgcaacggga aggtattcgt cctgcggcgc    1740
tgctggtaga taccattttt tccagcgatg gcgtgttctg tgcgccggaa ggcgaaatgg    1800
cacaggcggc ggcgttgatc cgtcaggcgg gcgggctgtt tattgcggat gaagtgcagc    1860
cgggcttcgg gcgcaccggg gaatcactgt ggggctttgc gcgccacaat gtcgtccctg    1920
atttggtgag tctagggaaa ccgatgggca acggacatcc catcgctgga ttggtggggc    1980
gttccgctct gttcgacgca tttggcgcg atgtgcgcta tttcaatacc tttggcggca    2040
atccggtttc ctgtcaggcg gcgcacgcgg tgctgcgggt gattcgggaa gagcagttgc    2100
agcagaatgc ccagcgggtc ggtgattatc tgcggcaagg gttgcagcaa ctggcgcagc    2160
atttcccgct gattggtgat attcgggctt acggcctgtt tattggtgcg gagctggtca    2220
gcgatcgcga aagtaaaacg ccggcaagtg aatccgcgtt gcaggtggtg aatgcgatgc    2280
gccaacgtgg tgtgctcatc agcgcgacgg ggccagcggc gaacatactg aaaattcgcc    2340
cgccgctggt gtttctggaa gaacacgccg atgtgttctt aaccacgctg agtgacgttt    2400
tagcgctcat cggcactcgt gcacagagat aa                                  2432
```